United States Patent
Freyne et al.

(10) Patent No.: US 8,394,955 B2
(45) Date of Patent: Mar. 12, 2013

(54) 2,4 (4,6) PYRIMIDINE DERIVATIVES

(75) Inventors: Eddy Jean Edgard Freyne, Rumst (BE); Marc Willems, Vosselaar (BE); Werner Constant Johan Embrechts, Beerse (BE); Kristof Van Emelen, Sint-Niklaas (BE); Sven Franciscus Anna Van Brandt, Nijlen (BE); Frederik Jan Rita Rombouts, Antwerp (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/277,651

(22) Filed: Oct. 20, 2011

(65) Prior Publication Data

US 2012/0065395 A1    Mar. 15, 2012

Related U.S. Application Data

(62) Division of application No. 11/720,681, filed as application No. PCT/EP2005/056606 on Dec. 8, 2005, now Pat. No. 8,148,388.

(60) Provisional application No. 60/634,291, filed on Dec. 8, 2004.

(30) Foreign Application Priority Data

Dec. 8, 2004  (EP) .................................... 04106384

(51) Int. Cl.
 *C07D 239/02* (2006.01)
(52) U.S. Cl. ........................ 544/294; 544/322; 544/329
(58) Field of Classification Search .................. 544/294, 544/322, 329
 See application file for complete search history.

(56) References Cited

U.S. PATENT DOCUMENTS 7,312,225 B2    12/2007   Luecking et al.

FOREIGN PATENT DOCUMENTS

WO    WO 2004/026881 A1    4/2004

OTHER PUBLICATIONS

Banks KC. Arylaminoheterocyclic compounds II. Journal of the American Chemical Society. 1944; 66: 1131.*
Shawver, LK., et.al., "Smart Drugs: Tyrosine kinase inhibitors in cancer therapy", Cancer Cell, (2002), vol. 1, p. 117.
International Search Report (date of mailing Apr. 3, 2006) for corresponding Patent Application No. PCT/EP2005/056606.

* cited by examiner

*Primary Examiner* — Paul Zarek

(57) ABSTRACT

The present invention is drawn to intermediates relating to 2,4 (4,6) pyrimidine derived macrocycles, pharmaceutical compositions thereof, and methods of making said compounds. The compounds disclosed herein are inhibitors of EGF receptor tyrosine kinases and are useful for treating cell proliferative disorders, including atherosclerosis, restenosis, and cancer.

4 Claims, No Drawings

2,4 (4,6) PYRIMIDINE DERIVATIVES

CROSS REFERENCE TO RELATED APPLICATIONS

This application is a divisional of U.S. patent application Ser. No. 11/720,681, filed Jun. 1, 2007, now U.S. Pat. No. 8,148,388, issued Apr. 3, 2012, which is a national stage of PCT Application No. PCT/EP2005/056606, filed Dec. 8, 2005, which claims priority from European Patent Application No. 04106384.3, filed Dec. 8, 2004, which claims priority from U.S. Provisional Application Ser. No. 60/634,291, filed Dec. 8, 2004, all of which are hereby incorporated by reference in their entirety.

The human genome encompasses some 2,000 proteins that utilize adenosine 5'-triphosphate (ATP) in one way or another and some 500 of these encode for protein kinases, i.e the protein-tyrosine and protein-serine/threonine kinases, that share a catalytic domain conserved in sequence and structure but which are notably different in how there catalysis is regulated. Substrate phosphorylation by these enzymes is nature's predominant molecular way of organizing cellular signal transduction and regulating biochemical processes in general. It is not surprising, therefore, that abnormal phosphorylation of cellular proteins is a hallmark of disease and that there is a growing interest in the use of kinase inhibitors as drugs for therapeutic intervention in may disease states such as cancer, diabetes, inflammation and arthritis.

In fact the search for such agents has recently culminated in the approval of the first kinase inhibitor drugs Herceptin® (Trastuzumab) and Gleevec™ (imatinib mesylate) for medical use. Herceptin® (Trastuzumab) is targeted against Her2/neu, a receptor tyrosine kinase found to be amplified up to 100-fold in about 30% of patients with invasive breast cancer. In clinical trials Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeted to receptor tyrosine kinases. The second example, Gleevec™ (imatinib mesylate), is targeted against the abelson tyrosine kinase (BcR-Abl), a constitutively active cytoplasmic tyrosine kinase present in virtually all patients with chronic myelogenous leukaemia (CML) and 15% to 30% of adult patients with acute lymphoblastic leukaemia. In clinical trials Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N., "Lessons learned from the development of an Abl tyrosine kinase inhibitor for chronic myelogenous leukaemia.", 2000, J. Clin. Invest. 105, 3).

In addition to the above, EGF receptor tyrosine kinases has been shown to be implicated in non-malignant proliferative disorders such as psoriasis (Elder et al., Science, 1989, 243; 811). It is therefore expected that inhibitors of EGF type receptor tyrosine kinases will be useful in the treatment of non-malignant diseases of excessive cellular proliferation such as psoriasis, benign prostatic hypertrophy, atherosclerosis and restenosis.

It is accordingly an object of the present invention to provide further kinase inhibitors useful in the manufacture of medicaments, in particular in the manufacture of medicaments for the treatment of cell proliferative related disorders.

This invention relates to 2,4 (4,6) pyrimidine derived macrocycles of formula (I) that have been found to have kinase inhibitory activity. In particular, the compounds of the present invention were found to have an anti-proliferative activity and are accordingly useful in methods of treatment of the human or animal body, for example in the manufacture of medicaments for use in hyper proliferative disorders such as atherosclerosis, restenosis and cancer. The invention also relates to processes for the manufacture of said pyrimidine derivatives, to pharmaceutical compositions containing them and to their use in the manufacture of medicaments of use in the production of anti-proliferative effect.

This invention concerns compounds of formula (I)

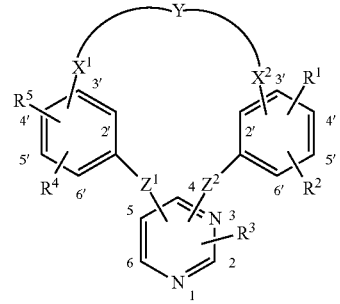

(I)

the N-oxide forms, the pharmaceutically acceptable addition salts and the stereochemically isomeric forms thereof, wherein $Z^1$ and $Z^2$ each independently represents $NR^{22}$; in particular $Z^1$ and $Z^2$ represents NH; in a more particular embodiment $Z^1$ and $Z^2$ are at positions 2,4 or 4,6 of the pyrimidine ring;

Y represents —$C_{3-9}$alkyl-; —$C_{3-9}$alkenyl-; —$C_{3-9}$alkynyl-;
—$C_{3-7}$alkyl-CO—NH— optionally substituted with amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-4}$alkyloxycarbonylamino-;
—$C_{3-7}$alkenyl-CO—NH— optionally substituted with amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-4}$alkyloxycarbonylamino-;
—$C_{3-7}$alkynyl-CO—NH— optionally substituted with amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-4}$alkyloxycarbonylamino-;
—$C_{1-5}$alkyl-oxy-$C_{1-5}$alkyl-; —$C_{1-5}$alkyl-$NR^6$—$C_{1-5}$alkyl-; —$C_{1-5}$alkyl-$NR^7$—CO—$C_{1-5}$alkyl-; —$C_{1-6}$alkyl-CO—NH—; —$C_{1-6}$alkyl-NH—CO—; —$C_{1-3}$alkyl-NH—CS—$Het^9$-; —$C_{1-3}$alkyl-NH—CO-$Het^3$-; $C_{1-2}$alkyl-CO-$Het^{10}$-CO—;
—$Het^4$-$C_{1-3}$alkyl-CO—NH—$C_{1-3}$alkyl-; —$C_{1-7}$alkyl-CO—; —$C_{1-6}$alkyl-CO—$C_{1-6}$alkyl-;
—$C_{1-2}$alkyl-NH—CO-$L^1$-NH—; —NH—CO-$L^2$-NH—; —$C_{1-2}$alkyl-CO—NH-$L^3$-CO—;
—$C_{1-2}$alkyl-NH—CO-$L^1$-NH—CO—$C_{1-3}$alkyl-; —$C_{1-2}$alkyl-NH—CO-$L^1$-NH—CO—;
—CO—NH-$L^2$-CO—; —$C_{1-2}$alkyl-CO—NH-$L^3$-CO—NH—$C_{1-3}$alkyl-;
—$C_{1-2}$alkyl-CO—NH-$L^3$-CO—NH—; —$C_{1-2}$alkyl-CO—$NR^{10}$—$C_{1-3}$alkyl-CO—;
—$C_{1-2}$alkyl-$NR^{11}$—$CH_2$—CO—NH—$C_{1-3}$alkyl-; —$NR^{12}$—CO—$C_{1-3}$alkyl-NH—;

Het⁵-CO—C$_{1-2}$alkyl-; —C$_{1-5}$alkyl-CO—NH—C$_{1-3}$alkyl-CO—NH—;
—C$_{1-5}$alkyl-NR$^{13}$—CO—C$_{1-3}$alkyl-NH—; -Het⁶-CO-Het⁷-; -Het⁸—NH—C$_{1-3}$alkyl-CO—NH—;
—C$_{1-3}$alkyl-NH—CO-Het$^{32}$-CO— or C$_{1-3}$alkyl-CO-Het$^{33}$-CO—NH—;

X¹ represents a direct bond, O, —O—C$_{1-2}$alkyl-, CO, —CO—C$_{1-2}$alkyl-, NR$^{16}$, —NR$^{16}$—C$_{1-2}$alkyl-, —CO—NR$^{17}$—, -Het$^{23}$-, -Het$^{23}$-C$_{1-2}$alkyl-, —O—N=CH— or —C$_{1-2}$alkyl-;

X² represents a direct bond, O, —O—C$_{1-2}$alkyl-, CO, —CO—C$_{1-2}$alkyl-, NR$^{18}$, —NR$^{18}$—C$_{1-2}$alkyl-, —CO—NR$^{19}$—, -Het$^{24}$-, -Het$^{24}$-C$_{1-2}$alkyl-, —O—N=CH— or —C$_{1-2}$alkyl-;

R¹ represents hydrogen, cyano, halo, hydroxy, formyl, C$_{1-6}$alkoxy-, C$_{1-6}$alkyl-,
halo-phenyl-carbonylamino-, Het$^{20}$,
C$_{1-6}$alkoxy- substituted with halo, Het¹ or C$_{1-4}$alkyloxy-, or R¹ represents
C$_{1-6}$alkyl substituted with one or where possible two or more substituents selected from hydroxy, Het$^{18}$ or halo;

R² represents hydrogen, cyano, halo, hydroxy, hydroxycarbonyl-, C$_{1-4}$alkyloxycarbonyl-, C$_{1-4}$alkylcarbonyl-, aminocarbonyl-, mono- or di(C$_{1-4}$alkyl)aminocarbonyl-, C$_{1-4}$alkyl-, C$_{2-6}$alkynyl-, C$_{3-6}$cycloalkyloxy-,
aminosulfonyl, mono- or di(C$_{1-4}$alkyl)aminosulfonyl, C$_{1-4}$alkylsulfide, C$_{1-4}$alkylsulfoxide, C$_{1-4}$alkylsulfide or C$_{1-6}$alkoxy-;

R³ represents hydrogen, cyano, nitro, C$_{1-4}$alkyl, or C$_{1-4}$alkyl substituted with one or more substituents selected from halo, C$_{1-4}$alkyloxy-, amino-, mono- or di(C$_{1-4}$alkyl)amino-, C$_{1-4}$alkyl-sulfonyl- or phenyl;

R⁴ represents hydrogen, cyano, halo, hydroxy, hydroxycarbonyl-,
C$_{1-4}$alkyloxycarbonyl-, C$_{1-4}$alkylcarbonyl-, aminocarbonyl-, mono- or di(C$_{1-4}$alkyl)aminocarbonyl-, C$_{1-4}$alkyl-, C$_{2-6}$alkynyl-, C$_{3-6}$cycloalkyloxy-, aminosulfonyl, mono- or di(C$_{1-4}$alkyl)aminosulfonyl, C$_{1-4}$alkylsulfide, C$_{1-4}$alkylsulfoxide, C$_{1-4}$alkylsulfide or C$_{1-6}$alkoxy-;

R⁵ represents hydrogen, cyano, halo, hydroxy, formyl, C$_{1-6}$alkoxy-, C$_{1-6}$alkyl-,
halo-phenyl-carbonylamino-, Het$^{21}$,
C$_{1-6}$alkoxy- substituted with halo, Het² or C$_{1-4}$alkyloxy-, or R⁵ represents
C$_{1-6}$alkyl substituted with one or where possible two or more substituents selected from hydroxy, Het$^{19}$ or halo;

R⁶ represents hydrogen, C$_{1-4}$alkyl, Het$^{11}$, Het$^{12}$-C$_{1-4}$alkyl-, phenyl-C$_{1-4}$alkyl- or phenyl wherein said R⁶ is optionally substituted with one or where possible two or more substituents selected from hydroxy, amino or C$_{1-4}$alkyloxy-;

R⁷ represents hydrogen, C$_{1-4}$alkyl, Het$^{13}$-C$_{1-4}$alkyl- or C$_{1-4}$alkyloxyC$_{1-4}$alkyl-;

R$^{10}$, R$^{12}$ and R$^{13}$ each independently represent hydrogen, or C$_{1-4}$alkyl optionally substituted with hydroxy, amino, mono- or di(C$_{1-4}$alkyl)amine, phenyl, Het$^{26}$ or C$_{1-4}$alkyloxy;

R$^{11}$ represents hydrogen, C$_{1-4}$alkyl or represent mono- or di(C$_{1-4}$alkyl)amino-C$_{1-4}$alkyl-carbonyl- optionally substituted with hydroxy, pyrimidinyl, mono- or di(C$_{1-4}$alkyl)amine or C$_{1-4}$alkyloxy;

R$^{16}$ and R$^{18}$ each independently represent hydrogen, C$_{1-4}$alkyl, C$_{1-4}$alkyl-oxy-carbonyl-, Het$^{16}$, Het$^{17}$-C$_{1-4}$alkyl- or phenyl-C$_{1-4}$alkyl-;

R$^{17}$ and R$^{19}$ each independently represent hydrogen, C$_{1-4}$alkyl, Het$^{14}$, Het$^{15}$-C$_{1-4}$alkyl- or phenyl-C$_{1-4}$alkyl-;

R$^{22}$ represents hydrogen, C$_{1-4}$alkyl- optionally substituted with one or where possible two or three substituents selected from halo, cyano and phenyl;

L¹ represents C$_{1-8}$alkyl optionally substituted one ore where possible two or more substituents selected from phenyl, indolyl, thienyl, pyridinyl, methylsulfide, hydroxy, thiol, cyano, thiazolyl, polyhaloC$_{1-4}$alkyl-phenyl-, C$_{1-4}$alkyloxy-, hydroxyphenyl, C$_{1-4}$alkyloxyphenyl-, aminocarbonyl, hydroxycarbonyl,
C$_{3-6}$cycloalkyl, amino, mono- or di(C$_{1-4}$alkyl)-amino-, imidazoyl or guanidino; in particular L¹ represents C$_{1-8}$alkyl optionally substituted one ore where possible two or more substituents selected from phenyl, indolyl, pyridinyl, methylsulfide, hydroxy, thiol, cyano, thiazolyl, polyhaloC$_{1-4}$alkyl-phenyl-, C$_{1-4}$alkyloxy-, hydroxyphenyl, C$_{1-4}$alkyloxyphenyl-, aminocarbonyl, hydroxycarbonyl, C$_{3-6}$cycloalkyl, amino, mono- or di(C$_{1-4}$alkyl)-amino-, imidazoyl or guanidino;

L² represents C$_{1-8}$alkyl optionally substituted one ore where possible two or more substituents selected from phenyl, indolyl, thienyl, pyridinyl, methylsulfide, hydroxy, thiol, cyano, thiazolyl, polyhaloC$_{1-4}$alkyl-phenyl-, C$_{1-4}$alkyloxy-, hydroxyphenyl, C$_{1-4}$alkyloxyphenyl-, aminocarbonyl, hydroxycarbonyl,
C$_{3-6}$cycloalkyl, amino, mono- or di(C$_{1-4}$alkyl)-amine-, imidazoyl or guanidino; in particular L² represents C$_{1-8}$alkyl optionally substituted one ore where possible two or more substituents selected from phenyl, indolyl, thienyl, methylsulfide, hydroxy, thiol, hydroxyphenyl, aminocarbonyl, hydroxycarbonyl, amino, mono- or di(C$_{1-4}$alkyl)-amino-, imidazoyl or guanidino;

L³ represents C$_{1-8}$alkyl optionally substituted one ore where possible two or more substituents selected from phenyl, indolyl, thienyl, pyridinyl, methylsulfide-, hydroxy, thiol, cyano, thiazolyl, polyhaloC$_{1-4}$alkyl-phenyl-, C$_{1-4}$alkyloxy-, hydroxyphenyl-, C$_{1-4}$alkyloxyphenyl-, aminocarbonyl-, hydroxycarbonyl-,
C$_{3-6}$cycloalkyl, amino, mono- or di(C$_{1-4}$alkyl)-amino-, imidazoyl or guanidino; in particular L³ represents C$_{1-8}$alkyl optionally substituted one ore where possible two or more substituents selected from phenyl, indolyl, thienyl, pyridinyl, methylsulfide-, hydroxy, thiol, cyano, hydroxyphenyl-, polyhaloC$_{1-4}$alkyl-phenyl-, C$_{1-4}$alkyloxy-, aminocarbonyl-, hydroxycarbonyl-, C$_{3-6}$cycloalkyl, amino, mono- or di(C$_{1-4}$alkyl)-amino-, imidazoyl or guanidino;

Het¹ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het¹ is optionally substituted with amino, C$_{1-4}$alkyl, hydroxy-C$_{1-4}$alkyl-, phenyl, phenyl-C$_{1-4}$alkyl-,
C$_{1-4}$alkyl-oxy-C$_{1-4}$alkyl-, mono- or di(C$_{1-4}$alkyl)amino- or amino-carbonyl-;

Het² represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het² is optionally substituted with amino, C$_{1-4}$alkyl, hydroxy-C$_{1-4}$alkyl-, phenyl, phenyl-C$_{1-4}$alkyl-,
C$_{1-4}$alkyl-oxy-C$_{1-4}$alkyl-, mono- or di(C$_{1-4}$alkyl)amino- or amino-carbonyl-;

Het³ and Het⁴ each independently represent a heterocycle selected from pyrrolidinyl,
2-pyrrolidinonyl, quinolinyl, isoquinolinyl, decahydroquinolinyl, piperazinyl or piperidinyl wherein said Het³ and Het⁴ are optionally substituted with one or where possible two or more substituents selected from hydroxy, $Het^{22}$-carbonyl, $C_{1-4}$alkyl, hydroxy-$C_{1-4}$alkyl- or polyhydroxy-$C_{1-4}$alkyl-;

$Het^5$ and $Het^6$ each independently represent a heterocycle selected from pyrrolidinyl,
2-pyrrolidinonyl, piperazinyl or piperidinyl wherein said $Het^5$ and $Het^6$ are optionally substituted with one or where possible two or more substituents selected from hydroxy, $C_{1-4}$alkyl, hydroxy-$C_{1-4}$alkyl- or polyhydroxy-$C_{1-4}$alkyl-;

$Het^7$ and $Het^8$ each independently represent a heterocycle selected from pyrrolidinyl,
2-pyrrolidinonyl, piperazinyl or piperidinyl wherein said $Het^7$ and $Het^8$ are optionally substituted with one or where possible two or more substituents selected from hydroxy, $C_{1-4}$alkyl, hydroxy-$C_{1-4}$alkyl- or polyhydroxy-$C_{1-4}$alkyl-;

$Het^9$ and $Het^{10}$ each independently represent a heterocycle selected from pyrrolidinyl, pyrrolyl, azetidinyl, 2-pyrrolidinonyl, piperazinyl or piperidinyl wherein said $Het^9$ and $Het^{10}$ are optionally substituted with one or where possible two or more substituents selected from hydroxy, $C_{1-4}$alkyl, hydroxy-$C_{1-4}$alkyl- or polyhydroxy-$C_{1-4}$alkyl-;

$Het^{11}$ represent a heterocycle selected from pyrrolidinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{12}$ represent a heterocycle selected from morpholinyl, pyrrolidinyl, piperazinyl or piperidinyl wherein said $Het^{12}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{13}$ represent a heterocycle selected from pyrrolidinyl or piperidinyl wherein said pyrrolidinyl or piperidinyl is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from pyrrolidinyl or piperidinyl wherein said pyrrolidinyl or piperidinyl is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from pyrrolidinyl or piperidinyl wherein said $Het^{16}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{17}$ represents a heterocycle selected from morpholinyl, pyrrolidinyl, piperazinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{18}$ or $Het^{19}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

$Het^{20}$ and $Het^{21}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{20}$ or $Het^{21}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

$Het^{22}$ represents a heterocycle selected from morpholinyl, pyrrolidinyl, piperazinyl or piperidinyl wherein said $Het^{22}$ is optionally substituted with one or where possible two or more substituents selected from hydroxy, $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{23}$ and $Het^{24}$ each independently represent a heterocycle selected from pyrrolidinyl, 2-pyrrolidinonyl, quinolinyl, isoquinolinyl, decahydroquinolinyl, piperazinyl or piperidinyl wherein said $Het^{23}$ or $Het^{24}$ is optionally substituted with one or where possible two or more substituents selected from hydroxy, $Het^{25}$, $Het^{22}$-carbonyl, $C_{1-4}$alkyl, hydroxy-$C_{1-4}$alkyl- or polyhydroxy-$C_{1-4}$alkyl-; and $Het^{25}$ and $Het^{26}$ each independently represent a heterocycle selected from morpholinyl, pyrrolidinyl, piperazinyl or piperidinyl wherein said $Het^{25}$ and $Het^{26}$ are optionally substituted with one or where possible two or more substituents selected from
$C_{1-4}$alkyl, $C_{3-6}$ cycloalkyl, hydroxy-$C_{1-4}$alkyl-, $C_{1-4}$alkyloxy$C_{1-4}$alkyl or polyhydroxy-$C_{1-4}$alkyl-;

$Het^{32}$ and $Het^{33}$ each independently represent a heterocycle selected from morpholinyl, pyrrolidinyl, 2-pyrrolidinonyl, piperazinyl or piperidinyl wherein said $Het^{32}$ and $Het^{33}$ are optionally substituted with one or where possible two or more substituents selected from hydroxy, $C_{1-4}$alkyl, hydroxy-$C_{1-4}$alkyl- or polyhydroxy-$C_{1-4}$alkyl-.

As used in the foregoing definitions and hereinafter,
halo is generic to fluoro, chloro, bromo and iodo;
$C_{1-2}$alkyl defines methyl or ethyl;
$C_{1-3}$alkyl defines straight and branched chain saturated hydrocarbon radicals having from 1 to 3 carbon atoms such as, for example, methyl, ethyl, propyl and the like;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;
$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;
$C_{1-6}$alkyl is meant to include $C_{1-5}$alkyl and the higher homologues thereof having 6 carbon atoms such as, for example hexyl, 1,2-dimethylbutyl, 2-methylpentyl and the like;
$C_{1-7}$alkyl defines straight and branched chain saturated hydrocarbon radicals having from 1 to 7 carbon atoms and is meant to include $C_{1-6}$alkyl and the higher homologues thereof having 7 carbon atoms such as, for example 1,2,3-dimethylbutyl, 1,2-methylpentyl and the like;
$C_{1-8}$alkyl defines straight and branched chain saturated hydrocarbon radicals having from 1 to 8 carbon atoms and is meant to include $C_{1-7}$alkyl and the higher homologues thereof having 8 carbon atoms such as, for example 2,3-dimethylhexyl, 2,3,4-trimethylpentyl, and the like;

$C_{3-9}$alkyl defines straight and branched chain saturated hydrocarbon radicals having from 3 to 9 carbon atoms such as propyl, butyl, pentyl, hexyl, heptyl, octyl, nonyl and the like;

$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;

$C_{3-9}$alkenyl defines straight and branched chain hydrocarbon radicals containing one double bond and having from 3 to 9 carbon atoms such as, for example 2-propenyl, 3-butenyl, 2-butenyl, 2-pentenyl, 3-pentenyl, 3-methyl-2-butenyl, 3-hexenyl and the like;

$C_{2-6}$alkynyl defines straight and branched chain hydrocarbon radicals containing one triple bond and having from 2 to 6 carbon atoms such as, for example, 2-propynyl, 3-butynyl, 2-butynyl, 2-pentynyl, 3-pentynyl, 3-methyl-2-butynyl, 3-hexynyl and the like;

$C_{3-6}$cycloalkyl is generic to cyclopropyl, cyclobutyl, cyclopentyl and cyclohexyl;

$C_{1-4}$alkyloxy defines straight or branched saturated hydrocarbon radicals such as methoxy, ethoxy, propyloxy, butyloxy, 1-methylethyloxy, 2-methylpropyloxy and the like;

$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;

polyhydroxy-$C_{1-4}$alkyl is generic to a $C_{1-4}$alkyl as defined hereinbefore, having two, three or were possible more hydroxy substituents, such as for example trifluoromethyl.

As used in the foregoing definitions and hereinafter, the term formyl refers to a radical of formula —CH(=O). When $X^1$ represent the divalent radical —O—N=CH—, said radical is attached with the carbon atom to the $R^3$, $R^4$ bearing cyclic moiety of the compounds of formula (I) and when $X^2$ represents the divalent radical —O—N=CH—, said radical is attached with the carbon atom to the $R^1$, $R^2$ bearing phenyl moiety of the compounds of formula (I).

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl. Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, trifluoroacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A first group of compounds are those compounds of formula (I) wherein one or more of the following restrictions apply;

$Z^1$ and $Z^2$ represents NH;

Y represents —$C_{3-9}$alkyl-; —$C_{3-9}$alkenyl-; —$C_{3-7}$alkyl-CO—NH— optionally substituted with amino, mono- or di($C_{1-4}$alkyl)amino or $C_{1-4}$alkyloxycarbonylamino-;
—$C_{1-5}$alkyl-oxy-$C_{1-5}$alkyl-; —$C_{1-5}$alkyl-NR$^6$—$C_{1-5}$alkyl-;
—$C_{1-5}$alkyl-NR$^7$—CO—$C_{1-5}$alkyl-; —$C_{1-6}$alkyl-CO—NH—; —$C_{1-6}$alkyl-NH—CO—;
—$C_{1-3}$alkyl-NH—CS-Het$^9$-; —$C_{1-3}$alkyl-NH—CO-Het$^3$-; $C_{1-2}$alkyl-CO-Het$^{10}$-CO—;
—Het$^4$-CH$_2$—CO—NH—$C_{1-3}$alkyl-; —$C_{1-7}$alkyl-CO—; —$C_{1-6}$alkyl-CO—$C_{1-6}$alkyl-;
—$C_{1-2}$alkyl-NH—CO-L$^1$-NH—; —$C_{1-2}$alkyl-CO—NH-L$^3$-CO—; —CO—NH-L$^2$-CO—;
$C_{1-2}$alkyl-NH—CO-L$^1$-NH—CO—; —$C_{1-2}$alkyl-NH—CO-L$^1$-NH—CO—$C_{1-3}$alkyl-CO—;

—$C_{1-2}$alkyl-CO—$NR^{10}$—$C_{1-3}$alkyl-CO—; —$C_{1-2}$alkyl-$NR^{11}$—$CH_2$—CO—NH—$C_{1-3}$alkyl-; —$NR^{12}$—CO—$C_{1-3}$alkyl-NH—; $Het^5$-CO—$C_{1-2}$alkyl-; —$C_{1-5}$alkyl-CO—NH—$C_{1-3}$alkyl-CO—NH—; —$C_{1-5}$alkyl-$NR^{13}$—CO—$C_{1-3}$alkyl-NH—; -$Het^6$-CO-$Het^7$-; -$Het^8$—NH—$C_{1-3}$alkyl-CO—NH—; $C_{1-3}$alkyl-NH—CO-$Het^{32}$-CO— or $C_{1-3}$alkyl-CO-$Het^{33}$-CO—NH—;

$X^1$ represents a direct bond, O, —O—$C_{1-2}$alkyl-, CO, —CO—$C_{1-2}$alkyl-, $NR^{16}$, —$NR^{16}$—$C_{1-2}$alkyl-, —CO—$NR^{17}$—, -$Het^{23}$-, -$Het^{23}$-$C_{1-2}$alkyl-, —O—N=CH— or —$C_{1-2}$alkyl-;

$X^2$ represents a direct bond, O, —O—$C_{1-2}$alkyl-, CO, —CO—$C_{1-2}$alkyl-, $NR^{18}$, —$NR^{18}$—$C_{1-2}$alkyl-, —CO—$NR^{19}$—, -$Het^{24}$-, -$Het^{24}$-$C_{1-2}$alkyl-, —O—N=CH— or —$C_{1-2}$alkyl-;

$R^1$ represents hydrogen, halo, $C_{1-6}$alkoxy-, $Het^{20}$ or $R^1$ represents $C_{1-6}$alkoxy- substituted with halo, $Het^1$ or $C_{1-4}$alkyloxy-;

$R^2$ represents hydrogen, halo or hydroxy;

$R^3$ represents hydrogen, nitro or cyano;

$R^4$ represents hydrogen or halo;

$R^5$ represents hydrogen, halo, $C_{1-6}$alkoxy-, $Het^{21}$ or $R^5$ represents $C_{1-6}$alkoxy- substituted with halo, $Het^2$ or $C_{1-4}$alkyloxy-;

$R^6$ represents hydrogen;

$R^7$ represents hydrogen, $C_{1-4}$alkyl, or $Het^{13}$-$C_{1-4}$alkyl-; in particular $R^7$ represents hydrogen or $Het^{13}$-$C_{1-4}$alkyl-;

$R^8$ and $R^9$ each independently represents hydrogen or $C_{1-4}$alkyl optionally substituted with phenyl, methylsulfide, hydroxy, thiol, amino, mono- or di($C_{1-4}$alkyl)-amino- or imidazoyl;

$R^{10}$, $R^{12}$ and $R^{13}$ each independently represent hydrogen or $C_{1-4}$alkyl optionally substituted with hydroxy or $C_{1-4}$alkyloxy;

$R^{11}$ represents hydrogen, or $C_{1-4}$alkyl;

$R^{16}$ and $R^{18}$ each independently represent hydrogen, $C_{1-4}$alkyl, $C_{1-4}$alkyl-oxy-carbonyl-, $Het^{16}$, $Het^{17}$-$C_{1-4}$alkyl- or phenyl-$C_{1-4}$alkyl-;

$R^{17}$ and $R^{19}$ each independently represent hydrogen, $C_{1-4}$alkyl, $Het^{14}$, $Het^{15}$-$C_{1-4}$alkyl- or phenyl-$C_{1-4}$alkyl-;

$L^1$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; in particular $L^1$ represents $C_{1-8}$alkyl optionally substituted one ore where possible two or more substituents selected from phenyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl;

$L^2$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; in particular $L^2$ represents $C_{1-8}$alkyl optionally substituted one ore where possible two or more substituents selected from phenyl, thienyl, methylsulfide, hydroxy, or mono- or di($C_{1-4}$alkyl)-amino-;

$L^3$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; in particular $L^3$ represents $C_{1-8}$alkyl optionally substituted one ore where possible two or more substituents selected from phenyl, pyridinyl, methylsulfide-, cyano, polyhalo$C_{1-4}$alkyl-phenyl-, $C_{1-4}$alkyloxy-, aminocarbonyl-, mono- or di($C_{1-4}$alkyl)-amino-, $C_{3-6}$ycolalkyl, thiazolyl or thienyl;

$Het^1$ and $Het^2$ each independently represent morpholinyl or pyridinyl, wherein said $Het^1$ or $Het^2$ are optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-; in particular $Het^1$ and $Het^2$ each independently represent morpholinyl;

$Het^3$ and $Het^4$ each independently represent a heterocycle selected from pyrrolidinyl, 2-pyrrolidinonyl, quinolinyl, isoquinolinyl, decahydroquinolinyl, piperazinyl or piperidinyl wherein said $Het^3$ and $Het^4$ are optionally substituted with one or where possible two or more hydroxy or $Het^{22}$-carbonyl-substituents;

$Het^5$ and $Het^6$ each independently represent a heterocycle selected from pyrrolidinyl, 2-pyrrolidinonyl, piperazinyl or piperidinyl wherein said $Het^5$ and $Het^6$ are optionally substituted with one or where possible two or more hydroxy substituents;

$Het^7$ and $Het^8$ each independently represent a heterocycle selected from pyrrolidinyl, 2-pyrrolidinonyl, piperazinyl or piperidinyl wherein said $Het^7$ and $Het^8$ are optionally substituted with one or where possible two or more hydroxy substituents;

$Het^9$ and $Het^{10}$ each independently represent a heterocycle selected from pyrrolidinyl, pyrrolyl, azetidinyl, 2-pyrrolidinonyl, piperazinyl or piperidinyl wherein said $Het^9$ and $Het^{10}$ are optionally substituted with one or where possible two or more hydroxy or $C_{1-4}$alkyl substituents;

$Het^{11}$ represent a heterocycle selected from pyrrolidinyl or piperidinyl wherein said $Het^{11}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{12}$ represent a heterocycle selected from morpholinyl, pyrrolidinyl, piperazinyl or piperidinyl wherein said $Het^{12}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{13}$ represent a heterocycle selected from pyrrolidinyl or piperidinyl wherein said pyrrolidinyl or piperidinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from pyrrolidinyl or piperidinyl wherein said pyrrolidinyl or piperidinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from pyrrolidinyl or piperidinyl wherein said $Het^{16}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{17}$ represents a heterocycle selected from morpholinyl, pyrrolidinyl, piperazinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$ and $Het^{21}$ each independently represent morpholinyl or pyridinyl;

$Het^{22}$ represents piperazinyl optionally substituted with $C_{1-4}$alkyl or hydroxy;

$Het^{23}$ and $Het^{24}$ each independently represent pyrrolidinyl, decahydroquinolinyl or piperidinyl wherein said $Het^{23}$ or $Het^{24}$ is optionally substituted with one or where possible two or more substituents selected from hydroxy, $Het^{22}$-carbonyl- or $C_{1-4}$alkyl;

$Het^{32}$ and $Het^{33}$ each independently represent a heterocycle selected from morpholinyl, pyrrolidinyl or piperidinyl.

Another group of compounds according to the present invention consists of those compounds of formula (I) wherein one or more of the following restrictions apply;

$Z^1$ and $Z^2$ represents NH;

Y represents —$C_{3-9}$alkyl-, —$C_{3-9}$alkenyl-, —$C_{3-7}$alkyl-CO—NH— optionally substituted with amino, mono- or di($C_{1-4}$alkyl)amino or $C_{1-4}$alkyloxycarbonylamino-, —$C_{1-5}$alkyl-oxy-$C_{1-5}$alkyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-CO—NH—, —$C_{1-6}$alkyl-NH—CO—, —$C_{1-3}$alkyl-NH—CS-$Het^9$-, —$C_{1-3}$alkyl-NH—CO-$Het^3$-, $C_{1-2}$alkyl-CO-$Het^{10}$-CO—, -$Het^4$-$CH_2$—CO—NH—$C_{1-3}$alkyl-, —$C_{1-7}$alkyl-CO—, —$C_{1-6}$alkyl-CO—$C_{1-6}$alkyl-, —$C_{1-2}$alkyl-NH—CO—$CR^8R^9$—NH—, —$C_{1-2}$alkyl-CO—NH—$CR^{20}R^{21}$—CO—, —$C_{1-2}$alkyl-CO—$NR^{10}$—$C_{1-3}$alkyl-CO—, —$C_{1-2}$alkyl-$NR^{11}$—$CH_2$—CO—NH—$C_{1-3}$alkyl-, —$NR^{12}$—CO—$C_{1-3}$alkyl-NH—, $Het^5$-CO—$C_{1-2}$alkyl-, —$C_{1-5}$alkyl-CO—NH—$C_{1-3}$alkyl-CO—NH—, —$C_{1-5}$alkyl-$NR^{13}$—CO—$C_{1-3}$alkyl-NH—, —CO—NH—$CR^{14}R^{15}$—CO—, -$Het^6$-CO-$Het^7$-, or -$Het^8$—NH—$C_{1-3}$alkyl-CO—NH—;

$X^1$ represents a direct bond, O, —O—$C_{1-2}$alkyl-, CO, —CO—$C_{1-2}$alkyl-, $NR^{16}$, —$NR^{16}$—$C_{1-2}$alkyl-, —CO—$NR^{17}$—, -$Het^{23}$-, -$Het^{23}$-$C_{1-2}$alkyl-, —O—N=CH— or —$C_{1-2}$alkyl-;

$X^2$ represents a direct bond, O, —O—$C_{1-2}$alkyl-, CO, —CO—$C_{1-2}$alkyl-, $NR^{18}$, —$NR^{18}$—$C_{1-2}$alkyl-, —CO—$NR^{19}$—, -$Het^{24}$-, -$Het^{24}$-$C_{1-2}$alkyl-, —O—N=CH— or —$C_{1-2}$alkyl-;

$R^1$ represents hydrogen, halo, $C_{1-6}$alkoxy-, $Het^{20}$ or $R^1$ represents $C_{1-6}$alkoxy- substituted with halo, $Het^1$ or $C_{1-4}$alkyloxy-;

$R^2$ represents hydrogen or halo;

$R^3$ represents hydrogen, nitro or cyano;

$R^4$ represents hydrogen or halo;

$R^5$ represents hydrogen, halo, $C_{1-6}$alkoxy-, $Het^{21}$ or $R^5$ represents $C_{1-6}$alkoxy- substituted with halo, $Het^2$ or $C_{1-4}$alkyloxy-;

$R^6$ represents hydrogen;

$R^7$ represents hydrogen, $C_{1-4}$alkyl, or $Het^{13}$-$C_{1-4}$alkyl-; in particular $R^7$ represents hydrogen or $Het^{13}$-$C_{1-4}$alkyl-;

$R^8$ and $R^9$ each independently represents hydrogen or $C_{1-4}$alkyl optionally substituted with phenyl, methylsulfide, hydroxy, thiol, amino, mono- or di($C_{1-4}$alkyl)-amino- or imidazoyl;

$R^{10}$, $R^{12}$ and $R^{13}$ each independently represent hydrogen or $C_{1-4}$alkyl optionally substituted with hydroxy or $C_{1-4}$alkyloxy;

$R^{11}$ represents hydrogen, or $C_{1-4}$alkyl;

$R^{14}$ and $R^{15}$ each independently represents hydrogen or $C_{1-4}$alkyl optionally substituted with mono- or di($C_{1-4}$alkyl)-amino-;

$R^{16}$ and $R^{18}$ each independently represent hydrogen, $C_{1-4}$alkyl, $C_{1-4}$alkyl-oxy-carbonyl-, $Het^{16}$, $Het^{17}$-$C_{1-4}$alkyl- or phenyl-$C_{1-4}$alkyl-;

$R^{17}$ and $R^{19}$ each independently represent hydrogen, $C_{1-4}$alkyl, $Het^{14}$, $Het^{15}$-$C_{1-4}$alkyl- or phenyl-$C_{1-4}$alkyl-;

$R^{20}$ and $R^{21}$ each independently represents hydrogen or $C_{1-4}$alkyl optionally substituted with mono- or di($C_{1-4}$alkyl)-amino-;

$Het^1$ and $Het^2$ each independently represent morpholinyl pyridinyl, wherein said $Het^1$ or $Het^2$ are optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-; in particular $Het^1$ and $Het^2$ each independently represent morpholinyl;

$Het^3$ and $Het^4$ each independently represent a heterocycle selected from pyrrolidinyl, 2-pyrrolidinonyl, quinolinyl, isoquinolinyl, decahydroquinolinyl, piperazinyl or piperidinyl wherein said $Het^3$ and $Het^4$ are optionally substituted with one or where possible two or more hydroxy substituents;

$Het^5$ and $Het^6$ each independently represent a heterocycle selected from pyrrolidinyl, 2-pyrrolidinonyl, piperazinyl or piperidinyl wherein said $Het^5$ and $Het^6$ are optionally substituted with one or where possible two or more hydroxy substituents;

$Het^7$ and $Het^8$ each independently represent a heterocycle selected from pyrrolidinyl, 2-pyrrolidinonyl, piperazinyl or piperidinyl wherein said $Het^7$ and $Het^8$ are optionally substituted with one or where possible two or more hydroxy substituents;

$Het^9$ and $Het^{10}$ each independently represent a heterocycle selected from pyrrolidinyl, 2-pyrrolidinonyl, piperazinyl or piperidinyl wherein said $Het^9$ and $Het^{10}$ are optionally substituted with one or where possible two or more hydroxy substituents;

$Het^{11}$ represent a heterocycle selected from pyrrolidinyl or piperidinyl wherein said $Het^{11}$ is optionally substituted with one or where possible two or more substituents selected from $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

$Het^{12}$ represent a heterocycle selected from morpholinyl, pyrrolidinyl, piperazinyl or piperidinyl wherein said $Het^{12}$ is optionally substituted with one or where possible two or more substituents selected from $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

$Het^{13}$ represent a heterocycle selected from pyrrolidinyl or piperidinyl wherein said pyrrolidinyl or piperidinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from pyrrolidinyl or piperidinyl wherein said pyrrolidinyl or piperidinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from pyrrolidinyl or piperidinyl wherein said $Het^{16}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{17}$ represents a heterocycle selected from morpholinyl, pyrrolidinyl, piperazinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$ and $Het^{21}$ each independently represent morpholinyl or pyridinyl; or $Het^{23}$ and $Het^{24}$ each independently represent pyrrolidinyl, decahydroquinolinyl or piperidinyl wherein said $Het^{23}$ or $Het^{24}$ is optionally substituted with one or where possible two or more substituents selected from hydroxy or $C_{1-4}$alkyl.

A further group of compounds according to the present invention consists of those compounds of formula (I) wherein one or more of the following restrictions apply;

$Z^1$ and $Z^2$ represents NH;

Y represents —$C_{3-9}$alkyl-, —$C_{3-9}$alkenyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-CO—NH—, —$C_{1-6}$alkyl-NH—CO—, —$C_{1-2}$alkyl-CO-$Het^{10}$-CO—, —$C_{1-3}$alkyl-NH—CO-$Het^3$-, -$Het^4$-$C_{1-3}$alkyl-CO—NH—$C_{1-3}$alkyl-, —$C_{1-2}$alkyl-NH—CO-$L^1$-NH—, —NH—CO-$L^2$-NH—, —$C_{1-2}$alkyl-CO—NH-$L^3$-CO—, —$C_{1-2}$alkyl-NH—CO-$L^1$-NH—CO—$C_{1-3}$alkyl-, —$C_{1-2}$alkyl-CO—NH-$L^3$-CO—NH—$C_{1-3}$alkyl-, —$C_{1-2}$alkyl-$NR^{11}$—$CH_2$—CO—NH—$C_{1-3}$alkyl-, $Het^5$-CO—$C_{1-2}$alkyl-, —$C_{1-5}$alkyl-CO—NH—$C_{1-3}$alkyl-CO—NH—, —$C_{1-5}$alkyl-$NR^{13}$—CO—$C_{1-3}$alkyl-NH—, —$C_{1-3}$alkyl-NH—CO-$Het^{32}$-CO—, or —$C_{1-3}$alkyl-CO-$Het^{33}$-CO—NH—;

$X^1$ represents a direct bond, O, —O—$C_{1-2}$alkyl-, —CO—$C_{1-2}$alkyl-, —$NR^{16}$—$C_{1-2}$alkyl-, —CO—$NR^{17}$—, $Het^{23}$-$C_{1-2}$alkyl- or $C_{1-2}$alkyl-;

$X^2$ represents a direct bond, O, —O—$C_{1-2}$alkyl-, —CO—$C_{1-2}$alkyl-, —$NR^{18}$—$C_{1-2}$alkyl-, —CO—$NR^{19}$—, $Het^{24}$-$C_{1-2}$alkyl- or $C_{1-2}$alkyl-;

$R^1$ represents hydrogen, halo, $C_{1-6}$alkyloxy- or $C_{1-6}$alkyloxy-substituted with $Het^1$ or $C_{1-4}$alkyloxy-;

$R^2$ represents hydrogen or halo;

$R^3$ represents hydrogen or cyano;

$R^4$ represents hydrogen or halo;

$R^5$ represents hydrogen, halo, $C_{1-6}$alkyloxy- or $C_{1-6}$alkyloxy-substituted with $Het^2$ or $C_{1-4}$alkyloxy-;

$R^6$ represents hydrogen;

$R^7$ represents hydrogen;

$R^{11}$ represents hydrogen or $C_{1-4}$alkyl;

$R^{13}$ represents hydrogen;

$R^{16}$ and $R^{18}$ represent hydrogen, $C_{1-4}$alkyl or $Het^{17}$-$C_{1-4}$alkyl-;

$R^{17}$ and $R^{19}$ represent hydrogen;

$L^1$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;

$L^2$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;

$L^3$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;

$Het^1$ represents morpholinyl, oxazolyl, isoxazolyl, or piperazinyl; in particular $Het^1$ represents morpholinyl or piperazinyl; more in particular $Het^1$ represents morpholinyl;

$Het^2$ represents morpholinyl, oxazolyl, isoxazolyl, or piperazinyl; in particular $Het^2$ represents morpholinyl or piperazinyl; more in particular $Het^2$ represents morpholinyl;

$Het^3$ represents morpholinyl, piperazinyl, piperidinyl or pyrrolidinyl; in particular $Het^3$ represents piperazinyl, piperidinyl or pyrrolidinyl;

$Het^4$ represents morpholinyl, piperazinyl, piperidinyl or pyrrolidinyl; in particular $Het^3$ represents piperazinyl or piperidinyl;

$Het^5$ represents morpholinyl, piperazinyl, piperidinyl or pyrrolidinyl, in particular $Het^5$ represents piperazinyl or piperidinyl, more in particular $Het^5$ represents piperazinyl;

$Het^{10}$ represents piperazinyl, piperidinyl, pyrrolidinyl or azetidinyl; in particular $Het^{10}$ represents pyrrolidinyl, piperazinyl or azetidinyl, more in particular $Het^{10}$ represents azetidinyl;

$Het^{17}$ represents morpholinyl, oxazolyl, isoxazolyl or piperazinyl; in particular $Het^{17}$ represents morpholinyl or piperazinyl;

$Het^{22}$ represents morpholinyl, oxazolyl, isoxazolyl or piperazinyl wherein said $Het^{22}$ is optionally substituted with $C_{1-4}$alkyl; in particular $Het^{22}$ represents morpholinyl or piperazinyl wherein said morpholinyl or piperazinyl or optionally substituted with $C_{1-4}$alkyl; more in particular $Het^{22}$ represents piperazinyl optionally substituted with $C_{1-4}$alkyl (methyl);

$Het^{23}$ and $Het^{24}$ each independently represent a heterocycle selected from pyrrolidinyl, piperazinyl or piperidinyl wherein said $Het^{23}$ or $Het^{24}$ are optionally substituted with $Het^{22}$-carbonyl;

$Het^{32}$ and $Het^{33}$ each independently represent a heterocycle selected from morpholinyl, piperazinyl, piperidinyl or pyrrolidinyl, in particular $Het^{32}$ and $Het^{33}$ are each independently selected from morpholinyl, piperazinyl or piperidinyl, more in particular $Het^{32}$ and $Het^{33}$ are each independently selected from morpholinyl or piperidinyl;

A further group of compounds according to the present invention consists of those compounds of formula (I) wherein one or more of the following restrictions apply;

$Z^1$ and $Z^2$ represents NH;

Y represents —$C_{3-9}$alkyl-, —$C_{1-5}$alkyl-$NR^7$—CO—$C_{1-5}$alkyl-, —$C_{1-6}$alkyl-CO—NH—, —$C_{1-6}$alkyl-NH—CO—, —$C_{1-2}$alkyl-CO-$Het^{10}$-CO—, -$Het^4$-$C_{1-3}$alkyl-CO—NH—$C_{1-3}$alkyl-, —$C_{1-2}$alkyl-CO—NH-$L^3$-CO—, —$C_{1-2}$alkyl-NH—CO-$L^1$-NH—CO—$C_{1-3}$alkyl, —$C_{1-2}$alkyl-CO—NH-$L^3$-CO—NH—$C_{1-3}$alkyl-, —$C_{1-3}$alkyl-NH—CO-$Het^{32}$-CO— or —$C_{1-3}$ alkyl-CO-$Het^{33}$-CO—NH—;

$X^1$ represents a direct bond, O, —O—$C_{1-2}$alkyl-, —CO—$C_{1-2}$alkyl-, —$NR^{16}$—$C_{1-2}$alkyl-, —CO—$NR^{17}$—, $Het^{23}$-$C_{1-2}$alkyl- or $C_{1-2}$alkyl; in particular $X^1$ represents a direct bond, O, —O—$C_{1-2}$alkyl-, —$NR^{16}$—$C_{1-2}$alkyl- or —$Het^{23}$-$C_{1-2}$alkyl-;

$X^2$ represents a direct bond, O, —O—$C_{1-2}$alkyl-, —CO—$C_{1-2}$alkyl-, —$NR^{18}$—$C_{1-2}$alkyl-, —CO—$NR^{19}$—, $Het^{24}$-$C_{1-2}$alkyl- or $C_{1-2}$alkyl; in particular $X^2$ represents a direct bond, O, —O—$C_{1-2}$alkyl-, —$NR^{18}$—$C_{1-2}$alkyl- or —$Het^{24}$-$C_{1-2}$alkyl-; more in particular $X^2$ represents O, —O—$C_{1-2}$alkyl-, —$NR^{18}$—$C_{1-2}$alkyl- or -$Het^{24}$-$C_{1-2}$alkyl-;

$R^1$ represents hydrogen, halo, $C_{1-6}$alkyloxy- or $C_{1-6}$alkyloxy-substituted with $Het^1$ or $C_{1-4}$alkyloxy-; in particular $R^1$ represents hydrogen, halo, $C_{1-6}$alkyloxy- or $C_{1-6}$alkyloxy- substituted with $Het^1$;

$R^2$ represents hydrogen or halo; in particular $R^2$ represents hydrogen;

$R^3$ represents hydrogen or cyano; in particular $R^3$ represents hydrogen;

$R^4$ represents hydrogen or halo; in particular $R^4$ represents hydrogen;

$R^5$ represents hydrogen, halo, $C_{1-6}$alkyloxy- or $C_{1-6}$alkyloxy-substituted with $Het^2$ or $C_{1-4}$alkyloxy-; in particular $R^5$ represents hydrogen or $C_{1-6}$alkyloxy-;

$R^7$ represents hydrogen;

$R^{16}$ and $R^{18}$ represent hydrogen, $C_{1-4}$alkyl or $Het^{17}$-$C_{1-4}$alkyl-;

$R^{17}$ and $R^{19}$ represent hydrogen;

$L^1$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;

in particular $L^1$ represents $C_{1-8}$alkyl optionally substituted with $C_{3-6}$ycloalkyl;

$L^3$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;

$Het^1$ represents morpholinyl, oxazolyl, isoxazolyl, or piperazinyl; in particular $Het^1$ represents morpholinyl or piperazinyl; more in particular $Het^1$ represents morpholinyl;

$Het^2$ represents morpholinyl, oxazolyl, isoxazolyl, or piperazinyl; in particular $Het^2$ represents morpholinyl or piperazinyl; more in particular $Het^2$ represents morpholinyl;

$Het^3$ represents morpholinyl, piperazinyl, piperidinyl or pyrrolidinyl; in particular $Het^3$ represents piperazinyl, piperidinyl or pyrrolidinyl; more in particular $Het^3$ represents piperazinyl or piperidinyl;

$Het^4$ represents morpholinyl, piperazinyl, piperidinyl or pyrrolidinyl; in particular $Het^4$ represents piperazinyl or piperidinyl;

$Het^5$ represents morpholinyl, piperazinyl, piperidinyl or pyrrolidinyl, in particular $Het^5$ represents piperazinyl or piperidinyl, more in particular $Het^5$ represents piperazinyl;

$Het^{10}$ represents piperazinyl, piperidinyl, pyrrolidinyl or azetidinyl; in particular $Het^{10}$ represents pyrrolidinyl, piperazinyl or azetidinyl, more in particular $Het^{10}$ represents azetidinyl;

$Het^{17}$ represents morpholinyl, oxazolyl, isoxazolyl or piperazinyl; in particular $Het^{17}$ represents morpholinyl or piperazinyl;

$Het^{22}$ represents morpholinyl, oxazolyl, isoxazolyl or piperazinyl wherein said $Het^{22}$ is optionally substituted with $C_{1-4}$alkyl; in particular $Het^{22}$ represents morpholinyl or piperazinyl wherein said morpholinyl or piperazinyl or optionally substituted with $C_{1-4}$alkyl; more in particular $Het^{22}$ represents piperazinyl optionally substituted with $C_{1-4}$alkyl;

$Het^{23}$ and $Het^{24}$ each independently represent a heterocycle selected from pyrrolidinyl, piperazinyl or piperidinyl wherein said $Het^{23}$ or $Het^{24}$ are optionally substituted with $Het^{22}$-carbonyl; in particular $Het^{23}$ and $Het^{24}$ each independently represent a heterocycle selected from piperazinyl or piperidinyl wherein said $Het^{23}$ and $Het^{24}$ are optionally substituted with $Het^{22}$-carbonyl;

$Het^{32}$ and $Het^{33}$ each independently represent a heterocycle selected from morpholinyl, piperazinyl, piperidinyl or pyrrolidinyl, in particular $Het^{32}$ and $Het^{33}$ are each independently selected from morpholinyl, piperazinyl or piperidinyl, more in particular $Het^{32}$ and $Het^{33}$ are each independently selected from morpholinyl or piperidinyl;

Another group of compounds are those compounds of formula (I) wherein one or more of the following restrictions apply;

$Z^1$ and $Z^2$ represents NH;

Y represents —$C_{3-9}$alkyl-, —$C_{3-9}$alkenyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-NH—CO—, —$C_{1-3}$alkyl-NH—CO-$Het^3$-, —$C_{1-2}$alkyl-NH—COC$R^8R^9$—NH—, —$C_{1-2}$alkyl-$NR^{11}$—$CH_2$CO—NH—$C_{1-3}$alkyl-, $Het^5$-CO—$C_{1-2}$alkyl-, or —$C_{1-5}$alkyl-CO—NH—$C_{1-3}$alkyl-CO—NH—;

$X^1$ represents a direct bond, O, —O—$C_{1-2}$alkyl-, —CO—$C_{1-2}$alkyl-, —$NR^{16}$—$C_{1-2}$alkyl-, —CO—$NR^{17}$— or $C_{1-2}$alkyl;

$X^2$ represents a direct bond, O, —O—$C_{1-2}$alkyl-, —CO—$C_{1-2}$alkyl-, —$NR^{18}$—$C_{1-2}$alkyl-, —CO—$NR^{19}$— or $C_{1-2}$alkyl;

$R^1$ represents hydrogen, halo, $C_{1-6}$alkyloxy- or $C_{1-6}$alkyloxy-substituted with $Het^1$ or $C_{1-4}$alkyloxy-;

$R^2$ represents hydrogen or halo;

$R^3$ represents hydrogen or cyano;

$R^4$ represents hydrogen or halo;

$R^5$ represents hydrogen, halo, $C_{1-6}$alkyloxy- or $C_{1-6}$alkyloxy-substituted with $Het^1$ or $C_{1-4}$alkyloxy-;

$R^6$ represents hydrogen;

$R^7$ represents hydrogen;

$R^8$ and $R^9$ each independently hydrogen or $C_{1-4}$alkyl;

$R^{11}$ represents hydrogen or $C_{1-4}$alkyl;

$R^{16}$ and $R^{18}$ represent hydrogen;

$R^{17}$ and $R^{19}$ represent hydrogen;

$Het^1$ represents morpholinyl;

$Het^2$ represents morpholinyl;

$Het^3$ represents pyrrolidinyl; or $Het^5$ represents piperazinyl

Another group of compounds are those compounds of formula (I) wherein one or more of the following restrictions apply;

$Z^1$ and $Z^2$ represent NH; in a particular embodiment $Z^1$ and $Z^2$ are at positions 2,4 or 4,6 of the pyrimidine ring;

Y represents —$C_{3-9}$alkyl-, —$C_{3-9}$alkenyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-CO—NH—, —$C_{1-6}$alkyl-NH—CO—, —$C_{1-2}$ alkyl-CO-$Het^{10}$-CO—, —$C_{1-3}$alkyl-NH—CO-$Het^3$-, -$Het^4$-$C_{1-3}$alkyl-CO—NH—$C_{1-3}$alkyl-, —$C_{1-2}$alkyl-NH—CO-$L^1$-NH—, —NH—CO-$L^2$-NH—, —$C_{1-2}$alkyl-CO—NH-$L^3$-CO—, —$C_{1-2}$alkyl-NH—CO-$L^1$-NH—CO—$C_{1-3}$alkyl-, —$C_{1-2}$alkyl-CO—NH-$L^3$-CO—NH—$C_{1-3}$alkyl-, —$C_{1-2}$alkyl-$NR^{11}$—$CH_2$—CO—NH—$C_{1-3}$alkyl-, $Het^5$-CO—$C_{1-2}$alkyl-, —C$_{1-5}$alkyl-CO—NH—C$_{1-3}$alkyl-CO—NH—, —C$_{1-5}$alkyl-NR$^{13}$—CO—C$_{1-3}$alkyl-NH—, —C$_{1-3}$alkyl-NH—CO-Het$^{32}$-CO—, or —C$_{1-3}$alkyl-CO-Het$^{33}$-CO—NH—;

X$^1$ represents a direct bond, O, —O—C$_{1-2}$alkyl-, —CO—C$_{1-2}$alkyl-, —NR$^{16}$—C$_{1-2}$alkyl-, —CO—NR$^{17}$—, Het$^{23}$-C$_{1-2}$alkyl- or C$_{1-2}$alkyl;

X$^2$ represents a direct bond, O, —O—C$_{1-2}$alkyl-, —CO—C$_{1-2}$alkyl-, —NR$^{18}$—C$_{1-2}$alkyl-, —CO—NR$^{19}$—, Het$^{24}$-C$_{1-2}$alkyl- or C$_{1-2}$alkyl;

R$^1$ and R$^5$ each independently represent hydrogen, halo, C$_{1-6}$alkyloxy- or C$_{1-6}$alkyloxy- substituted with Het$^1$ or C$_{1-4}$alkyloxy-;

R$^2$ and R$^4$ each independently represent hydrogen or halo;

R$^3$ represents hydrogen or cyano;

R$^6$, R$^7$, R$^{13}$, R$^{17}$ and R$^{19}$ represent hydrogen;

R$^{11}$ represents hydrogen or C$_{1-4}$alkyl;

R$^{16}$ and R$^{18}$ represent hydrogen, C$_{1-4}$alkyl or Het$^{17}$-C$_{1-4}$alkyl-;

L$^1$, L$^2$ and L$^3$ each independently represents C$_{1-8}$alkyl optionally substituted with one or where possible two or more substituents selected from phenyl, methylsulfide, cyano, polyhaloC$_{1-4}$alkyl-phenyl-, C$_{1-4}$alkyloxy, pyridinyl, mono- or di(C$_{1-4}$alkyl)-amino- or C$_{3-6}$cycloalkyl;

Het$^1$, Het$^2$, Het$^{17}$ each independently represent morpholinyl, oxazolyl, isoxazolyl, or piperazinyl;

Het$^3$, Het$^4$, Het$^5$ each independently represent morpholinyl, piperazinyl, piperidinyl or pyrrolidinyl;

Het$^{10}$ represents piperazinyl, piperidinyl, pyrrolidinyl or azetidinyl;

Het$^{22}$ represents morpholinyl, oxazolyl, isoxazolyl or piperazinyl wherein said Het$^{22}$ is optionally substituted with C$_{1-4}$alkyl;

Het$^{23}$ and Het$^{24}$ each independently represent a heterocycle selected from pyrrolidinyl, piperazinyl or piperidinyl wherein said Het$^{23}$ or Het$^{24}$ are optionally substituted with Het$^{22}$-carbonyl;

Het$^{32}$ and Het$^{33}$ each independently represent a heterocycle selected from morpholinyl, piperazinyl, piperidinyl or pyrrolidinyl.

In a further object, the present invention provides the 2,4-pyrimidine derivatives of the formula (I) compounds, hereinafter referred to as the compounds of formula

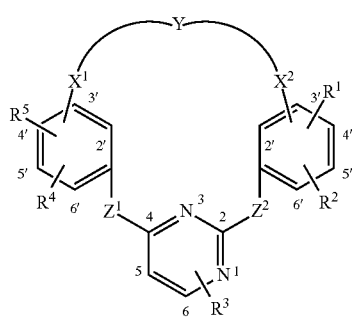

(I$^a$)

the N-oxide forms, the pharmaceutically acceptable addition salts and the stereochemically isomeric forms thereof, wherein Y, Z$^1$, Z$^2$, X$^1$, X$^2$, R$^1$, R$^2$, R$^3$, R$^4$ and R$^5$ are defined as for the compounds of formula (I) hereinbefore, including any of the limitations as provided for the different groups of compounds of formula (I) as defined hereinbefore.

In particular those compounds of formula (r) wherein one or more of the following restrictions apply;

Z$^1$ and Z$^2$ represents NH;

Y represents —C$_{3-9}$alkyl-, —C$_{3-9}$alkenyl-, —C$_{1-6}$alkyl-CO—NH—, —C$_{1-5}$alkyl-NR$^7$—CO—C$_{1-5}$alkyl, —C$_{1-3}$alkyl-NH—CO-Het$^3$- or —C$_{1-2}$alkyl-NR$^{11}$—CH$_2$—CO—NH—C$_{1-3}$alkyl-; in particular Y represents C$_{3-9}$alkyl-, —C$_{3-9}$alkenyl-, —C$_{1-6}$alkyl-CO—NH—, —C$_{1-3}$alkyl-NH—CO-Het$^3$- or —C$_{1-2}$alkyl-NR$^{11}$—CH$_2$—CO—NH—C$_{1-3}$alkyl- X$^1$ represents a direct bond, O, —O—C$_{1-2}$alkyl-, —NR$^{16}$—C$_{1-2}$alkyl-, Het$^{23}$-C$_{1-2}$alkyl or —CO—NR$^{17}$—; in particular X$^1$ represents a direct bond, O, —O—C$_{1-2}$alkyl-, or —CO—NR$^{17}$—

X$^2$ represents a direct bond, O, —O—C$_{1-2}$alkyl-, —NR$^{18}$—C$_{1-2}$alkyl-, Het$^{24}$-C$_{1-2}$alkyl or —CO—NR$^{19}$—; in particular X$^2$ represents a direct bond, O, —O—C$_{1-2}$alkyl-, or —CO—NR$^{19}$—;

R$^1$ represents hydrogen, halo, C$_{1-6}$alkoxy-, or R$^1$ represents C$_{1-6}$alkoxy- substituted with halo, Het$^1$ or C$_{1-4}$alkyloxy-; in particular R$^1$ represents hydrogen or halo;

R$^2$ represents hydrogen or halo;

R$^3$ represents hydrogen, or cyano;

R$^4$ represents hydrogen or halo;

R$^5$ represents hydrogen, halo, C$_{1-6}$alkoxy-, or R$^5$ represents C$_{1-6}$alkoxy- substituted with halo, Het$^2$ or C$_{1-4}$alkyloxy-;

R$^7$ represents hydrogen;

R$^{11}$ represents hydrogen or C$_{1-4}$alkyl-;

R$^{16}$ and R$^{18}$ each independently represent hydrogen, C$_{1-4}$alkyl or Het$^{17}$-C$_{1-4}$alkyl-;

R$^{17}$ represents hydrogen;

R$^{19}$ represents hydrogen;

Het$^3$ represents pyrrolidinyl;

Het$^{17}$ represents morpholinyl or piperazinyl wherein said Het$^{17}$ is optionally substituted with C$_{1-4}$alkyl;

Het$^{23}$ and Het$^{24}$ each independently represent a heterocycle selected from pyrrolidinyl or piperazinyl.

A further group of compounds according to the present invention consists of those compounds of formula (I$^a$) wherein one or more of the following restrictions apply;

Z$^1$ and Z$^2$ represents NH;

Y represents —C$_{3-9}$alkyl-, —C$_{3-9}$alkenyl-, —C$_{1-5}$alkyl-NR$^7$—CO—C$_{1-5}$alkyl-, —C$_{1-6}$alkyl-NH—CO—, —C$_{1-3}$alkyl-NH—CO-Het$^3$- or —C$_{1-2}$alkyl-NR$^{11}$—CH$_2$CO—NH—C$_{1-3}$alkyl-;

X$^1$ represents a direct bond, O, —NR$^{16}$—C$_{1-2}$alkyl- or C$_{1-2}$alkyl;

X$^2$ represents a direct bond, O, —NR$^{18}$—C$_{1-2}$alkyl- or C$_{1-2}$alkyl;

R$^1$ represents hydrogen, halo or C$_{1-6}$alkyloxy-;

R$^2$ represents hydrogen or halo;

R$^3$ represents hydrogen or cyano;

R$^4$ represents hydrogen or halo;

R$^5$ represents hydrogen, halo or C$_{1-6}$alkyloxy-;

R$^6$ represents hydrogen;

R$^7$ represents hydrogen;

R$^{11}$ represents hydrogen or C$_{1-4}$alkyl;

R$^{16}$ and R$^{18}$ represent hydrogen; and

R$^{17}$ and R$^{19}$ represent hydrogen;

Het$^3$ represents pyrrolidinyl.

In a further object, the present invention provides the 4,6-pyrimidine derivatives of the formula (I) compounds, hereinafter referred to as the compounds of formula

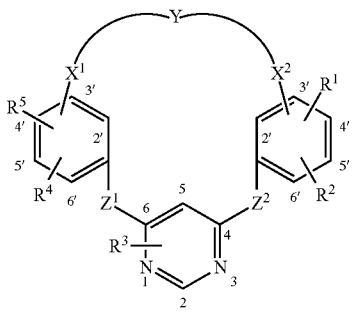
(I$^b$)

the N-oxide forms, the pharmaceutically acceptable addition salts and the stereochemically isomeric forms thereof, wherein Y, $Z^1$, $Z^2$, $X^1$, $X^2$, $R^1$, $R^2$, $R^3$, $R^4$ and $R^5$ are defined as for the compounds of formula (I) hereinbefore, including any of the limitations as provided for the different groups of compounds of formula (I) as defined hereinbefore.

In particular those compounds of formula (I$^b$) wherein one or more of the following restrictions apply;

$Z^1$ and $Z^2$ represents NH;

Y represents —$C_{3-9}$alkyl-, —$C_{3-9}$alkenyl-, —$C_{3-7}$alkyl-CO—NH— optionally substituted with amino, mono- or di($C_{1-4}$alkyl)amino or $C_{1-4}$alkyloxycarbonylamino-,
—$C_{1-5}$alkyl-oxy-$C_{1-5}$alkyl-, —$C_{1-5}$alkyl-NR$^6$—$C_{1-5}$alkyl-,
—$C_{1-5}$alkyl-NR$^7$—CO—$C_{1-5}$alkyl-, —$C_{1-6}$alkyl-CO—NH—, —$C_{1-6}$alkyl-NH—CO—, —$C_{1-3}$alkyl-NH—CS-Het$^9$-, —$C_{1-3}$alkyl-NH—CO-Het$^3$-, $C_{1-2}$alkyl-CO-Het$^{10}$-CO—,
-Het$^4$-CH$_2$—CO—NH—$C_{1-3}$alkyl-, —$C_{1-7}$alkyl-CO—, —$C_{1-6}$alkyl-CO—$C_{1-6}$alkyl-,
—$C_{1-2}$alkyl-NH—CO-L$^1$-NH—, —$C_{1-2}$alkyl-CO—NH-L$^3$-CO—, —CO—NH-L$^2$-CO—,
—$C_{1-2}$alkyl-NH—CO-L$^1$-NH—CO—, —$C_{1-2}$alkyl-NH—CO-L$^1$-NH—CO—$C_{1-3}$alkyl-CO—,
—$C_{1-2}$alkyl-CO—NR$^{10}$—$C_{1-3}$alkyl-CO—, —$C_{1-2}$alkyl-NR$^{11}$—CH$_2$—CO—NH—$C_{1-3}$alkyl-,
—NR$^{12}$—CO—$C_{1-3}$alkyl-NH—, Het$^5$-CO—$C_{1-2}$alkyl-, —$C_{1-5}$alkyl-CO—NH—$C_{1-3}$alkyl-CO—NH—, —$C_{1-5}$alkyl-NR$^{13}$—CO—$C_{1-3}$alkyl-NH—, -Het$^6$-CO-Het$^7$-, -Het$^8$—NH—$C_{1-3}$alkyl-CO—NH—,
$C_{1-3}$alkyl-NH—CO-Het$^{32}$-CO—, or $C_{1-3}$alkyl-CO-Het$^{33}$-CO—NH—;

$X^1$ represents a direct bond, O, —O—$C_{1-2}$alkyl-, CO, —CO—NR$^{16}$, —NR$^{16}$—$C_{1-2}$alkyl-, —CO—NR$^{17}$—, -Het$^{23}$-, -Het$^{23}$-$C_{1-2}$alkyl-, —O—N=CH— or —$C_{1-2}$alkyl-; in particular $X^1$ represents a direct bond, O, —O—$C_{1-2}$alkyl-, CO, —CO—$C_{1-2}$alkyl-, NR$^{16}$, —NR$^{16}$—$C_{1-2}$alkyl-, —CO—NR$^{17}$—, -Het$^{23}$-, -Het$^{23}$-$C_{1-2}$alkyl-, —O—N=CH— or —$C_{1-2}$alkyl-;

$X^2$ represents a direct bond, O, —O—$C_{1-2}$alkyl-, CO, —CO—NR$^{18}$, —NR$^{18}$—$C_{1-2}$alkyl-, —CO—NR$^{19}$—, -Het$^{24}$-, -Het$^{24}$-$C_{1-2}$alkyl-, —O—N=CH— or —$C_{1-2}$alkyl-; in particular $X^2$ represents a direct bond, O, —O—$C_{1-2}$alkyl-, CO, —CO—$C_{1-2}$alkyl-, NR$^{18}$, —NR$^{18}$—$C_{1-2}$alkyl, —CO—NR$^{19}$—, -Het$^{24}$-, -Het$^{24}$-$C_{1-2}$ alkyl-, —O—N=CH— or —$C_{1-2}$alkyl-;

$R^1$ represents hydrogen, halo, $C_{1-6}$alkoxy-, Het$^{20}$ or $R^1$ represents
$C_{1-6}$alkoxy- substituted with halo, Het$^1$ or $C_{1-4}$alkyloxy-; in particular $R^1$ represents hydrogen halo or $C_{1-4}$alkyloxy-;

$R^2$ represents hydrogen, halo or hydroxy; in particular $R^2$ represents hydrogen or halo;

$R^3$ represents hydrogen, nitro or cyano; in particular $R^3$ represents hydrogen or cyano;

$R^4$ represents hydrogen or halo;

$R^5$ represents hydrogen, halo, $C_{1-6}$alkoxy-, Het$^{21}$ or $R^5$ represents
$C_{1-6}$alkoxy- substituted with halo, Het$^2$ or $C_{1-4}$alkyloxy-; in particular $R^5$ represents hydrogen, halo or $C_{1-6}$alkyloxy-;

$R^6$ represents hydrogen;

$R^7$ represents hydrogen, $C_{1-4}$alkyl, or Het$^{13}$-$C_{1-4}$alkyl-; in particular $R^7$ represents hydrogen or Het$^{13}$-$C_{1-4}$alkyl-;

$R^8$ and $R^9$ each independently represents hydrogen or $C_{1-4}$alkyl optionally substituted with phenyl, methylsulfide, hydroxy, thiol, amino, mono- or di($C_{1-4}$alkyl)-amino- or imidazoyl; in particular $R^7$ represents hydrogen, $C_{1-4}$alkyl, or Het$^{13}$-$C_{1-4}$alkyl-; even more particular $R^7$ represents hydrogen or Het$^{13}$-$C_{1-4}$alkyl-;

$R^{10}$, $R^{12}$ and $R^{13}$ each independently represent hydrogen or $C_{1-4}$alkyl optionally substituted with hydroxy or $C_{1-4}$alkyloxy; in particular $R^{13}$ represents hydrogen, or $C_{1-4}$alkyl;

$R^{11}$ represents hydrogen, or $C_{1-4}$alkyl;

$R^{16}$ and $R^{18}$ each independently represent hydrogen, $C_{1-4}$alkyl, $C_{1-4}$alkyl-oxy-carbonyl-, Het$^{16}$, Het$^{17}$-$C_{1-4}$ alkyl- or phenyl-$C_{1-4}$alkyl-;

$R^{17}$ and $R^{19}$ each independently represent hydrogen, $C_{1-4}$alkyl, Het$^{14}$, Het$^{15}$-$C_{1-4}$alkyl- or phenyl-$C_{1-4}$alkyl-;

$L^1$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; in particular $L^1$ represents $C_{1-8}$alkyl optionally substituted one ore where possible two or more substituents selected from phenyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; more in particular $L^1$ represents $C_{1-8}$alkyl optionally substituted with phenyl, methylsulfide, hydroxy, thiol, amino, mono- or di($C_{1-4}$alkyl)-amino- or imidazoyl;

$L^2$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-, $C_{1-4}$alkyloxyphenyl-, aminocarbonyl, $C_{3-6}$cycloalkyl, amino, mono- or di($C_{1-4}$alkyl)-amine-, or imidazoyl; in particular $L^2$ represents $C_{1-8}$alkyl optionally substituted one ore where possible two or more substituents selected from phenyl, thienyl, methylsulfide, hydroxy, or mono- or di($C_{1-4}$alkyl)-amino-; more in particular $L^2$ represents $C_{1-8}$alkyl optionally substituted with
mono- or di($C_{1-4}$alkyl)-amino-;

$L^3$ represents $C_{1-8}$alkyl optionally substituted one ore where possible two or more substituents selected from phenyl, thienyl, pyridinyl, methylsulfide, hydroxy, thiol, thiazolyl, cyano, hydroxyphenyl, polyhalo$C_{1-4}$alkyl-phenyl-, $C_{1-4}$alkyloxy-,
$C_{1-4}$alkyloxyphenyl-, aminocarbonyl, $C_{3-6}$cycloalkyl, amino, mono- or di($C_{1-4}$alkyl)-amine-, or imidazoyl; in particular $L^3$ represents $C_{1-8}$alkyl optionally substituted one ore where possible two or more substituents selected from phenyl, pyridinyl, methylsulfide-, cyano, polyhaloC$_{1-4}$alkyl-phenyl-, C$_{1-4}$alkyloxy-, aminocarbonyl-, mono- or di(C$_{1-4}$alkyl)-amino-, C$_{3-6}$ycoloalkyl, thiazolyl or thienyl; more in particular L$^3$ represents C$_{1-8}$alkyl optionally substituted with mono- or di(C$_{1-4}$alkyl)-amino-;

Het$^1$ and Het$^2$ each independently represent morpholinyl pyridinyl, wherein said Het$^1$ or Het$^2$ are optionally substituted with amino, C$_{1-4}$alkyl, hydroxy-C$_{1-4}$alkyl-, phenyl, phenyl-C$_{1-4}$alkyl-, C$_{1-4}$alkyl-oxy-C$_{1-4}$alkyl-mono- or di(C$_{1-4}$alkyl)amino- or amino-carbonyl-; in particular Het$^1$ and Het$^2$ each independently represent morpholinyl;

Het$^3$ and Het$^4$ each independently represent a heterocycle selected from pyrrolidinyl,
2-pyrrolidinonyl, quinolinyl, isoquinolinyl, decahydroquinolinyl, piperazinyl or piperidinyl wherein said Het$^3$ and Het$^4$ are optionally substituted with one or where possible two or more hydroxy or Het$^{22}$-carbonyl-substituents; in particular Het$^3$ and Het$^4$ each independently represent a heterocycle selected from pyrrolidinyl, 2-pyrrolidinonyl, quinolinyl, isoquinolinyl, decahydroquinolinyl, piperazinyl or piperidinyl wherein said Het$^3$ and Het$^4$ are optionally substituted with one or where possible two or more hydroxy substituents;

Het$^5$ and Het$^6$ each independently represent a heterocycle selected from pyrrolidinyl,
2-pyrrolidinonyl, piperazinyl or piperidinyl wherein said Het$^5$ and Het$^6$ are optionally substituted with one or where possible two or more hydroxy substituents;

Het$^7$ and Het$^8$ each independently represent a heterocycle selected from pyrrolidinyl,
2-pyrrolidinonyl, piperazinyl or piperidinyl wherein said Het$^7$ and Het$^8$ are optionally substituted with one or where possible two or more hydroxy substituents;

Het$^9$ and Het$^{10}$ each independently represent a heterocycle selected from pyrrolidinyl, pyrrolyl, azetidinyl, 2-pyrrolidinonyl, piperazinyl or piperidinyl wherein said Het$^9$ and Het$^{10}$ are optionally substituted with one or where possible two or more hydroxy or C$_{1-4}$alkyl substituents;

Het$^{11}$ represent a heterocycle selected from pyrrolidinyl or piperidinyl wherein said Het$^{11}$ is optionally substituted with one or where possible two or more substituents selected from C$_{1-4}$alkyl, C$_{3-6}$cycloalkyl, hydroxy-C$_{1-4}$allyl-, C$_{1-4}$alkyloxyC$_{1-4}$alkyl or polyhydroxy-C$_{1-4}$alkyl-;

Het$^{12}$ represent a heterocycle selected from morpholinyl, pyrrolidinyl, piperazinyl or piperidinyl wherein said Het$^{12}$ is optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{13}$ represent a heterocycle selected from pyrrolidinyl or piperidinyl wherein said pyrrolidinyl or piperidinyl are optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{14}$ represent a heterocycle selected from pyrrolidinyl or piperidinyl wherein said pyrrolidinyl or piperidinyl are optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{15}$ represents a heterocycle selected from morpholinyl, pyrrolidinyl, piperazinyl or piperidinyl wherein said Het$^{15}$ is optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{16}$ represent a heterocycle selected from pyrrolidinyl or piperidinyl wherein said Het$^{16}$ is optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{17}$ represents a heterocycle selected from morpholinyl, pyrrolidinyl, piperazinyl or piperidinyl wherein said Het$^{17}$ is optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$alkyl-;

Het$^{20}$ and Het$^{21}$ each independently represent morpholinyl or pyridinyl;

Het$^{22}$ represents piperazinyl or piperidinyl optionally substituted with C$_{1-4}$alkyl or hydroxy;

Het$^{23}$ and Het$^{24}$ each independently represent pyrrolidinyl, decahydroquinolinyl or piperidinyl wherein said Het$^{23}$ or Het$^{24}$ is optionally substituted with one or where possible two or more substituents selected from hydroxy, Het$^{22}$-carbonyl- or C$_{1-4}$alkyl; in particular Het$^{23}$ and Het$^{24}$ each independently represent pyrrolidinyl, decahydroquinolinyl or pyridinyl wherein said Het$^{23}$ or Het$^{24}$ is optionally substituted with one or where possible two or more substituents selected from hydroxy or C$_{1-4}$alkyl;

Het$^{32}$ and Het$^{33}$ each independently represent a heterocycle selected from morpholinyl, pyrrolidinyl or piperidinyl.

A further group of compounds according to the present invention consists of those compounds of formula (I$^b$) wherein one or more of the following restrictions apply;

Z$^1$ and Z$^2$ represents NH;

Y represents —C$_{3-9}$alkyl-, —C$_{3-9}$alkenyl-, —C$_{1-5}$alkyl-NR$^6$—C$_{1-5}$alkyl-, —C$_{1-5}$alkyl-NR$^7$—CO—C$_{1-5}$alkyl-, —C$_{1-6}$alkyl-CO—NH—, —C$_{1-6}$alkyl-NH—CO—, —C$_{1-2}$ alkyl-CO -Het$^{10}$-CO—, —C$_{1-3}$alkyl-NH—CO-Het$^3$-, -Het$^4$-C$_{1-3}$alkyl-CO—NH—C$_{1-3}$alkyl-, —C$_{1-2}$alkyl-NH—CO-L$^1$-NH—, —NH—CO-L$^2$-NH—, —C$_{1-2}$alkyl-CO—NH-L$^3$-CO—, —C$_{1-2}$alkyl-NH—CO-L$^1$-NH—CO—C$_{1-3}$alkyl-, —C$_{1-2}$alkyl-CO—NH-L$^3$-CO—NH—C$_{1-3}$alkyl-, —C$_{1-2}$alkyl-NR$^{11}$—CH$_2$—CO—NH—C$_{1-3}$alkyl-, Het$^5$-CO—C$_{1-2}$alkyl-, —C$_{1-5}$alkyl-CO—NH—C$_{1-3}$alkyl-CO—NH—, —C$_{1-5}$alkyl-NR$^{13}$—CO—C$_{1-3}$alkyl-NH—, —C$_{1-3}$alkyl-NH—CO-Het$^{32}$-CO—, or —C$_{1-3}$alkyl-CO-Het$^{33}$-CO—NH—; in particular Y represents —C$_{3-9}$alkyl-, —C$_{1-5}$alkyl-NR$^6$—C$_{1-5}$alkyl-, —C$_{1-5}$alkyl-NR$^7$—CO—C$_{1-5}$alkyl-, —C$_{1-6}$alkyl-NH—CO—, —C$_{1-2}$alkyl-NH—CO-L$^1$-NH—, Het$^5$-CO—C$_{1-2}$alkyl-, or —C$_{1-5}$alkyl-CO—NH—C$_{1-3}$alkyl-CO—NH—;

X$^1$ represents a direct bond, O, —O—C$_{1-2}$alkyl-, —CO—C$_{1-2}$ alkyl-, —NR$^{16}$—C$_{1-2}$alkyl-, —CO—NR$^{17}$—, Het$^{23}$-C$_{1-2}$alkyl- or C$_{1-2}$alkyl; in particular X$^1$ represents a direct bond, O, —O—C$_{1-2}$alkyl-, —CO—C$_{1-2}$alkyl-, —NR$^{16}$—C$_{1-2}$alkyl-, —CO—NR$^{17}$— or C$_{1-2}$alkyl;

X$^2$ represents a direct bond, O, —O—C$_{1-2}$alkyl-, —CO—C$_{1-2}$ alkyl-, —NR$^{18}$—C$_{1-2}$alkyl-, —CO—NR$^{19}$—, Het$^{24}$-C$_{1-2}$alkyl- or C$_{1-2}$alkyl; in particular X$^2$ represents a direct bond, O, —O—C$_{1-2}$alkyl-, —CO—C$_{1-2}$alkyl-, —NR$^{18}$—C$_{1-2}$alkyl-, —CO—NR$^{19}$— or C$_{1-2}$alkyl;

R$^1$ represents hydrogen, halo, C$_{1-6}$alkyloxy- or C$_{1-6}$alkyloxy-substituted with Het$^1$ or C$_{1-4}$alkyloxy-;

R$^2$ represents hydrogen or halo;

$R^3$ represents hydrogen or cyano;
$R^4$ represents hydrogen or halo;
$R^5$ represents hydrogen, halo, $C_{1-6}$alkyloxy- or $C_{1-6}$alkyloxy- substituted with $Het^2$ or $C_{1-4}$alkyloxy-;
$R^6$ represents hydrogen;
$R^7$ represents hydrogen;
$R^{11}$ represents hydrogen or $C_{1-4}$alkyl;
$R^{13}$ represents hydrogen;
$R^{16}$ and $R^{18}$ represent hydrogen, $C_{1-4}$alkyl or $Het^{17}$-$C_{1-4}$alkyl-; in particular $R^{16}$ and $R^{18}$ represent hydrogen;
$R^{17}$ and $R^{19}$ represent hydrogen;
$L^1$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl; in particular $L^1$ represents $C_{1-8}$alkyl;
$L^2$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;
$L^3$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl;
$Het^1$ represents morpholinyl, oxazolyl, isoxazolyl, or piperazinyl; in particular $Het^1$ represents morpholinyl or piperazinyl; more in particular $Het^1$ represents morpholinyl;
$Het^2$ represents morpholinyl, oxazolyl, isoxazolyl, or piperazinyl; in particular $Het^2$ represents morpholinyl or piperazinyl; more in particular $Het^2$ represents morpholinyl;
$Het^3$ represents morpholinyl, piperazinyl, piperidinyl or pyrrolidinyl; in particular $Het^3$ represents piperazinyl, piperidinyl or pyrrolidinyl;
$Het^4$ represents morpholinyl, piperazinyl, piperidinyl or pyrrolidinyl; in particular $Het^3$ represents piperazinyl or piperidinyl;
$Het^5$ represents morpholinyl, piperazinyl, piperidinyl or pyrrolidinyl, in particular $Het^5$ represents piperazinyl or piperidinyl, more in particular $Het^5$ represents piperazinyl;
$Het^{10}$ represents piperazinyl, piperidinyl, pyrrolidinyl or azetidinyl; in particular $Het^{10}$ represents pyrrolidinyl, piperazinyl or azetidinyl, more in particular $Het^{10}$ represents azetidinyl;
$Het^{17}$ represents morpholinyl, oxazolyl, isoxazolyl or piperazinyl; in particular $Het^{17}$ represents morpholinyl or piperazinyl;
$Het^{22}$ represents morpholinyl, oxazolyl, isoxazolyl or piperazinyl wherein said $Het^{22}$ is optionally substituted with $C_{1-4}$alkyl; in particular $Het^{22}$ represents morpholinyl or piperazinyl wherein said morpholinyl or piperazinyl or optionally substituted with $C_{1-4}$alkyl; more in particular $Het^{22}$ represents piperazinyl optionally substituted with $C_{1-4}$alkyl;
$Het^{23}$ and $Het^{24}$ each independently represent a heterocycle selected from pyrrolidinyl, piperazinyl or piperidinyl wherein said $Het^{23}$ or $Het^{24}$ are optionally substituted with $Het^{22}$-carbonyl;
$Het^{32}$ and $Het^{33}$ each independently represent a heterocycle selected from morpholinyl, piperazinyl, piperidinyl or pyrrolidinyl, in particular $Het^{32}$ and $Het^{33}$ are each independently selected from morpholinyl, piperazinyl or piperidinyl, more in particular $Het^{32}$ and $Het^{33}$ are each independently selected from morpholinyl or piperidinyl;

A further group of compounds according to the present invention consists of those compounds of formula (I) wherein one or more of the following restrictions apply;
$Z^1$ and $Z^2$ represents NH;
Y represents —$C_{3-9}$alkyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-NH—CO—, —$C_{1-2}$alkyl-NH—CO-$L^1$-NH—, $Het^5$-CO—$C_{1-2}$alkyl-, NH—CO-$L^2$-NH— or —$C_{1-5}$alkyl-CO—NH—$C_{1-3}$alkyl-CO—NH—; in particular Y represents —$C_{3-9}$alkyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-NH—CO—, —$C_{1-2}$alkyl-NH—CO-$L^1$-NH— or —NH—CO-$L^2$-NH—;
$X^1$ represents O, —O—$C_{1-2}$alkyl-, —CO—$C_{1-2}$alkyl- or $Het^{23}$-$C_{1-2}$alkyl-; in particular $X^1$ represents O, —O—$C_{1-2}$alkyl- or —CO—$C_{1-2}$alkyl-;
$X^2$ represents O, —O—$C_{1-2}$alkyl-, —CO—$C_{1-2}$alkyl- or $Het^{24}$-$C_{1-2}$alkyl-; in particular $X^2$ represents O, —O—$C_{1-2}$alkyl- or —CO—$C_{1-2}$alkyl-;
$R^1$ represents hydrogen, halo, $C_{1-6}$alkyloxy- or $C_{1-6}$alkyloxy- substituted with $Het^1$;
$R^2$ represents hydrogen or halo;
$R^3$ represents hydrogen or cyano;
$R^4$ represents hydrogen or halo;
$R^5$ represents hydrogen, halo, $C_{1-6}$alkyloxy- or $C_{1-6}$alkyloxy- substituted with $Het^2$;
$R^6$ represents hydrogen;
$R^7$ represents hydrogen;
$R^{11}$ represents hydrogen or $C_{1-4}$alkyl;
$R^{13}$ represents hydrogen;
$L^1$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl; in particular $L^1$ represents $C_{1-8}$alkyl;
$L^2$ represents $C_{1-8}$alkyl optionally substituted with one or where possible two or more substituents selected from phenyl, methylsulfide, cyano, polyhalo$C_{1-4}$alkyl-phenyl-, $C_{1-4}$alkyloxy, pyridinyl, mono- or di($C_{1-4}$alkyl)-amino- or $C_{3-6}$cycloalkyl; in particular $L^2$ represents $C_{1-8}$alkyl;
$Het^1$ represents morpholinyl, oxazolyl, isoxazolyl, or piperazinyl; in particular $Het^1$ represents morpholinyl or piperazinyl; more in particular $Het^1$ represents morpholinyl;
$Het^2$ represents morpholinyl, oxazolyl, isoxazolyl, or piperazinyl; in particular $Het^2$ represents morpholinyl or piperazinyl; more in particular $Het^2$ represents morpholinyl;
$Het^5$ represents morpholinyl, piperazinyl, piperidinyl or pyrrolidinyl, in particular $Het^5$ represents piperazinyl or piperidinyl, more in particular $Het^5$ represents piperazinyl;
$Het^{22}$ represents morpholinyl, oxazolyl, isoxazolyl or piperazinyl wherein said $Het^{22}$ is optionally substituted with $C_{1-4}$alkyl; in particular $Het^{22}$ represents morpholinyl or piperazinyl wherein said morpholinyl or piperazinyl or optionally substituted with $C_{1-4}$alkyl; more in particular $Het^{22}$ represents piperazinyl optionally substituted with $C_{1-4}$alkyl;
$Het^{23}$ and $Het^{24}$ each independently represent a heterocycle selected from pyrrolidinyl, piperazinyl or piperidinyl wherein said $Het^{23}$ or $Het^{24}$ are optionally substituted with $Het^{22}$-carbonyl; in particular $Het^{23}$ and $Het^{24}$ represent pyrrolidinyl.

In a further embodiment of the present invention the compounds of formula (I) are selected from the group consisting of;
1H,7H-6, 2:12,8-dimetheno-13,1,3,5,7,16,19-benzoxahexaazacyclotricosine-17,20(14H)-dione, 24-chloro-15, 16,18,19,21-pentahydro-11-methoxy- 6, 2:12,8-dimetheno-7H-13,1,3,5,7,17,20-benzoxahexaaza-cyclotetracosine-18,21-dione, 25-chloro-1,14,15,16,17,19,20,22-octahydro-11-methoxy-19-(2-methylpropyl)-, (19S)—

1H,7H-2,6:12,8-dimetheno-13,20,1,3,5,7-benzodioxatet-raazacyclodocosine, 23-bromo-14,15,16,17,18,19-hexahydro-11-methoxy- 1H,7H-6,2:8,12-dimetheno-13,20,1,3,5,7-benzodioxatet-raazacyclodocosine, 23-bromo-14,15,16,17,18,19-hexahydro-10-methoxy- 1H,7H-2,6:12,8-dimetheno-14H-13,19,1,3,5,7-benzodiox-atetraazacycloheneicosine, 22-bromo-15,16,17,18-tet-rahydro-11-methoxy- 1H,7H-6,2:8,12-dimetheno-13,20,1,3,5,7,17-benzodioxap-entaazacyclodocosine, 23-chloro-14,15,16,17,18,19-hexahydro-11-methoxy- 6,2:8,12-dimetheno-7H-13,1,3,5,7,17,20-benzoxahexaaza-cyclotetracosine-18,21-dione, 25-chloro-1,14,15,16,17,19,20,22-octahydro-11-methoxy-19,19-dimethyl- 1H-7H-6,2:8,12-dimetheno-13,1,3,5,7,16,19-benzoxa-hexaazacyclotricosine-17,20(14H)-dione, 24-chloro-15,16,18,19,21-pentahydro-18,18-dimethyl-11-[3-(4-mor-pholinyl)propoxy]-

1H,7H-6,2:8,12-dimetheno-13,1,3,5,7,16,19-benzoxa-hexaazacyclotricosine-17,20(14H)-dione, 24-chloro-15,16,18,19,21-pentahydro-11-[3-(4-morpholinyl)propoxy]-

14,21-dioxa-2,4,8,17,28-pentaazatetracyclo[20.3.1.1~3,7~0.1~9,13~]octacosa-1(26),3,5,7(28),9,11,13(27),22,24-nonaene-6-carbonitrile, 16-oxo- 14,19-dioxa-2,4,8,26-tetraazatetracyclo[18.3.1.1~3,7~0.1~9,13~]hexacosa-1(24),3,5,7(26),9,11,13(25),20,22-nonaene-6-carbonitrile 14,21-dioxa-2,4,8,18,28-pentaazatetracyclo[20.3.1.1~3,7~0.1~9,13~]octacosa-1(26),3,5,7(28),9,11,13(27),22,24-nonaen-19-one 21,17-metheno-15,11-nitrilo-16H-pyrrolo[2,1-r][13,1,5,7,16,19]benzoxapentaazacyclodocosine-12-carbonitrile, 8-chloro-7-fluoro-1,2,3,5,10,23,24,25,26,26a-decahydro-20-methoxy-26-oxo-, (26aS)—

14,22-dioxa-2,4,8,19,29-pentaazatetracyclo[21.3.1.1~3,7~0.1~9,13~]nonacosa-1(27),3,5,7(29),9,11,13(28),23,25-nonaen-20-one 12,8-metheno-6,2-nitrilo-7H-13,1,5,7,16,19-benzoxapen-taazacyclodocosine-3-carbonitrile, 23-chloro-1,14,15,16,17,18,19,20-octahydro-11-methoxy-19-methyl-17-oxo- 1H,7H-12,8-metheno-6,2-nitrilo-13,1,5,7,17,20-benzoxap-entaazacyclotricosine-3-carbonitrile, 24-chloro-14,15,16,17,18,19,20,21-octahydro-11-methoxy-20-methyl-18-oxo- Other special group of compounds are:

those compounds of formula (I) wherein —$X^1$— or —$X^2$— represents —O—;

those compounds of formula (I) wherein —$X^1$— represents —$C_{1-2}$alkyl-$NR^{16}$—;

those compounds of formula (I) wherein —$X^2$— represents —$C_{1-2}$alkyl-$NR^{17}$—;

those compounds of formula (I) wherein —$X^1$— represents either of a direct bond, —O—, —O—$C_{1-2}$alkyl- or —$NR^{16}$—$C_{1-2}$alkyl- and wherein —$X^2$— represents either of —O—, —O—$C_{1-2}$alkyl-, —$NR^{17}$—$C_{1-2}$alkyl or —$Het^{24}$-$C_{1-2}$alkyl-;

those compounds of formula (I) wherein —$X^1$— represents —O— or —$NR^{16}$—$C_{1-2}$alkyl- and wherein —$X^2$— represents —$NR^{17}$—$C_{1-2}$alkyl or —$Het^{24}$-$C_{1-2}$alkyl-;

those compounds of formula (I) wherein —$X^1$— represents —CO—$NR^{17}$—, in particular CO—NH;

those compounds of formula (I) wherein —$X^2$— represents —CO—$NR^{18}$—, in particular CO—NH;

those compounds of formula (I) wherein $R^1$ represent fluor and $R^2$ represents Cl;

those compounds of formula (I) wherein $R^2$ represents Cl;

those compounds of formula (I) wherein $R^2$ represents hydrogen;

those compounds of formula (I) wherein $R^1$ represents chloro or fluoro;

those compounds of formula (I) wherein $R^5$ represents hydrogen or $C_{1-4}$alkyloxy-;

those compounds of formula (I0 wherein $R^5$ represents $C_{1-4}$alkyloxy-, in particular methoxy;

those compounds of formula (I) wherein $R^4$ represents hydrogen;

those compounds of formula (I) wherein Y represents $C_{3-9}$alkyl and $R^1$ and $R^2$ each independently represent —O— or CO—NH;

those compounds of formula (I) wherein Y represents —$C_{1-5}$alkyl-$NR^7$—CO—$C_{1-5}$alkyl, —$C_{1-2}$alkyl-NH—CO-$L^1$-NH—, —$C_{1-2}$alkyl-CO—NH-$L^3$-CO—, —$C_{1-2}$alkyl-NH—CO-$L^1$-NH—CO—, —$C_{1-2}$alkyl-NH—CO-$L^1$-NH—CO—$C_{1-3}$alkyl-, —$C_{1-2}$alkyl-CO—NH-$L^3$-CO—NH—, —$C_{1-2}$alkyl-CO—NH-$L^3$-CO—NH—$C_{1-3}$alkyl-, —CO—NH-$L^2$-CO— or —NH—CO-$L^2$-NH—;

those compounds of formula (I) wherein Y represents —$C_{1-5}$alkyl-$NR^7$—CO—$C_{1-5}$alkyl, —$C_{1-2}$alkyl-CO—NH-$L^3$-CO—, —$C_{1-2}$alkyl-CO—NH-$L^3$-CO—NH—$C_{1-3}$alkyl-, —$C_{1-3}$alkyl-CO-$Het^{28}$-CO—NH—, —$C_{1-6}$alkyl-CO—NH—, —$C_{1-2}$alkyl-CO-$Het^{10}$-CO—, —$C_{1-3}$alkyl-NH—CO-$Het^{27}$-CO— or —$Het^4$-$C_{1-3}$alkyl-CO—NH—$C_{1-3}$alkyl-;

those compounds of formula (I) wherein Y represents —$C_{1-5}$alkyl-$NR^7$—CO—$C_{1-5}$alkyl, —$C_{1-2}$alkyl-NH—CO-$L^1$-NH—, —$C_{1-2}$alkyl-CO—NH-$L^3$-CO—, —$C_{1-2}$alkyl-NH—CO-$L^1$-NH—CO—, —$C_{1-2}$alkyl-NH—CO-$L^1$-NH—CO—$C_{1-3}$alkyl-, —$C_{1-2}$alkyl-CO—NH-$L^3$-CO—NH—, —$C_{1-2}$alkyl-CO—NH-$L^3$-CO—NH—$C_{1-3}$alkyl-, —CO—NH-$L^2$-CO—, —NH—CO-$L^2$-NH—, —$C_{1-3}$alkyl-CO-$Het^{28}$-CO—NH—, —$C_{1-6}$alkyl-CO—NH—, —$C_{1-2}$alkyl-CO-$Het^{10}$-CO—, —$C_{1-3}$alkyl-NH—CO-$Het^{27}$-CO— or -$Het^4$-$C_{1-3}$alkyl-CO—NH—$C_{1-3}$alkyl-;

In a further embodiment of the present invention the $X^2$ substituent is at position 3', the $R^1$ substituent represents hydrogen or halo and is at position 4', the $R^2$ substituent represents halo and is at position 5', the $X^1$ substituent is at position 3', the $R^5$ substituent is at position 4' and represents hydrogen or $C_{1-4}$alkyloxy- and the $R^4$ substituent at position 5' of the structure of formula (I). Alternatively, the $X^2$ substituent is at position 2', the $R^1$ substituent represents hydrogen or halo and is at position 4', the $R^2$ substituent represents halo and is at position 5', the $X^1$ substituent is at position 3', the $R^5$ substituent is at position 4' and represents hydrogen or $C_{1-4}$alkyloxy- and the $R^4$ substituent at position 5' of the structure of formula (I).

The compounds of this invention can be prepared by any of several standard synthetic processes commonly used by those skilled in the art of organic chemistry and include both solution phase and solid phase chemistry techniques. These standard synthetic processes are for example described in the following references; "Heterocyclic Compounds"—Vol. 24

(part 4) p 261-304 Fused pyrimidines, Wiley—Interscience; Chem. Pharm. Bull., Vol 41 (2) 362-368 (1993); J. Chem. Soc., Perkin Trans. 1, 2001, 130-137. In brief, in a first step a 2,4 or 4,6-di-I or di-Cl-pyrimidine (II) is aminated with an appropriate aniline of formula (III) to yield the anilinopyrimidine of general formula (IV). In a second step this anilinopyrimidine is further substituted with a further aniline of general formula (V) which provides the bis(aniline)pyrimidines of formula (VI). Deprotection and ring closure provides the compounds of the present invention.

The aniline derivatives of formula (III) or (V) are either known structures or obtained using standard synthetic processes commonly used by those skilled in the art of organic chemistry, in particular departing from suitable nitrobenzaldehydes or nitrophenols. See for example the general synthesis schemes 6-12 hereinafter.

In case of solid phase chemistry the compounds of the present invention are generally prepared according to Scheme 1.

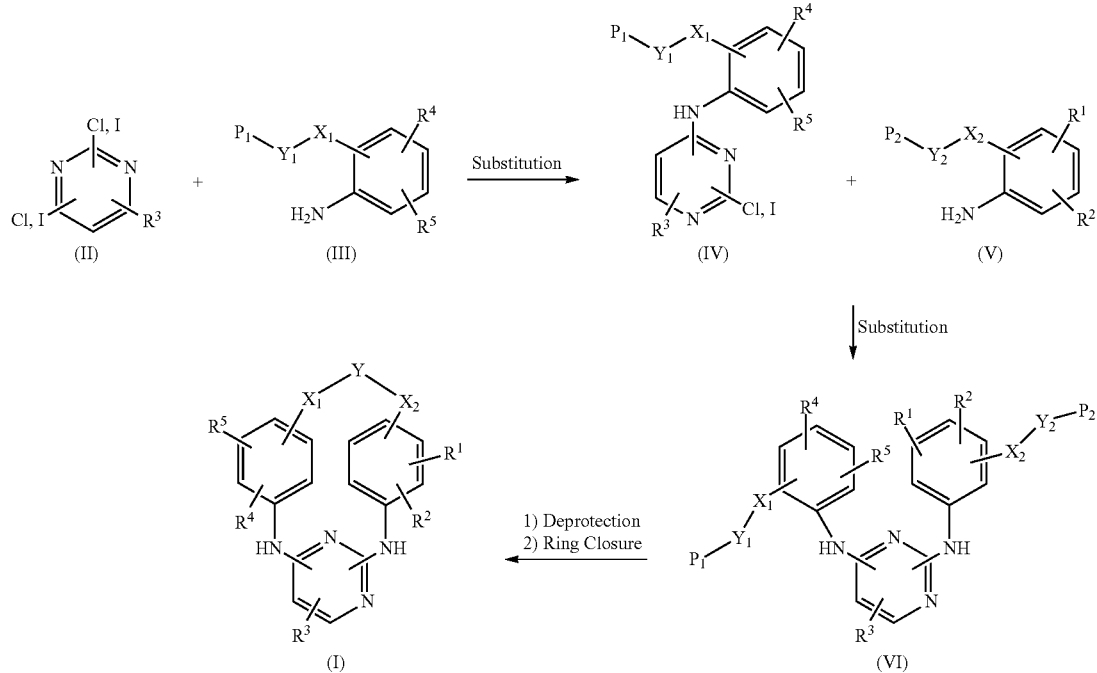

Wherein $Y_1$ and $Y_2$ each independently represent $C_{1-7}$alkyl, $C_{3-7}$alkenyl or $C_{3-7}$alkynyl wherein said $C_{1-7}$alkyl, $C_{3-7}$alkenyl, $C_{3-7}$alkynyl are optionally substituted with one or where possible two or more substituents selected from amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfonyl and $C_{1-4}$alkyloxycarbonylamino; or $Y_1$ and $Y_2$ each independently represent Het', Het'-CO,
Het'-$C_{1-5}$alkyl, $CR^8R^9$—NH, $CR^8R^9$—NH—CO, $CR^{20}R^{21}$—CO, $CR^{20}R^{21}$—CO—NH, CO—$C_{1-3}$alkyl, NH—CO—$C_{1-3}$alkyl, $C_{1-3}$alkyl-$NR^{11}$—$CH_2$, $CH_2$—CO—NH—$C_{1-3}$alkyl or $C_{1-3}$alkyl-NH, wherein $R^8$, $R^9$, $R^{11}$, $R^{20}$ and $R^{21}$ are as defined for the compounds of formula (I) hereinbefore and wherein Het[1] represents a heterocycle selected from the group consisting of pyrrolidinyl, 2-pyrrolidinyl, quinolinyl, isoquinolinyl, decahydroquinolinyl, piperazinyl or piperidinyl wherein said Het[1] is optionally substituted with one or where possible two or more substituents selected from hydroxy, Het[22]-carbonyl, $C_{1-4}$alkyl, hydroxy-$C_{1-4}$alkyl or polyhydroxy-$C_{1-4}$alkyl, wherein Het[22] is as defined for the compounds of formula (I).

$P_1$ and $P_2$ each independently represent optionally protected functional groups, such as for example a primary or secondary amine, hydroxy, hydroxycarbonyl or halo (Cl, Br or I), which upon reaction produce together with the $Y_1$ respectively $Y_2$ substituent to which they are attached, the divalent Y radical as defined for the compounds of formula (I) hereinbefore.

In a first step, a formyl functionalized polystyrene such as for example 2-(3,5-dimethoxy-4-formylphenoxy)ethoxymethyl polystyrene (1) is aminated with an appropriate Boc-protected amino aniline of formula (A) by reductive amination using art known conditions, such as for example using $NaBH_4$ and titanium(iv)isopropoxide as reducing agents in $CH_2Cl_2/CH_3COOH$ 1% or $DMF/CH_3COOH$ 1% as solvent. This reaction is typically performed overnight at room temperature.

The thus obtained secondary amine (2) is subsequently coupled to 2,4 or 4,6-di-I or di-Cl-pyrimidine by stirring the reagens in an appropriate solvent such as propanol or 1-butanol at an elevated temperature (at 60-90° C.) for about 40 hours in the presence of N-ethyl-N-(1-methylethyl)-2-propanamine (DIPEA).

To obtain the bis(anilino)pyrimidine scaffold of the present invention, the intermediate resin (3) is further reacted with an appropriate aniline ester (B) using the Pd/BINAP catalyzed amination reaction, i.e. typically performed in toluene or dioxane as a solvent, using $Pd_2(dba)_3$ or $Pd(OAc)_2$ as precatalyst at a ratio of BINAP to Pd in the range of 5.0-1.0, optionally in the presence of a weak base such as for example $Cs_2CO_3$. This reaction is performed under $N_2$ and shaken for 10-20 h at a temperature ranging from 65 to 110° C.

Deprotection provides the intermediates 4 or 4' which after ring closure provides the compounds of formula I[i] or are further elongated with Boc-protected amino acids (C) to yield the compounds of formula I[ii].

Scheme 1
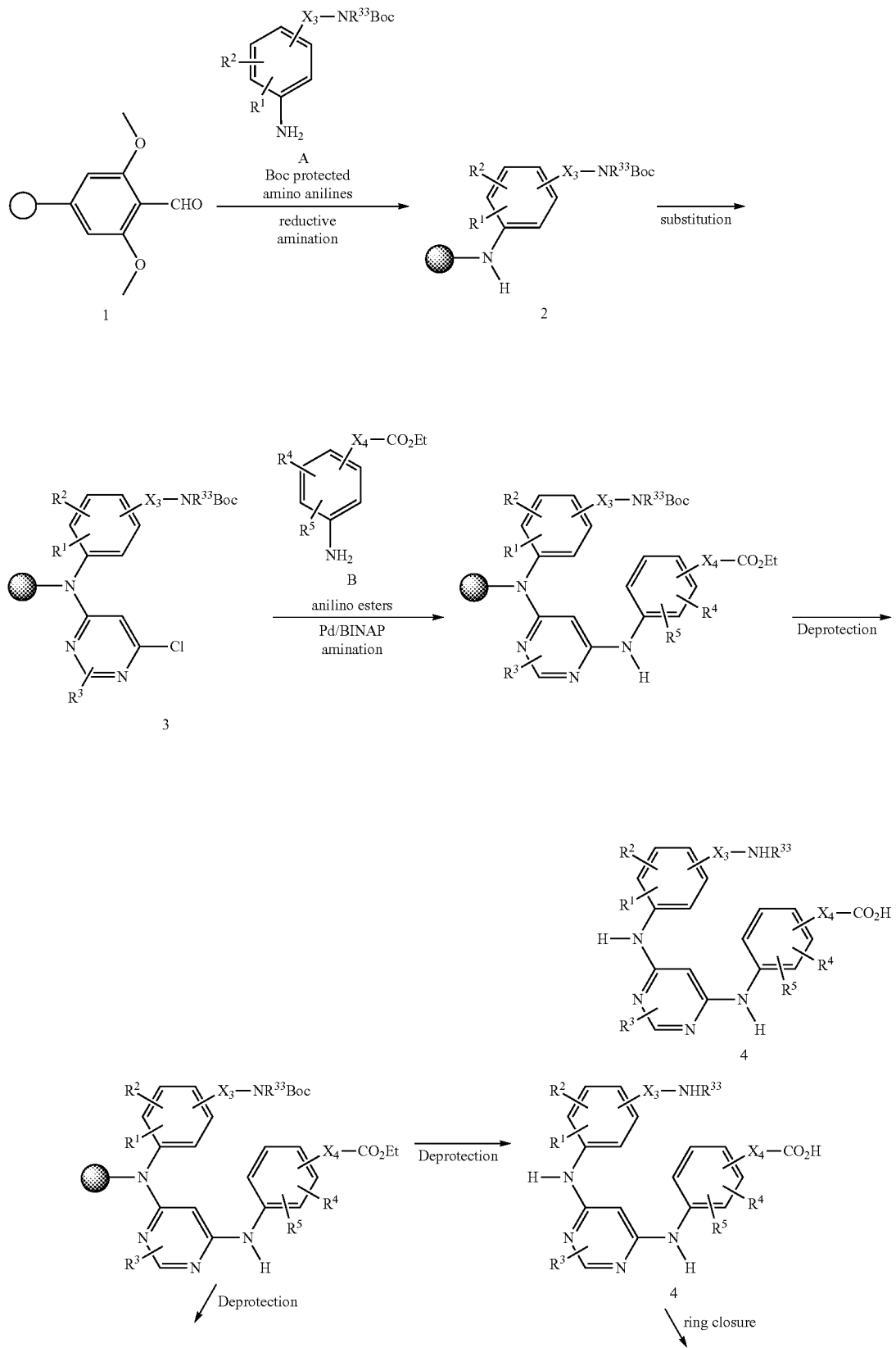

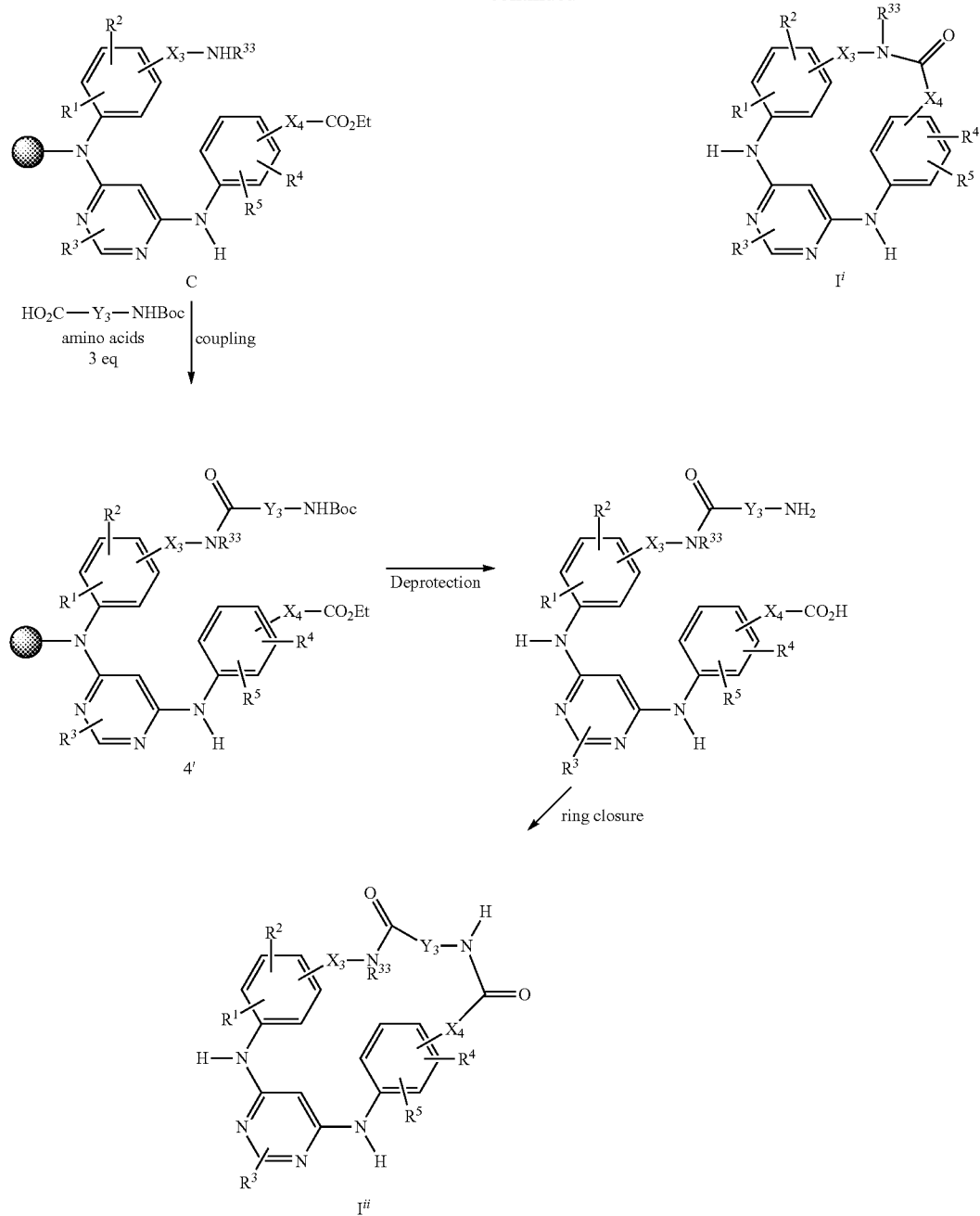

Wherein $X_3$ and $X_4$ each independently represent a direct bond, $C_{1-7}$alkyl, $C_{3-7}$alkenyl, $C_{3-7}$alkynyl, $C_{1-5}$alkyl-O—$C_{1-5}$alkyl, $C_{1-5}$alkyl-$NR^{30}$—$C_{1-5}$alkyl, $C_{1-2}$alkyl-CO-$Het^{10}$, $Het^{23}$, O—$C_{1-2}$alkyl or $CR^8R^9$; wherein $Het^{10}$, $Het^{23}$ $R^8$ and $R^9$ are defined as for the compounds of formula (I). Wherein $Y_3$ represents $Het^6$-CO-$Het^7$, $C_{1-6}$alkyl, $C_{1-6}$alkyl-CO—NH—$C_{1-6}$alkyl or $CR^{31}R^{32}$; wherein $R^{31}$ and $R^{32}$ each independently represent hydrogen or $C_{1-4}$alkyl optionally substituted with phenyl, indolyl, methylsulfide, hydroxyl, thiol, hydroxyphenyl, $C_{1-4}$alkyloxyphenyl, aminocarbonyl, hydroxycarbonyl, amino, mono- or di($C_{1-4}$ alkyl)amine, imidazoyl or guandino; and wherein $Het^6$ and $Het^7$ are defined as for the compounds of formula (I). Wherein $R^{30}$ represents hydrogen, $C_{1-4}$alkyl, $Het^{11}$, $Het^{12}$-$C_{1-4}$alkyl, phenyl-$C_{1-4}$alkyl, phenyl or mono- or di($C_{1-4}$alkyl)amino-$C_{1-4}$alkyl-carbonyl wherein said $R^{30}$ is optionally substituted with hydroxy, amino, mono- or di($C_{1-4}$alkyl)amino, pyrimidinyl or $C_{1-4}$alkyloxy. Wherein $R^{33}$ represents hydrogen, $C_{1-4}$alkyl, $Het^{14}$ or $C_{1-4}$alkyl substituted with one or where possible two or more substituents selected from hydroxy, amino, mono- or di($C_{1-4}$alkyl)amino, phenyl, $Het^{15}$ or $C_{1-2}$alkyloxy and wherein ● represents 2-(3,5-dimethoxy-4-formylphenoxy)ethoxymethyl polystyrene (1).

In case of solution phase chemistry the compounds of the present invention are generally prepared according to reaction scheme 2.

Scheme 2

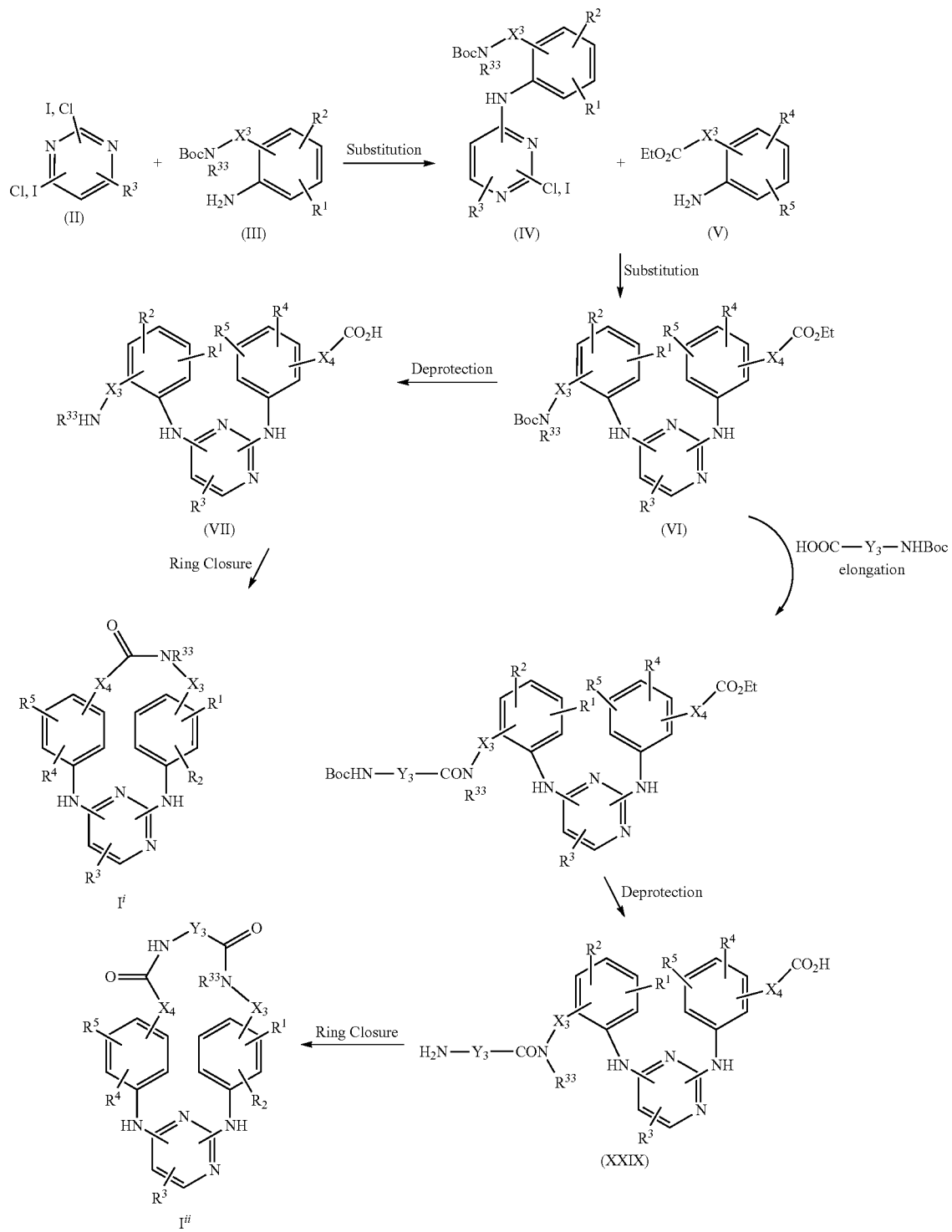

Wherein $X_3$ and $X_4$ each independently represent a direct bond, $C_{1-7}$alkyl, $C_{3-7}$alkenyl, $C_{3-7}$alkynyl, $C_{1-5}$alkyl-O—$C_{1-5}$alkyl, $C_{1-5}$alkyl-NR$^{30}$—$C_{1-5}$alkyl, $C_{1-2}$alkyl-CO-Het$^{10}$, Het$^{23}$, O—$C_{1-2}$alkyl or $CR^8R^9$; wherein Het$^{10}$, Het$^{23}$ $R^8$ and $R^9$ are defined as for the compounds of formula (I). Wherein $Y_3$ represents Het$^6$-CO-Het$^7$, $C_{1-6}$alkyl, $C_{1-6}$alkyl-CO—NH—$C_{1-6}$alkyl or $CR^{31}R^{32}$; wherein $R^{31}$ and $R^{32}$ each independently represent hydrogen or $C_{1-4}$alkyl optionally substituted with phenyl, indolyl, methylsulfide, hydroxyl, thiol, hydroxyphenyl, $C_{1-4}$alkyloxyphenyl, aminocarbonyl, hydroxycarbonyl, amino, mono- or di($C_{1-4}$alkyl)amine, imidazoyl or guandino; and wherein Het$^6$ and Het$^7$ are defined as for the compounds of formula (I). Wherein $R^{30}$ represents hydrogen, $C_{1-4}$alkyl, $Het^{11}$, $Het^{12}$-$C_{1-4}$alkyl, phenyl-$C_{1-4}$alkyl, phenyl or mono- or di($C_{1-4}$alkyl)amino-$C_{1-4}$alkyl-carbonyl wherein said $R^{30}$ is optionally substituted with hydroxy, amino, mono- or di($C_{1-4}$alkyl)amino, pyrimidinyl or $C_{1-4}$alkyloxy. Wherein $R^{33}$ represents hydrogen, $C_{1-4}$alkyl, $Het^{14}$ or $C_{1-4}$alkyl substituted with one or where possible two or more substituents selected from hydroxy, amino, mono- or di($C_{1-4}$alkyl)amino, phenyl, $Het^{15}$ or $C_{1-2}$alkyloxy.

In a first substitution reaction a Boc-protected amino aniline (III) is coupled to the 2,4 or 4,6-di-I or di-Cl-pyrimidine (II) by stirring for example the reagens in an appropriate solvent such as propanol or 1-butanol at an elevated temperature (at 60-90° C.) for about 40 hours in the presence of N-ethyl-N-(1-methylethyl)-2-propanamine (DIPEA), yielding the anilinopyrimidines of general formula IV. In a second substitution reaction under comparable reaction conditions, said intermediate (IV) is coupled to the aniline ester of general formula (V) yielding the bis(anilino)pyrimidine of formula (VI). Deprotection provides the intermediates of formula VII which after ring closure provides the compounds of formula I′. Further elongation of the amine in VII with Boc-protected amino acids under art known conditions, see for example the synthesis of intermediate 36 in example A10c, yields after deprotection and ring closure the compounds of formula I″. Ring closure is typically performed in the presence of a coupling reagent such as for example 1,3-dicyclohexylcarbodiimide (DCC), N,N′-carbonyldiimidazole (CDI), $POCl_3$, $TiCl_4$, sulfur chloride fluoride ($SO_2ClF$) or 1-(3-dimethylaminopropyl)-3-ethylcarbodiimide (EDCI) in the presence or absence of 1-hydroxybenzotriazole (HOBt).

As further exemplified in the experimental part of the description, a particular group of compounds are those compounds of formula (I) were —$X^1$— and —$X^2$— represent —C=O—$NR^{17}$— and —C=O—$NR^{19}$— respectively, hereinafter referred to as compounds of formula (I′) which are generally prepared using the following synthesis scheme (scheme 3).

As for the general synthesis scheme (Scheme 2) hereinbefore, in a first substitution reaction an aniline ester (V) is coupled to the 2,4 or 4,6-di-I or di-Cl-pyrimidine by stirring for example the reagens in an appropriate solvent such as propanol or 1-butanol at an elevated temperature (at 60-90° C.) for about 40 hours in the presence of N-ethyl-N-(1-methylethyl)-2-propanamine (DIPEA), yielding the anilinopyrimidines of general formula VIII. In a second substitution reaction an amino benzoic acid (IX) was coupled to the anilinopyrimidine of formula VIII under art known conditions, such as for example using hydrochloric acid (6N) in isopropanol as solvent and stirring for 1-3 h at an elevated temperature ranging from 110-170° C., to yield the bis(anilino)pyrimidines intermediates of formula X. To obtain the diamide-linker in the final compounds, said bis(aniline)pyrimidine is subsequently elongated by amidation with an appropriate Boc-protected diamine using standard coupling reagents such as 1,3-dicyclohexylcarbodiimide (DCC), N,N′-carbonyldiimidazole (CDI), $POCl_3$, $TiCl_4$, sulfur chloride fluoride ($SO_2ClF$) or 1-(3-dimethylaminopropyl)-3-ethylcarbodiimide (EDCI) in the presence or absence of 1-hydroxybenzotriazole (HOBt) Deprotection and ring closure by macrolactamization (see above) yields compounds according to the invention.

Scheme 3

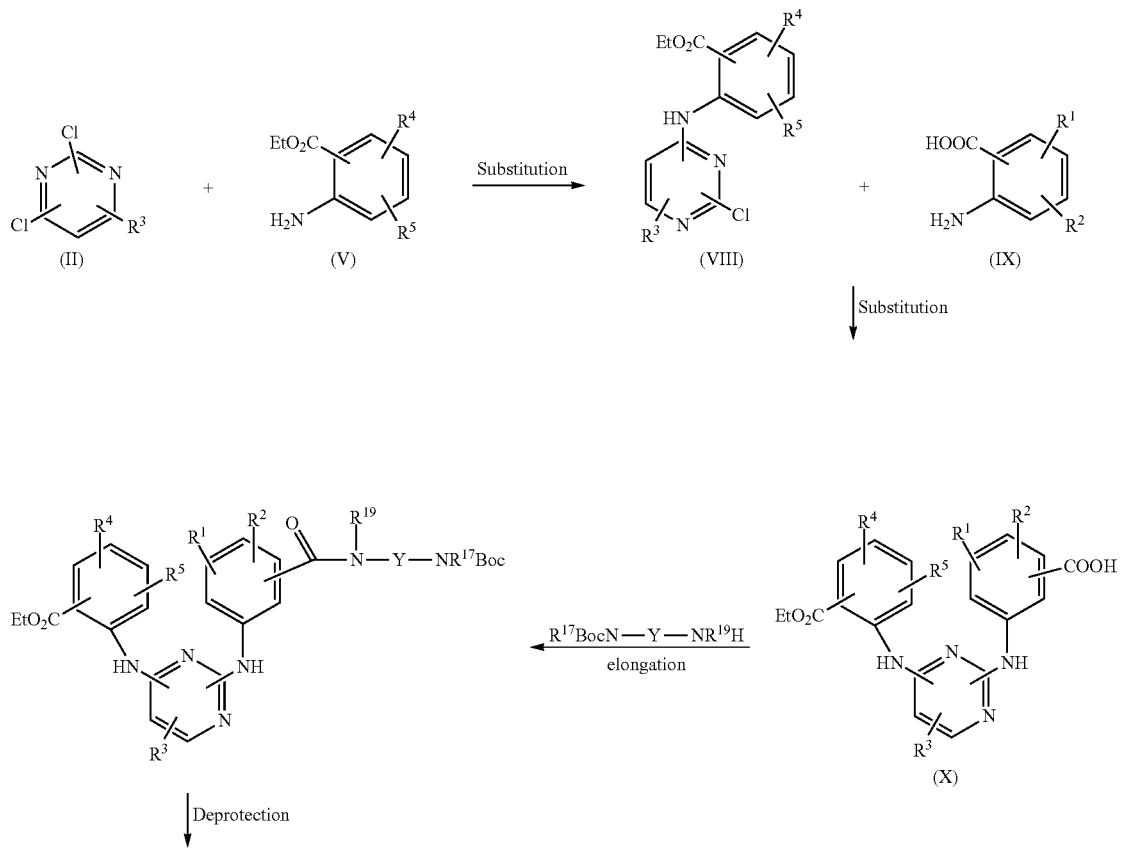

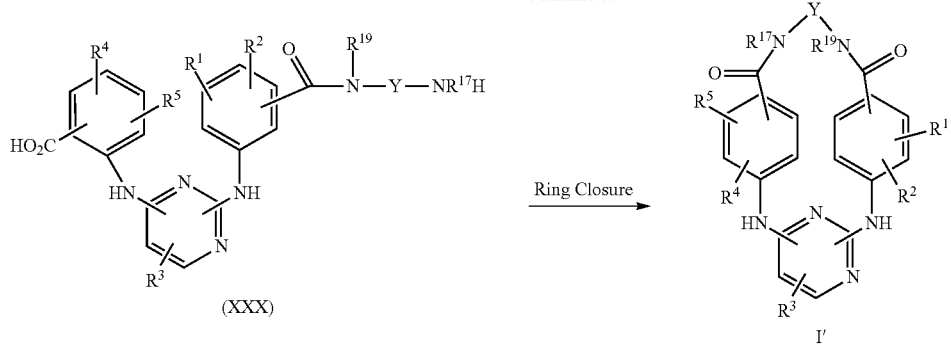

Wherein Y, $R^1$, $R^2$, $R^3$, $R^4$, $R^5$, $R^{17}$ and $R^{19}$ are defined as for the compounds of formula (I)

An alternative synthesis route for the compounds of the present invention, in particular for the 2,4-bis(aniline)-5-cyano-pyrimidine derivatives of formula I' supra, comprises the use of 4-chloro-2-(methylthio)pyrimidine-5-carbonitrile instead of 2,4-dichloro-pyrimidine-5-carbonitrile as building block (Scheme 4). This building block allows for selective introduction of one aniline in the 4-position. The second aniline can then be introduced after oxidation of the sulfur atom. Because of the known sensitivity of the nitrile function towards hydrolysis, a tBu ester, which can be deprotected under anhydrous conditions, is preferred.

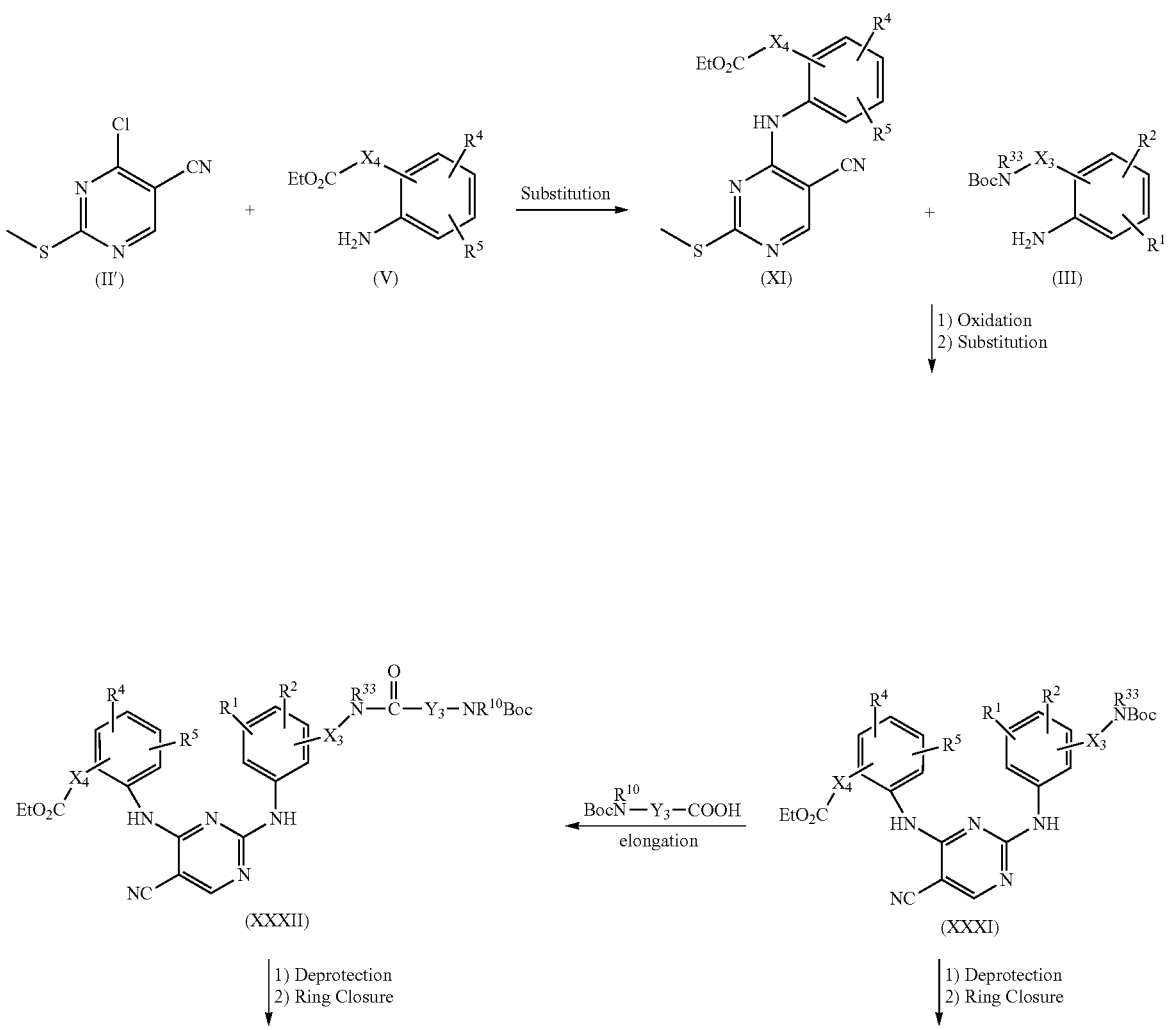

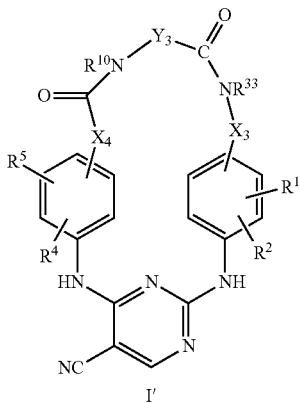

I'

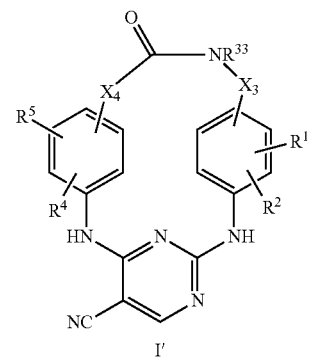

I'

Wherein $X_3$, $X_4$ and $Y_3$ are defined as for schemes 1&2 hereinbefore and wherein $R^1$, $R^2$, $R^4$, $R^5$ and $R^{10}$ are defined as for the compounds of formula (I).

As for the general synthesis scheme (Scheme 2) hereinbefore, in a first substitution reaction an aniline ester (V) is coupled to the 4-chloro-2-methylsulfide-pyrimidine-5-carbonitrile (II') by stirring for example the reagens in an appropriate solvent such as propanol or 1-butanol at an elevated temperature (at 60-90° C.) for about 40 hours in the presence of N-ethyl-N-(1-methylethyl)-2-propanamine (DIPEA), yielding the anilinopyrimidines of general formula XI. The second Boc-protected amino aniline (III) is introduced at the 2-position after oxidizing the sulphur atom of XI. This oxidation is typically performed with m-chloroperbenzoic acid in $CH_2Cl_2$ (DCM) or $CH_2Cl$—$CH_2Cl$ (DCE) under art known conditions as exemplified in the synthesis examples hereinafter. Deprotection and ring closure by macrolactamization (see above) yields the compounds according to the invention.

For the synthesis of those compounds of formula (I) wherein Y represents $Het^5$-CO—$C_{1-2}$alkyl or $Het^6$-CO-$Het^7$ hereinafter referred to as the compounds of formula I'', the following synthesis scheme is generally applied (Scheme 5). As used herein,

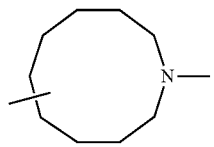

represents a heterocycle selected from pyrrolidinyl, 2-pyrrolidinoyl, piperazinyl or piperidinyl optionally substituted with one or where possible two or more substituents selected from hydroxyl, $C_{1-4}$alkyl, hydroxyl-$C_{1-4}$alkyl or polyhydroxy-$C_{1-4}$alkyl. $X_5$ and $X_4$ represent a direct bond, —O—, —O—$C_{1-6}$alkyl-, $C_{1-2}$alkyl, $Het^7$-$C_{1-2}$alkyl-, $C_{1-4}$alkyl-$NR^{16}$—$C_{1-2}$alkyl or $C_{1-2}$alkyl-$Het^1$-$C_{1-2}$alkyl; $Y_4$ represents $C_{1-6}$alkyl-, $C_{1-6}$alkyl-CO—NH—$C_{1-4}$alkyl or $CR^8R^9$; wherein $Het^7$, $R^1$, $R^2$, $R^3$, $R^4$, $R^5$, $R^8$, $R^9$ and $R^{16}$ are defined as for the compounds of formula (I) and wherein

⬤ represents 2-(3,5-dimethoxy-4-formylphenoxy)ethoxymethyl polystyrene (1).

This reactions scheme only differs from the general solid phase reaction scheme 1 in that in the first step, the formyl functionalized polystyrene such as for example 2-(3,5-dimethoxy-4-formylphenoxy)ethoxymethyl polystyrene (1) is aminated with an appropriate Boc-protected aniline of formula (A) by reductive amination. As for scheme 1, the next steps consist of a first coupling with the appropriate 2,4 or 4,6-di-I or di-Cl-pyrimidine followed by a substitution with the appropriate anailine ester (B) to yield the bis(aniline) pyrimidine scaffold of the present invention. Deprotection and optional elongation, provides after ring closure the compounds of formula (I''') and (I'''') respectively.

Scheme 5
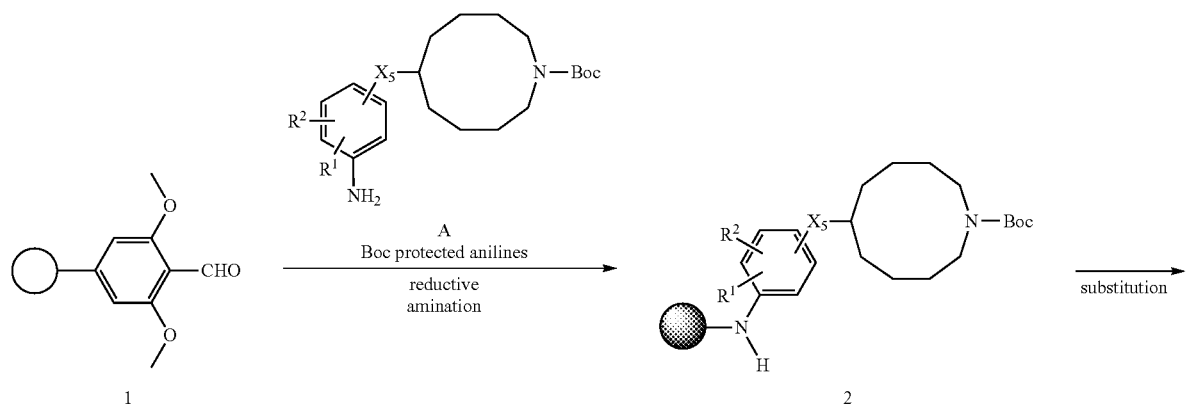
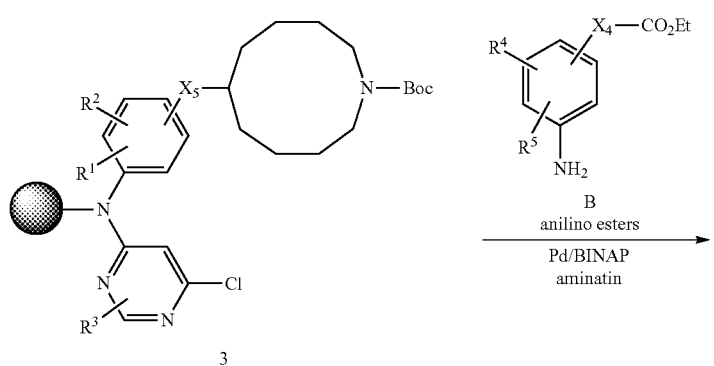
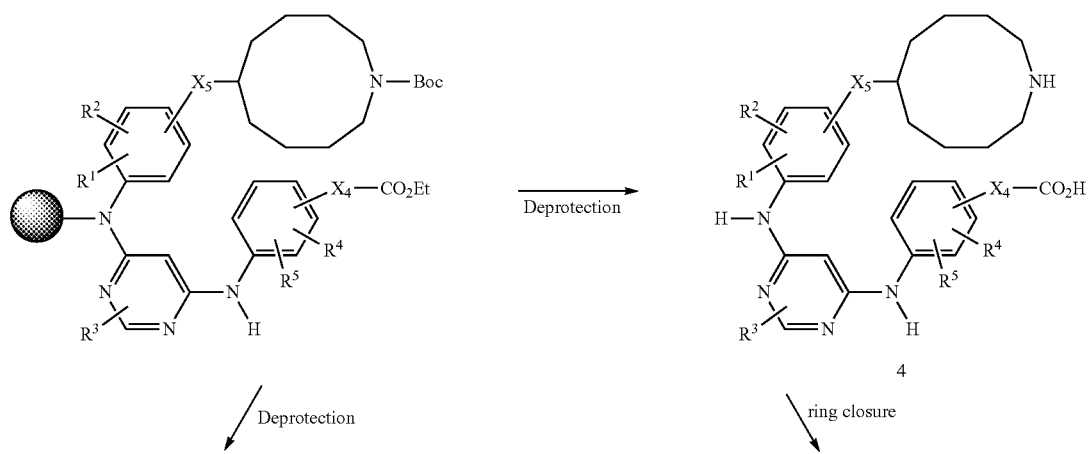

-continued
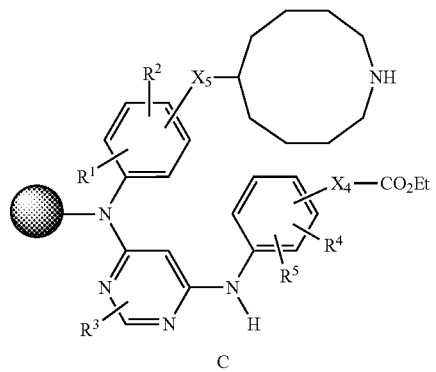
C
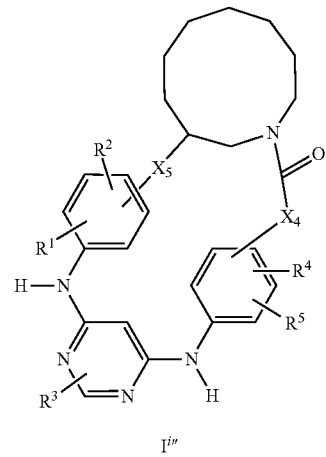
I$^{i''}$
HO$_2$C—Y—NHBoc
amino acids 3 eq | coupling
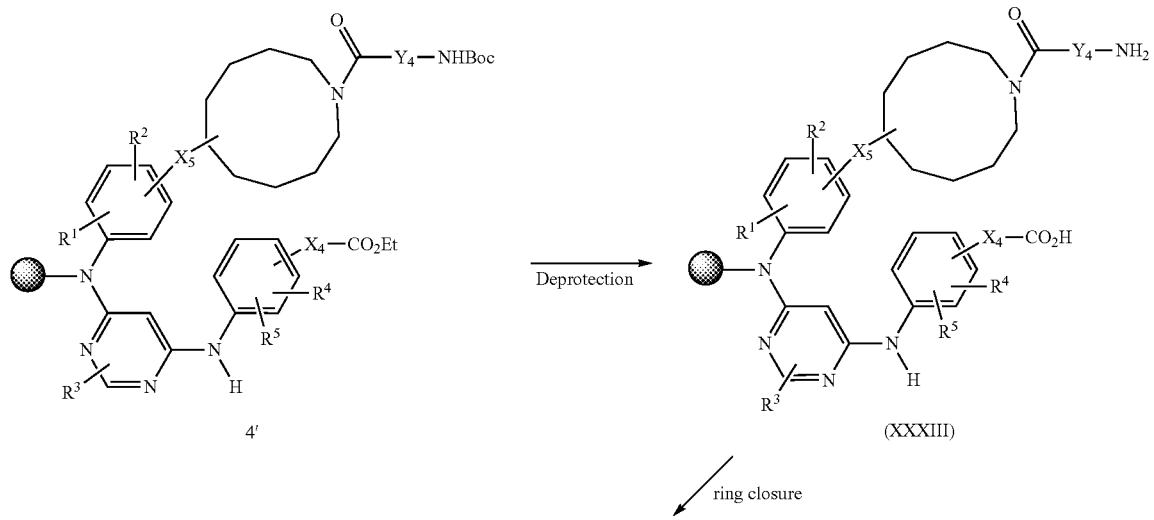
4'　　　　　　　　　　(XXXIII)
Deprotection
ring closure
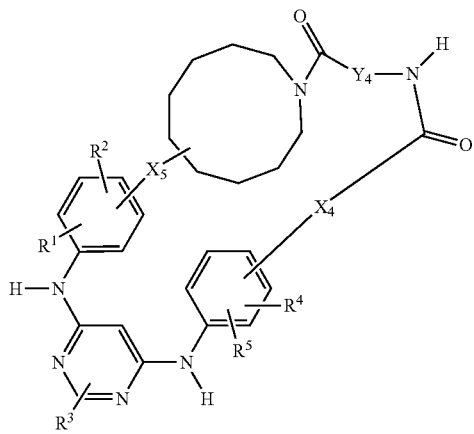
I$^{ii''}$ For those compounds where $X^1$ or $X^2$ represents —O—, the suitable Boc-protected amino anilines (III$^a$) are generally prepared by alkylation from the known nitrophenols (XII), with a Boc-protected aminoalkylhalide followed by hydrogenolysis of the nitro group using art known procedures (Scheme 6).

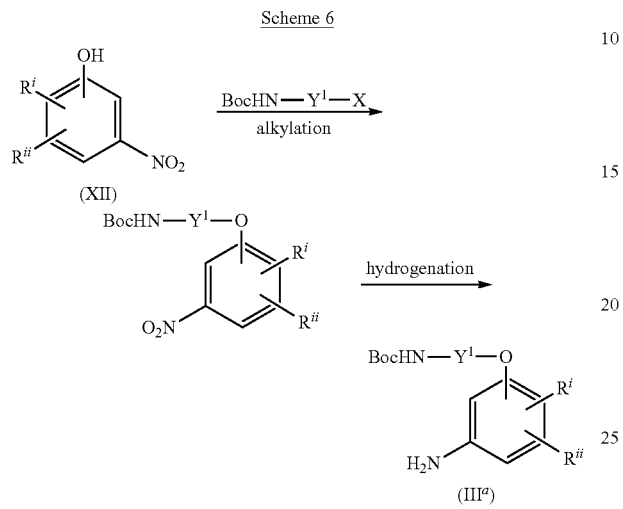

as used in scheme 6, R$^i$ represents either R$^1$ or R$^5$ as defined for the compounds of formula (I) hereinbefore and R$^{ii}$ represents either R$^2$ or R$^4$ as defined for the compounds of formula (I) hereinbefore.

For those compounds where $X^1$ or $X^2$ represents NR$^{12}$—C$_{1-2}$alkyl-, the suitable aniline esters of formula (V$^b$) are generally prepared from the known nitro-benzaldehydes (XIII) and an amine (XIV) by reductive amination under standard conditions (Scheme 7), for example using NaBH$_4$ and titanium(iv)isopropoxide as reducing agents in ethanol as solvent, yielding in a first step the nitro-benzylamines of formula (XV). Subsequent hydrogenolysis of the nitro group provides the intermediates of the present invention.

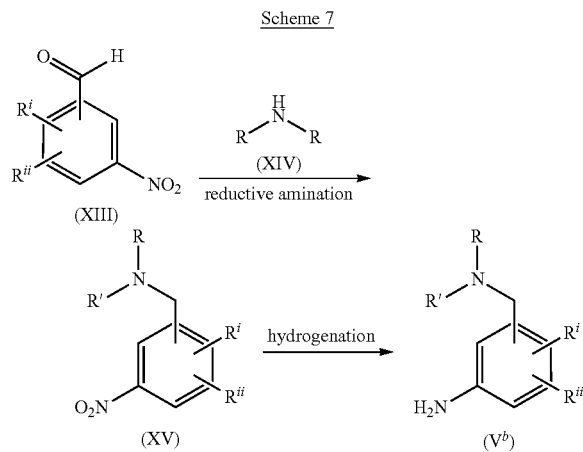

as used in scheme 7, R$^i$ represents either R$^1$ or R$^5$ as defined for the compounds of formula (I) hereinbefore and R$^{ii}$ represents either R$^2$ or R$^4$ as defined for the compounds of formula (I) hereinbefore.

Alternatively for those compounds (I) where $X^1$ or $X^2$ represents —O—, the suitable substituted anilines of formula (III$^a$) are generally prepared from the commercially available nitro-phenols (XVI) and the .-protected halogenated alcohols (XVII) under alkaline conditions in a reaction inert solvent, for example, using dimethylacetamide (DMA) in the presence of K$_2$CO$_3$. The resulting nitro-phenyl derivative (XVIII) is subsequently reduced according to standard conditions, for example, using iron/acetic acid, to yield the substituted anilines of formula (III$^a$) (Scheme 8).

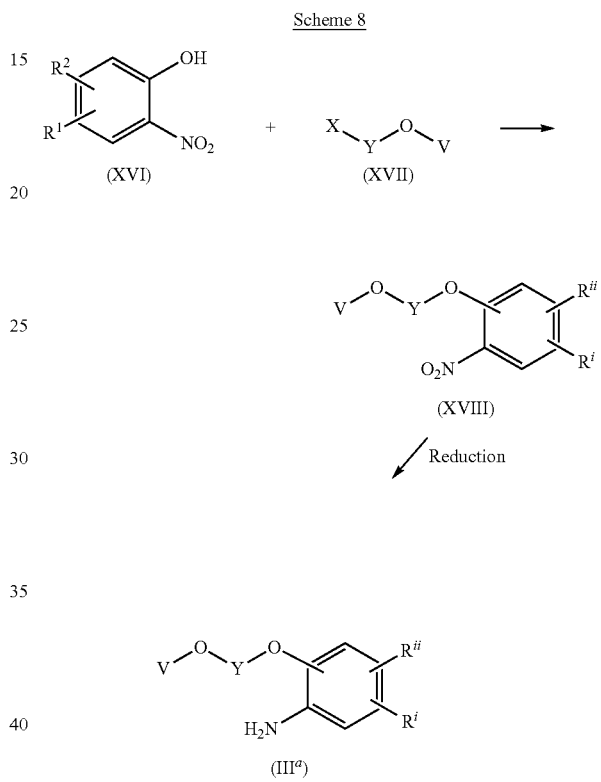

X represents a halogen such as for example, Cl, Br, and I
V represents a protective group such as for example methylcarbonyl
R$^i$ represents either R$^1$ or R$^5$ as defined for the compounds of formula (I) hereinbefore and R$^{ii}$ represents either R$^2$ or R$^4$ as defined for the compounds of formula (I) hereinbefore.

For those compounds of formula (I) where $X^1$ or $X^2$ represents NR$^{16}$—C$_{1-2}$alkyl- or —NR$^{18}$—C$_{1-2}$alkyl- respectively, the suitable substituted anilines of formula (III$^b$) are generally prepared from the commercially available 2-nitro-benzaldehydes (XIII) and the amine substituted alcohols (XIX) by reductive amination under standard conditions, for example using NaBH$_4$ and titanium(iv)isopropoxide as reducing agents in ethanol as solvent, yielding in a first step the nitro-benzylamines of formula (XX).

Next the primary free alcohol is protected using art known procedures, for example, using an esterification reaction with acetic anhydride in the presence of pyridine.

The thus obtained intermediate of formula (XXI) is subsequently reduced according to standard conditions, for example, using iron/acetic acid to yield the substituted anilines of formula (III$^b$) (Scheme 9).

Scheme 9

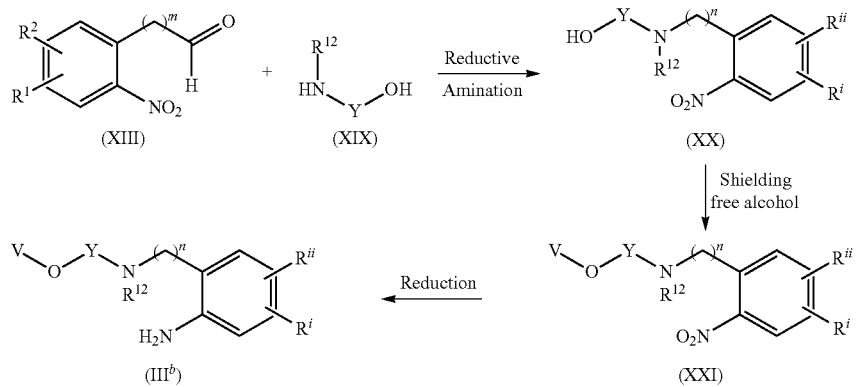

V represents a protective group such as for example methylcarbonyl
m = 0 or 1 and n = 1 or 2
$R^i$ represents either $R^1$ or $R^5$ as defined for the compounds of formula (I) hereinbefore and $R^{ii}$ represents either $R^2$ or $R^4$ as defined for the compounds of formula (I) hereinbefore.

For those compounds of formula (I) where $X^1$ or $X^2$ represents —O—N=CH—, the suitable substituted anilines of formula (III$^c$) are generally prepared according to reaction scheme 10.

In a first step the known 2-nitro-benzaldehydes (XIII) are converted into the corresponding oxime (XXII) using, for example, the art known condensation reaction with hydroxylamine.

Next said oxime of formula XXII is allowed to react with an halogenated alkylacetate under alkaline conditions, for example using $K_2CO_3$ in DMSO, followed by reducing the nitro group, for example, with iron/acetic acid, to provide the suitable substituted aniline of formula (III$^c$).

Scheme 10

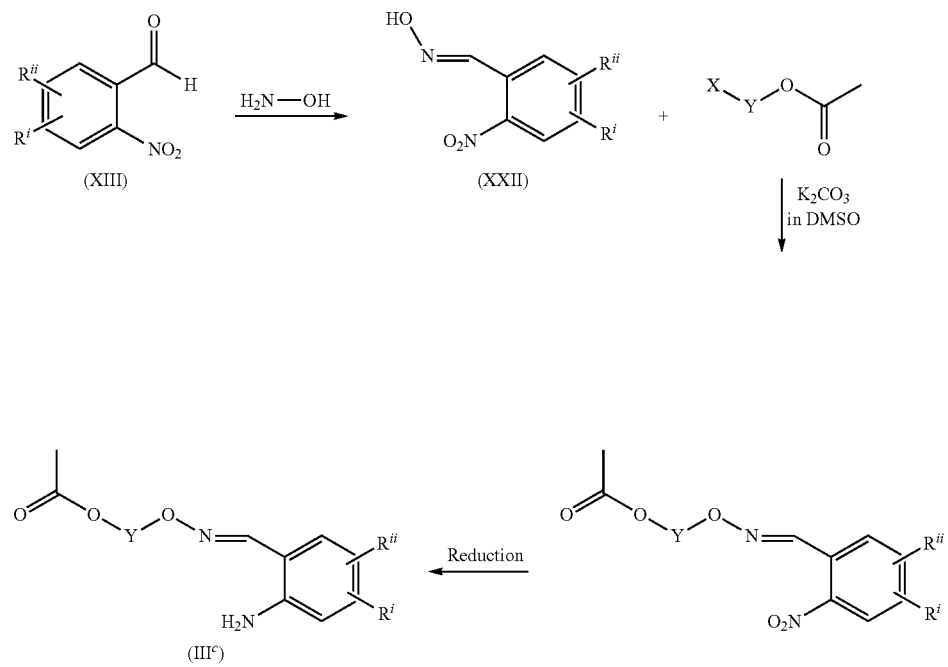

X represents a halogen such as for example Cl, Br, or I
$R^i$ represents either $R^1$ or $R^5$ as defined for the compounds of formula (I) hereinbefore and $R^{ii}$ represents either $R^2$ or $R^4$ as defined for the compounds of formula (I) hereinbefore.

For those compounds where $X^1$ represents —O—, $X^2$ represents a direct bond and Y represents $C_{1-6}$alkyl-NH—CO—, the suitable substituted anilines of formula (III$^d$) are generally prepared according to reaction scheme 11.

In a first step the known 2-nitro-benzoic acids (XXIII) are amidated to the intermediates of formula (XXIV) under art known conditions, for example, using a hydroxylated amine of formula (XIX') that is added dropwise to a mixture of (XXIII) in $CH_2Cl_2$ in the presence of 1,1'carbonylbis-1H-imidazole.

Next the primary free alcohol is protected using art known procedures, for example, using an esterification reaction with acetic anhydride in the presence of pyridine.

The thus obtained intermediate of formula (XXV) is subsequently reduced according to standard conditions, for example, using iron/acetic acid to yield the substituted anilines of formula (III$^d$).

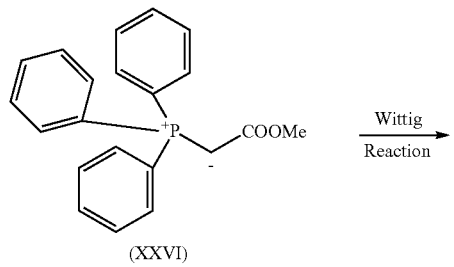

(XXVI)

Scheme 11

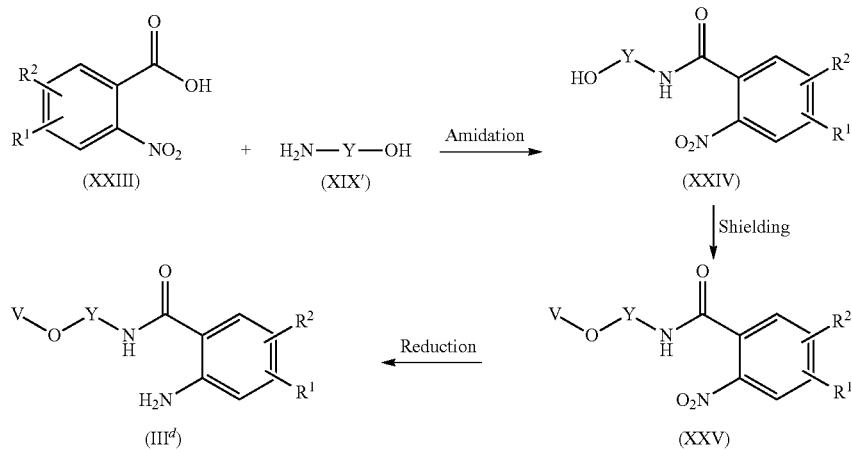

V represents a protective group such as for example methylcarbonyl

For those compounds where $X^2$ represents a direct bond the suitable substituted anilines of formula (III$^e$) are generally prepared according to reaction scheme 12.

In a first step the known 2-nitro-benzaldehydes (XIII) are alkenated to the intermediates of formula (XXVII) under art known conditions, for example, using the Wittig Reaction with the appropriate phosphonium salt of formula (XXVI).

Following esterification of the free carboxylic acid under standard conditions for example, using ethanol under acidic conditions, the intermediate of formula (XXVIII) are reduced to yield the desired substituted anilines of formula (III$^e$).

Scheme 12

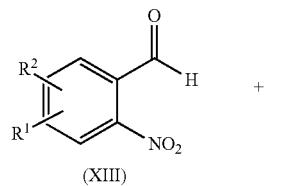

(XIII)

-continued

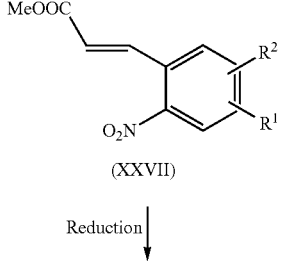

(XXVII)

Reduction ↓

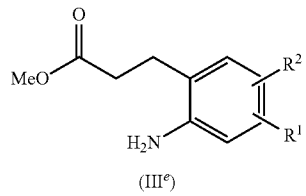

(III$^e$)

More specific examples for the synthesis of compounds of formula (I) are provided in the examples hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The protection and deprotection of functional groups may take place before or after a reaction step. The use of protecting groups is fully described in 'Protective Groups in Organic Synthesis' $2^{nd}$ edition, T W Greene & P G M Wutz, Wiley Interscience (1991).

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I) can also be converted into each other following art— known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures. However, in the synthesis of the compounds of formula (I), the present invention further provides;
a) the intermediates of formula (III)

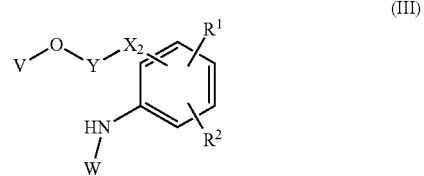

(III)

the pharmaceutically acceptable addition salts and the stereochemically isomeric forms thereof, wherein
V represents hydrogen or a protective group preferably selected from the group consisting of methylcarbonyl, t-butyl, methyl, ethyl, benzyl or trialkylsilyl;
W represents hydrogen or a protective group preferably selected from the group consisting of t-butyloxycarbonyl or benzyloxycarbony;
Y represents —O—$C_{1-5}$alkyl- with the oxygen atom attached to the phenyl ring, —$C_{1-5}$alkyl-CO—NH—, $C_{1-3}$alkyl-CO—NH—, —$C_{1-5}$alkyl-NR$^{13}$—CO—$C_{1-3}$alkyl-NH—, —CO—NH—CR$^{14}$R$^{15}$—CO—, or -Het$^6$-CO—, Het$^8$—NH—$C_{1-3}$alkyl-CO—NH—;
$X_2$ represents a direct bond, —O—$C_{1-2}$alkyl- with the oxygen atom attached to the phenyl ring, CO, —CO—$C_{1-2}$alkyl-, NR$^{18}$, —NR$^{18}$—$C_{1-2}$alkyl-, —CO—NR$^{19}$—, -Het$^{24}$-, -Het$^{24}$-$C_{1-2}$alkyl-, —O—N=CH— or —$C_{1-2}$alkyl-;
$R^1$ represents hydrogen, cyano, halo, hydroxy, formyl, $C_{1-6}$alkoxy-, $C_{1-6}$alkyl-, halo-phenyl-carbonylamino-, Het$^{20}$, $C_{1-6}$alkoxy- substituted with halo, Het$^1$ or $C_{1-4}$alkyloxy-, or $R^1$ represents $C_{1-6}$alkyl substituted with one or where possible two or more substituents selected from hydroxy, Het[18] or halo;

$R^2$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^{13}$ each represents hydrogen, or $C_{1-4}$alkyl optionally substituted with hydroxy, amino, mono- or di($C_{1-4}$alkyl)amine, phenyl or $C_{1-4}$alkyloxy;

$R^{14}$ and $R^{15}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amino, mono- or di($C_{1-4}$alkyl)-amino-, imidazoyl or guanidino;

$R^{18}$ and $R^{19}$ each independently represent hydrogen, $C_{1-4}$alkyl, $C_{1-4}$alkyl-oxy-carbonyl-, Het[16], Het[17]-$C_{1-4}$alkyl- or phenyl-$C_{1-4}$alkyl-;

Het[6] represents a heterocycle selected from pyrrolidinyl, 2-pyrrolidinonyl, piperazinyl or piperidinyl wherein said Het[6] is optionally substituted with one or where possible two or more substituents selected from hydroxy, $C_{1-4}$alkyl, hydroxy-$C_{1-4}$alkyl- or polyhydroxy-$C_{1-4}$alkyl-;

Het[8] represents a heterocycle selected from pyrrolidinyl, 2-pyrrolidinonyl, piperazinyl or piperidinyl wherein said Het[8] is optionally substituted with one or where possible two or more substituents selected from hydroxy, $C_{1-4}$alkyl, hydroxy-$C_{1-4}$alkyl- or polyhydroxy-$C_{1-4}$alkyl-;

Het[16] represent a heterocycle selected from pyrrolidinyl or piperidinyl wherein said Het[16] is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het[17] represents a heterocycle selected from morpholinyl, pyrrolidinyl, piperazinyl or piperidinyl wherein said Het[17] is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het[20] represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het[20] is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

Het[22] represents a heterocycle selected from morpholinyl, pyrrolidinyl, piperazinyl or piperidinyl wherein said Het[22] is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het[24] represents a heterocycle selected from pyrrolidinyl, 2-pyrrolidinonyl, quinolinyl, isoquinolinyl, decahydroquinolinyl, piperazinyl or piperidinyl wherein said Het[24] is optionally substituted with one or where possible two or more substituents selected from hydroxy, Het[25], Het[22]-carbonyl, $C_{1-4}$alkyl, hydroxy-$C_{1-4}$alkyl- or polyhydroxy-$C_{1-4}$alkyl-; and Het[25] represents a heterocycle selected from morpholinyl, pyrrolidinyl, piperazinyl or piperidinyl wherein said Het[25] is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-.

b) the intermediates of formula (IV)

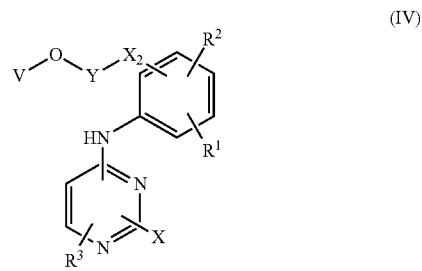

(IV)

the pharmaceutically acceptable addition salts and the stereochemically isomeric forms thereof, wherein V represents hydrogen or a protective group preferably selected from the group consisting of methylcarbonyl, t-butyl, methyl, ethyl, benzyl or trialkylsilyl;

Y represents —O—$C_{1-5}$alkyl- with the oxygen atom attached to the phenyl ring, —$C_{1-5}$alkyl-CO—NH—, $C_{1-3}$alkyl-CO—NH—, —$C_{1-5}$alkyl-NR[13]—CO—$C_{1-3}$alkyl-NH—, —CO—NH—CR[14]R[15]—CO—, or Het[8]—NH—$C_{1-3}$alkyl-CO—NH—;

X represents halo, in particular chloro or X represents $C_{1-4}$alkyl-sulfide or $C_{1-4}$alkylsulfoxide;

$X_2$ represents a direct bond, —O—$C_{1-2}$alkyl- with the oxygen atom attached to the phenyl ring, CO, —CO—$C_{1-2}$alkyl-, NR[18], —NR[18]—$C_{1-2}$alkyl-, —CO—NR[19]—, -Het[24]-, -Het[24]-$C_{1-2}$alkyl-, —O—N=CH— or —$C_{1-2}$alkyl-;

$R^1$ represents hydrogen, cyano, halo, hydroxy, formyl, $C_{1-6}$alkoxy-, $C_{1-6}$alkyl-, halo-phenyl-carbonylamino-, Het[20], $C_{1-6}$alkoxy- substituted with halo, Het[1] or $C_{1-4}$alkyloxy-, or $R^1$ represents $C_{1-6}$alkyl substituted with one or where possible two or more substituents selected from hydroxy, Het[18] or halo;

$R^2$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^3$ represents hydrogen, cyano, nitro, $C_{1-4}$alkyl- or $C_{1-4}$alkyl substituted with one or more substituents selected from halo, $C_{1-4}$alkyloxy or phenyl;

$R^{13}$ each represents hydrogen, or $C_{1-4}$alkyl optionally substituted with hydroxy, amino, mono- or di($C_{1-4}$alkyl)amine, phenyl or $C_{1-4}$alkyloxy;

$R^{14}$ and $R^{15}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amino, mono- or di($C_{1-4}$alkyl)-amino-, imidazoyl or guanidino;

$R^{18}$ and $R^{19}$ each independently represent hydrogen, $C_{1-4}$alkyl, $C_{1-4}$alkyl-oxy-carbonyl-, Het[16], Het[17]-$C_{1-4}$alkyl- or phenyl-$C_{1-4}$alkyl-;

Het[6] represents a heterocycle selected from pyrrolidinyl, 2-pyrrolidinonyl, piperazinyl or piperidinyl wherein said Het[6] is optionally substituted with one or where possible two or more substituents selected from hydroxy, $C_{1-4}$alkyl, hydroxy-$C_{1-4}$alkyl- or polyhydroxy-$C_{1-4}$alkyl-;

Het⁸ represents a heterocycle selected from pyrrolidinyl, 2-pyrrolidinonyl, piperazinyl or piperidinyl wherein said Het⁸ is optionally substituted with one or where possible two or more substituents selected from hydroxy, $C_{1-4}$alkyl, hydroxy-$C_{1-4}$alkyl- or polyhydroxy-$C_{1-4}$alkyl-;

Het¹⁶ represent a heterocycle selected from pyrrolidinyl or piperidinyl wherein said Het¹⁶ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het¹⁷ represents a heterocycle selected from morpholinyl, pyrrolidinyl, piperazinyl or piperidinyl wherein said Het¹⁷ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het²⁰ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het²⁰ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

Het²² represents a heterocycle selected from morpholinyl, pyrrolidinyl, piperazinyl or piperidinyl wherein said Het²² is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het²⁴ represents a heterocycle selected from pyrrolidinyl, 2-pyrrolidinonyl, quinolinyl, isoquinolinyl, decahydroquinolinyl, piperazinyl or piperidinyl wherein said Het²⁴ is optionally substituted with one or where possible two or more substituents selected from hydroxy, Het²⁵, Het²²-carbonyl, $C_{1-4}$alkyl, hydroxy-$C_{1-4}$alkyl- or polyhydroxy-$C_{1-4}$alkyl-; and Het²⁵ represents a heterocycle selected from morpholinyl, pyrrolidinyl, piperazinyl or piperidinyl wherein said Het²⁵ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-.

In particular the intermediates of formula (III) or (IV) wherein one or more of the following restrictions apply;

i) V represents hydrogen, methyl, t-butyl or ethyl;
ii) Y represents —O—$C_{1-5}$alkyl-, —$C_{1-5}$alkyl-CO—NH—, $C_{1-3}$alkyl-CO—NH—, —$C_{1-5}$alkyl-NR¹³—CO—$C_{1-3}$alkyl-NH—, —CO—NH—CR¹⁴R¹⁵—CO—, or Het⁸-NH—$C_{1-3}$alkyl-CO—NH—;
iii) X² represents a direct bond, —O—$C_{1-2}$alkyl-, NR¹⁸, —NR¹⁸—$C_{1-2}$alkyl-, —CH₂—, —CO—NR¹⁹—, Het²⁴ or -Het²⁴-$C_{1-2}$alkyl-;
iv) X² represents CO—NR¹⁹— or -Het²⁴-$C_{1-2}$alkyl-;
v) R¹ represents hydrogen, halo, $C_{1-6}$alkoxy-, Het²⁰ or R¹ represents $C_{1-6}$alkoxy- substituted with halo, Het¹ or $C_{1-4}$alkyloxy-;
vi) R² represents hydrogen, cyano, halo or hydroxy, preferably halo, more in particular fluoro or chloro;
vii) R¹³ represents hydrogen or $C_{1-4}$alkyl;
viii) R¹⁴ and R¹⁵ each independently represent hydrogen or $C_{1-4}$alkyl optionally substituted with mono- or di($C_{1-4}$alkyl)-amino-;
ix) R¹⁸ and R¹⁹ each independently represent hydrogen, $C_{1-4}$alkyl, $C_{1-4}$alkyl-oxy-carbonyl-, Het¹⁶, Het¹⁷-$C_{1-4}$alkyl- or phenyl-$C_{1-4}$alkyl; in particular hydrogen;

x) Het⁶ represents a heterocycle selected from pyrrolidinyl, piperazinyl or piperidinyl wherein said heterocycle is optionally substituted with hydroxy;
xi) Het⁸ represents a heterocycle selected from pyrrolidinyl, piperazinyl or piperidinyl wherein said heterocycle is optionally substituted with hydroxy;
xii) Het²⁰ represents morpholinyl;
xiii) Het²² represents pyrrolidinyl, quinolinyl, isoquinolinyl, morpholinyl, piperazinyl or piperidinyl;
xiv) Het²⁴ represents pyrrolidinyl, quinolinyl, isoquinolinyl, decahydroquinolinyl, piperazinyl or piperidinyl wherein said Het²⁴ is optionally substituted with hydroxy or Het²²-carbonyl.

c) the intermediates of formula (VI)

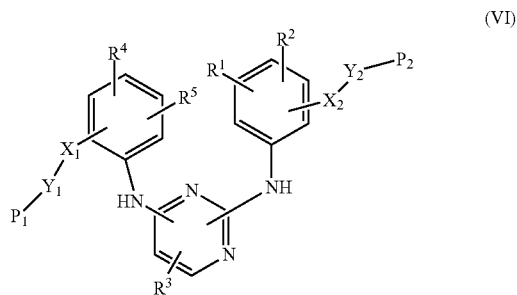

(VI)

the pharmaceutically acceptable addition salts and the stereochemically isomeric forms thereof, wherein $P_1$ and $P_2$ each independently represent hydroxy, halo, hydroxycarbonyl-, halocarbonyl-, amino or —NHR²⁹;

$Y_1$ and $Y_2$ each independently represent $C_{1-7}$alkyl, $C_{3-7}$alkenyl or $C_{3-7}$alkynyl wherein said $C_{1-7}$alkyl, $C_{3-7}$alkenyl, $C_{3-7}$alkynyl are optionally substituted with one or where possible two or more substituents selected from amino, mono- or
di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfonyl and $C_{1-4}$alkyloxycarbonylamino;

or $Y_1$ and $Y_2$ each independently represent Het²⁷, Het²⁸-CO, Het²⁹-$C_{1-5}$alkyl, CR⁸R⁹—NH, CR²³R²⁴—NH—CO, CR²⁰R²¹—CO, CR²⁵R²⁶—CO—NH, CO—$C_{1-3}$alkyl, NH—CO—$C_{1-3}$alkyl, $C_{1-3}$alkyl-NR¹¹—CH₂, CH₂—CO—NH—$C_{1-3}$alkyl or $C_{1-3}$alkyl-NH;

X¹ represents a direct bond, O, —O—$C_{1-2}$alkyl-, CO, —CO—$C_{1-2}$alkyl-, NR¹⁶, —NR¹⁶—$C_{1-2}$alkyl-, —CH₂—, —CO—NR¹⁷—, -Het²³-, -Het²³-$C_{1-2}$alkyl-, —O—N=CH— or —$C_{1-2}$alkyl-;

X² represents a direct bond, O, —O—$C_{1-2}$alkyl-, CO, —CO—$C_{1-2}$alkyl-, NR¹⁸, —NR¹⁸—$C_{1-2}$alkyl-, —CH₂—, —CO—NR¹⁹—, -Het²⁴-, -Het²⁴-$C_{1-2}$alkyl-, —O—N=CH— or —$C_{1-2}$alkyl-;

R¹ represents hydrogen, cyano, halo, hydroxy, formyl, $C_{1-6}$alkoxy-, $C_{1-6}$alkyl-, halo-phenyl-carbonylamino-, Het²⁰, $C_{1-6}$alkoxy- substituted with halo, Het¹ or $C_{1-4}$alkyloxy-, or R¹ represents
$C_{1-6}$alkyl substituted with one or where possible two or more substituents selected from hydroxy, Het¹⁸ or halo;

R² represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^3$ represents hydrogen, cyano, nitro, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

$R^4$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^5$ represents hydrogen, cyano, halo, hydroxy, formyl, $C_{1-6}$alkoxy-, $C_{1-6}$alkyl-, halo-phenyl-carbonylamino-, $Het^{21}$, $C_{1-6}$alkoxy- substituted with halo, $Het^2$ or $C_{1-4}$alkyloxy-, or $R^5$ represents
$C_{1-6}$alkyl substituted with one or where possible two or more substituents selected from hydroxy, $Het^{19}$ or halo;

$R^8$, $R^9$, $R^{23}$ and $R^{24}$ each independently represents hydrogen or $C_{1-4}$alkyl optionally substituted with cyano, phenyl, indolyl, methylsulfide, hydroxy, thiol, hydroxyphenyl, polyhalo$C_{1-4}$alkylphenyl, $C_{1-4}$alkyloxy, pyridinyl, $C_{3-6}$cycloalkyl,
$C_{1-4}$alkyloxyphenyl-, aminocarbonyl, hydroxycarbonyl, amino, mono- or
di($C_{1-4}$alkyl)-amine-, imidazoyl or guanidino;

$R^{11}$ represents hydrogen, $C_{1-4}$alkyl or represent mono- or di($C_{1-4}$alkyl)amino-$C_{1-4}$alkyl-carbonyl- optionally substituted with hydroxy, pyrimidinyl, mono- or di($C_{1-4}$alkyl)amine or $C_{1-4}$alkyloxy;

$R^{16}$ and $R^{18}$ each independently represent hydrogen, $C_{1-4}$alkyl, $C_{1-4}$alkyl-oxy-carbonyl-, $Het^{16}$, $Het^{17}$-$C_{1-4}$alkyl- or phenyl-$C_{1-4}$alkyl-;

$R^{17}$ and $R^{19}$ each independently represent hydrogen, $C_{1-4}$alkyl, $Het^{14}$, $Het^{15}$-$C_{1-4}$alkyl- or phenyl-$C_{1-4}$alkyl-;

$R^{20}$, $R^{21}$, $R^{25}$ and $R^{26}$ each independently represents hydrogen or $C_{1-4}$alkyl optionally substituted with cyano, phenyl, indolyl, methylsulfide, hydroxy, thiol, hydroxyphenyl, polyhalo$C_{1-4}$alkylphenyl, $C_{1-4}$alkyloxy, pyridinyl, $C_{3-6}$cycloalkyl,
aminocarbonyl, hydroxycarbonyl, amino, mono- or di($C_{1-4}$ alkyl)-amino-, imidazoyl or guanidino;

$R^{29}$ represents phenyl, $Het^{30}$ or $C_{1-4}$alkyl wherein said $R^{29}$ is optionally substituted with one or where possible two or more substituents selected from hydroxy, amino, mono- or di($C_{1-4}$alkyl)amino, phenyl, $Het^{31}$ or $C_{1-4}$alkyloxy-;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-,
$C_{1-4}$alkyl-oxy-$C_{1-4}$alkyl-mono- or di($C_{1-4}$alkyl)amino- or amino-carbonyl-;

$Het^2$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^2$ is optionally substituted with amino, $C_{1-4}$alkyl, hydroxy-$C_{1-4}$alkyl-, phenyl, phenyl-$C_{1-4}$alkyl-,
$C_{1-4}$alkyl-oxy-$C_{1-4}$alkyl-mono- or di($C_{1-4}$alkyl)amino- or amino-carbonyl-;

$Het^{17}$ represent a heterocycle selected from pyrrolidinyl or piperidinyl wherein said pyrrolidinyl or piperazinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from pyrrolidinyl or piperidinyl wherein said pyrrolidinyl or piperidinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{17}$ represents a heterocycle selected from morpholinyl, pyrrolidinyl, piperazinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{18}$ or $Het^{19}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{20}$ and $Het^{21}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{20}$ or $Het^{21}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{22}$ represents a heterocycle selected from morpholinyl, pyrrolidinyl, piperazinyl or piperidinyl wherein said $Het^{22}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{23}$ and $Het^{24}$ each independently represent a heterocycle selected from pyrrolidinyl, 2-pyrrolidinonyl, quinolinyl, isoquinolinyl, decahydroquinolinyl, piperazinyl or piperidinyl wherein said $Het^{23}$ or $Het^{24}$ is optionally substituted with one or where possible two or more substituents selected from hydroxy, $Het^{25}$, $Het^{22}$-carbonyl, $C_{1-4}$alkyl, hydroxy-$C_{1-4}$alkyl- or polyhydroxy-$C_{1-4}$alkyl-;

$Het^{25}$ represents a heterocycle selected from morpholinyl, pyrrolidinyl, piperazinyl or piperidinyl wherein said $Het^{25}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{27}$ and $Het^{29}$ each independently represent a heterocycle selected from pyrrolidinyl, -pyrrolidinonyl, quinolinyl, isoquinolinyl, decahydroquinolinyl, piperazinyl or piperidinyl wherein said $Het^{27}$ and $Het^{29}$ are optionally substituted with one or where possible two or more substituents selected from hydroxy, $Het^{22}$-carbonyl-, $C_{1-4}$alkyl, hydroxy-$C_{1-4}$alkyl- or polyhydroxy-$C_{1-4}$alkyl-;

Het$^{28}$ represents a heterocycle selected from pyrrolidinyl, 2-pyrrolidinonyl, piperazinyl or piperidinyl wherein said Het$^{28}$ is optionally substituted with one or where possible two or more substituents selected from hydroxy, $C_{1-4}$alkyl, hydroxy-$C_{1-4}$alkyl- or polyhydroxy-$C_{1-4}$alkyl-;

Het$^{30}$ represents a heterocycle selected from pyrrolidinyl, 2-pyrrolidinonyl, piperazinyl or piperidinyl wherein said heterocycle is optionally substituted with one or where possible two or more substituents selected from hydroxy, $C_{1-4}$alkyl,
  $C_{3-6}$ cycloalkyl, hydroxy-$C_{1-4}$alkyl, $C_{1-4}$alkyloxy-$C_{1-4}$alkyl or polyhydroxy$C_{1-4}$alkyl-; and Het$^{31}$ represents a heterocycle selected from morpholinyl, pyrrolidinyl, 2-pyrrolidinonyl, piperazinyl or piperidinyl wherein said Het$^{31}$ is optionally substituted with one or where possible two or more substituents selected from hydroxy, $C_{1-4}$alkyl, $C_{3-6}$cycloalkyl, hydroxy-$C_{1-4}$alkyl, $C_{1-4}$alkyloxy-$C_{1-4}$alkyl or polyhydroxy$C_{1-4}$alkyl-.

In another embodiment the present invention provides the intermediates of formula (VI) wherein one or more of the following restrictions apply;

$P_1$ and $P_2$ each independently represent hydroxy, halo, hydroxycarbonyl-, halocarbonyl-, amino or NHR$^{29}$;

$Y_1$ and $Y_2$ each independently represent $C_{1-7}$alkyl, $C_{3-7}$alkenyl, Het$^{27}$, Het$^{28}$-CO, CR$^8$R$^9$—NH, CR$^{23}$R$^{24}$NH—CO, CO—$C_{1-3}$alkyl, NH—CO—$C_{1-3}$alkyl,
  $C_{1-3}$alkyl-NR$^{11}$—CH$_2$, CH$_2$—CO—NH—$C_{1-3}$alkyl or $C_{1-3}$alkyl-NH; in particular $Y_1$ and $Y_2$ each independently represent $C_{1-7}$alkyl, $C_{3-7}$alkenyl, Het$^{27}$, Het$^{28}$-CO,
  CR$^8$R$^9$—NH,
  CO—$C_{1-3}$alkyl, $C_{1-3}$alkyl-NR$^{11}$—CH$_2$ or CH$_2$—CO—NH—$C_{1-3}$alkyl; in a more particular embodiment $Y_1$ and $Y_2$ each independently represent Het$^{27}$, Het$^{28}$-CO, CR$^8$R$^9$—NH,
  CO—$C_{1-3}$alkyl, $C_{1-3}$alkyl-NR$^{11}$—CH$_2$ or CH$_2$—CO—NH—$C_{1-3}$alkyl;

$X^1$ represents a direct bond, O, O—$C_{1-2}$alkyl, CO—$C_{1-2}$alkyl, NR$^{16}$—$C_{1-2}$alkyl or CO—NR$^{17}$;

$X^2$ represents a direct bond, O, O—$C_{1-2}$alkyl, CO—$C_{1-2}$alkyl, NR$^{18}$—$C_{1-2}$alkyl, CO—NR$^{19}$, or Het$^{24}$-$C_{1-2}$alkyl;

$R^1$ represents hydrogen, halo, $C_{1-6}$alkyloxy-, or $C_{1-6}$alkyloxy substituted with Het$^1$ or $C_{1-4}$alkyloxy;

$R^2$ represents hydrogen of halo;

$R^3$ represents hydrogen, cyano or nitro; in particular hydrogen or cyano;

$R^4$ represents hydrogen or halo;

$R^5$ represents hydrogen, halo, $C_{1-6}$alkyloxy-, or $C_{1-6}$alkyloxy substituted with Het$^2$ or $C_{1-4}$alkyloxy;

$R^8$, $R^9$, $R^{23}$ and $R^{24}$ each independently represents hydrogen or $C_{1-4}$alkyl optionally substituted with phenyl, methylsulfide, hydroxy, thiol, amino, mono- or di($C_{1-4}$alkyl)-amine or imidazoyl; in particular $R^8$, $R^9$, $R^{23}$ and $R^{24}$ each independently represents hydrogen or $C_{1-4}$alkyl;

$R^{11}$ represents hydrogen or $C_{1-4}$alkyl;

$R^{16}$, $R^{17}$, $R^{18}$ and $R^{19}$ represent hydrogen;

$R^{29}$ represents hydrogen, $C_{1-4}$alkyl, or Het$^{31}$-$C_{1-4}$alkyl; in particular $R^{29}$ represents hydrogen or Het$^{31}$-$C_{1-4}$alkyl;

Het$^1$ represents morpholinyl;

Het$^2$ represents morpholinyl;

Het$^{27}$ represents pyrrolidinyl or piperazinyl;

Het$^{28}$ represents pyrrolidinyl or piperazinyl; or

Het$^{31}$ represents morpholinyl, pyrrolidinyl, piperazinyl or piperidinyl wherein said Het$^{31}$ is optionally substituted with hydroxy.

It is also an object of the present invention to provide the intermediates of formula (VII) wherein;

$P_1$ and $P_2$ each independently represent hydroxy, halo, hydroxycarbonyl-, halocarbonyl-, amino or —NHR$^{29}$;

$Y_1$ and $Y_2$ each independently represent $C_{1-7}$alkyl, $C_{3-7}$alkenyl, Het$^{27}$, Het$^{28}$-CO,
  Het$^{29}$-$C_{1-5}$alkyl, L$^2$-NH, L$^1$-NH—CO, L$^3$-CO, L$^3$-CO—NH, CO—$C_{1-6}$alkyl, NH—CO—$C_{1-3}$alkyl, $C_{1-3}$alkyl-NR$^{11}$—CH$_2$, or CH$_2$—CO—NH—$C_{1-3}$alkyl; in particular $Y_1$ and $Y_2$ each independently represent $C_{1-7}$alkyl, $C_{3-7}$alkenyl, Het$^{27}$, Het$^{28}$-CO,
  L$^1$-NH, CO—$C_{1-3}$alkyl, $C_{1-3}$alkyl-NR$^{11}$—CH$_2$ or CH$_2$—CO—NH—$C_{1-3}$alkyl; in a more particular embodiment $Y_1$ and $Y_2$ each independently represent Het$^{27}$, Het$^{28}$-CO, L$^1$-NH, CO—$C_{1-3}$alkyl, $C_{1-3}$alkyl-NR$^{11}$—CH$_2$ or CH$_2$—CO—NH—$C_{1-3}$alkyl;

$X^1$ represents a direct bond, O, —O—$C_{1-2}$alkyl, CO, CO—$C_{1-2}$alkyl, NR$^{16}$—$C_{1-2}$alkyl,
  CO—NR$^{17}$, Het$^{23}$-$C_{1-2}$alkyl, or $C_{1-2}$alkyl;

$X^2$ represents a direct bond, O, —O—$C_{1-2}$alkyl, CO, CO—$C_{1-2}$alkyl, NR$^{18}$—$C_{1-2}$alkyl,
  CO—NR$^{16}$, Het$^{24}$-$C_{1-2}$alkyl, or $C_{1-2}$alkyl;

$R^1$ represents hydrogen, halo, $C_{1-6}$alkyloxy or $C_{1-6}$alkyloxy substituted with Het$^1$ or $C_{1-4}$alkyloxy;

$R^2$ represents hydrogen or halo;

$R^3$ represents hydrogen or cyano;

$R^4$ represents hydrogen or halo;

$R^5$ represents hydrogen, halo, $C_{1-6}$alkyloxy or $C_{1-6}$alkyloxy substituted with Het$^2$ or $C_{1-4}$alkyloxy;

$R^{11}$ represents hydrogen or $C_{1-4}$alkyl or Het$^{17}$-$C_{1-4}$alkyl;

$R^{16}$ and $R^{18}$ each independently represent hydrogen, $C_{1-4}$alkyl or Het$^{17}$-$C_{1-4}$alkyl;

$R^{17}$ and $R^{19}$ each independently represent hydrogen;

$L^1$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl; in particular L$^1$ represents $C_{1-8}$alkyl optionally substituted with phenyl, methylsulfide, hydroxy, thiol, amino, mono- or di($C_{1-4}$alkyl)-amine or imidazoyl $L^2$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$L^3$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

Het$^1$ represents morpholinyl, oxazolyl, isoxazolyl, or piperazinyl; in particular Het$^1$ represents morpholinyl or piperazinyl; more in particular Het$^1$ represents morpholinyl;

Het$^2$ represents morpholinyl, oxazolyl, isoxazolyl, or piperazinyl; in particular Het$^2$ represents morpholinyl or piperazinyl; more in particular Het$^2$ represents morpholinyl;

Het$^{22}$ represents a heterocycle selected from morpholinyl, piperazinyl or piperidinyl wherein said Het$^{22}$ is optionally substituted with $C_{1-4}$alkyl;

Het$^{23}$ and Het$^{24}$ each independently represent a heterocycle selected from pyrrolidinyl, piperazinyl or piperidinyl, wherein said Het$^{23}$ and Het$^{24}$ is optionally substituted with Het$^{22}$-carbonyl;

Het$^{27}$ and Het$^{29}$ each independently represent a heterocycle selected from morpholinyl, pyrrolidinyl, -pyrrolidinonyl, quinolinyl, isoquinolinyl, decahydroquinolinyl, piperazinyl or piperidinyl wherein said Het$^{27}$ and Het$^{29}$ are optionally substituted with one or where possible two or more substituents selected from hydroxy, Het$^{22}$-carbonyl-, $C_{1-4}$alkyl, hydroxy-$C_{1-4}$alkyl- or polyhydroxy-$C_{1-4}$alkyl-; in particular Het$^{27}$ and Het$^{29}$ are each independently selected from morpholinyl, piperazinyl or pyrrolidinyl; more in particular Het$^{27}$ and Het$^{29}$ are each independently selected from piperazinyl or pyrrolidinyl;

Het$^{28}$ represents a heterocycle selected from morpholinyl, pyrrolidinyl, 2-pyrrolidinonyl, piperazinyl or piperidinyl wherein said Het$^{28}$ is optionally substituted with one or where possible two or more substituents selected from hydroxy, $C_{1-4}$alkyl, hydroxy-$C_{1-4}$alkyl- or polyhydroxy-$C_{1-4}$alkyl-; in particular Het$^{28}$ is selected from morpholinyl, piperazinyl or pyrrolidinyl; more in particular Het$^{27}$ and Het$^{29}$ is selected from piperazinyl or pyrrolidinyl.

d) the intermediate of formula (VII)

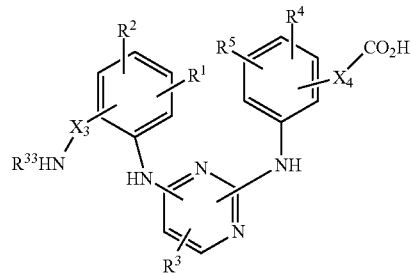

(VII)

the pharmaceutically acceptable addition salts and the stereochemically isomeric forms thereof, wherein $X_3$ and $X_4$ each independently represent a direct bond, $C_{1-7}$alkyl, $C_{3-7}$alkenyl, $C_{3-7}$alkynyl, wherein said $C_{1-7}$alkyl, $C_{3-7}$alkenyl, $C_{3-7}$alkynyl are optionally substituted with one or where possible two or more substituents selected from amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfonyl and $C_{1-4}$alkyloxycarbonylamino;

or $X_3$ and $X_4$ each independently represent $C_{1-5}$alkyl-O—$C_{1-5}$alkyl, $C_{1-5}$alkyl-NR$^{30}$—$C_{1-5}$alkyl, $C_{1-2}$alkyl-CO-Het$^{10}$, Het$^{23}$, O—$C_{1-2}$alkyl with the oxygen atom attached to the phenyl ring or CR$^8$R$^9$;

R$^1$ represents hydrogen, cyano, halo, hydroxy, formyl, $C_{1-6}$alkoxy-, $C_{1-6}$alkyl-, halo-phenyl-carbonylamino-, Het$^{20}$, $C_{1-6}$alkoxy- substituted with halo, Het$^1$ or $C_{1-4}$alkyloxy-, or R$^1$ represents $C_{1-6}$alkyl substituted with one or where possible two or more substituents selected from hydroxy, Het$^{18}$ or halo;

R$^2$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

R$^3$ represents hydrogen, cyano, nitro, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

R$^4$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

R$^5$ represents hydrogen, cyano, halo, hydroxy, formyl, $C_{1-6}$alkoxy-, $C_{1-6}$alkyl-, halo-phenyl-carbonylamino-, Het$^{21}$, $C_{1-6}$alkoxy- substituted with halo, Het$^2$ or $C_{1-4}$alkyloxy-, or R$^5$ represents $C_{1-6}$alkyl substituted with one or where possible two or more substituents selected from hydroxy, Het$^{19}$ or halo;

R$^8$ and R$^9$ each independently represents hydrogen or $C_{1-4}$alkyl optionally substituted with phenyl, indolyl, methylsulfide, hydroxy, thiol, hydroxyphenyl, $C_{1-4}$alkyloxyphenyl-, aminocarbonyl, hydroxycarbonyl, amino, mono- or di($C_{1-4}$alkyl)-amine-, imidazoyl, cyano, polyhalo$C_{1-4}$alkylphenyl, $C_{1-4}$alkyloxy, pyridinyl, $C_{3-6}$cycloalkyl or guanidino; in particular R$^8$ and R$^9$ each independently represent hydrogen or $C_{1-4}$alkyl optionally substituted with phenyl, indolyl, methylsulfide, hydroxy, thiol, hydroxyphenyl, $C_{1-4}$alkyloxyphenyl-, aminocarbonyl, hydroxycarbonyl, amino, mono- or di($C_{1-4}$alkyl)-amine-, imidazoyl, or guanidino; even more particular R$^8$ and R$^9$ each independently represent hydrogen or $C_{1-4}$alkyl optionally substituted with phenyl, methylsulfide or mono- or di($C_{1-4}$alkyl)amine;

R$^{30}$ represents hydrogen, $C_{1-4}$alkyl, Het$^{11}$, Het$^{12}$-$C_{1-4}$alkyl, phenyl-$C_{1-4}$alkyl, phenyl or mono- or di($C_{1-4}$alkyl)amino-$C_{1-4}$alkyl-carbonyl wherein said R$^{30}$ is optionally substituted with hydroxy, amino, mono- or di($C_{1-4}$alkyl)amino, pyrimidinyl or $C_{1-4}$alkyloxy;

R$^{33}$ represents hydrogen, $C_{1-4}$alkyl, Het$^{14}$ or $C_{1-4}$alkyl substituted with one or where possible two or more substituents selected from hydroxy, amino, mono- or di($C_{1-4}$alkyl)amino, phenyl, Het$^{15}$ or $C_{1-2}$alkyloxy;

Het$^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

Het$^2$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^2$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

Het$^{10}$ represents a heterocycle selected from pyrrolidinyl, 2-pyrrolidinonyl, piperazinyl or piperidinyl wherein said Het$^{10}$ is optionally substituted with one or where possible two or more substituents selected from hydroxy, $C_{1-4}$alkyl, hydroxy-$C_{1-4}$alkyl- or polyhydroxy-$C_{1-4}$alkyl-;

Het$^{11}$ represent a heterocycle selected from pyrrolidinyl or piperidinyl wherein said Het$^{11}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{12}$ represent a heterocycle selected from morpholinyl, pyrrolidinyl, piperazinyl or piperidinyl wherein said Het$^{12}$ is optionally substituted with one or where possible two or more substituents selected from $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

$Het^{14}$ represent a heterocycle selected from pyrrolidinyl or piperidinyl wherein said pyrrolidinyl or piperazinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{18}$ or $Het^{19}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{20}$ and $Het^{21}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{20}$ or $Het^{21}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{22}$ represents a heterocycle selected from morpholinyl, pyrrolidinyl, piperazinyl or piperidinyl wherein said $Het^{22}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{23}$ represents a heterocycle selected from pyrrolidinyl, 2-pyrrolidinonyl, quinolinyl, isoquinolinyl, decahydroquinolinyl, piperazinyl or piperidinyl wherein said $Het^{23}$ is optionally substituted with one or where possible two or more substituents selected from hydroxy, $Het^{25}$, $Het^{22}$-carbonyl, $C_{1-4}$alkyl, hydroxy-$C_{1-4}$alkyl- or polyhydroxy-$C_{1-4}$alkyl-; and $Het^{25}$ represents a heterocycle selected from morpholinyl, pyrrolidinyl, piperazinyl or piperidinyl wherein said $Het^{25}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-, provided that said intermediate of formula (VII) is other than 2-[[2-[(3-aminophenyl)amino]-4-pyrimidinyl]amino]-Benzoic acid [604801-24-3].

In another embodiment the present invention provides the intermediates of formula (VII) wherein one or more of the following restrictions apply;

$X_3$ and $X_4$ each independently represent a direct bond, $C_{1-7}$alkyl, $C_{3-7}$alkenyl, $C_{1-5}$alkyl-$NR^{30}$—$C_{1-5}$alkyl, $Het^{23}$, $CR^8R^9$, or O—$C_{1-2}$alkyl with the oxygen atom attached to the phenyl ring;

$R^1$ represents hydrogen, halo, $C_{1-6}$alkyloxy-, or $C_{1-6}$alkyloxy substituted with $Het^1$ or $C_{1-4}$alkyloxy;

$R^2$ represents hydrogen of halo;

$R^3$ represents hydrogen, cyano or nitro; in particular hydrogen or cyano;

$R^4$ represents hydrogen or halo;

$R^5$ represents hydrogen, halo, $C_{1-6}$alkyloxy-, or $C_{1-6}$alkyloxy substituted with $Het^2$ or $C_{1-4}$alkyloxy;

$R^8$ and $R^9$ each independently represents hydrogen or $C_{1-4}$alkyl optionally substituted with phenyl, methylsulfide, hydroxy, thiol, amino, mono- or di($C_{1-4}$alkyl)-amine-, or imidazoyl;

$R^{30}$ represents hydrogen, $C_{1-4}$alkyl or $Het^{12}$-$C_{1-4}$alkyl;

$R^{33}$ represents hydrogen, $C_{1-4}$alkyl or $Het^{15}$-$C_{1-4}$alkyl;

$Het^1$ represents morpholinyl;

$Het^2$ represents morpholinyl;

$Het^{12}$ represents pyrrolidinyl or piperazinyl wherein said $Het^{12}$ is optionally substituted with one or where possible two or more substituents selected from $C_{1-4}$alkyl, $C_{3-6}$ cycloalkyl, hydroxy-$C_{1-4}$allyl-, $C_{1-4}$alkyloxy$C_{1-4}$alkyl or polyhydroxy-$C_{1-4}$alkyl-; in particular $Het^{12}$ represents pyrrolidinyl or piperazinyl;

$Het^{15}$ represents pyrrolidinyl or piperazinyl wherein said $Het^{15}$ is optionally substituted with one or where possible two or more substituents selected from $C_{1-4}$alkyl, $C_{3-6}$ cycloalkyl, hydroxy-$C_{1-4}$allyl-, $C_{1-4}$alkyloxy$C_{1-4}$alkyl or polyhydroxy-$C_{1-4}$alkyl-; in particular $Het^{15}$ represents pyrrolidinyl or piperazinyl; or $Het^{23}$ represents a heterocycle selected from pyrrolidinyl, decahydroquinolinyl or pyridinyl wherein said $Het^{23}$ is optionally substituted with one or where possible two or more substituents selected from hydroxy or $C_{1-4}$alkyl.

In a further embodiment of the present invention, the intermediates of formula (VII) are characterized in that the two aniline residues are bound to the pyrimidine ring at positions 2,4 or 4,6 respectively; $X_3$ and $X_4$ substituent are at position 3'; $R^1$ and $R^4$ are at position 4' and $R^2$ and $R^5$ are at position 5'.

It is also an object of the present invention to provide the use of the intermediates of formula (III), (IV), (VI), (VII), (XXIX), (XXX), (XXXI), (XXXII), (XXXIII) in the synthesis of a macrocyclic kinase inhibitor such as for the compounds of formula (I).

As described in the experimental part hereinafter, the growth inhibitory effect and anti-tumour activity of the present compounds has been demonstrated in vitro, in enzymatic assays on the receptor tyrosine kinases EGFR, ErbB2, ErbB4, F1T3, BLK or the Sar kinase family such as for example Lyn, Yes cSRC. In an alternative assay, the growth inhibitory effect of the compounds was tested on a number of carcinamo cell lines, in particular in the ovarian carcinoma cell line SKOV3 and the squamous carcinoma cell line A431 using art known cytotoxicity assays such as MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restenosis, cancer and diabetic complications e.g. retinopathy.

In view of the utility of the compounds according to the invention, there is provided a method of treating a cell proliferative disorder such as atherosclerosis, restenosis and cancer, the method comprising administering to an animal in need of such treatment, for example, a mammal including humans, suffering from a cell proliferative disorder, a therapeutically effective amount of a compound according to the present invention.

Said method comprising the systemic or topical administration of an effective amount of a compound according to the invention, to animals, including humans. One skilled in the art will recognize that a therapeutically effective amount of the kinase inhibitors of the present invention is the amount sufficient to induce the growth inhibitory effect and that this amount varies inter alia, depending on the size, the type of the neoplasia, the concentration of the compound in the therapeutic formulation, and the condition of the patient. Generally, an amount of kinase inhibitor to be administered as a therapeutic agent for treating cell proliferative disorder such as atherosclerosis, restenosis and cancer, will be determined on a case by case by an attending physician.

Generally, a suitable dose is one that results in a concentration of the kinase inhibitor at the treatment site in the range of 0.5 nM to 200 µM, and more usually 5 nM to 10 µM. To obtain these treatment concentrations, a patient in need of treatment likely will be administered between 0.01 mg/kg to 500 mg/kg body weight, in particular from 10 mg/kg to 250 mg/kg body weight. As noted above, the above amounts may vary on a case-by-case basis. In these methods of treatment the compounds according to the invention are preferably formulated prior to admission. As described herein below, suitable pharmaceutical formulations are prepared by known procedures using well known and readily available ingredients.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.01 mg/kg to 500 mg/kg body weight, in particular from 10 mg/kg to 250 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

EXPERIMENTAL PART

The following examples illustrate the present invention.

Hereinafter, "BINAP" is defined as [1,1'-binaphthalene]-2,2'-diylbis[diphenyl-phosphine, "DMF" is defined as N,N-dimethylformamide, "DCM" is defined as dichloromethane, 'DIAD" is defined as diazenedicarboxylic acid, bis(1-methylethyl) ester, "DIPE" is defined as diisopropyl ether, "DIPEA" (=DIEA, CAS 7087-68-5) is defined as N-ethyl-N-(1-methylethyl)-2-propanamine, "DMSO" is defined as dimethylsulfoxide, "DMF" is defined as N,N-dimethylformamide, "EDC" is defined as N'-(ethylcarbonimidoyl)-N,N-dimethyl-1,3-propanediamine, monohydrochloride, "EtOAc" is defined as ethyl acetate, "EtOH" is defined as ethanol, "HBTU" is defined as 1-[bis(dimethylamino)methylene]-1H-Benzotriazolium, hexafluorophosphate(1-), 3-oxide, "MeOH" is defined as methanol, "NMP" is defined as 1-methyl-2-pyrrolidinone, "TFA" is defined as trifluoroacetic acid, "THF" is defined as tetrahydrofuran, "TIS" is defined as triisopropylsilane A. Preparation of the Intermediates Example A1

| Preparation of intermediate 1 | 5-pyrimidinecarbonitrile, 2,4-bis[[3-(2-propenyloxy)phenyl]amino]- |
|---|---|

A mixture of 3-(2-propenyloxy)-benzenamine (max. 0.02 mol), 2,4-dichloro-5-pyrimidinecarbonitrile (0.009 mol) and DIPEA (0.03 mol) in acetonitrile (200 ml) was stirred and refluxed for 16 hours. The solvent was evaporated under reduced pressure. The residue was taken up into diglyme and stirred for 4 hours at 100° C., then stirred overnight at 100° C. The solvent was evaporated under reduced pressure. The residue was purified twice by column chromatography over silica gel (eluent: DCM/MeOH from 99/1 to 97/3). The product fractions were collected and the solvent was evaporated under reduced pressure, yielding 1.2 g (33.4%) of intermediate 1.

Example A2

| a) Preparation of intermediate 2 | benzoic acid, 3-[[5-cyano-2-(methylthio)-4-pyrimidinyl]amino]-, 1,1-dimethylethyl ester |
|---|---|

A mixture of 4-chloro-2-(methylthio)-5-pyrimidinecarbonitrile (0.010 mol), 3-amino-benzoic acid, 1,1-dimethylethyl ester (0.010 mol) and DIPEA (0.010 mol) in 2-propanol p.a. (50 ml) was stirred and refluxed for 1 hour, then a small amount of ice was added and the obtained cloudy mixture was allowed to cool. The precipitate was filtered off and dried, yielding 2.816 g (82%) of intermediate 2, melting point 162-164° C.

| b) Preparation of intermediate 3 | benzoic acid, 3-[[5-cyano-2-(methylsulfonyl)-4-pyrimidinyl]amino]-, 1,1-dimethylethyl ester |
|---|---|

A mixture of intermediate 2 (0.0082 mol) in DCM p.a. (80 ml) and MeOH p.a. (10 ml) was stirred at room temperature, then 3-chlorobenzenecarboperoxoic acid (0.020 mol) was added in small portions over 30 minutes and the reaction mixture was stirred for 4 hours at room temperature. The mixture was washed with a $NaHCO_3$ soln. (0.020 mol) and the layers were separated. The organic layer was washed again with water, dried, filtered off and the solvent was evaporated. The residue was purified by Flash column chromatography (eluent: DCM/MeOH 100/0 to 98/2). The product fractions were collected and the solvent was evaporated. The residue was crystallised from DIPE/acetonitrile (10/1), then the precipitate was filtered off and dried, yielding 1.742 g (56%) of intermediate 3.

| c) Preparation of intermediate 4 | benzoic acid, 3-[[5-cyano-2-[[3-[2-[[(1,1-dimethylethoxy)carbonyl]amino]ethoxy]phenyl]amino]-4-pyrimidinyl]amino]-, 1,1-dimethylethyl ester |
|---|---|

A mixture of intermediate 3 (0.001 mol) and [2-(3-aminophenoxy)ethyl]-carbamic acid, 1,1-dimethylethyl ester (0.001 mol) in DMSO p.a. dried on molecular sieves (5 ml) was stirred for 2 hours at 120° C. and then the reaction mixture was allowed to cool. The mixture was poured out into water and stirred overnight. The resulting precipitate was filtered off and dried, yielding 0.700 g of intermediate 4, which was combined with another fraction which was made on the same way and further purified by column chromatography (eluent: DCM/MeOH 98/2). The desired product fractions were collected and the solvent was evaporated, yielding 0.700 g of intermediate 4.

| d) Preparation of intermediate 5 | benzoic acid, 3-[[2-[[3-(2-aminoethoxy)phenyl]amino]-5-cyano-4-pyrimidinyl]amino]- trifluoroacetic acid salt |
|---|---|

A mixture of intermediate 4 (0.00128 mol) in DCM (15 ml) was stirred at room temperature and then a mixture of TFA (0.5 ml) in DCM (5 ml) was added dropwise. The resulting mixture was stirred for 20 hours at room temperature and extra TFA (0.5 ml) in DCM (4.5 ml) was added. The reaction mixture was stirred and refluxed for 20 hours and then again extra TFA (2 ml) was added. The mixture was stirred and refluxed for 6 hours more and was then left to stand over the weekend. The solvent was evaporated and the obtained residue was stirred in DIPE/acetonitrile. The resulting precipitate was filtered off and dried. yielding 0.534 g (82%) of intermediate 5, isolated as a trifluoroacetic acid salt.

Example A3

| a) Preparation of intermediate 6 | carbamic acid, [4-(3-nitrophenoxy)butyl]-, 1,1-dimethylethyl ester |
|---|---|

A mixture of (4-hydroxybutyl)-carbamic acid, 1,1-dimethylethyl ester (0.063 mol), 3-nitro-phenol (0.05 mol) and triphenyl-phosphine (0.05 mol) in THF (250 ml) was stirred at 0° C., then bis(1-methylethyl)diazenedicarboxylate (0.05 mol) was added dropwise at 0° C. and the reaction mixture was allowed to reach room temperature. After stirring for 1 hour at ambient temperature, the solvent was evaporated and the obtained residue was purified by short column chromatography (eluent: DCM). The product fractions were collected and the solvent was evaporated. This residue (13 g) was then crystallised from petroleum-benzin/DIPE and the desired product was collected, yielding 16 g of intermediate 6, melting point 90° C.

| b) Preparation of intermediate 7 | carbamic acid, [4-(3-aminophenoxy)butyl]-, 1,1-dimethylethyl ester |
|---|---|

A mixture of intermediate 6 (0.06 mol) in MeOH (250 ml) was hydrogenated at 50° C. with Pd/C (2 g) as a catalyst in the presence of thiophene solution (1 ml). After uptake of $H_2$ (3 equiv.), the catalyst was filtered over dicalite and the filtrate was evaporated, yielding 14 g (100%) of intermediate 7.

| c) Preparation of intermediate 8 | carbamic acid, [4-[3-[(2-chloro-4-pyrimidinyl)amino]phenoxy]butyl]-, 1,1-dimethylethyl ester |
|---|---|

A mixture of 2,4-dichloro-pyrimidine (0.01 mol), intermediate 7 ((0.011 mol) and DIPEA (0.015 mol) in EtOH (150 ml) was stirred and refluxed for 20 hours and then the solvent was evaporated. The obtained residue was dissolved in water and the solution was extracted with DCM. The organic layer was separated, dried (MgSO$_4$) and the solvent was evaporated. The residue was crystallised from DIPE and the resulting precipitate was collected, yielding 2.1 g (55.3%) of intermediate 8.

| d) Preparation of intermediate 9 | acetic acid, [3-[[4-[[3-(4-aminobutoxy)phenyl]amino]-2-pyrimidinyl]amino]phenoxy]- |
|---|---|

A mixture of intermediate 8 ((0.0023 mol), (3-aminophenoxy)-acetic acid, 1,1-dimethylethyl ester (0.0030 mol) and HCl/2-propanol (2 drops) in 2-propanol/water (4/1) (100 ml) was stirred and refluxed over the weekend and then HCl/2-propanol (10 ml) was added. The reaction mixture was stirred and refluxed for 2 hours, then cooled and neutralised to pH 7 with a 36% HCl solution. The resulting precipitate was filtered off, washed with water and dried (vac.) The obtained solids (1.2 g) were dissolved in sodium hydroxide 10% solution (100 ml) and then the resulting mixture was stirred and refluxed for 20 hours. After neutralising the mixture with a 36% HCl solution, the precipitate was filtered off, washed with water and dried (vac.), yielding 1.2 g (100%) of intermediate 9.

Example A4

| a) Preparation of intermediate 10 | carbamic acid, [2-[[(3-nitrophenyl)methyl]amino]-2-oxoethyl]-, 1,1-dimethylethyl ester |
|---|---|

EDC (0.031 mol) was added to a mixture of 3-nitro-benzenemethanamine, monohydrochloride (0.026 mol), N-[(1,1-dimethylethoxy)carbonyl]-glycine (0.031 mol) and triethylamine (0.065 mol) in DMF (q.s.) at room temperature and then the reaction mixture was reacted for 3 hours at room temperature. After an aqueous work-up with a 10% citric acid solution, with water, with an aqueous NaHCO$_3$ solution and with NaCl, the organic layer was dried and the solvent was evaporated, yielding 3.66 g (46%) of intermediate 10.

| b) Preparation of intermediate 11 | carbamic acid, [2-[[(3-aminophenyl)methyl]amino]-2-oxoethyl]-, 1,1-dimethylethyl ester |
|---|---|

A mixture of intermediate 10 (0.012 mol) in MeOH (30 ml) and THF (20 ml) was hydrogenated with Pd/C 10% (1 g) as a catalyst in the presence of thiophene solution (1 ml). After uptake of H$_2$ (3 equiv.), the catalyst was filtered off and the filtrate was evaporated, yielding 3 g of intermediate 11.

| c) Preparation of intermediate 12 | benzoic acid, 3-[[5-cyano-2-[[3-[[[[[(1,1-dimethylethoxy)carbonyl]amino]acetyl]amino]methyl]phenyl]amino]-4-pyrimidinyl]amino]-, 1,1-dimethylethyl ester |
|---|---|

A mixture of intermediate 2 (0.0003 mol) and 3-chlorobenzenecarboperoxoic acid (0.00072 mol) in DCM (q.s.) was reacted for 2 hours, then intermediate 11 (0.00036 mol) was added and the reaction mixture was stirred for 1 hour at room temperature. Finally, the mixture was heated to 60° C. and the desired product was collected, yielding intermediate 12.

| d) Preparation of intermediate 13 | benzoic acid, 3-[[2-[[3-[[(aminoacetyl)amino]methyl]phenyl]amino]-5-cyano-4-pyrimidinyl]amino]- |
|---|---|

A mixture of intermediate 12 (0.03 mol) in 50% TFA in DCM (4 ml) was reacted for 1 hour at room temperature and then the solvent was evaporated, yielding intermediate 13.

Example A5

| a) Preparation of intermediate 14 | carbamic acid, [3-(2-methoxy-5-nitrophenoxy)propyl]-, 1,1-dimethylethyl ester |
|---|---|

A mixture of 2-methoxy-5-nitro-phenol, (0.0766 mol), (3-bromopropyl)-carbamic acid, 1,1-dimethylethyl ester (0.092 mol) and potassium carbonate (0.092 mol) in DMF (130 ml) was stirred at 60° C. for 18 hours. Water was added. The mixture was extracted with EtOAc/diethyl ether. The organic layer was separated, dried (MgSO$_4$), filtered, and the solvent was evaporated till dryness. The crude crystals were taken up in diethyl ether/DIPE. The precipitate was filtered off and dried, yielding 24 g (96%) of intermediate 14.

| b) Preparation of intermediate 15 | carbamic acid, [3-(5-amino-2-methoxyphenoxy)propyl]-, 1,1-dimethylethyl ester |
|---|---|

A mixture of intermediate 14 (0.0735 mol) and Raney Nickel (20 g) in MeOH (400 ml) was hydrogenated at room temperature for 2 hours under a 3 bar pressure, then filtered. The filtrate was evaporated till dryness, yielding 24.1 g (>100%) of intermediate 15.

Example A6

| a) Preparation of intermediate 16 | L-proline, 1-[(4-chloro-5-fluoro-2-nitrophenyl)methyl]-, 1,1-dimethylethyl ester |
|---|---|

A solution of L-proline, 1,1-dimethylethyl ester (0.010 mol) and 4-chloro-5-fluoro-2-nitrobenzaldehyde (0.010 mol)

in DCM (30 ml) was cooled to 0° C. and titanium tetrakis(2-propanolato) (0.010 mol) was added, then the mixture was stirred for 1 hour at room temperature and NaBH(OAc)$_3$ (0.011 mol) was added. The reaction mixture was stirred for 3 hours at room temperature and extra titanium tetrakis(2-propanolato) (0.001 mol) and NaBH(OAc)$_3$ (0.001 mol) were added. After stirring for another 5 hours, water was added and the mixture was filtered. The organic layer was separated, dried (K$_2$CO$_3$), and the solvent was evaporated, yielding intermediate 16 (S) (used as such in the next reaction step).

| b) Preparation of intermediate 17 | L-proline, 1-[(2-amino-4-chloro-5-fluorophenyl)methyl]-, 1,1-dimethylethyl ester |
|---|---|

A mixture of intermediate 16 (0.009 mol) in EtOAc (150 ml) was hydrogenated with Pt/C$_5$% (1 g) as a catalyst in the presence of thiophene solution (1 ml). After uptake of H$_2$ (3 equiv.), the catalyst was filtered off and the filtrate was evaporated. The residue was purified by reversed phase high-performance liquid chromatography (NH$_4$OAc buffer), then the product fractions were collected and the organic component of the eluent was evaporated. The obtained precipitate was filtered off, washed with water and dried in vacuo, to give 1.1286 g (34%) of intermediate 17.

| c) Preparation of intermediate 18 | L-proline, 1-[[4-chloro-2-[[5-cyano-2-(methylthio)-4-pyrimidinyl]amino]-5-fluorophenyl]methyl]-, 1,1-dimethylethyl ester |
|---|---|

DIPEA (0.00026 mol) was added to a solution of 4-chloro-2-(methylthio)-5-pyrimidinecarbonitrile (0.00013 mol) and intermediate 17 (0.00014 mol) in 2-propanol (q.s.) and then the reaction mixture was stirred overnight at 60° C. LCMS monitoring indicated slow progression and the reaction had to be brought to 80° C. for 27 hours to effect completion. Next, the solvent was evaporated, yielding intermediate 18 (used as such in the next reaction step). In another run intermediate 18 was isolated in 30% yield following reversed phase HPLC (NH$_4$OAc buffer), mp. 116.7-118.2° C.

| d) Preparation of intermediate 19 | L-proline, 1-[[4-chloro-2-[[5-cyano-2-[[3-[3-[[(1,1-dimethylethoxy)carbonyl]amino]propoxy]-4-methoxyphenyl]amino]-4-pyrimidinyl]amino]-5-fluorophenyl]methyl]-, 1,1-dimethylethyl ester |
|---|---|

A solution of 3-chlorobenzenecarboperoxoic acid (0.000173 mol) in 1,2-dichloro-ethane (q.s.) was dried with anhydrous MgSO$_4$ and filtered, to give Residue I.

Residue I was added to a solution of intermediate 18 (0.000157 mol) in 1,2-dichloro-ethane (q.s.) and the resulting mixture was stirred for 1 hour at room temperature. Upon addition of extra Residue I was added and the mixture was stirred for another 30 min. Intermediate 15 (0.000173 mol) was added and the reaction mixture was stirred overnight at 65° C. After cooling to room temperature, a saturated. NaHCO$_3$ soln. was added and the organic layer was separated and dried. Finally, the solvent was evaporated yielding intermediate 19, which was used as such in the next reaction step, (S).

| e) Preparation of intermediate 20 | L-proline, 1-[[2-[[2-[[3-(3-aminopropoxy)-4-methoxyphenyl]amino]-5-cyano-4-pyrimidinyl]amino]-4-chloro-5-fluorophenyl]methyl]- trifluoroacetic acid salt |
|---|---|

A solution of intermediate 19 (0.000157 mol) in TFA/DCM (50/50) (5 ml) was reacted for 5 hours and then the solvent was evaporated at 30° C., yielding intermediate 20 (S), isolated as a trifluoroacetic acid salt (used as such in the next reaction step).

Example A7

| a) Preparation of intermediate 21 | 1-hexanol, 6-(4-chloro-2-nitrophenoxy)-, acetate (ester) |
|---|---|

A solution of 4-chloro-2-nitrophenol (0.10 mol) in N,N-dimethylacetamide (200 ml) was treated for 15 minutes with potassium carbonate (17 g) at 90° C., then 6-bromo-1-hexanol, acetate (0.12 mol) was added at 60° C. and the reaction mixture was stirred overnight at 60° C. The mixture was poured out into ice-water (500 ml) and extracted with toluene (2×250 ml). The organic layers were combined, dried (MgSO$_4$), filtered off and the solvent was evaporated, yielding 42.3 g (>100%) of intermediate 21.

| b) Preparation of intermediate 22 | 1-hexanol, 6-(2-amino-4-chlorophenoxy)-, acetate (ester) |
|---|---|

A mixture of intermediate 21 (max. 0.11 mol) in THF (400 ml) was hydrogenated with Pt/C (5.0 g) as a catalyst in the presence of thiophene solution (3 ml). After uptake of H$_2$ (3 equiv.), the catalyst was filtered off and the filtrate was evaporated. The obtained residue was dissolved in DIPE (300 ml) and treated with 2-propanol/(6N HCl). After stirring for 1 hour, the resulting white solids were collected and dried, yielding 30.0 g of intermediate 22.

| c) Preparation of intermediate 23 | 1-hexanol, 6-[4-chloro-2-[(6-chloro-4-pyrimidinyl)amino]phenoxy]-, acetate (ester) |
|---|---|

A mixture of 4,6-dichloropyrimidine (0.01 mol), intermediate 22 (0.012 mol) and DIPEA (0.025 mol) in EtOH (50 ml) was heated for 3 days on an oil bath at 80° C., then the solvent was evaporated and the obtained residue was purified by column chromatography. The desired product fractions were collected and the solvent was evaporated, yielding intermediate 23.

| d) Preparation of intermediate 24 | phenol, 5-[[6-[[5-chloro-2-[(6-hydroxyhexyl)oxy]phenyl]amino]-4-pyrimidinyl]amino]-2-methoxy- |
|---|---|

A solution of intermediate 23 (0.0015 mol), 5-amino-2-methoxy-phenol (0.0015 mol) and HCl (cat. quant.) in butanol (50 ml) was stirred for 48 hours at reflux temperature and after completion, the solvent was evaporated under reduced pressure. The crude residue was filtered over silica gel (eluent: DCM/MeOH 92/8), then the desired product fractions were collected and the solvent was evaporated to dryness, yielding 0.300 g of intermediate 24.

Example A8 a) Preparation of intermediate 25

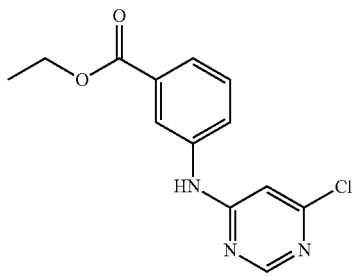

Ethyl 3-aminobenzoate (0.080 mol) was added to 2,4-dichloropyrimidine (0.066 mol) in isopropanol (80 ml), DIPEA (0.133 mol) was added. The reaction mixture was stirred and heated in the microwave for 3 hours at 160° C. The cooled reaction mixture was poured into a flask at room temperature, isopropanol (100 ml) was added, the reaction mixture was stirred at room temperature. The crystallized solid was filtered and dried at 50° C. under vacuum, yielding 11.3 g of intermediate 25, melting point 152° C.

| b) Preparation of intermediate 26 | benzoic acid, 3,3'-(4,6-pyrimidinediyldiimino)bis-, ethyl ester, hydrochloric acid salt |
|---|---|

To a solution of intermediate 25 (0.0072 mol) in isopropanol (50 ml), 3-aminobenzoic acid (0.0086 mol) was added. Hydrochloric acid in isopropanol (6N, 1.5 ml) was added. The reaction mixture was stirred and heated in the microwave for 2.5 hours at 130° C. The reaction mixture was concentrated, crystallized from acetonitrile/isopropanol. The precipitate was filtered off and dried at 50° C. under vacuum, yielding 1.9 g of intermediate 26 isolated as a hydrochloric acid salt, melting point 248-250° C.

| c) Preparation of intermediate 27 | benzoic acid, 3-[[6-[[3-[[[6-[[(1,1-dimethylethoxy)carbonyl]amino]hexyl]amino]carbonyl]phenyl]amino]-4-pyrimidinyl]amino]-, ethyl ester |
|---|---|

To a solution of intermediate 26 (1.32 mmol) in DCM (50 ml), N-Boc-1,6-hexanediamine (1.88 mmol) was added. 1-Hydroxybenzotriazole (1.88 mmol), N-(3-Dimethylaminopropyl)-N-ethylcarbodiimide hydrochloride (1.88 mmol), triethylamine (0.805 ml) was added. The reaction mixture was stirred for 48 hours at room temperature. A precipitate was formed in the reaction mixture. The solid was filtered and dried at 40° C. under vacuum, yielding 430 mg of intermediate 27, melting point 163° C.

| d) Preparation of intermediate 28 | benzoic acid, 3-[[6-[[3-[[(6-aminohexyl)amino]carbonyl]phenyl]amino]-4-pyrimidinyl]amino]-, ethyl ester, trifluoroacetic acid salt |
|---|---|

To a solution of intermediate 27 (0.69 mmol) in DCM (10 ml), a solution of 20% TFA in DCM was added. The reaction mixture was stirred for 1 hour at room temperature. The solvent was evaporated. toluene was added, the solvent was evaporated, ethanol was added. the solvent was evaporated. The product was used without further purification, yielding intermediate 28, isolated as a trifluoroacetic acid salt.

| e) Preparation of intermediate 29 | benzoic acid, 3-[[6-[[3-[[(6-aminohexyl)amino]carbonyl]phenyl]amino]-4-pyrimidinyl]amino]- Lithium charged |
|---|---|

To a solution of intermediate 28 (0.69 mmol) in EtOH (20 ml), 1 ml water and LiOH (4.5 mmol) was added. The reaction mixture was stirred for 6.5 hours at 40° C. The solvent was evaporated. The product was used without further purification, yielding intermediate 29, isolated as Lithium charged.

Example A9 a) Preparation of intermediate 30

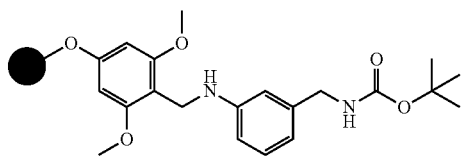

A mixture of Novabiochem 01-64-0261 commercial resin (2 g, loading: 0.94 mmol/g, 0.0018 mol) was washed with DCM (50 ml), then a solution of 3-tert-butoxycarbonylaminomethylaniline (0.009 mol) in DCM/CH$_3$COOH 1% (25 ml) was added and the resulting mixture was shaken for 10 minutes at room temperature. Sodium triacetoxyborohydride (0.009 mol) was added, followed by addition of DCM/CH$_3$COOH 1% (25 ml) and the reaction mixture was shaken gently for 48 hours at room temperature. After filtration, the resin was washed 3 times with MeOH and 3 times with DCM, 3× MeOH, 3×DCM, 3× MeOH, 3×DCM, 3× MeOH, 3×DCM, 3× MeOH, 3×DCM, yielding intermediate 30, which was used in next reaction step.

b) Preparation of intermediate 31

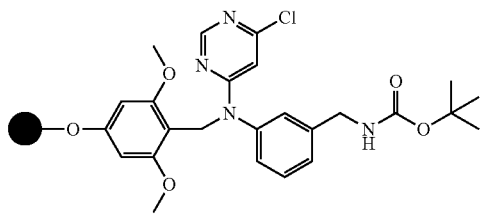

Intermediate 30 was washed with 1-butanol, to intermediate 30 was added 4,6-dichloropyrimidine (0.018 mol) and DIPEA (0.018 mol) in 1-butanol (50 ml). The reaction mixture was shaken for 40 hours at 90° C. under N$_2$, then the resin was filtered off and washed 3× with MeOH, 3×DCM, 3× MeOH, 3×DCM, 3× MeOH, 3×DCM, 3× MeOH, 3×DCM.

This procedure was repeated: to intermediate 30 was added 4,6-dichloropyrimidine [1193-21-1] (0.018 mol) and DIPEA (0.018 mol) in 1-butanol (50 ml). The reaction mixture was shaken gently for 24 hours at 90° C., under N₂, then the resin was filtered off and washed 3× with MeOH, 3×DCM, 3× MeOH, 3×DCM, 3× MeOH, 3×DCM, 3× MeOH, 3×DCM, 3× MeOH, 3×DCM, yielding intermediate 31, which was used in next reaction step.

c) Preparation of intermediate 32

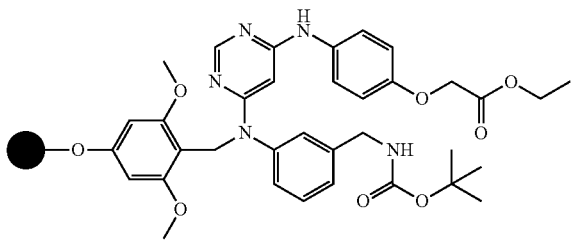

Intermediate 31 was washed with toluene, to intermediate 31 was added a mixture of ethyl (4-aminophenoxy)acetate (0.018 mol), Tris(dibenzylideneacetone)dipalladium(0) (0.00036 mol), (+/−)-2,2'-Bis(diphenylphosphino)-1,1'-binaphthalene (0.0018 mol) and cesium carbonate (0.027 mol) in toluene (50 ml). The reaction was brought under nitrogen. The reaction mixture was shaken for 18 hours at 110° C., under N₂, then the resin was filtered off hot and washed 3 times with hot DMF (at 70° C.), 3 times with hot water (at 50° C.), 3 times with DMF and 3 times with water, 3 times with DMF and 3 times with water, 3 times with DMF and 3 times with DCM. Finally, washed 3 times with MeOH and 3 times with DCM, 3 times with MeOH and 3 times with DCM. The residue was dried under vacuum at 30° C., yielding intermediate 32.

| d) Preparation of intermediate 33 | acetic acid, [4-[[6-[[3-(aminomethyl)phenyl]amino]-4-pyrimidinyl]amino]phenoxy]- |
|---|---|

Intermediate 32 was washed with THF, to intermediate 32 (300 mg) was added lithiumhydroxide (0.0049 mol) in THF (8 ml) and water (2 ml). The reaction mixture was shaken for 48 hours at 50° C., then the resin was filtered off and washed 3 times with water, 3 times with MeOH, 3 times with water and 3 times with DMF, 3 times with water and 3 times with DMF, 3 times with MeOH and 3 times with DCM, 3 times with MeOH and 3 times with DCM, 3 times with MeOH and 3 times with DCM. The residue was cleaved with TFA/TIS/DCM (25/2/73) for 4 hours, then the resin was filtered off and shaked for 1 hour with TFA/TIS/DCM (25/2/73). The resin was filtered off and washed 3 times with DCM. Finally, the combined solvents were blown dry under nitrogen at 50° C., 3 times DCM (5 ml) was added and blown dry under nitrogen at 50° C., yielding intermediate 33, isolated as a TFA-salt.

Example A10 a) Preparation of intermediate 34

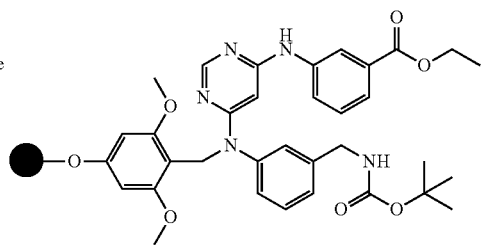

Intermediate 31 was washed with toluene, to intermediate 31 was added a mixture of ethyl 3-aminobenzoate (0.018 mol), Tris(dibenzylideneacetone)dipalladium(0) (0.00036 mol), (+/−)-2,2'-Bis(diphenylphosphino)-1,1'-binaphthalene (0.0018 mol) and cesium carbonate (0.027 mol) in toluene (50 ml). The reaction was brought under nitrogen. The reaction mixture was shaken for 18 hours at 110° C., under N₂, then the resin was filtered off hot and washed 3 times with hot DMF (at 70° C.), 3 times with hot water (at 50° C.), 3 times with DMF and 3 times with water, 3 times with DMF and 3 times with water, 3 times with DMF and 3 times with DCM. Finally, washed 3 times with MeOH and 3 times with DCM, 3 times with MeOH and 3 times with DCM. The residue was dried under vacuum at 30° C., yielding intermediate 34.

b) Preparation of intermediate 35

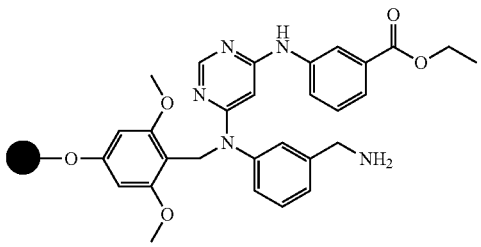

Intermediate 34 (400 mg) was washed with DCM, to intermediate 34 was added 10 ml of a solution of Trimethylsilyl trifluoromethanesulfonate/2,6-lutidine (1M/1.5M) in DCM. The resin was shaked gently for 3 hours at room temperature. The resin was filtered, washed with 3× MeOH, 3×DCM, 3× MeOH, 3×DCM, 3× MeOH, 3×DCM, 3× MeOH, 3×DCM, 3× MeOH, 3×DCM, yielding intermediate 35, which was used in next reaction step.

c) Preparation of intermediate 36

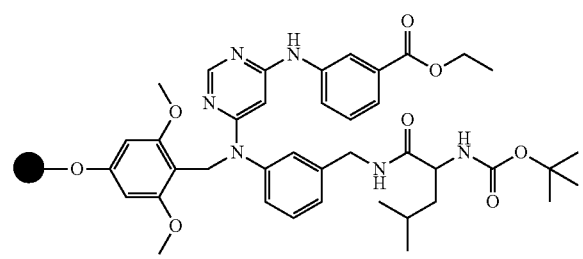

Intermediate 35 was washed with DMF. To intermediate 35 was added a mixture of N-(tert-Butoxycarbonyl)-L-leucine (0.00108 mol), Fluoro-N,N,N',N'-tetramethylformamidinium hexafluorophosphate (0.00108 mol) and DIPEA (0.0018 mol) in DMF (10 ml). The reaction mixture was shaken 48 hours at room temperature, then the resin was filtered off and washed with 3× MeOH, 3×DCM, 3× MeOH, 3×DCM, 3× MeOH, 3×DCM, 3× MeOH, 3×DCM, 3× MeOH, 3×DCM, yielding (RS) intermediate 36, which was used in next reaction step.

d) Preparation of intermediate 37

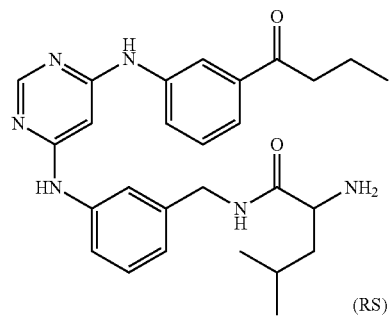

Intermediate 36 was washed with THF, intermediate 36 was added lithiumhydroxide (0.0049 mol) in THF (8 ml) and water (2 ml). The reaction mixture was shaken for 48 hours at 50° C., then the resin was filtered off and washed 3 times with water, 3 times with MeOH, 3 times with water and 3 times with DMF, 3 times with water and 3 times with DMF, 3 times with MeOH and 3 times with DCM, 3 times with MeOH and 3 times with DCM, 3 times with MeOH and 3 times with DCM. The resin was cleaved with TFA/TIS/DCM (25/2/73) for 4 hours, then the resin was filtered off and shaked for 1 hour with TFA/TIS/DCM (25/2/73). The resin was filtered off and washed 3 times with DCM. Finally, the combined solvents were blown dry under nitrogen at 50° C., 3 times DCM (5 ml) was added and blown dry under nitrogen at 50° C., yielding intermediate 37 (RS), isolated as a TFA-salt.

Example A11

| a) Preparation of intermediates 38 and 39 | phenol, 5-[(6-chloro-4-pyrimidinyl)amino]-2-methoxy-<br>Free base: intermediate 38<br>•HCl: intermediate 39 |
|---|---|

A solution of 4,6-dichloropyrimidine (0.1 mol), 5-amino-2-methoxyphenol (0.1 mol) and DIPEA (0.2 mol) in 2-propanol (200 ml) was heated in a microwave oven (divided in 5 portions) for 30 minutes at 130° C. Then the solvent was evaporated and the obtained residue was stirred in acetonitrile. The resulting precipitate was filtered off, washed with acetonitrile/DIPE and dried (vac.) at 60° C., yielding 15.01 g (60%) of intermediate 38. If desired, the compound can be converted to the HCl salt by stirring in 6 N HCl/2-propanol and collecting and drying the obtained precipitate, yielding intermediate 39.

| b) Preparation of intermediate 40 | benzenemethanol, 3-[[6-[(3-hydroxy-4-methoxyphenyl)amino]-4-pyrimidinyl]amino]- |
|---|---|

A mixture of intermediate 39 (0.05 mol, HCl salt) and 3-aminobenzenemethanol (0.05 mol) in n-butanol (80 ml) was equally divided over 2 microwave reaction vessels and each reaction mixture was heated for 30 minutes at 130° C. Extra 3-aminobenzenemethanol (0.0025 mol) was then added to each vessel and the resulting mixtures were heated for another 20 minutes at 130° C. 2-propanol and 6 N HCl/2-propanol was added to the combined mixtures, after which they were stirred overnight. The formed precipitate was collected and purified by reversed-phase high-performance liquid chromatography ($NH_4OAc$ buffer). After evaporation of the organic component of the eluent, a white precipitation was obtained, filtered off and dried in the oven, yielding 9.2444 g (55%) of intermediate 40, melting point 232.0-232.1° C.

| c) Preparation of intermediate 41 | carbamic acid, [2-[5-[[6-[[3-(hydroxymethyl)phenyl]amino]-4-pyrimidinyl]amino]-2-methoxyphenoxy]ethyl]-, 1,1-dimethylethyl ester |
|---|---|

A suspension of intermediate 40 (0.0075 mol) and cesium carbonate (0.0375 mol) in DMF (50 ml) was stirred for 1 hour at room temperature. Then (2-bromoethyl)-carbamic acid, 1,1-dimethylethyl ester (0.0090 mol) was added and the reaction mixture was stirred overnight. Extra (2-bromoethyl)-carbamic acid, 1,1-dimethylethyl ester (0.14 g) was added and the resulting mixture was stirred at 50° C. After 9 hours, the solvent was evaporated and DCM and water were added. The mixture was extracted 2 times with DCM and the combined organic layers were dried (anhydrous $K_2CO_3$). The product was purified over a pad of silica gel (eluent: DCM/EtOAc 60/40 to 0/100). The product fractions were collected and the solvent was evaporated. The obtained residue was triturated with DIPE and after filtration the desired product was dried (vac.) at 60° C., yielding 2.92 g (81%) of intermediate 41.

| d) Preparation of intermediate 42 | glycine, N-[[3-[[6-[[3-[2-[[(1,1-dimethylethoxy)carbonyl]amino]ethoxy]-4-methoxyphenyl]amino]-4-pyrimidinyl]amino]phenyl]methyl]-N-methyl-, methyl ester |
|---|---|

A suspension of intermediate 41 (0.0020 mol) and sodium iodide (0.0020 mol) in dry acetonitrile (50 ml) was stirred at room temperature, then methanesulfonyl chloride (0.0024 mol) and DIPEA (0.060 mol) were added dropwise. After 15 minutes sarcosine methyl ester hydrochloride (0.0030 mol) was added. The reaction mixture was stirred for 16 hours at 65° C. and, upon cooling to room temperature, PS—N=C=O (Aldrich, cat. 473685) (0.0030 mol) was added together with DCM (q.s.) and acetonitrile (q.s.). The mixture was shaken for 24 hours and then the resin was filtered off and washed with DCM, with MeOH, with DCM, with MeOH and with DCM again. The solvent was evaporated and the obtained residue was used as such in the next reaction step, yielding intermediate 42.

intermediate 94

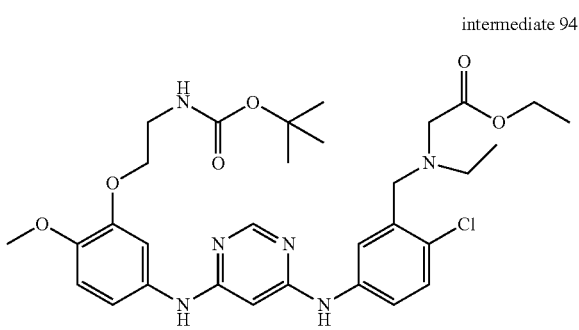 [SMILES: CCOC(=O)CN(CC)Cc1cc(Nc2cc(Nc3ccc(OC)c(OCCNC(=O)OC(C)(C)C)c3)ncn2)ccc1Cl]

intermediate 96

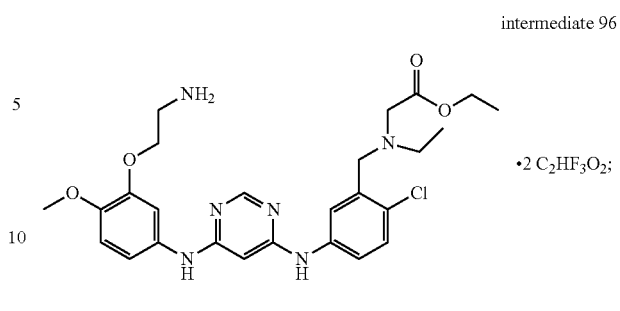

·2 C₂HF₃O₂;

Example A12

| e) Preparation of intermediate 43 | glycine, N-[[3-[[6-[[3-[2-[[(1,1-dimethylethoxy)carbonyl]amino]ethoxy]-4-methoxyphenyl]amino]-4-pyrimidinyl]amino]phenyl]methyl]-N-methyl- |
|---|---|

Lithium hydroxide monohydrate (0.010 mol) was added to a solution of intermediate 42 (0.002 mol) in EtOH/water (8/2) (50 ml) and the reaction mixture was stirred overnight at 65° C. Extra lithium hydroxide monohydrate (0.010 mol) was added, then the mixture was stirred for 4 hours at 65° C. and the solvent was evaporated to dryness, yielding intermediate 43, used as such in the next reaction step.

| a) Preparation of intermediate 45 | L-leucine, N-[(4-chloro-2-nitrophenyl)acetyl]-, 1,1-dimethylethyl ester |
|---|---|

A mixture of 4-chloro-2-nitro-benzeneacetic acid (0.0134 mol), L-leucine, 1,1-dimethylethyl ester, hydrochloride (0.0161 mol), triethylamine (0.0161 mol), EDC (0.0161 mol) and 1-hydroxy-1H-benzotriazole (0.0161 mol) in DCM/THF (60 ml) was stirred at room temperature overnight, water was added then the mixture was extracted with DCM. The organic layer was separated, dried (MgSO₄), filtered, and the solvent was evaporated till dryness. The residue (6.5 g) was crystallized from EtOAc/DIPE. The precipitate was filtered, washed with DIPE and air dried, yielding 3.2 g (63%) of intermediate 45.

intermediate 95

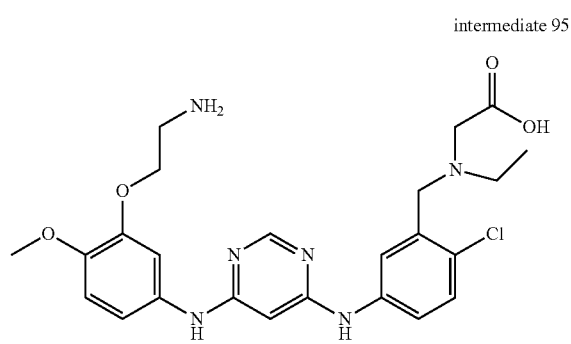 [SMILES: CCN(CC(=O)O)Cc1cc(Nc2cc(Nc3ccc(OC)c(OCCN)c3)ncn2)ccc1Cl]

| b) Preparation of intermediate 46 | L-leucine, N-[(2-amino-4-chlorophenyl)acetyl]-, 1,1-dimethylethyl ester |
|---|---|

A mixture of intermediate 45 (0.0072 mol) and Pt/C₅% (0.28 g) in thiophene solution 10% in EtOH (1.4 ml) and THF (100 ml) was hydrogenated at 50° C. for 72 hours under a 3 bar pressure, then filtered over celite. The filtrate was evaporated. The residue (3.4 g) was purified by column chromatography over silica gel (eluent: DCM/MeOH 100/0 to 98/2; 15-40 μm). The pure fractions were collected and the solvent was evaporated, yielding 2 g (77%) of intermediate 46 (L).

| c) Preparation of intermediate 47 | L-leucine, N-[[4-chloro-2-[(6-iodo-4-pyrimidinyl)amino]phenyl]acetyl]-, 1,1-dimethylethyl ester |
|---|---|

| f) Preparation of intermediate 44 | glycine, N-[[3-[[6-[[3-(2-aminoethoxy)-4-methoxyphenyl]amino]-4-pyrimidinyl]amino]phenyl]methyl]-N-methyl-trifluoroacetic acid salt |
|---|---|

A solution of intermediate 43 (0.002 mol) in TFA/DCM/TIS (49/49/2) (50 ml) was stirred for 1 hour at room temperature and then the solvent was evaporated, yielding intermediate 44, isolated as a trifluoroacetic acid salt, used as such in the next reaction step.

A mixture of intermediate 46 (L) (0.0028 mol), 4,6-diiodo-pyrimidine (0.0056 mol) and DIPEA (0.0056 mol) in NMP (20 ml) was heated in a microwaves (P=100 W) at 170° C. for 45 minutes, then cooled to room temperature, poured out into water and extracted with EtOAc/diethyl ether. The organic layer was washed with saturated NaCl, dried (MgSO₄), filtered, and the solvent was evaporated till dryness. The residue (4 g) was purified by column chromatography over silica gel (eluent: DCM/MeOH 100/0 to 98/2; 15-40 μm). The pure fractions were collected and the solvent was evaporated, yielding intermediate 47 (L).

| d) Preparation of intermediate 48 | L-leucine, N-[[4-chloro-2-[[6-[[3-[3-[[(1,1-dimethylethoxy)carbonyl]amino]propoxy]-4-methoxyphenyl]amino]-4-pyrimidinyl]amino]phenyl]acetyl]-, 1,1-dimethylethyl ester |
|---|---|

A mixture of intermediate 47 (L) (0.0017 mol), intermediate 15 (0.0021 mol) and HCl/2-propanol 5N (6 drops) in t-butanol (20 ml) was stirred and refluxed for 18 hours, then cooled to room temperature, poured out into water and extracted with DCM. The organic layer was washed with potassium carbonate 10%, dried (MgSO$_4$), filtered, and the solvent was evaporated till dryness. The residue (1.46 g) was purified by column chromatography over silica gel (eluent: DCM/MeOH/NH$_4$OH 100/0/0 to 97/3/0.1; 15-40 µm). The pure fractions were collected and the solvent was evaporated, yielding 0.54 g (41%) of intermediate 48 (L).

| e) Preparation of intermediate 49 | L-leucine, N-[[2-[[6-[[3-(3-aminopropoxy)-4-methoxyphenyl]amino]-4-pyrimidinyl]amino]-4-chlorophenyl]acetyl]-trifluoroacetic acid salt |
|---|---|

A mixture of intermediate 48 (L) (0.0007 mol) in TFA (2 ml) and DCM (10 ml) was stirred at room temperature for 18 hours. The solvent was evaporated till dryness, yielding intermediate 49, isolated as a trifluoroacetic acid salt. This product was used directly in the next reaction step.

Example A13

| a) Preparation of intermediate 50 | carbamic acid, (5-chloro-2-hydroxyphenyl)-, 1,1-dimethylethyl ester |
|---|---|

A solution of di-tert-butyl dicarbonate ester (0.0696 mol) in THF (50 ml) was added at 0° C. to a solution of 2-amino-4-chlorophenol (0.0697 mol) in THF (100 ml). The mixture was stirred at room temperature for 1 hour, then left at room temperature for 48 hours and evaporated in vacuo. The residue was purified by column chromatography over silica gel (eluent: DCM 100). The pure fractions were collected and the solvent was evaporated, yielding 13.6 g (80%) of intermediate 50.

| b) Preparation of intermediate 51 | carbamic acid, [2-(2-bromoethoxy)-5-chlorophenyl]-, 1,1-dimethylethyl ester |
|---|---|

A mixture of intermediate 50 (0.0615 mol), 1,2-dibromoethane (0.0313 mol) and cesium carbonate (0.0615 mol) in DMF (150 ml) was stirred at room temperature for 48 hours, then poured out into water and extracted three times with diethyl ether and brine. The organic layer was separated, dried (MgSO$_4$), filtered, and the solvent was evaporated in vacuo, yielding intermediate 51. This product was used directly in the next reaction step.

| c) Preparation of intermediate 52 | carbamic acid, [5-chloro-2-[2-[(3-hydroxypropyl)amino]ethoxy]phenyl]-, 1,1-dimethylethyl ester |
|---|---|

A mixture of intermediate 51 (0.0615 mol) and 3-amino-1-propanol (0.612 mol) in EtOH (300 ml) was stirred and refluxed for 48 hours, then condensed in vacuo, poured out into water and extracted three times with DCM. The organic phase was separated, washed with brine, dried (MgSO$_4$), filtered, and the solvent was evaporated in vacuo. The residue was purified by column chromatography over silica gel (eluent: DCM/MeOH/NH$_4$OH 95/5/0.5). The pure fractions were collected and the solvent was evaporated, yielding 6.4 g (30%) of intermediate 52.

| d) Preparation of intermediate 53 | carbamic acid, [2-[4-chloro-2-[[(1,1-dimethylethoxy)carbonyl]amino]phenoxy]ethyl](3-hydroxypropyl)-, phenylmethyl ester |
|---|---|

A solution of benzyl chloroformate (0.022 mol) in DCM (10 ml) was added at 0° C. to a mixture of intermediate 52 (0.0183 mol) and triethylamine (0.0226 mol) in DCM (200 ml). The mixture was stirred at room temperature overnight and was poured out into water. NaHCO$_3$ (50 ml) was added. The organic layer was separated, dried (MgSO$_4$), filtered, and the solvent was evaporated in vacuo. The residue was purified by column chromatography over silica gel (eluent: DCM/MeOH 100/0 to 98/2). The pure fractions were collected and the solvent was evaporated, yielding 8.2 g (94%) of intermediate 53.

| e) Preparation of intermediate 54 | acetic acid, trifluoro-, 3-[[2-(2-amino-4-chlorophenoxy)ethyl][(phenylmethoxy)carbonyl]amino] propyl ester |
|---|---|

TFA (15 ml) was added at 0° C. to a stirring mixture of intermediate 53 (0.0173 mol) in DCM (100 ml) and the resulting reaction mixture was stirred for 16 hours at room temperature, then evaporated in vacuo, yielding 8.2 g (99%) of intermediate 54. This product was used directly in the next reaction step.

| f) Preparation of intermediate 55 | carbamic acid, [2-[4-chloro-2-[[6-[(3-hydroxy-4-methoxyphenyl)amino]-4-pyrimidinyl]amino]phenoxy]ethyl](3-hydroxypropyl)-, phenylmethyl ester |
|---|---|

A mixture of intermediate 38 (0.019 mol), intermediate 54 (0.017 mol) and HCl/2-propanol (20 drops, 5M) in 2-methyl-2-pentanol (25 ml) was stirred and refluxed for 20 hours, then evaporated in vacuo. The residue was dissolved in DCM. TFA was added. The mixture was stirred overnight. TFA was added. The mixture was stirred at room temperature for 3 days, then evaporated in vacuo. The residue was dissolved in EtOH. Potassium hydroxide (30 ml, 2M solution) was added. The mixture was stirred and refluxed, then evaporated in vacuo. HCl 3N was added to neutralize the mixture then water (200 ml) was added. The mixture was extracted three times with DCM. The organic layer was separated, dried (MgSO$_4$), filtered, and the solvent was evaporated. The residue was purified by column chromatography over silica gel (eluent:

DCM/MeOH/NH$_4$OH 97/3/0.1). The pure fractions were collected and the solvent was evaporated, yielding 8.3 g (73%) of intermediate 55.

| g) Preparation of intermediate 56 | phenol, 5-[[6-[[5-chloro-2-[2-[(3-hydroxypropyl)amino]ethoxy]phenyl]amino]-4-pyrimidinyl]amino]-2-methoxy- |
|---|---|

A mixture of intermediate 55 (0.013 mol) in potassium hydroxide 40% (0.3 ml) and EtOH (2 ml) was stirred and refluxed for 1 hour. A solution of NH$_4$Cl was added. The solvent was removed in vacuo. The mixture was partitioned between DCM and saturated NaCl. The insoluble material was removed by filtration, dissolved in a mixture of CH$_2$Cl$_2$/MeOH/NH$_4$OH (80/20/3), filtered on a cake of silica and concentrated in vacuo. The residue was suspended in CH$_2$Cl$_2$ (200 ml) and DIEA (20 ml) was added. The mixture was stirred 16 hours at room temperature, then water (200 ml) was added. The organic extract was dried (MgSO$_4$) then concentrated in vacuo to yield 3.9 g of intermediate 56, melting point 170° C.

Example A14

| Preparation of intermediate 57 | benzoic acid, 3-[(6-chloro-4-pyrimidinyl)amino]-, 1,1-dimethylethyl ester |
|---|---|

A mixture of 4,6-dichloropyrimidine (0.0168 mol), 3-aminobenzoic acid, 1,1-dimethylethyl ester (0.034 mol) and DIPEA (0.034 mol) in 2-propanol (60 ml) was reacted overnight at 90° C. and then the solvent was evaporated. The residue was treated with 1N HCl and washed 3 times and then the organic solvent was evaporated. The obtained product was dissolved in DCM and washed 3 times with 1N HCl. The organic layer was separated, dried (MgSO$_4$) and the solvent was evaporated, yielding 5.61 g of intermediate 57.

Example A15

| a) Preparation of intermediate 58 | carbamic acid, [2-[[(4-methoxy-3-nitrophenyl)methyl]amino]ethyl]-, 1,1-dimethylethyl ester |
|---|---|

A mixture of 4-methoxy-3-nitro-benzaldehyde (0.00625 mol) and (2-aminoethyl)-carbamic acid, 1,1-dimethylethyl ester (0.00625 mol) in MeOH (30 ml) was reacted for 2 hours at room temperature, then sodium tetrahydroborate (0.0069 mol) was added and the reaction mixture was stirred overnight. Water was added and the resulting mixture was extracted 3 times with toluene. The organic layer was separated, dried (MgSO$_4$) and the solvent was evaporated, yielding intermediate 58.

| b) Preparation of intermediate 59 | carbamic acid, [2-[[(3-amino-4-methoxyphenyl)methyl]amino]ethyl]-, 1,1-dimethylethyl ester |
|---|---|

A mixture of intermediate 58 (0.001 mol) in MeOH (q.s.) was hydrogenated with Pd/C (0.1 g) as a catalyst in the presence of thiophene solution (0.1 ml). After uptake of H$_2$ (3 equiv.), the catalyst was filtered off and the filtrate was evaporated. After extraction with DCM, the organic layer was separated, dried (MgSO$_4$) and the solvent was evaporated (vac.), yielding 1.579 g of intermediate 59.

| c) Preparation of intermediate 60 | benzoic acid, 3-[[6-[[5-[[[2-[[(1,1-dimethylethoxy)carbonyl]amino]ethyl]amino]methyl]-2-methoxyphenyl]amino]-4-pyrimidinyl]amino]-, 1,1-dimethylethyl ester |
|---|---|

A mixture of intermediate 59 (0.00305 mol), intermediate 57 (0.00254 mol), 2-methyl-2-propanol, sodium salt (0.00305 mol), tris(dibenzylideneacetone)dipalladium(0) (0.00013 mol) and BINAP (0.00026 mol) in toluene (40 ml) was reacted overnight at 90° C., then the solvent was evaporated and the residue was purified by reversed-phase high-performance liquid chromatography. The desired product fraction was collected and extracted, yielding 0.122 g of intermediate 60.

| d) Preparation of intermediate 61 | benzoic acid, 3-[[6-[[5-[[[2-[[(1,1-dimethylethoxy)carbonyl]amino]ethyl][(9H-fluoren-9-ylmethoxy)carbonyl]amino]methyl]-2-methoxyphenyl]amino]-4-pyrimidinyl]amino]-, 1,1-dimethylethyl ester |
|---|---|

A mixture of intermediate 60 (0.00021 mol) and 1-[[(9H-fluoren-9-ylmethoxy)carbonyl]oxy]-2,5-pyrrolidinedione (0.00024 mol) in DCM (10 ml) was reacted for 3 hours at room temperature and then the reaction mixture was treated with an aq. NaHCO$_3$ soln. The organic layer was separated, dried (MgSO$_4$) and the solvent was evaporated, yielding 0.169 g of intermediate 61, used as such in the next reaction step).

| e) Preparation of intermediate 62 | benzoic acid, 3-[[6-[[5-[[(2-aminoethyl)[(9H-fluoren-9-ylmethoxy)carbonyl]amino]methyl]-2-methoxyphenyl]amino]-4-pyrimidinyl]amino]- |
|---|---|

A mixture of intermediate 61 (0.00021 mol) in TFA (50% in DCM) (5 ml) was reacted for 5 hours at room temperature and then the solvent was evaporated, yielding intermediate 62.

Example A16

| a) Preparation of intermediate 63 | phenylalanine, N-[[3-[[6-[[3-[2-[[(1,1-dimethylethoxy)carbonyl]amino]ethoxy]-4-methoxyphenyl]amino]-4-pyrimidinyl]amino]phenyl]methyl]-, methyl ester |
|---|---|

Methanesulfonyl chloride (0.0006 mol) was added to a suspension of intermediate 41 (0.0005 mol) and sodium iodide (0.0005 mol) in acetonitrile (15 ml). Then DIPEA (0.0015 mol) was added and the reaction mixture was stirred for 15 minutes at room temperature. Next, phenylalanine methyl ester hydrochloride (q.s.) was added and the resulting mixture was stirred for 19 hours at 65° C. LCMS monitoring showed slow progression and the reaction had to be warmed to 80° C. for 9 more hours to effect completion. After cooling to room temperature, DCM was added in the same quantity, then PS-benzaldehyde (Argonaut Technologies, cat. 800361) (0.003 mol) was added and the reaction mixture was shaken for 40 hours at room temperature. The resin was filtered off and then washed with DCM, with heptane, with DCM, with heptane again and finally with DCM again, yielding intermediate 63 (used as such in the next reaction step).

| b) Preparation of intermediate 64 | phenylalanine, N-[[3-[[6-[[3-(2-aminoethoxy)-4-methoxyphenyl]amino]-4-pyrimidinyl]amino]phenyl]methyl]- |
|---|---|

A solution of intermediate 63 (0.0005 mol) in HCl 6 N (10 ml) and dioxane (10 ml) was stirred for 48 hours at 65° C. Since LCMS monitoring showed slow progression, the solvent was concentrated, HCl (37%) was added and the resulting mixture was stirred again overnight at 65° C. to effect completion. Finally, the solvent was evaporated, yielding intermediate 64 (RS), which was used as such in the next reaction step.

Example A17

Preparation of intermediate 65 phenol, 5-amino-2-(2-methoxyethoxy)-

A mixture of 2-(2-methoxyethoxy)-5-nitrophenol (0.0356 mol) and Raney Nickel (7.6 g) in MeOH (150 ml) was hydrogenated at room temperature for 6 hours under a 3 bar pressure, then filtered. The filtrate was evaporated till dryness, yielding 6.5 g (100%) of intermediate 65.

Example A18

| a) Preparation of intermediate 66 | 1-pentanol, 5-[[(4-chloro-5-fluoro-2-nitrophenyl)methyl]amino]- |
|---|---|

A mixture of 4-chloro-5-fluoro-2-nitrobenzaldehyde (0.0295 mol) and 5-amino-1-pentanol (0.0295 mol) in MeOH (100 ml) was stirred at room temperature for 18 hours. NaBH$_3$CN (3 ml) and acetic acid (100 ml) were added. The mixture was stirred at room temperature overnight, then quenched with water, poured out into saturated NaHCO$_3$ and extracted with DCM. The organic layer was separated, dried (MgSO$_4$), filtered, and the solvent was evaporated till dryness, yielding 7.5 g (87%) of intermediate 66. This product was used directly in the next reaction step.

| b) Preparation of intermediate 67 | 1-pentanol, 5-[[(4-chloro-5-fluoro-2-nitrophenyl)methyl]methylamino]- |
|---|---|

A mixture of intermediate 66 (0.0179 mol), formaldehyde 37% aqueous (0.0447 mol) and formic acid (0.0447 mol) was stirred at 50° C. for 3 hours, then cooled to room temperature and diluted in water. pH was adjusted to 7 with saturated NaHCO$_3$. The mixture was extracted with DCM. The organic layer was separated, dried (MgSO$_4$), filtered, and the solvent was evaporated till dryness, yielding 4.1 g (75%) of intermediate 67.

| c) Preparation of intermediate 68 | 1-pentanol, 5-[[(2-amino-4-chloro-5-fluorophenyl)methyl]methylamino]- |
|---|---|

A mixture of intermediate 67 (0.0135 mol), iron (0.0673 mol) and ammonium chloride (0.135 mol) in THF/MeOH/water (400 ml) was stirred and refluxed for 18 hours, then cooled to room temperature and filtered. The filtrate was diluted in DCM and washed with potassium carbonate 10%. The organic layer was separated, dried (MgSO$_4$), filtered, and the solvent was evaporated till dryness. The residue (3.5 g) was purified by column chromatography DCM/MeOH/NH$_4$OH 95/5/0.1; 70-200 µm). The pure fractions were collected and the solvent was evaporated, yielding 1.2 g (32%) of intermediate 68.

| d) Preparation of intermediate 69 | 1-pentanol, 5-[[[4-chloro-2-[(6-chloro-4-pyrimidinyl)amino]-5-fluorophenyl]methyl]methylamino]- |
|---|---|

A mixture of intermediate 68 (0.0043 mol), 4,6-dichloropyrimidine (0.0087 mol) and DIPEA (0.0096 mol) in NMP (25 ml) was stirred at 170° C. for 1 hour, then cooled to room temperature, poured out into water and extracted three times with diethyl ether. The organic layer was separated, dried (MgSO$_4$), filtered, and the solvent was evaporated till dryness. The residue was purified by column chromatography over silica gel (eluent: DCM/MeOH/NH$_4$OH 98/2/1; 15-40 µm). The pure fractions were collected and the solvent was evaporated, yielding 1.3 g (77%) of intermediate 69.

| e) Preparation of intermediate 70 | phenol, 5-[[6-[[5-chloro-4-fluoro-2-[[(5-hydroxypentyl)methylamino]methyl]phenyl]amino]-4-pyrimidinyl]amino]-2-(2-methoxyethoxy)- |
|---|---|

A mixture of intermediate 69 (0.0033 mol), intermediate 65 (0.0039 mol) and HCl/2-propanol 5N (3 drops) in t-butanol (25 ml) was refluxed for 16 hours, then evaporated till dryness. The residue was dissolved in 2-methyl-2-pentanol (15 ml). The mixture was stirred and refluxed overnight, then cooled to room temperature, poured out into saturated NaHCO$_3$ and extracted with DCM. The organic layer was separated, dried (MgSO$_4$), filtered, and the solvent was evaporated till dryness. The crude oil (1.7 g) was crystallized from DCM/MeOH (95/5). The precipitate was filtered off and dried, yielding 0.46 g (25%) of intermediate 70.

Example A19 a) Preparation of intermediate 71

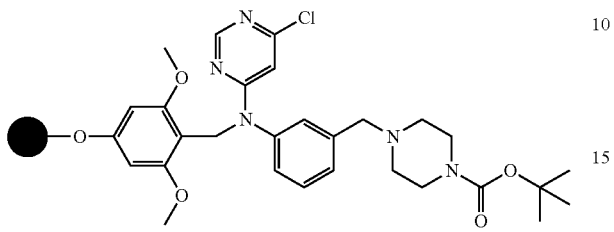

Intermediate 71 was prepared in exact the same manner as intermediate 31, only as starting material 3-(1-Boc-piperazin-4-yl-methyl)-aniline [361345-40-6] was used in the synthesis.

b) Preparation of intermediate 72

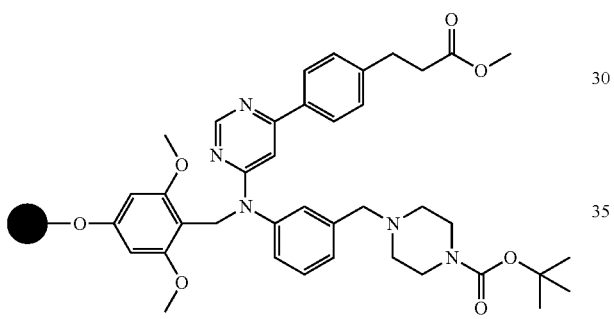

Intermediate 71 was washed with dioxane. To intermediate 71 (400 mg) was added a mixture of [4-(2-methoxycarbonylethyl)phenyl]boronic acid (0.0018 mol), tris(dibenzylideneacetone)dipalladium(0) (0.000036 mol), 1,3-Bis(2,4,6-trimethylphenyl)-4,5-dihydroimidazolium chloride (0.000036 mol) and cesium carbonate (0.0036 mol) in dioxane (10 ml). The reaction was brought under nitrogen. The reaction mixture was shaken for 18 hours at 90° C., under N₂, then the resin was filtered off hot and washed 3 times with hot DMF (at 70° C.), 3 times with hot water (at 50° C.), 3 times with DMF and 3 times with water, 3 times with DMF and 3 times with DCM. Finally, washed 3 times with MeOH and 3 times with DCM, 3 times with MeOH and 3 times with DCM, yielding intermediate 72, which was used in next reaction step.

| c) Preparation of intermediate 73 | benzenepropanoic acid, 4-[6-[[3-(1-piperazinylmethyl)phenyl]amino]-4-pyrimidinyl]- |
|---|---|

Intermediate 72 was washed with THF, to intermediate 72 was added lithiumhydroxide (0.0049 mol) in THF (8 ml) and water (2 ml). The reaction mixture was shaken for 48 hours at 50° C., then the resin was filtered off and washed 3 times with water, 3 times with MeOH, 3 times with water and 3 times with DMF, 3 times with water and 3 times with DMF, 3 times with MeOH and 3 times with DCM, 3 times with MeOH and 3 times with DCM, 3 times with MeOH and 3 times with DCM. The resin was cleaved with TFA/TIS/DCM (25/2/73) for 4 hours, then the resin was filtered off and shaked for 1 hour with TFA/TIS/DCM (25/2/73). The resin was filtered off and washed 3 times with DCM. Finally, the combined solvents were blown dry under nitrogen at 50° C., 3 times DCM (5 ml) was added and blown dry under nitrogen at 50° C., yielding intermediate 73 isolated as a TFA-salt.

Example A20 a) Preparation of intermediate 74

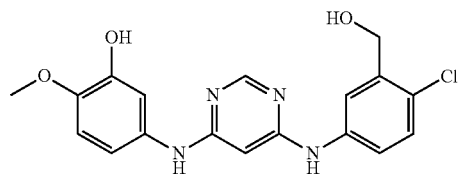

Intermediate 39 (0.027 mol) and 5-amino-2-chloro-benzenemethanol (0.032 mol) were dissolved in DMF (60 ml). The reaction solution was stirred and heated at 140° C. for 5 hours, yielding intermediate 74, (mixture used in next reaction step, without further work-up/purification).

b) Preparation of intermediate 75

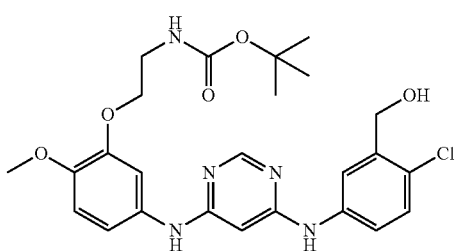

To intermediate 74 (crude reaction mixture containing max. 0.027 mol of intermediate) was added DMF (200 ml) and Cesium carbonate (0.162 mol). The resulting suspension was stirred for one hour at room temperature. Then (2-bromoethyl)-carbamic acid, 1,1-dimethylethyl ester (0.054 mol) was added and the reaction mixture was stirred for 24 hours at room temperature. The mixture was filtered through a flitted funnel. The filtrate's solvent was evaporated on the Rotavap. The residue (dark oil) was purified by column chromatography. The product fractions were collected and the solvent was evaporated, yielding 6.73 g (48%) of intermediate 75.

c) Preparation of intermediate 76

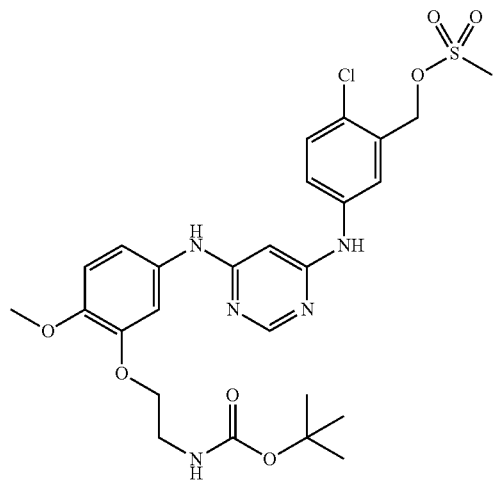

Intermediate 75 (0.001750 mol) was suspended in a mixture of DIPEA (0.00525 mol) and acetonitrile (33.5 ml). Methanesulfonyl chloride (0.002275 mol) was added and the resulting homogeneous solution was stirred for 30 minutes, yielding intermediate 76, (mixture used in next reaction step, without further work-up/purification).

d) Preparation of intermediate 77

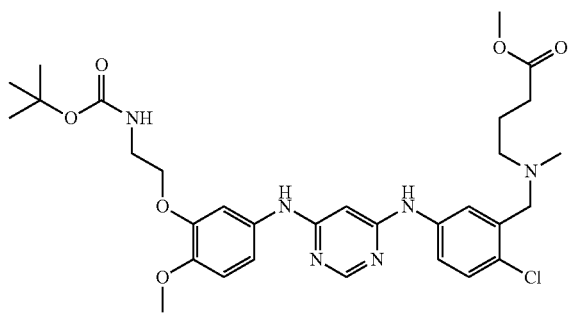

4-(methylamino)-butanoic acid, methyl ester (0.000500 mol) and DIPEA (0.000750 mol) were added to intermediate 76 (±0.000250 mol) in acetonitrile (5 ml) in a tube. The tube was capped with a silicon stopper and the reaction mixture was shaken for 24 hours at 65° C. The mixture was allowed to cool to room temperature, and diluted with 5 ml of DCM. Scavenger was added and the mixture was shaken overnight at room temperature. The solvent was removed, yielding intermediate 77.

e) Preparation of intermediate 78

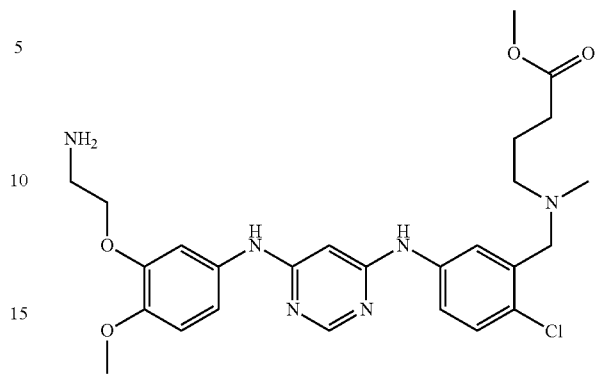

Intermediate 77 (±0.000250 mol) was taken up into a mixture of TFA/DCM/TIS 49/49/2 v/v/v (5 ml). The reaction mixture was stirred overnight at room temperature. The solvent and excess of TFA was evaporated. The residue was dried (oil-pump vacuum; 65° C.), yielding intermediate 78.

f) Preparation of intermediate 79

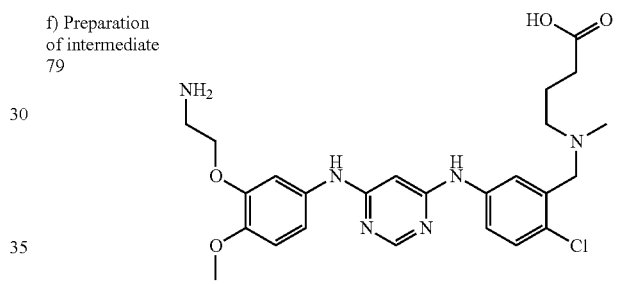

Intermediate 78 (±0.000250 mol) was taken up into a mixture of THF/water 8/1 (10 ml). Lithium hydroxide monohydrate (0.00250 mol; 10 equiv) was added. The reaction mixture was stirred overnight at 65° C. The solvent was evaporated. The residue was dried (oil-pump vacuum). The residue was taken up into dry DMF (10 ml), filtered off, then used as such in next reaction step, yielding intermediate 79.

Example A21 a) Preparation of intermediate 80

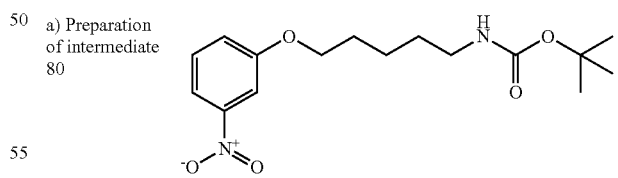

A mixture of (5-hydroxypentyl)-carbamic acid, 1,1-dimethylethyl ester (0.06 mol), 3-nitro-phenol (0.05 mol) and triphenylphosphine (0.05 mol) in THF (300 ml) was stirred at 0° C. and bis(1-methylethyl)diazenedicarboxylate (0.05 mol) was added dropwise at 0° C. The reaction mixture was stirred for 15 minutes at 0° C. and was then allowed to reach room temperature. The mixture was stirred at ambient temperature for 1 hour and the solvent was evaporated. The residue was purified by short column chromatography (eluent: DCM). The product fractions were collected and the solvent was evaporated. The obtained residue (12 g) was precipitated from petroleum benzin and the resulting precipitate was collected, yielding 9.3 g of intermediate 80, melting point 65° C.

b) Preparation of intermediate 81

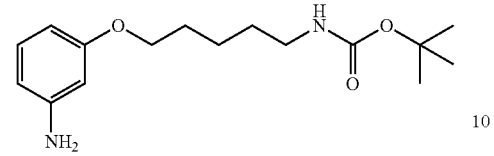

A mixture of intermediate 80 (0.028 mol) in MeOH (250 ml) was hydrogenated at 50° C. with Pd/C 10% (2 g) as a catalyst in the presence of thiophene solution (1 ml). After uptake of H$_2$ (3 equiv.), the catalyst was filtered over dicalite and the filtrate was evaporated, yielding 9 g of intermediate 81.

c) Preparation of intermediate 82

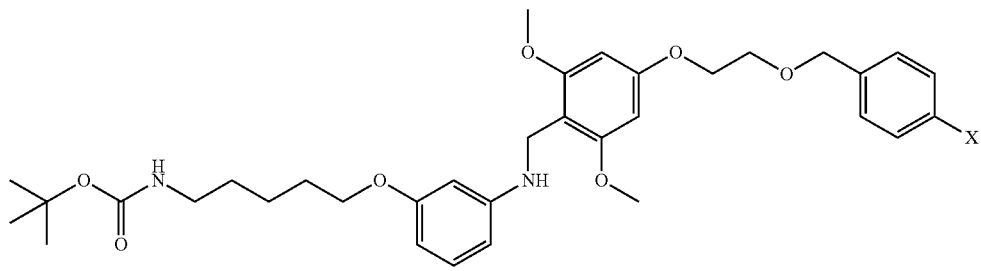

2-(3,5-Dimethoxy-4-formylphenoxy)ethoxymethyl polystyrene (Novabiochem; 01-64-0261) (0.0018 mol) was washed with 1% acetic acid in DCM (50 ml), then a solution of intermediate 81 (0.009 mol) in 1% acetic acid in DCM (25 ml) was added and the resulting mixture was shaken for 10 minutes at room temperature. Tris(acetato-α-O)-hydroborate (1-), sodium (0.009 mol) was added, followed by addition of 1% acetic acid in DCM (25 ml) and the reaction mixture was shaken for 2 days at room temperature. After filtration, the resin was washed 4×[3 times with MeOH and 3 times with DCM], yielding intermediate 82.

d) Preparation of intermediate 83

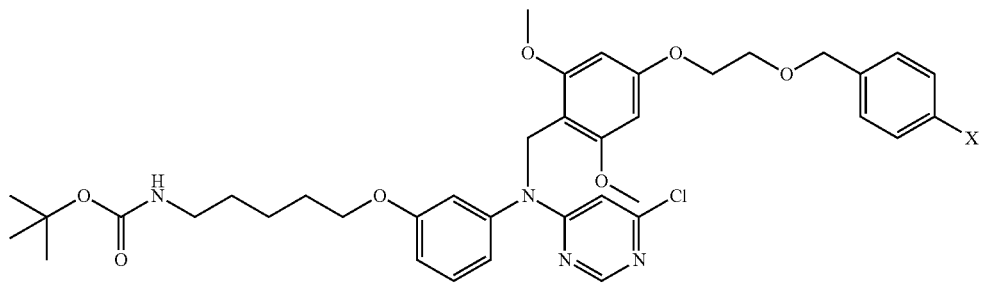

A mixture of intermediate 82 (max. 0.0018 mol; previously washed with butanol (q.s.)), 4,6-dichloro-pyrimidine (0.018 mol) and DIPEA (0.018 mol) in butanol (50 ml) was shaken for 40 hours at 90° C. and under N$_2$, then the resin was filtered off, yielding (without cleavage), intermediate 83.

e) Preparation of intermediate 84

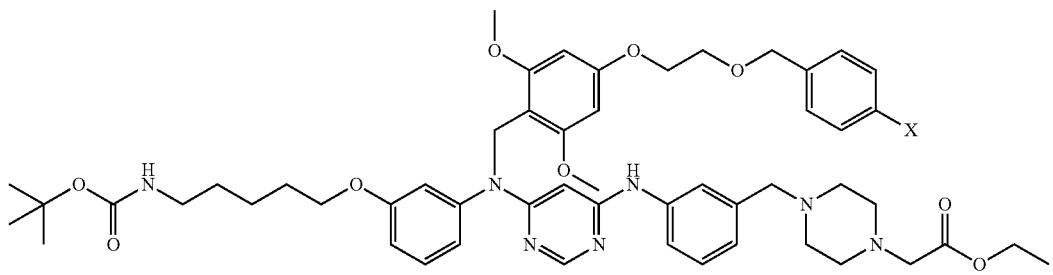

A mixture of intermediate 83 (max. 0.0018 mol; previously washed 2× with toluene), 4-[(3-aminophenyl)methyl]-1-piperazineacetic acid, ethyl ester (0.018 mol), $Pd_2(dba)_3$ [cas number 51364-51-3] (0.00036 mol), BINAP (0.0018 mol) and cesium carbonate (0.027 mol) in toluene (p.a., dry, 50 ml) was shaken for 18 hours at 110° C. and under $N_2$, then the resin was filtered off hot and washed 3 times with hot DMF, 3 times with hot DMF/water, 3× with hot DMF, 3 times with water and 3 times with DMF, 3× with DCM, 3× with DMF, washed 2×[3 times with DCM and 3 times with MeOH], and 3× with DCM. A sample was cleaved with TFA/TIS/DCM (25/2/73). After evaporation, the obtained residue was dried (vac.) at 30° C., yielding intermediate 84.

N-methyl-glycine, ethyl ester (0.326 mol) was added to a mixture of 3-nitro-benzaldehyde (0.326 mol) in 1,2-dichloroethane (1000 ml). 2-propanol, titanium(4+) salt (0.39 mol) was added and the reaction mixture was stirred for 10 minutes at room temperature. Tris(acetato-α-O) hydroborate (1-), sodium (0.82 mol) was added and the reaction mixture was stirred for 2 hours at room temperature under $N_2$ atmosphere. Water (500 ml) was added carefully. DCM (500 ml) was added. The biphasic mixture was filtered through dicalite. The filtrate was separated into it's layers. The organic phase was washed with water, dried ($MgSO_4$), filtered and the solvent was evaporated. The residue was concentrated with f) Preparation of intermediate 85

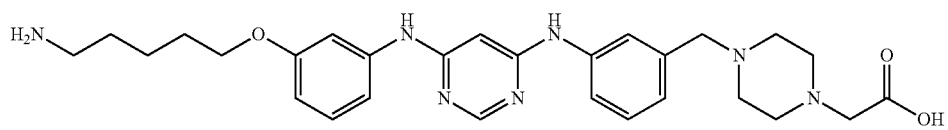

A mixture of intermediate 84 (0.4 g; max. 0.00018 mol) and lithium hydroxide monohydrate (0.0048 mol) in THF (8 ml) and water (2 ml) was shaken for 48 hours at 50° C., then the resin was filtered off, washed 3 times with water (50° C.), 3 times with DMF, then 3× with DCM. The reaction mixture was cleaved with TFA/TIS/DCM (25/2/73) over 4 hours, then filtered and the filtrate was collected. The resin was shaken again for 1 hour with TFA/TIS/DCM 25/2/73, then filtered and the filtrate was collected. The filtrates were combined and the solvent was evaporated at 70° C. under $N_2$ flow, yielding intermediate 85.

Example A22 a) Preparation of intermediate 86

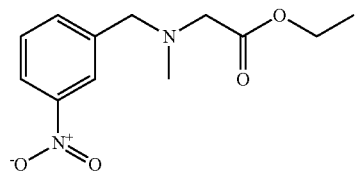

DIPE, then with toluene, yielding intermediate 86 (quantitative yield, used in next reaction step, without further purification).

b) Preparation of intermediate 87

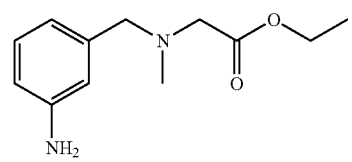

A mixture of intermediate 86 (max. 0.326 mol) in EtOH (600 ml) was hydrogenated at 50° C. with Pd/C 10% (4 g) as a catalyst in the presence of thiophene solution (2 ml). After uptake of $H_2$ (3 equiv), the catalyst was filtered off over dicalite and the filtrate was evaporated. The residue was purified by column chromatography over silica gel (eluent: DCM/MeOH 97/3). The product fractions were collected and the solvent was evaporated, yielding 44 g (58%) of intermediate 87.

Example A23 a) Preparation of intermediate 88

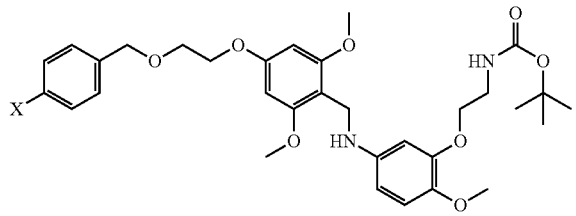

2-(3,5-Dimethoxy-4-formylphenoxy)ethoxymethyl polystyrene (Novabiochem; 01-64-0261) (0.0018 mol) was washed with 1% acetic acid in DCM (50 ml), then a solution of [2-(5-amino-2-methoxyphenoxy)ethyl]-carbamic acid, 1,1-dimethylethyl ester (0.009 mol) in 1% acetic acid in DCM (25 ml) was added and the resulting mixture was shaken for 10 minutes at room temperature. Tris(acetato-α-O)-hydroborate (1-), sodium (0.009 mol) was added, followed by addition of 1% acetic acid in DCM (25 ml) and the reaction mixture was shaken over the weekend at room temperature. After filtration, the resin was washed 4×[3 times with MeOH and 3 times with DCM], yielding intermediate 88.

intermediate 97

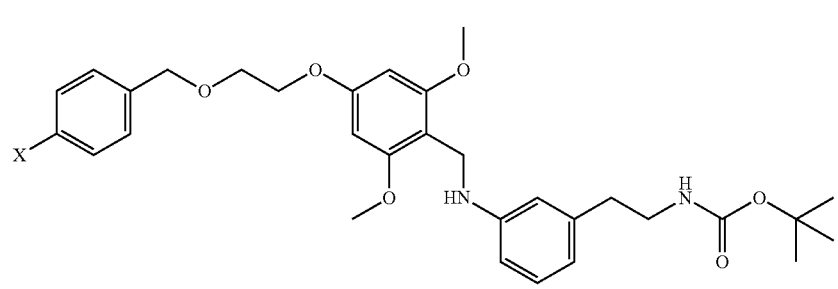

b) Preparation of intermediate 89

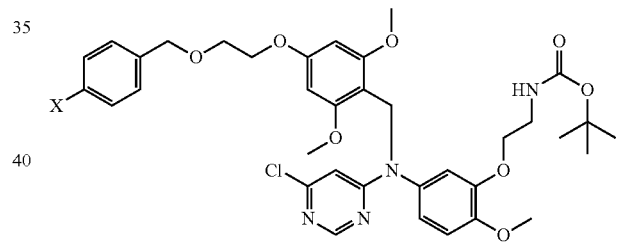

A mixture of intermediate 88 (max. 0.0018 mol; previously washed with butanol (q.s.)), 4,6-dichloro-pyrimidine (0.018 mol) and DIPEA (0.018 mol) in butanol (50 ml) was shaken for 40 hours at 90° C. and under $N_2$, then the resin was filtered off and washed 4×[3 times with DCM and 3 times with MeOH] and finally 3 times with DCM. A sample of the resin was cleaved with TFA/TIS/DCM (25/2/73) for 1 hour and then the solvent was evaporated, yielding intermediate 89.

intermediate 98

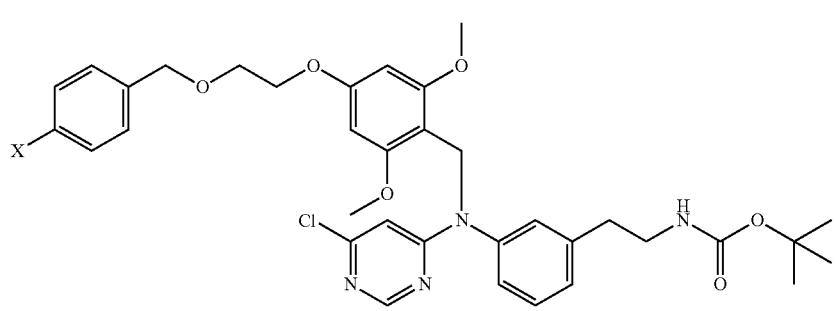

c) Preparation of intermediate 90

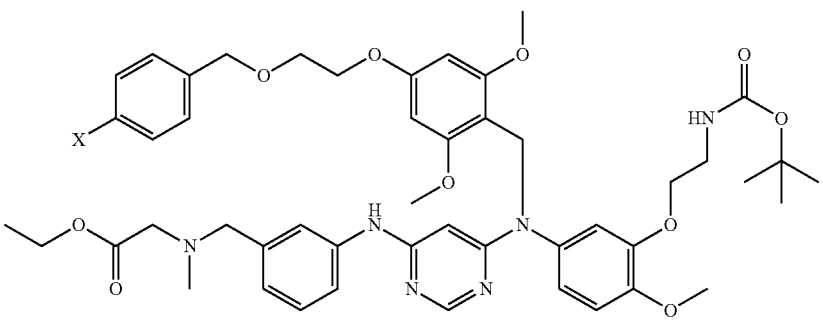

A mixture of intermediate 89 (max. 0.0018 mol), intermediate 87 (0.018 mol), $Pd_2(dba)_3$ [cas number 51364-51-3] (0.00036 mol), BINAP (0.0018 mol) and cesium carbonate (0.027 mol) in toluene (p.a., dry, 50 ml) was shaken for 18 hours at 110° C. and under $N_2$, then the resin was filtered off hot and washed 3 times with hot DMF (at 70° C.), 3 times with hot water (at 50° C.), 2×[3 times with DMF and 3 times with water], 3 times with DMF and 3 times with DCM. Finally, washed 2×[3 times with MeOH and 3 times with DCM]. A sample was cleaved with TFA/TIS/DCM (25/2/73) and LCMS-analyses showed an impurity. The residue was washed again 5×[3 times with MeOH and 3 times with DCM], then a sample was cleaved with TFA/TIS/DCM (25/2/73). After evaporation, the obtained residue was dried (vac.) at 30° C., yielding intermediate 90.

d) Preparation of intermediate 91

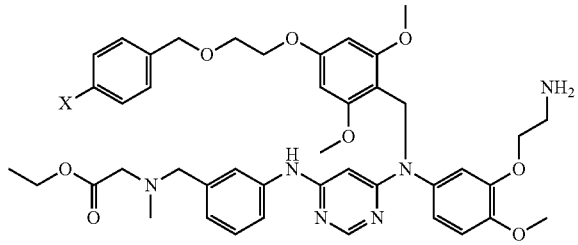

intermediate 99

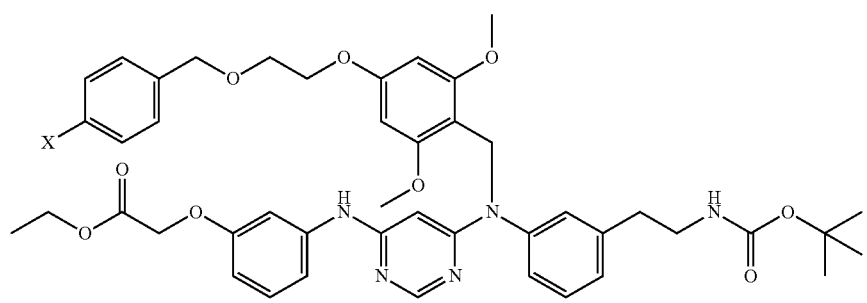

intermediate 100

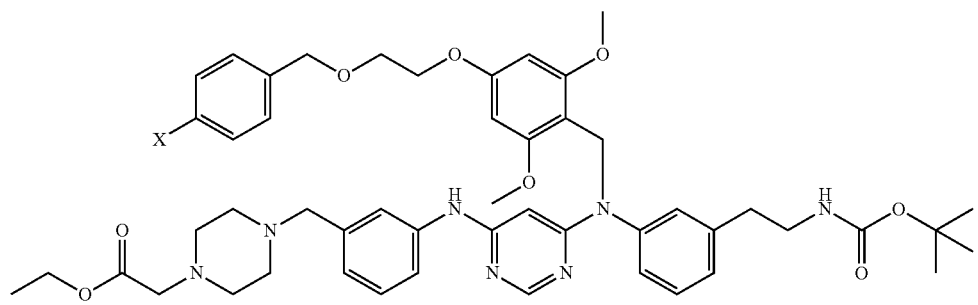

Intermediate 90 (0.400 g of crude resin, previously washed with DCM) was shaken in trifluoro-methanesulfonic acid, trimethylsilyl ester/2,6-dimethyl-pyridine/DCM (1.5 M/1 M/10 ml) for 4 hours at room temperature. The resin was filtered off, washed with DCM (1×), MeOH (3×), [DCM (3×), MeOH (3×)][4×], washed with DCM (3×), then dried, yielding intermediate 91.
intermediate 101
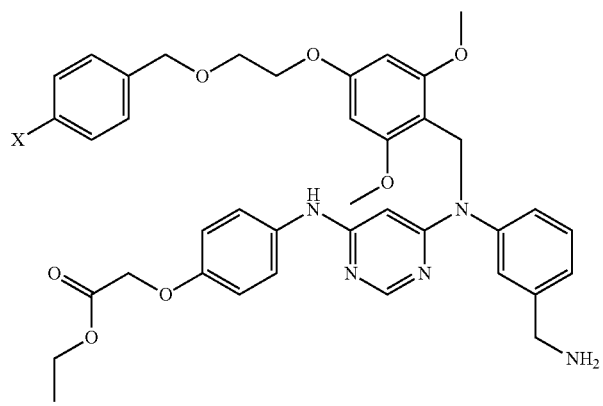
intermediate 102
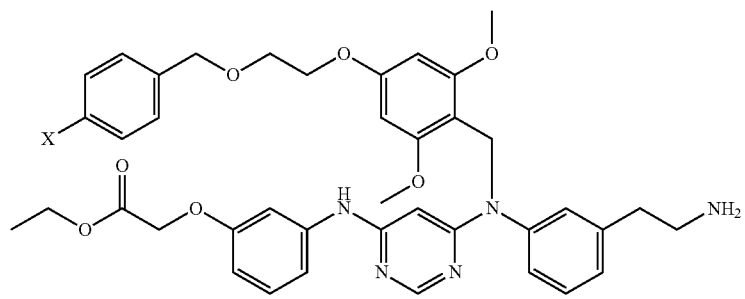
intermediate 103
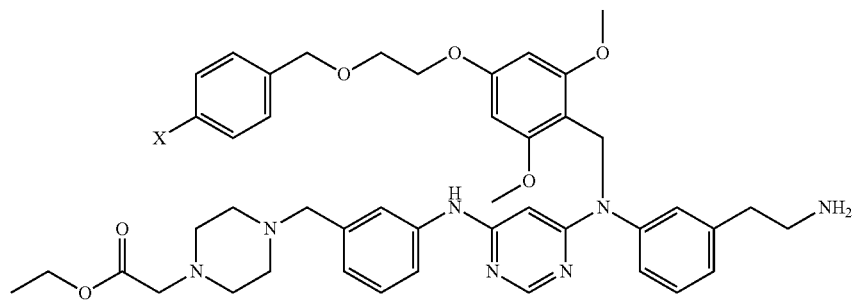

e) Preparation of intermediate 92

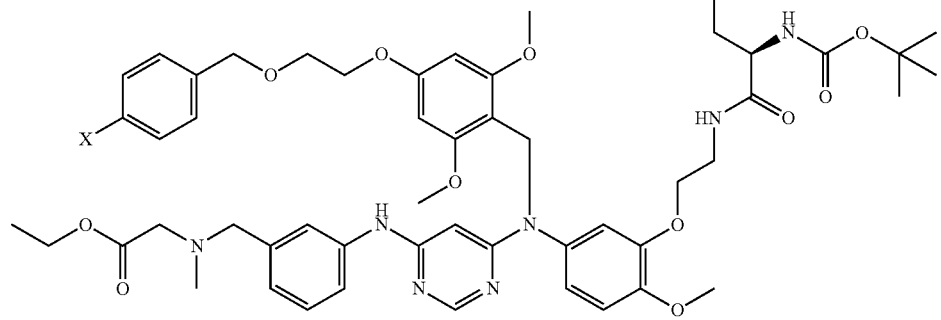

A solution of N-[(1,1-dimethylethoxy)carbonyl]-4-(trifluoromethyl)-L-phenylalanine (0.00108 mol), tetramethylfluoroformamidinium hexafluorophosphate (0.00108 mol) and DIPEA (0.0018 mol) in DMF dry (10 ml) was added to resin intermediate 91 (crude; previously washed 2× with dry DMF) and the whole was shaken for 48 hours at room temperature. The resin was filtered off, washed with DCM (3×), with [MeOH (3×), DCM (3×)][5 x], then dried, yielding intermediate 92.

intermediate 104

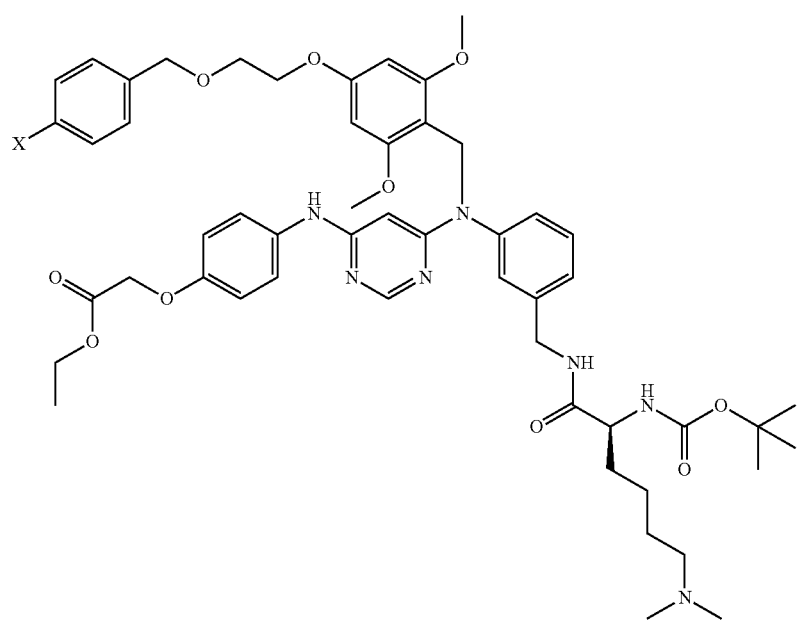

-continued

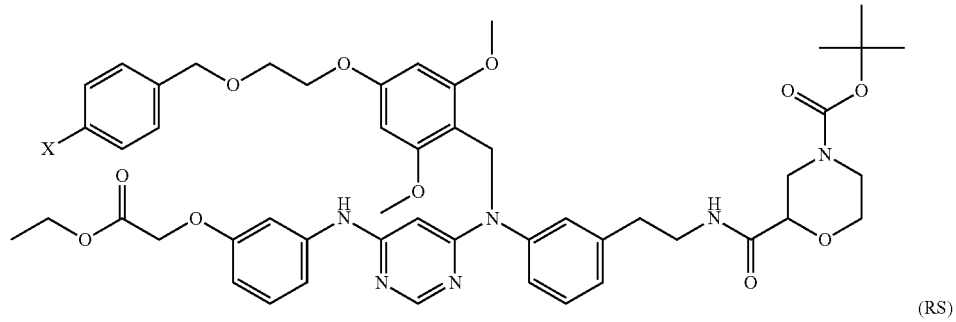

intermediate 105

(RS)

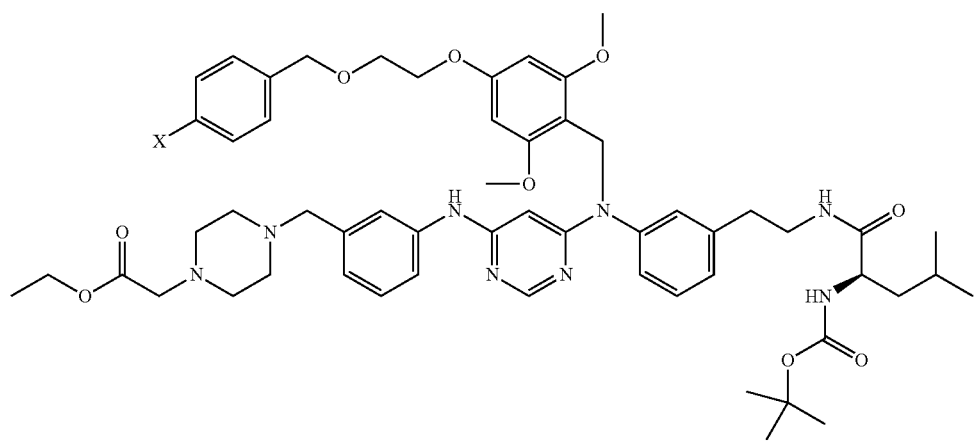

intermediate 106 f) Preparation of intermediate 93

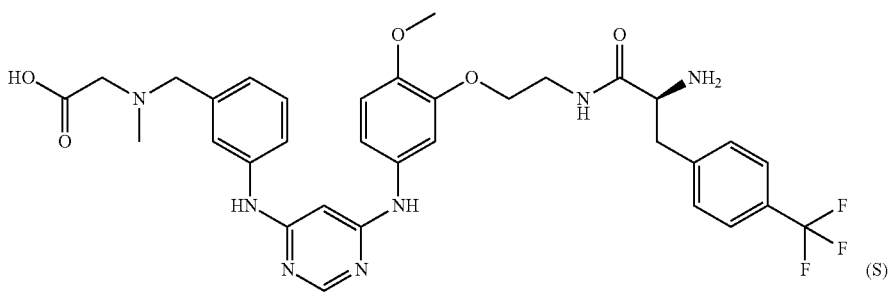

A mixture of intermediate 92 (crude, previously washed with THF) and lithium hydroxide monohydrate (0.0048 mol) in THF (8 ml) and water (2 ml) was shaken for 48 hours at 50° C., then the resin was filtered off, washed 3 times with water (50° C.), 3 times with DMF (50° C.), then 1× with MeOH and 3× with DCM. The reaction mixture was cleaved with TFA/TIS/DCM (25/2/73) over 4 hours, then filtered and the filtrate was collected. The resin was shaken again for 1 hour with TFA/TIS/DCM 25/2/73, then filtered and the filtrate was collected. The filtrates were combined and the solvent was evaporated at 50° C. under $N_2$ flow. Acetonitrile was added to the residue, then concentrated again at 50° C. (2×), yielding intermediate 93.

intermediate 107

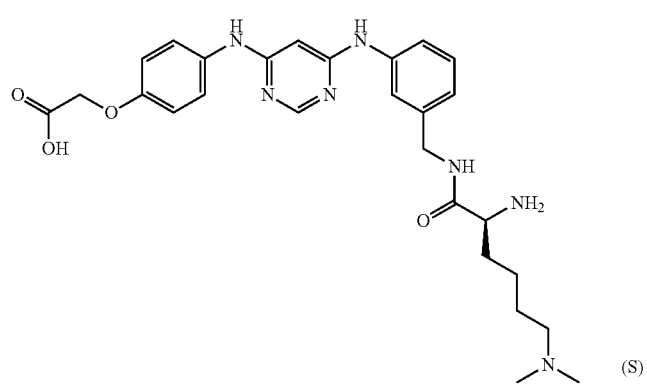

intermediate 108 intermediate 109

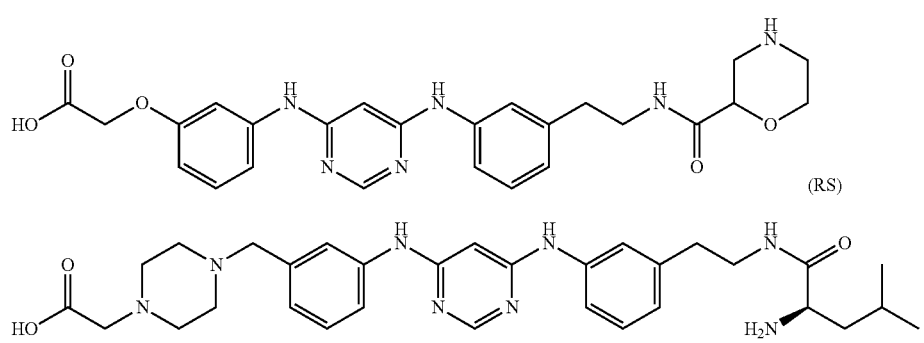

B. Preparation of the Final Compounds

Example B1

| Preparation of compound 1 | 14,19-dioxa-2,4,8,26-tetraazatetracyclo[18.3.1.1~3,7~.1~9,13~]hexacosa-1(24),3,5,7(26),9,11,13(25),16,20,22-decaene-6-carbonitrile, (16Z)- |

Grubbs' catalyst (0.00008 mol, Registry Number: 172222-30-9) was added to intermediate 1 (0.0006 mol) in DCM p.a. (200 ml). The reaction mixture was stirred for 16 hours at 50° C. The solvent was evaporated under reduced pressure. The residue was purified by column chromatography. The product fractions were collected and the solvent was evaporated, yielding 0.0081 g of compound 1.

Example B2

| Preparation of compound 2 | 14,19-dioxa-2,4,8,26-tetraazatetracyclo[18.3.1.1~3,7~.1~9,13~]hexacosa-1(24),3,5,7(26),9,11,13(25),20,22-nonaene-6-carbonitrile |

A solution of 2,4-dichloro-5-pyrimidinecarbonitrile (0.003 mol) in diglyme (100 ml) was added in one portion to a solution of 3,3'-[1,4-butanediylbis(oxy)]bis-benzenamine (0.003 mol) in diglyme (400 ml) at 90° C. The reaction mixture was stirred and refluxed for 16 hours and then cooled. The solvent was evaporated under reduced pressure and the residue was purified on a silica gel filter (eluent: DCM/MeOH 99.5/0.5). The product fractions were collected and the solvent was evaporated under reduced pressure. The residue was stirred in DCM/MeOH (98/2), the resulting precipitate was filtered off and dried, yielding 0.1806 g (16%) of compound 2.

Example B3

| Preparation of compound 3 | 18-oxa-2,4,8,15,25-pentaazatetracyclo[17.3.1.1~3,7~.1~9,13~]pentacosa-1(23),3,5,7(25),9,11,13(24),19,21-nonaene-6-carbonitrile, 14-oxo- |

A mixture of HBTU (0.0004 mol) in DMF extra dry (50 ml) was stirred under $N_2$ at room temperature, then a mixture of intermediate 5 (0.0004 mol) and DIPEA (0.004 mol) in DMF extra dry (50 ml) was added dropwise over 1 hour and the reaction mixture was stirred overnight. The solvent was evaporated and the residue was stirred in boiling MeOH (10 ml) and water (5 ml). The mixture was allowed to cool under stirring and the resulting precipitate was filtered off. The filtrate was evaporated and the obtained residue was taken up in DCM/MeOH, then washed with 0.1N HCl and 2 times with 0.1N NaOH. The organic layer was separated, dried, filtered off and the solvent was evaporated. The residue was purified by RediSep®-Flash column chromatography (eluent: DCM/(MeOH/NH$_3$) 99/1 to 97/3). The desired product fractions were collected and the solvent was evaporated. The residue was stirred in boiling acetonitrile, then the precipitate was filtered off and dried, yielding 0.022 g (15%) of compound 3, melting point>260° C.

| | |
|---|---|
| 21-oxa-2,4,8,15,28-pentaazatetracyclo[20.3.1.1~3,7~.1~9,13~]octacosa-1(26),3,5,7(28),9,11,13(27),22,24-nonaene-6-carbonitrile, 14-oxo- | Compound 18 mp. >260° C. |
| 14-oxa-2,4,8,19,27-pentaazatetracyclo[19.3.1.1~3,7~.1~9,13~]heptacosa-1(25),3,5,7(27),9,11,13(26),21,23-nonaen-20-one | Compound 19 |
| 14-oxa-2,4,8,17,25-pentaazatetracyclo[17.3.1.1~3,7~.1~9,13~]pentacosa-1(23),3,5,7(25),9,11,13(24),19,21-nonaene-6-carbonitrile, 18-oxo- | Compound 20 mp. >260° C. |
| 14-oxa-2,4,8,21,29-pentaazatetracyclo[21.3.1.1~3,7~.1~9,13~]nonacosa-1(27),3,5,7(29),9,11,13(28),23,25-nonaen-22-one | Compound 21 mp. 262° C. |
| 14-oxa-2,4,8,20,28-pentaazatetracyclo[20.3.1.1~3,7~.1~9,13~]octacosa-1(26),3,5,7(28),9,11,13(27),22,24-nonaen-21-one | Compound 22 mp. >260° C. |
| 18-oxa-2,4,8,15,25-pentaazatetracyclo[17.3.1.1~3,7~.1~9,13~]pentacosa-1(23),3,5,7(25),9,11,13(24),19,21-nonaen-16-one | Compound 23 mp. >260° C. |
| 2,4,8,15,23-pentaazatetracyclo[15.3.1.1~3,7~.1~9,13~]tricosa-1(21),3,5,7(23),9,11,13(22),17,19-nonaen-16-one | Compound 24 mp. >250° C. |

Example B4

| | |
|---|---|
| Preparation of compound 4 | 14,22-dioxa-2,4,8,19,29-pentaazatetracyclo[21.3.1.1~3,7~.1~9,13~]nonacosa-1(27),3,5,7(29),9,11,13(28),23,25-nonaen-20-one |

A mixture of intermediate 9 (0.0023 mol) and DIPEA (0.0057 mol) in DMF (100 ml) was added dropwise to a mixture of HBTU (0.0057 mol) in DMF (200 ml) at room temperature and then the reaction mixture was stirred for 2 hours at room temperature. The solvent was evaporated and the obtained residue was dissolved in DCM/MeOH (8/2) (500 ml). This solution was washed with water, then the organic layer was separated, dried (MgSO$_4$), filtered off and the solvent was evaporated. The residue was purified by reversed-phase high-performance liquid chromatography (Standard method, gradient eluent). The product fractions were collected and the solvent was evaporated. The residue was dissolved in DCM and washed with water. The organic layer was separated, dried (MgSO$_4$), filtered off and the solvent was evaporated. The residual fraction was crystallised from acetonitrile, then the precipitate was filtered off, washed with a small amount of acetonitrile and dried (vac.), yielding 0.085 g (9%) of compound 4.

| | |
|---|---|
| 14,21-dioxa-2,4,8,17,28-pentaazatetracyclo[20.3.1.1~3,7~.1~9,13~]octacosa-1(26),3,5,7(28),9,11,13(27),22,24-nonaene-6-carbonitrile, 16-oxo- | Compound 25 mp. >260° C. |
| 14,22-dioxa-2,4,8,17,29-pentaazatetracyclo[21.3.1.1~3,7~.1~9,13~]nonacosa-1(27),3,5,7(29),9,11,13(28),23,25-nonaene-6-carbonitrile, 16-oxo- | Compound 26 mp. >260° C. |
| 14,20-dioxa-2,4,8,17,27-pentaazatetracyclo[19.3.1.1~3,7~.1~9,13~]heptacosa-1(25),3,5,7(27),9,11,13(26),21,23-nonaene-6-carbonitrile, 16-oxo- | Compound 27 mp. 260° C. |
| 14,21-dioxa-2,4,8,18,28-pentaazatetracyclo[20.3.1.1~3,7~.1~9,13~]octacosa-1(26),3,5,7(28),9,11,13(27),22,24-nonaene-6-carbonitrile, 19-oxo- | Compound 28 mp. 236° C. |
| 14,21-dioxa-2,4,8,18,28-pentaazatetracyclo[20.3.1.1~3,7~.1~9,13~]octacosa-1(26),3,5,7(28),9,11,13(27),22,24-nonaen-19-one | Compound 29 mp. 262° C. |

Example B5

| | |
|---|---|
| Preparation of compound 5 | 2,4,8,15,18,26-hexaazatetracyclo[18.3.1.1~3,7~.1~9,13~]hexacosa-1(24),3,5,7(26),9,11,13(25),20,22-nonaene-6-carbonitrile, 14,17-dioxo- |

Intermediate 13 (0.0009 mol) and DIPEA (0.0036 mol) were slowly added over 2 hours to a mixture of HBTU (0.00225 mol) in DMF (40 ml), then the reaction mixture was reacted for 1 hour at room temperature. After 3 hours, the reaction mixture was treated with water and the solvent was evaporated. The residue was purified by reversed-phase high-performance liquid chromatography. The pure fractions were collected and the solvent was evaporated, yielding 0.017 g (14%) of compound 5.

Example B6

| | |
|---|---|
| Preparation of compound 6 | 21,17-metheno-15,11-nitrilo-1H,16H-pyrrolo[2,1-s][13,1,5,7,17,20]benzoxapentaazacyclotricosine-12-carbonitrile, 8-chloro-7-fluoro-2,3,5,10,23,24,25,26,27,27a-decahydro-20-methoxy-27-oxo-, (27aS)- |

DIPEA (0.001884 mol) was added to a solution of intermediate 20 (0.000157 mol) in DMF dry (q.s.) and the mixture was stirred for 10 minutes, to give Solution (I). Solution (I) was added dropwise to a solution of HBTU (0.000471 mol) in dry DMF (40 ml) and the reaction mixture was stirred for 1 hour at room temperature. The solvent was evaporated and satd. aq. NaHCO$_3$ soln. with Na$_2$CO$_3$ (solid) was added to the residue. After extraction with DCM, the combined organic layers were dried (K$_2$CO$_3$), and the solvent was evaporated. The obtained residue was purified by reversed phase high-performance liquid chromatography (TFA-buffer). After evaporation of the organic component of the eluent, NaHCO$_3$ was added and the product was isolated by extraction with DCM, yielding 0.011 g of compound 6.

| | |
|---|---|
| 1H,7H-12,8-metheno-6,2-nitrilo-1,3,7,14,17-benzopentaazacycloeicosine-5-carbonitrile, 21-chloro-13,14,15,16,17,18-hexahydro-17-methyl-15-oxo- | Compound 30 |
| 21,17-metheno-15,11-nitrilo-16H-pyrrolo[2,1-r][13,1,5,7,16,19]benzoxapentaazacyclodocosine-12-carbonitrile, 8-chloro-7-fluoro-1,2,3,5,10,23,24,25,26,26a-decahydro-20-methoxy-26-oxo-, (26aS)- | Compound 31 |
| 12,8-metheno-6,2-nitrilo-7H-13,1,5,7,16,19-benzoxapentaazacyclodocosine-3-carbonitrile, 23-chloro-1,14,15,16,17,18,19,20-octahydro-11-methoxy-19-methyl-17-oxo- | Compound 32 |
| 1H,7H-12,8-metheno-6,2-nitrilo-13,1,5,7,17,20-benzoxapentaazacyclotricosine-3-carbonitrile, 24-chloro-14,15,16,17,18,19,20,21-octahydro-11-methoxy-20-methyl-18-oxo- | Compound 33 mp. 182.7-184.5° C. |

Example B7

Preparation of compound 7: 1H,7H-6,2:12,8-dimetheno-13,20,1,3,5,7-benzodioxatetraazacyclodocosine, 23-chloro-14,15,16,17,18,19-hexahydro-11-methoxy- A solution of intermediate 24 (0.00014 mol), 1,1'-(azodicarbonyl)bis-piperidine (0.00021 mol) and tributyl-phosphine (0.00021 mol) in THF (10 ml) was stirred for 2 hours at room temperature and then the solvent was evaporated under reduced pressure. The obtained residue was purified by high-performance liquid chromatography. The product fractions were collected and the solvent was evaporated, yielding 0.009 g of compound 7.

| Name | Compound |
|---|---|
| 11H-6,10-metheno-5H-dibenzo[b,k][1,13,4,6,8,10]dioxatetraazacyclononadecine, 13-chloro-17,18,19,20,21,22-hexahydro-2-methoxy- | Compound 34 mp. 206° C. |
| 1H,7H-2,6:12,8-dimetheno-14H-13,19,1,3,5,7-benzodioxatetraazacycloheneicosine, 22-bromo-15,16,17,18-tetrahydro-11-methoxy- | Compound 35 |
| 1H,7H-2,6:12,8-dimetheno-13,20,1,3,5,7-benzodioxatetraazacyclodocosine, 23-bromo-14,15,16,17,18,19-hexahydro-11-methoxy- | Compound 36 |
| 1H,7H-2,6:12,8-dimetheno-14H-13,21,1,3,5,7-benzodioxatetraazacyclotricosine, 24-bromo-15,16,17,18,19,20-hexahydro-11-methoxy- | Compound 37 |
| 1H,7H-2,6:12,8-dimetheno-13,22,1,3,5,7-benzodioxatetraazacyclotetracosine, 25-bromo-14,15,16,17,18,19,20,21-octahydro-11-methoxy- | Compound 38 |
| 1H,7H-2,6:12,8-dimetheno-14H-13,23,1,3,5,7-benzodioxatetraazacyclopentacosine, 26-chloro-15,16,17,18,19,20,21,22-octahydro-11-methoxy- | Compound 39 |
| 1H,7H-6,2:8,12-dimetheno-13,20,1,3,5,7-benzodioxatetraazacyclodocosine, 23-bromo-14,15,16,17,18,19-hexahydro-10-methoxy- | Compound 40 |

Example B8

Preparation of compound 8: 2,4,6,8,15,22-hexaazatetracyclo[22.3.1.1~3,7~.1~9,13~]triaconta-1(28),3,5,7(30),9,11,13(29),24,26-nonaene-14,23-dione To a solution of intermediate 29 (0.69 mmol) in DMF (100 ml), DIPEA (6.90 mmol) was added. This solution was added dropwise during 1 hour to a solution of (Benzotriazol-1-yloxy)tripyrrolidinophosphonium hexafluorophosphate (2.1 mmol) in DMF (100 ml) at room temperature. The reaction mixture was stirred further for 30 min at room temperature. The solvent was evaporated. The residue was dissolved in DCM, washed with 10% NaHCO$_3$ solution, then dried (MgSO$_4$), filtered and the solvent was evaporated. The residue was suspended from acetonitrile, the precipitate was filtered off. The solid was recrystallized from acetonitrile, after cooling the solid was filtered off and dried in vacuum at 50° C., yielding 100 mg of compound 8, melting point 307° C.

| Name | Compound |
|---|---|
| 2,4,6,8,15,21-hexaazatetracyclo[21.3.1.1~3,7~.1~9,13~]nonacosa-1(27),3,5,7(29),9,11,13(28),23,25-nonaene-14,22-dione | Compound 41 mp. 328° C. |

Example B9

Preparation of compound 9: 18-oxa-2,4,6,8,15-pentaazatetracyclo[17.2.2.1~3,7~.1-9,13~]pentacosa-3,5,7(25),9,11,13(24),19,21,22-nonaen-16-one, trifluoroacetic acid salt A solution of intermediate 33 in DMF (20 ml) was added dropwise to a solution of HBTU (0.0003 mol) and DIPEA (0.0015 mol) in DMF (10 ml) while stirring. The reaction mixture was stirred for 30 minutes, the solvent was evaporated at 50° C. under N$_2$. The obtained residue was purified by column chromatography [some residues were first purified with a NH$_4$OAc buffer and then with a TFA-buffer on a RP-column; other residues were purified directly with a TFA-buffer on a RP-column]. The product fractions were collected and then the solvent was evaporated and co-evaporated with CH$_3$CN/MeOH, yielding 0.034 g of compound 9, isolated as a trifluoroacetic acid salt (1:1).

| Name | Compound |
|---|---|
| 20-oxa-1,8,10,12,14,23-hexaazapentacyclo[21.2.2.1~3,7~.1~9,13~.1~15,19~]triaconta-3,5,7(30),9,11,13(29),15,17,19(28)-nonaen-22-one | Compound 42 |
| 1,8,10,12,14,23-hexaazapentacyclo[21.2.2.1~3,7~.1~9,13~.1~15,19~]triaconta-3,5,7(30),9,11,13(29),15,17,19(28)-nonaen-22-one | Compound 43 |
| 1,8,10,12,14,23-hexaazapentacyclo[21.2.2 .2~15,18~.1~3,7~.1~9,13~]hentriaconta-3,5,7(31),9,11,13(30),15,17,28-nonaen-22-one, trifluoroacetic acid salt | Compound 44 |
| 1,8,10,12,14,22-hexaazapentacyclo[20.2.2.1~3,7~.1~9,13~.1~15,19~]nonacosa-3,5,7(29),9,11,13(28),15,17,19(27)-nonaen-21-one | Compound 45 |
| 14,20-dioxa-2,4,6,8,17-pentaazatetracyclo[19.2.2.1~3,7~.1~9,13~]heptacosa-3,5,7(27),9,11,13(26),21,23,24-nonaen-18-one, 12-methoxy-, trifluoroacetic acid salt (1:1) | Compound 46 |
| 2,4,6,8,15-pentaazatetracyclo[16.3.1.1~3,7~.1~9,13~]tetracosa-1(22),3,5,7(24),9,11,13(23),18,20-nonaen-16-one, trifluoroacetic acid salt (1:1) | Compound 47 |
| 14-oxa-2,4,6,8,17-pentaazatetracyclo[18.3.1.1~3,7~.1~9,13~]hexacosa-1(24),3,5,7(26),9,11,13(25),20,22-nonaen-18-one, 12-methoxy-, trifluoroacetic acid salt (1:1) | Compound 48 |
| | Compound 49 |

| | |
|---|---|
| 2,4,6,8,15,18-hexaazatetracyclo[18.3.1.1~3,7~.1~9,13~]hexacosa-1(24),3,5,7(26),9,11,13(25),20,22-nonaen-16-one, 18-methyl-, trifluoroacetic acid salt (1:1) | Compound 50 |
| 2,4,6,8,15,18,21-heptaazatetracyclo[21.3.1.1~3,7~.1-9,13~]nonacosa-1(27),3,5,7(29),9,11,13(28),23,25-nonaen-17-one, 21-ethyl-15-methyl-, trifluoroacetic acid salt (1:3) | Compound 51 |
| 1,8,10,12,14,21,24-heptaazapentacyclo[22.2.2.1~3,7~.1~9,13~.1~15,19~]hentriaconta-3,5,7(31),9,11,13(30),15,17,19(29)-nonaen-23-one, 21-methyl-, trifluoroacetic acid salt (1:3) | Compound 52 |
| 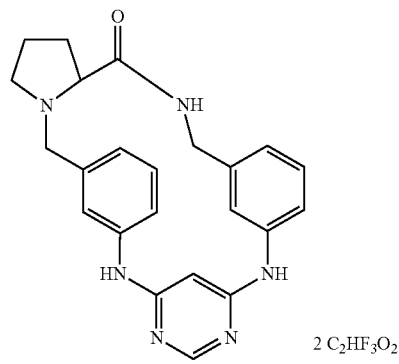 [SMILES: O=C1NCc2cccc(c2)Nc2cc(ncn2)Nc2cccc(c2)CN2CCCC12] | Compound 53 |
| 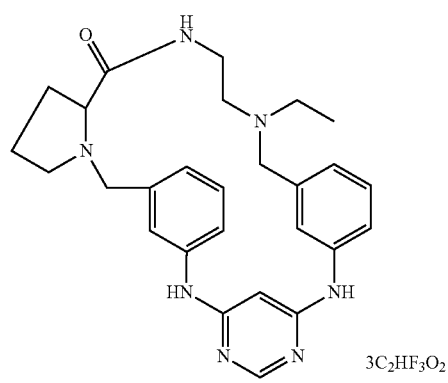 [SMILES: CCN1CCNC(=O)C2CCCN2Cc2cccc(c2)Nc2cc(ncn2)Nc2cccc(c2)C1] | Compound 54 |
| 2,4,6,8,15,18-hexaazatetracyclo[19.3.1.1~3,7~.1~9,13~]heptacosa-1(25),3,5,7(27),9,11,13(26),21,23-nonaen-19-one, 15-ethyl-, trifluoroacetic acid salt (1:2) | Compound 55 |
| 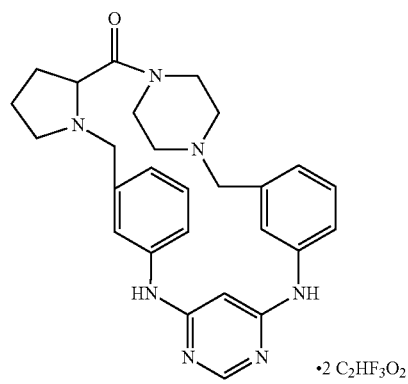 [SMILES: O=C1C2CCCN2Cc2cccc(c2)Nc2cc(ncn2)Nc2cccc(c2)CN2CCN1CC2] | Compound 56 |

Example B10

| | |
|---|---|
| Preparation of compound 10 | (RS)-2,4,6,8,15,18-hexaazatetracyclo[18.3.1.1~3,7~.1~9,13~]hexacosa-1(24),3,5,7(26),9,11,13(25),20,22-nonaene-14,17-dione, 16-(2-methylpropyl)-trifluoroacetic acid salt |

A solution of intermediate 37 in DMF (20 ml) was added dropwise to a solution of HBTU (0.0004 mol) and DIPEA (0.300 ml) in DMF (10 ml) while stirring. The reaction mixture was stirred for 30 minutes at room temperature, the solvent was evaporated at 50° C. under $N_2$. The obtained residue was purified by column chromatography [some residues were first purified with a $NH_4OAc$ buffer and then with a TFA-buffer on a RP-column; other residues were purified directly with a TFA-buffer on a RP-column]. The product fractions were collected and then the solvent was evaporated and co-evaporated with $CH_3CN/MeOH$, yielding 0.069 g of compound 10, isolated as a trifluoroacetic acid salt (1:1).

| | |
|---|---|
| 2,4,6,8,15,23-hexaazatetracyclo[23.3.1.1~3,7~.1~9,13~]hentriaconta-1(29),3,5,7(31),9,11,13(30),25,27-nonaene-14,22-dione | Compound 57 |
| 2,4,6,8,15,21-hexaazatetracyclo[21.3.1.1~3,7~.1~9,13~]nonacosa-1(27),3,5,7(29),9,11,13(28),23,25-nonaene-14,20-dione | Compound 58 |
| 2,4,6,8,15,18-hexaazatetracyclo[18.3.1.1~3,7~.1~9,13~]hexacosa-1(24),3,5,7(26),9,11,13(25),20,22-nonaene-14,17-dione, 16-[4-(dimethylamino)butyl]- | Compound 59 |
| 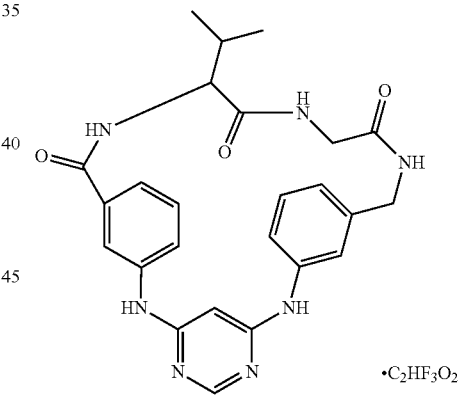 | Compound 60 |
| 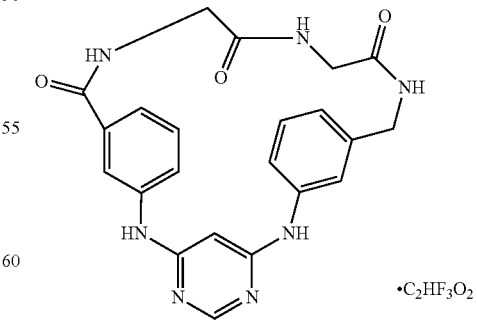 | Compound 61 |
| 2,4,6,8,15,18-hexaazatetracyclo[18.3.1.1~3,7~.1~9,13~]hexacosa-1(24),3,5,7(26),9,11,13(25),20,22-nonaene-14,17-dione, 16-[2-(methylthio)ethyl]- | Compound 62 |

| | |
|---|---|
| 2,4,6,8,15,18-hexaazatetracyclo[18.3.1.1~3,7~.1~9,13~]hexacosa-1(24),3,5,7(26),9,11,13(25),20,22-nonaene-14,17-dione, 15-methyl-, trifluoroacetic acid salt (1:1) | Compound 63 |
| 2,4,6,8,15,18-hexaazatetracyclo[18.3.1.1~3,7~.1~9,13~]hexacosa-1(24),3,5,7(26),9,11,13(25),20,22-nonaene-14,17-dione, 16-(1-hydroxyethyl)-, trifluoroacetic acid salt (1:1) | Compound 64 |
| 2,4,6,8,15,18-hexaazatetracyclo[18.3.1.1~3,7~.1~9,13~]hexacosa-1(24),3,5,7(26),9,11,13(25),20,22-nonaene-14,17-dione, 16-(1H-imidazol-4-ylmethyl)-, trifluoroacetic acid salt (1:1) | Compound 65 |

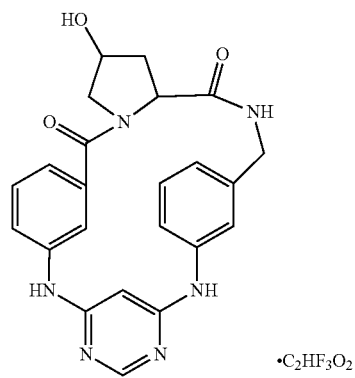

•C₂HF₃O₂

Compound 66

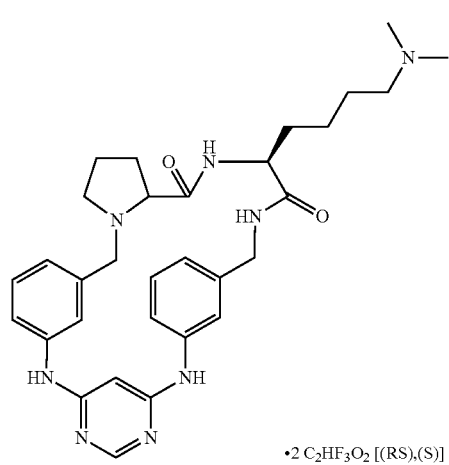 [SMILES: CN(C)CCCC[C@@H]1NC(=O)C2CCCN2Cc2cccc(c2)Nc2cc(ncn2)Nc2cccc(c2)CNC1=O]

•2 C₂HF₃O₂ [(RS),(S)]

Compound 67

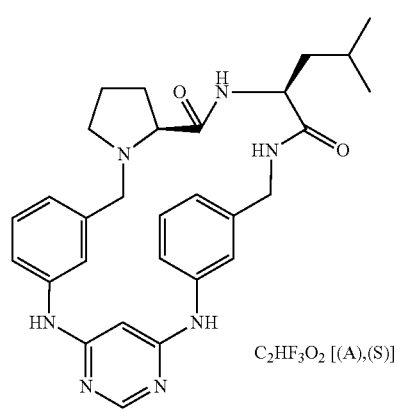 [SMILES: CC(C)C[C@@H]1NC(=O)[C@@H]2CCCN2Cc2cccc(c2)Nc2cc(ncn2)Nc2cccc(c2)CNC1=O]

C₂HF₃O₂ [(A),(S)]

Compound 68

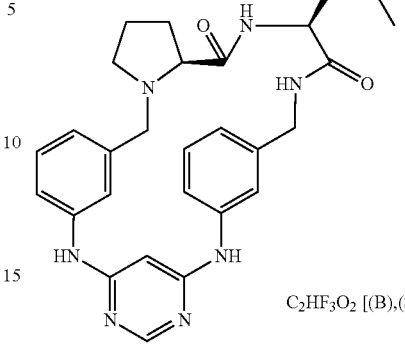

C₂HF₃O₂ [(B),(S)]

Compound 69

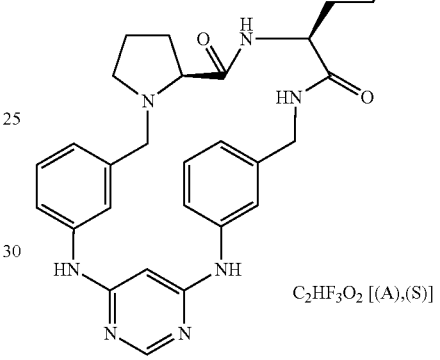

C₂HF₃O₂ [(A),(S)]

Compound 70

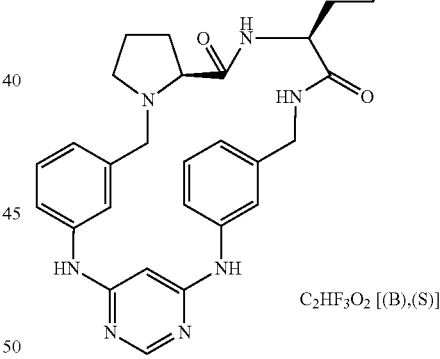

C₂HF₃O₂ [(B),(S)]

Compound 71

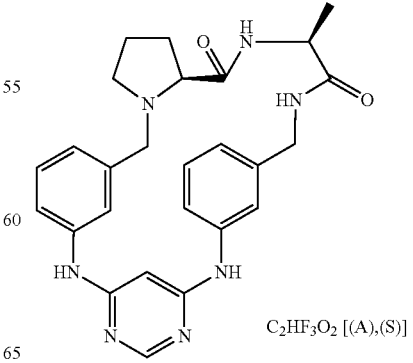

C₂HF₃O₂ [(A),(S)]

Compound 72

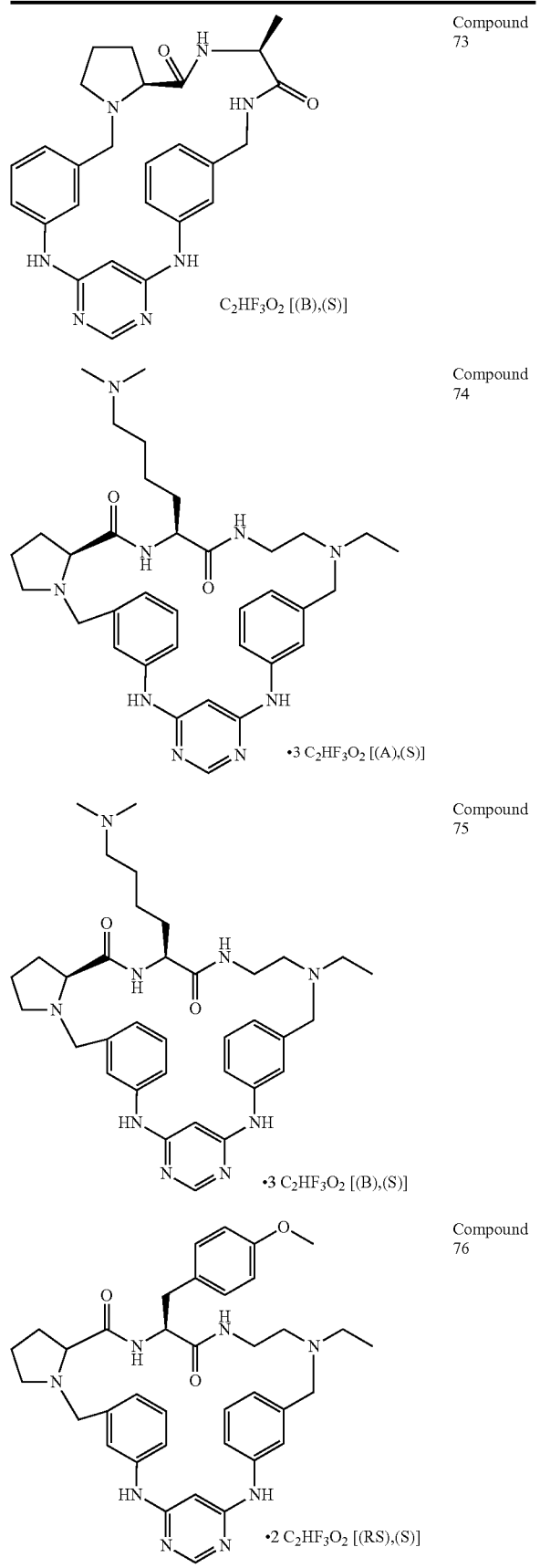
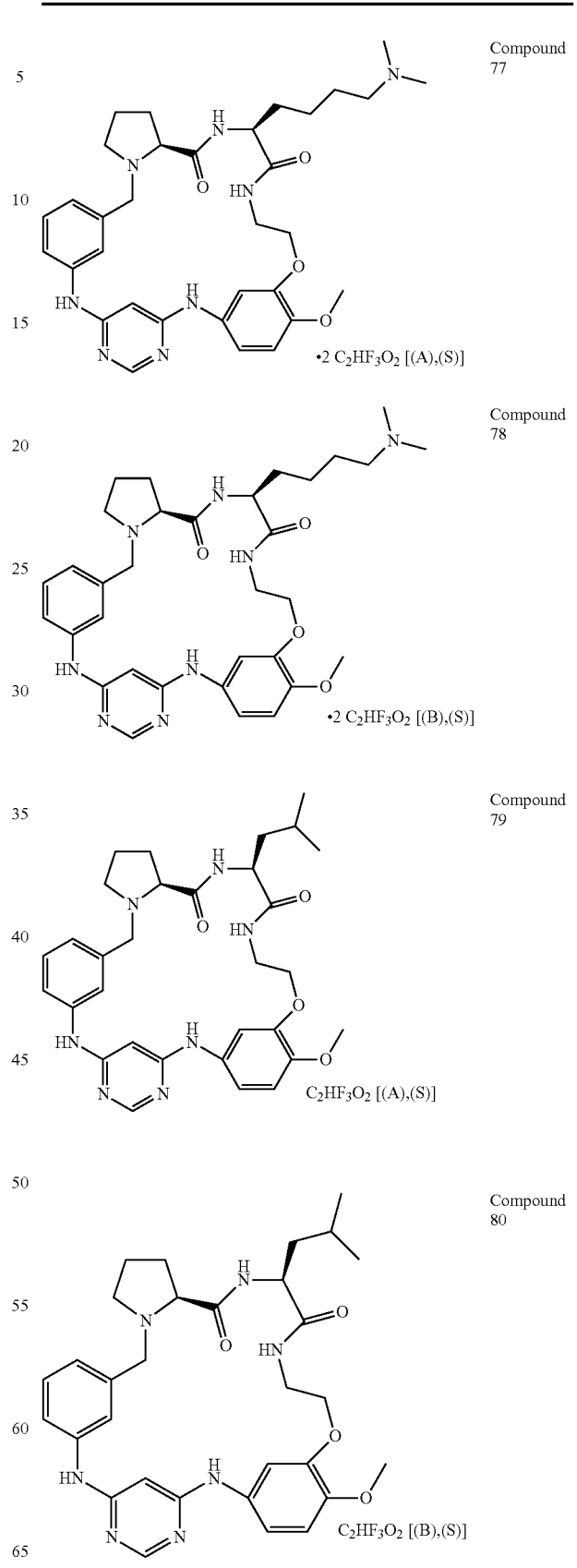

| | |
|---|---|
| 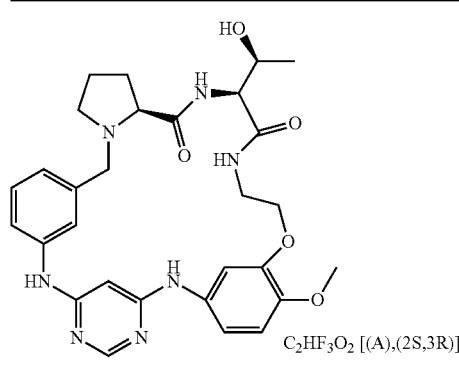 C₂HF₃O₂ [(A),(2S,3R)] | Compound 81 |
| 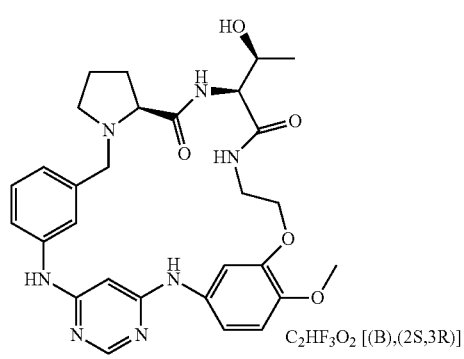 [SMILES: COc1ccc2cc1OCCNC(=O)[C@H]([C@H](C)O)NC(=O)[C@@H]1CCCN1Cc1cccc(c1)Nc1cc(ncn1)N2] C₂HF₃O₂ [(B),(2S,3R)] | Compound 82 |
| 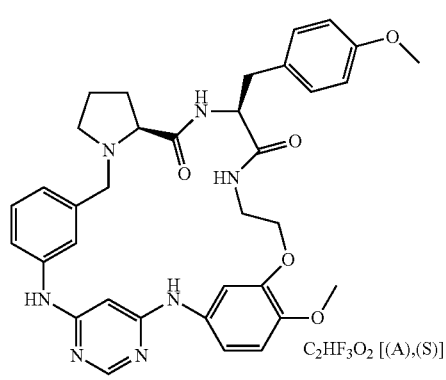 [SMILES: COc1ccc(C[C@@H]2NC(=O)[C@@H]3CCCN3Cc3cccc(c3)Nc3cc(ncn3)Nc3ccc(OC)c(c3)OCCNC2=O)cc1] C₂HF₃O₂ [(A),(S)] | Compound 83 |
| 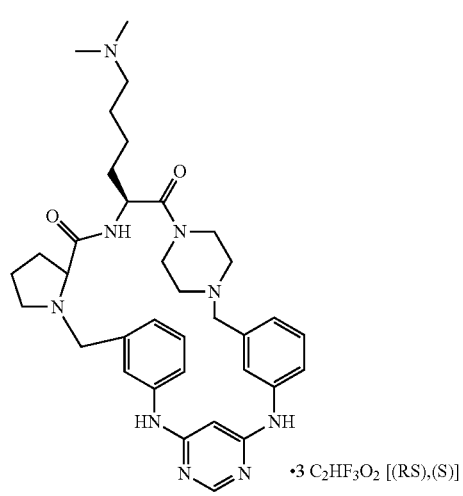 [SMILES: CN(C)CCCC[C@@H]1NC(=O)C2CCCN2Cc2cccc(c2)Nc2cc(ncn2)Nc2cccc(c2)CN2CCN(CC2)C1=O] ·3 C₂HF₃O₂ [(RS),(S)] | Compound 84 |
| 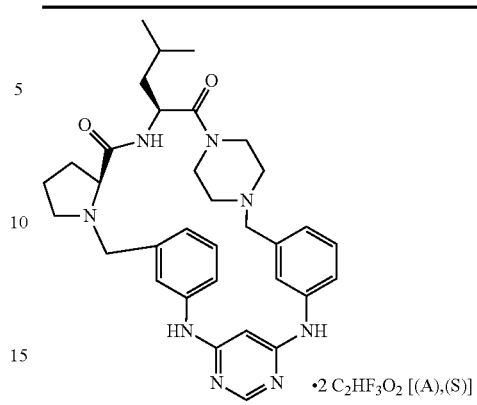 ·2 C₂HF₃O₂ [(A),(S)] | Compound 85 |
| 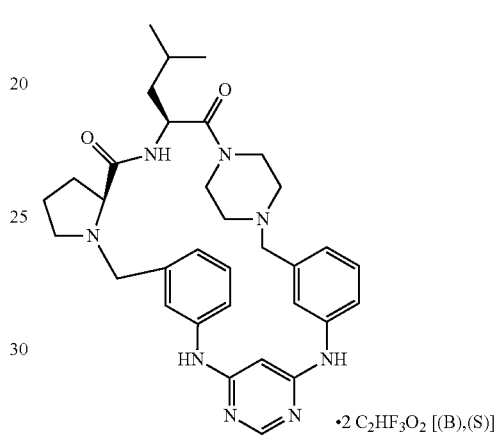 ·2 C₂HF₃O₂ [(B),(S)] | Compound 86 |
| 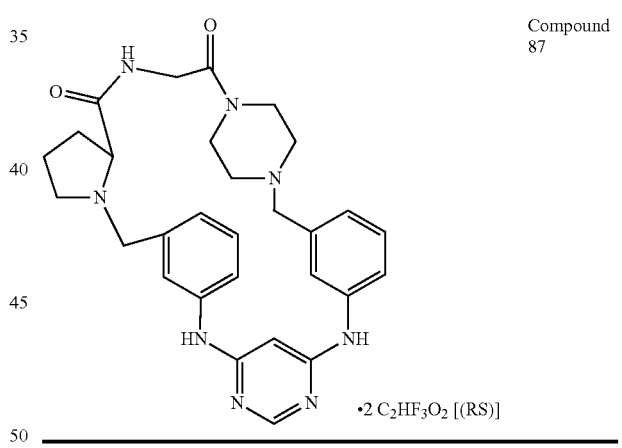 ·2 C₂HF₃O₂ [(RS)] | Compound 87 |

Example B11

| | |
|---|---|
| Preparation of compound 11 | 14-oxa-2,4,6,8,17,20-hexaazatetracyclo[20.3.1.1~3,7~.1~9,13~]octacosa-1(26),3,5,7(28),9,11,13(27),22,24-nonaen-18-one, 12-methoxy-20-methyl- |

DIPEA (0.012 mol) was added to a solution of intermediate 44 (0.002 mol) in 50 mL of dry DMF (q.s.) and then this solution was added dropwise to a mixture of HBTU (0.006 mol) in 150 mL of dry DMF (q.s.). The resulting mixture was stirred for 30 minutes at room temperature and the solvent was evaporated. PS-NMe₃(+)HCO₃(−) (Novabiochem, cat.

01-64-0419) was added and the mixture was shaken overnight. After filtration, Silica-SO₃H (Acros, cat. 360220050) (0.016 mol) was added portionwise to "catch" the product, then the reaction mixture was filtered over a plug of silica gel and washed with DCM/MeOH (9:1). The product was then released by washing with DCM/7 N NH₃ in MeOH (9:1) and, upon evaporation of the solvent, triturated with MeOH. Filtration of the precipitate provided 0.1024 g of the pure product. The mother liquor and washings of the silica gel were combined and purified by reversed phase HPLC (NH₄OAc buffer) yielding a second batch of product, yielding 0.0581 g of compound 11.

The compound could be isolated in two ways:

1. Catch and release: The solvent was concentrated to about 100 mL after which PS-NMe₃(+)HCO₃(−) (Novabiochem, cat. 01-64-0419) (0.012 mol) was added. The resulting suspension was shaken overnight to scavenge 1-hydroxybenzotriazole (HOBt). After filtration and washing with DMF, Silica-SO₃H (Acros, cat. 360220050) (0.016 mol) was added portionwise to catch the compound, then the reaction mixture was filtered over silica gel and washed with DCM/MeOH (90/10). The desired product was then released by washing with 10% 7 N NH₃/MeOH in DCM. After evaporation of the solvent, MeOH was added, and the resulting precipitate was filtered off giving pure compound 11 (0.1024 g, 12% from intermediate 63).

Reversed Phase HPLC: Alternatively, the reaction mixture after macrocyclization can be evaporated to dryness and directly purified by high-performance liquid chromatography (NH₄OAc buffer). In this case compound 11 can be obtained in 20% yield from intermediate 63, mp. 286.3-288.1° C.

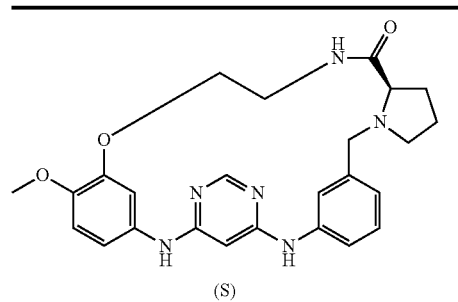

Compound 88
mp. 279.0-281.2° C.
(S)

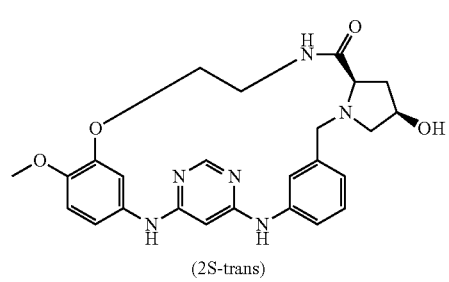

Compound 89
mp. 287.8-289.1° C.
(2S-trans)

Compound 90
mp. 292.9-295.5° C.
(RS)

20-oxa-1,8,10,12,14,23-hexaazapentacyclo[23.3.1.1~3,7~.1~9,13~.1-15,19~]dotriaconta-3,5,7(32),9,11,13(31),15,17,19(30)-nonaen-24-one, 18-methoxy-(RS) — Compound 91 mp. 281.0-285.6° C.

20-oxa-1,8,10,12,14,23-hexaazapentacyclo[23.2.2.1~3,7~.1~9,13~.1~15,19~]dotriaconta-3,5,7(32),9,11,13(31),15,17,19(30)-nonaen-24-one, 18-methoxy- — Compound 92 mp. 297.9-298.2° C.

20-oxa-1,8,10,12,14,23-hexaazapentacyclo[24.2.2.1~3,7~.1~9,13~.1~15,19~]tritriaconta-3,5,7(33),9,11,13(32),15,17,19(31)-nonaen-24-one, 18-methoxy- — Compound 93 mp. 296.9-299.5° C.

20-oxa-1,8,10,12,14,23,26-heptaazapentacyclo[24.2.2.1~3,7~.1~9,13~.1~15,19~]tritriaconta-3,5,7(33),9,11,13(32),15,17,19(31)-nonaen-24-one, 18-methoxy- — Compound 94 mp. 267.7-269.0° C.

Compound 95
(2S,4S)

Compound 96
(R)

20-oxa-1,8,10,12,14,23,27-heptaazapentacyclo[26.2.2.1~3,7~.1~9,13~.1~15,19~]pentatriaconta-3,5,7(35),9,11,13(34),15,17,19(33)-nonaen-24-one, 18-methoxy- — Compound 97

14-oxa-2,4,6,8,17,21-hexaazatetracyclo[21.3.1.1~3,7~.1~9,13~]nonacosa-1(27),3,5,7(29),9,11,13(28),23,25-nonaen-18-one, 12-methoxy-21-(phenylmethyl)- — Compound 98

20-oxa-1,8,10,12,14,23-hexaazapentacyclo[23.3.1.1~3,7~.1~9,13~.1~15,19~]dotriaconta-3,5,7(32),9,11,13(31),15,17,19(30)-nonaen-24-one, 26-hydroxy-18-methoxy- — Compound 99

14-oxa-2,4,6,8,17,20-hexaazatetracyclo[20.3.1.1~3,7~.1~9,13~]octacosa-1(26),3,5,7(28),9,11,13(27),22,24-nonaen-18-one, 20-ethyl-12-methoxy- — Compound 100

| | |
|---|---|
| 14-oxa-2,4,6,8,17,22-hexaazatetracyclo[22.3.1.1~3,7~.1~9,13~]triaconta-1(28),3,5,7(30),9,11,13(29),24,26-nonaen-18-one, 12-methoxy-22-methyl- | Compound 101 |
| 14-oxa-2,4,6,8,17,21-hexaazatetracyclo[21.3.1.1~3,7~.1~9,13~]nonacosa-1(27),3,5,7(29),9,11,13(28),23,25-nonaen-18-one, 12-methoxy-21-phenyl- | Compound 102 |

Example B12

| | |
|---|---|
| Preparation of compound 12 | 6,2:12,8-dimetheno-7H-13,1,3,5,7,17,20-benzoxahexaazacyclotetracosine-18,21-dione, 25-chloro-1,14,15,16,17,19,20,22-octahydro-11-methoxy-19-(2-methylpropyl)-, (19S)- |

A mixture of intermediate 49 (0.0062 mol), HBTU (0.0081 mol) and triethylamine (0.0187 mol) in DCM/THF/DMF (170 ml) was stirred at room temperature for 4 hours, poured out into water and extracted with EtOAc. The organic layer was washed with saturated $NaHCO_3$, dried ($MgSO_4$), filtered, and the solvent was evaporated till dryness. The residue was crystallized from DCM/MeOH. The precipitate was filtered off, washed with DCM, diethyl ether then dried in vacuo. The solid was recrystallized in THF. Addition of DIPE to the filtrate gave a second batch of compound 12 (L)-(S), melting point 191° C.

| | |
|---|---|
| 1H,7H-6,2:12,8-dimetheno-13,1,3,5,7,16,19-benzoxahexaazacyclotricosine-17,20(14H)-dione, 24-chloro-15,16,18,19,21-pentahydro-11-methoxy- | Compound 103 mp. 240° C. |
| 6,2:12,8-dimetheno-7H-13,1,3,5,7,17,20-benzoxahexaazacyclotetracosine-18,21-dione, 1,14,15,16,17,19,20,22-octahydro-11-methoxy-17-[2-(4-morpholinyl)ethyl]-, trifluoroacetic acid salt | Compound 104 mp. 154° C. |
| 6,2:8,12-dimetheno-7H-13,1,3,5,7,17,20-benzoxahexaazacyclotetracosine-18,21-dione, 25-chloro-1,14,15,16,17,19,20,22-octahydro-11-methoxy-19,19-dimethyl- | Compound 105 mp. >250° C. |
| 1H,7H-6,2:8,12-dimetheno-13,1,3,5,7,16,19-benzoxahexaazacyclotricosine-17,20(14H)-dione, 24-chloro-15,16,18,19,21-pentahydro-18,18-dimethyl-11-[3-(4-morpholinyl)propoxy]- | Compound 106 mp. >260° C. |
| 1H,7H-6,2:8,12-dimetheno-13,1,3,5,7,16,19-benzoxahexaazacyclotricosine-17,20(14H)-dione, 24-chloro-15,16,18,19,21-pentahydro-11-[3-(4-morpholinyl)propoxy]-, hydrochloric acid salt (1:2) | Compound 107 mp. 180° C. |

Example B13

| | |
|---|---|
| Preparation of compound 13 | 1H,7H-6,2:8,12-dimetheno-13,20,1,3,5,7,17-benzodioxapentaazacyclodocosine, 23-chloro-14,15,16,17,18,19-hexahydro-11-methoxy- |

Intermediate 56 (0.0083 mol) was dissolved in DCM/MeOH. Toluene was added. The mixture was evaporated in vacuo. The residue was suspended in THF (160 ml). Triphenylphosphine (0.0248 mol) was added. A solution of DIAD (0.0247 mol) in THF (50 ml) was added dropwise. The mixture was stirred at room temperature overnight then evaporated in vacuo. The residue was partitioned between water and EtOAc/diethyl ether. The organic layer was separated, dried ($MgSO_4$), filtered, and the solvent was evaporated in vacuo. The residue was purified by column chromatography over silica gel (eluent: DCM/MeOH/$NH_4OH$ 96/4/0.3; 20-45 µm), yielding 1.44 g of a off white solid. It was then triturated with acetonitrile/isopropyl ether, filtered off and dried in vacuo, yielding 0.995 g of compound 13, mp. >260° C.

| | |
|---|---|
| 14,20-dioxa-2,4,6,8,17-pentaazatetracyclo[19.3.1.1~3,7~.1~9,13~]heptacosa-1(25),3,5,7(27),9,11,13(26),21,23-nonaen-16-one, 12,22-dimethoxy- | Compound 108 mp. 257° C. |

Example B14

| | |
|---|---|
| Preparation of compound 14 | 2,4,6,8,15,18-hexaazatetracyclo[18.3.1.1~3,7~.1~9,13~]hexacosa-1(24),3,5,7(26),9,11,13(25),20,22-nonaen-14-one, 23-methoxy- |

A mixture of intermediate 62 (0.00021 mol), HBTU (0.00053 mol) and DIPEA (0.00084 mol) in DMF (100 ml) and piperidine (10 ml) was reacted for 3 hours at room temperature, then morpholine (10 ml) was added and after 90 minutes the solvent was evaporated. The residue was purified by reversed-phase high-performance liquid chromatography. The desired product fractions were collected and the solvent was evaporated, yielding 0.008 g of compound 14.

| | |
|---|---|
| 14-oxa-2,4,6,8,17-pentaazatetracyclo[17.3.1.1~3,7~.1~9,13~]pentacosa-1(23),3,5,7(25),9,11,13(24),19,21-nonaen-18-one, 12-methoxy- | Compound 109 |

Example B15

| | |
|---|---|
| Preparation of compound 15 | 14-oxa-2,4,6,8,17,20-hexaazatetracyclo[20.3.1.1~3,7~.1~9,13~]octacosa-1(26),3,5,7(28),9,11,13(27),22,24-nonaen-18-one, 12-methoxy-19-(phenylmethyl)- |

DIPEA (0.0050 mol) was added to a solution of intermediate 64 (0.0005 mol) in DMF dry (30 ml) and the mixture was stirred, then the obtained solution was added dropwise to a solution of HBTU (0.0015 mol) in DMF dry (100 ml) and after 1 hour the solvent was evaporated. DCM, water and potassium carbonate were added and the reaction mixture was shaken. The organic layer was separated and the aqueous layer was extracted 2 times with DCM. The organic layers were combined, dried (anhydrous potassium carbonate), filtered off and the solvent was evaporated to dryness. The obtained residue was purified by reversed-phase high-performance liquid chromatography ($NH_4OAc$). The product fractions were collected and the solvent was evaporated. The residue (0.0491 g-19%) was dissolved in MeOH/DCM (10/

90), then the resulting mixture was filtered through Extrelut and the solvent was evaporated, yielding 0.0353 g (14%) of compound 15.

Example B16

| Preparation of compound 16 | 6,2:12,8-dimetheno-7H-13,1,3,5,7,19-benzoxapentaazacyclodocosine, 23-chloro-22-fluoro-1,14,15,16,17,18,19,20-octahydro-11-(2-methoxyethoxy)-19-methyl- |
|---|---|

A solution of 1,1'-(azodicarbonyl)bis-piperidine (0.0013 mol) in THF (3 ml) and a solution of tributyl-phosphine (0.0013 mol) in THF (3 ml) were added dropwise simultaneously to a solution of intermediate 70 (0.0008 mol) in THF/DMF 80/20 (22 ml) over a period of 30 minutes. The mixture was stirred at room temperature over the week-end, then poured out into potassium carbonate 10% and extracted with EtOAc. The organic layer was separated, dried (MgSO$_4$), filtered, and the solvent was evaporated till dryness. The crude oil (1.9 g) was crystallized from acetonitrile. The precipitate was filtered off and dried. The residue (0.46 g) was purified by column chromatography over silica gel (eluent: DCM 100 then DCM/MeOH 98/2; 15-40 µm). The pure fractions were collected and the solvent was evaporated. The residue (0.23 g, 52%) was crystallized from acetonitrile. The precipitate was filtered off and dried, yielding 0.197 g (44%) of compound 16, melting point 203° C.

Example B17

| Preparation of compound 17 | 3,5,7,14,17-pentaazapentacyclo[19.2.2.2~14,17~.1~2,6~.1~8,12~]nonacosa-2,4,6(29),8,10,12(28),21,23,24-nonaen-18-one, trifluoroacetic acid salt |
|---|---|

A solution of intermediate 73 in DMF (20 ml) was added dropwise to a solution of HBTU (0.0004 mol) and DIPEA (0.300 ml) in DMF (10 ml) while stirring. The reaction mixture was stirred for 30 minutes, the solvent was evaporated at 50° C. under N$_2$. The obtained residue was purified by column chromatography [some residues were first purified with a NH4OAc buffer and then with a TFA-buffer on a RP-column; other residues were purified directly with a TFA-buffer on a RP-column] The product fractions were collected and then the solvent was evaporated and co-evaporated with acetonitrile/MeOH, yielding 0.014 g of compound 17, isolated as a trifluoroacetic acid salt (1:1).

| 1,8,10,12,22-pentaazapentacyclo[20.2.2.1~3,7~.1~9,13~.1~14,18~]nonacosa-3,5,7(29),9,11,13(28),14,16,18(27)-nonaen-21-one, trifluoroacetic acid salt (1:1) | Compound 110 |
|---|---|

Example B18

Preparation of compound 111

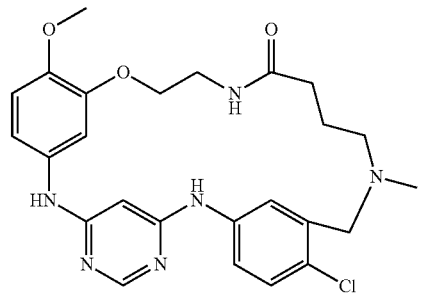

•C$_2$HF$_3$O$_2$ (1:1)

DIPEA (0.000750 mol) was added to mixture intermediate 79 (0.000250 mol) in 10 ml of DMF. This mixture was added dropwise to a solution of HBTU (0.000750 mol) in DMF (20 ml) over a 2-hour period. The reaction mixture was stirred for 30 minutes. The solvent was evaporated (oil-pump vacuum). The residue was purified by HPLC. The product fractions were collected and the solvent was evaporated, yielding compound 111.

Example B19

Preparation of compound 112

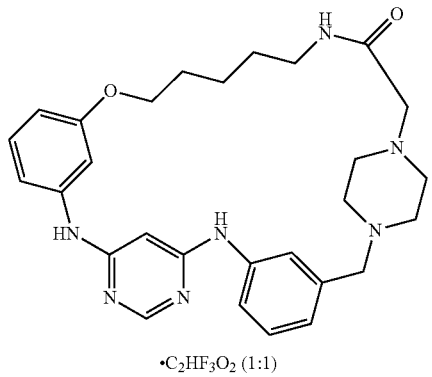

•C$_2$HF$_3$O$_2$ (1:1)

A solution of intermediate 85 (crude) in DMF (20 ml) was added dropwise to a solution of HBTU (0.00040 mol) and DIPEA (0.300 ml) in DMF (10 ml) and after stirring for 10 minutes at room temperature, the solvent was evaporated. The obtained residue was purified by reversed-phase high-performance liquid column chromatography [first purified with a NH$_4$OAc buffer and then desalted with a TFA-buffer on a RP-column] The product fractions were collected and then the solvent was evaporated (GeneVac), yielding 0.061 g of compound 112.

Example B20

Preparation of compound 113

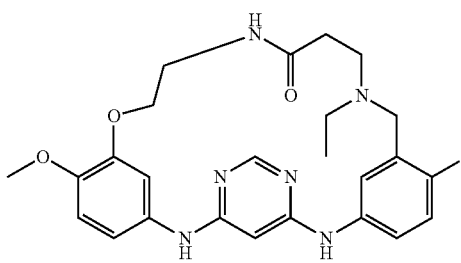

DIPEA (0.015 mol) was added to a solution of intermediate 95 (0.0025 mol) in DMF dry (10 mL) and this solution was added dropwise to a mixture of HBTU (0.0075 mol) in DMF dry (20 mL) The resulting mixture was stirred for 30 minutes at room temperature and the solvent was evaporated. The residue was purified by reversed phase HPLC (NH$_4$OAc buffer), yielding 0.014 g of compound 113.

Example B21

Preparation of compound 114

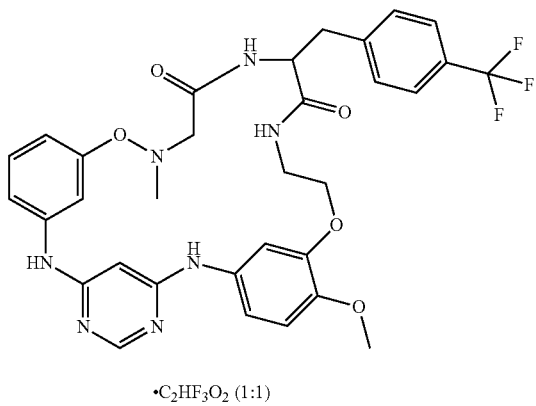

•C$_2$HF$_3$O$_2$ (1:1)

A solution of intermediate 93 (crude) in DMF (20 ml) was added dropwise to a solution of HBTU (0.00040 mol) and DIPEA (0.300 ml) in DMF (10 ml) and after stirring for 10 minutes at room temperature, the solvent was evaporated. The obtained residue was purified by reversed-phase high-performance liquid column chromatography using an eluent with an NH$_4$OAc buffer on preplines. The product fractions were collected and then the solvent was evaporated. The residues were desalted then by reversed-phase HPLC using a TFA buffer. The product fractions were collected and the solvent was evaporated (Genevac), yielding 0.008 g of compound 114.

Example B22

Preparation of compound 115

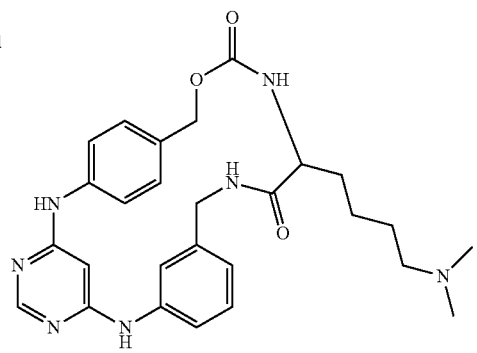

•C$_2$HF$_3$O$_2$ (1:1)

A solution of intermediate 107 (crude) in DMF (20 ml) was added dropwise to a solution of HBTU (0.00040 mol) and DIPEA (0.300 ml) in DMF (10 ml) and after stirring for 30 minutes at room temperature, the solvent was evaporated under a N$_2$ flow at 70° C. The obtained residue was purified by reversed-phase high-performance liquid column chromatography using an eluent with an NH$_4$OAc buffer on preplines. The product fractions were collected and then the solvent was evaporated. The residues were desalted then by reversed-phase HPLC on preplines using a TFA buffer. The product fractions were collected and the solvent was evaporated (Genevac), yielding 0.007 g of compound 115.

Example B23

Preparation of compound 116

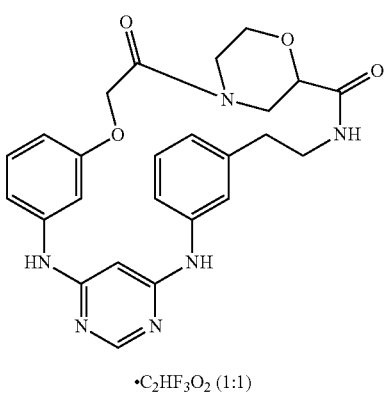

•C$_2$HF$_3$O$_2$ (1:1)
(RS)

A solution of intermediate 108 (crude) in DMF (20 ml) was added dropwise (using a multichannel pump) to a solution of HBTU (0.00040 mol) and DIPEA (0.300 ml) in D (10 ml) and after stirring for 10 minutes at room temperature, the solvent was evaporated. The obtained residue was purified by reversed-phase high-performance liquid column chromatography [first purified with a NH$_4$OAc buffer (by preplines) and then desalted with a TFA-buffer on a RP-column (by preplines)]. The product fractions were collected and then the solvent was evaporated, yielding 0.009 g of compound 116.

Example B24

Preparation of compound 117

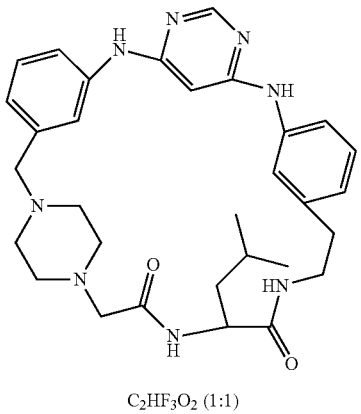

C₂HF₃O₂ (1:1)

A solution of intermediate 109 (crude) in DMF (20 ml) was added dropwise (using a Watson-Marlow multichannel pump) to a solution of HBTU (0.00040 mol) and DIPEA (0.300 ml) in DMF (10 ml) and after stirring for 10 minutes at room temperature, the solvent was evaporated. The obtained residue was purified by reversed-phase high-performance liquid column chromatography [first purified with a NH₄OAc buffer (by preplines) and then desalted with a TFA-buffer on a RP-column (by preplines)]. The product fractions were collected and then the solvent was evaporated, yielding 0.023 g of compound 117.

Table F-1 lists the compounds that were prepared according to one of the above Examples. The following abbreviations were used in the tables: .C₂HF₃O₂ stands for the trifluoroacetate salt.

TABLE F-1

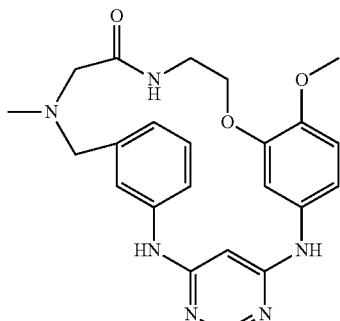

•2 C₂HF₃O₂; Co. No. 118; Ex. [B20]

TABLE F-1-continued

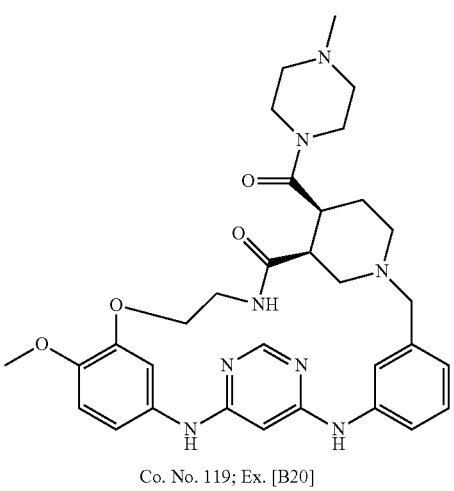 [SMILES: COc1ccc2cc1OCCNC(=O)[C@@H]1CN(CC[C@@H]1C(=O)N1CCN(C)CC1)Cc1cccc(c1)Nc1cc(ncn1)N2]

Co. No. 119; Ex. [B20]

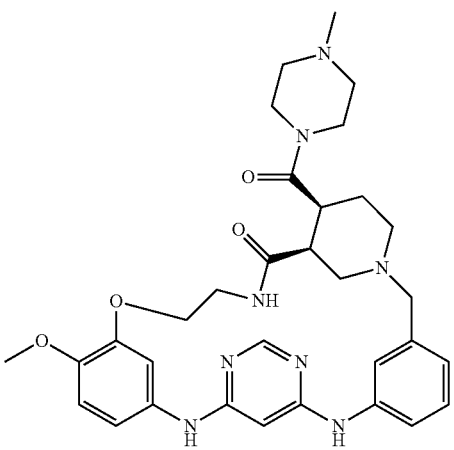

Co. No. 120; Ex. [B20]

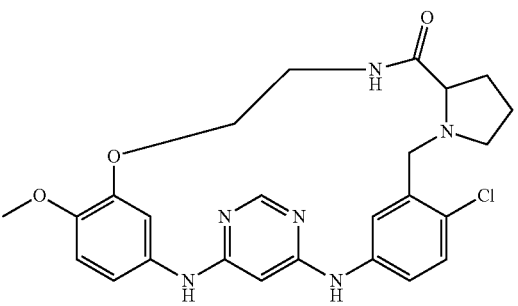

Co. No. 121; Ex. [B20]

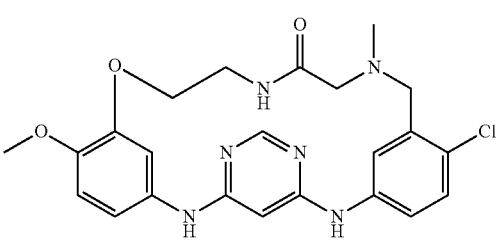

Co. No. 122; Ex. [B20]

TABLE F-1-continued
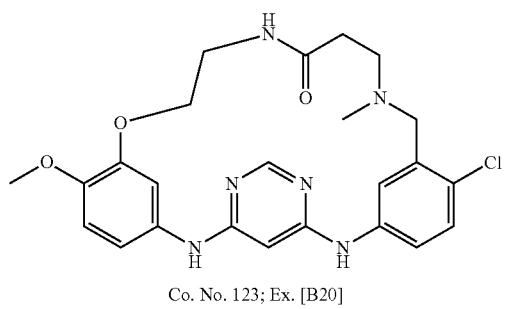 [SMILES: COc1ccc2cc1OCCNC(=O)CCN(C)Cc1cc(ccc1Cl)Nc1cc(ncn1)N2]
Co. No. 123; Ex. [B20]
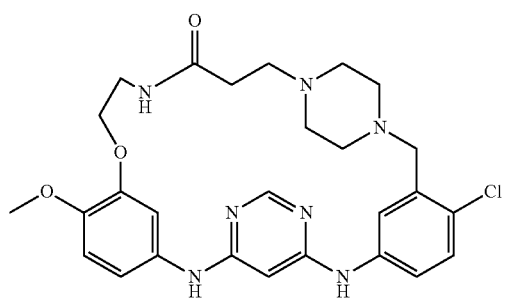
Co. No. 124; Ex. [B19]
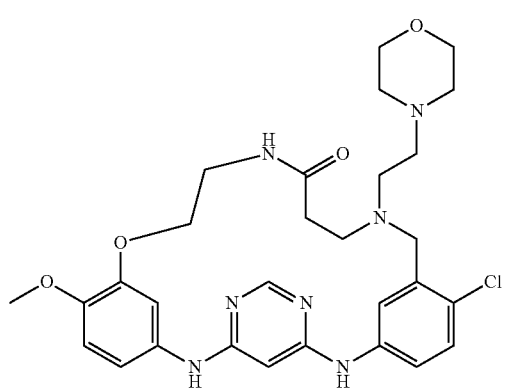
Co. No. 125; Ex. [B20]
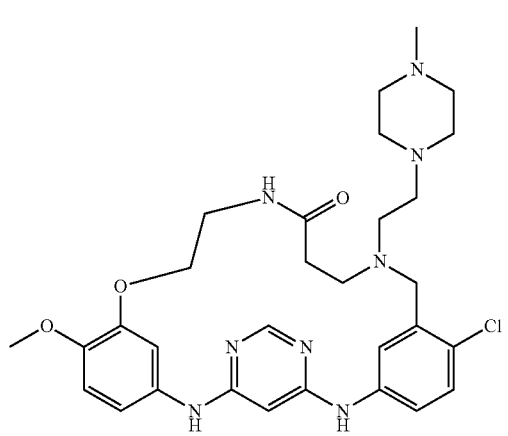
Co. No. 126; Ex. [B20]
TABLE F-1-continued
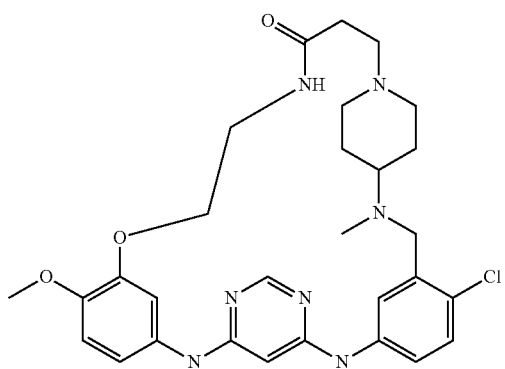
Co. No. 127; Ex. [B20]
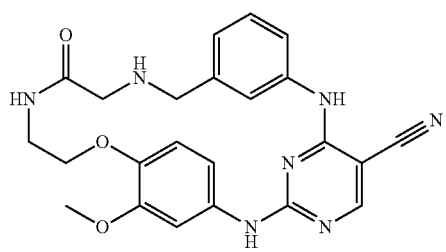
Co. No. 128; Ex. [B20]
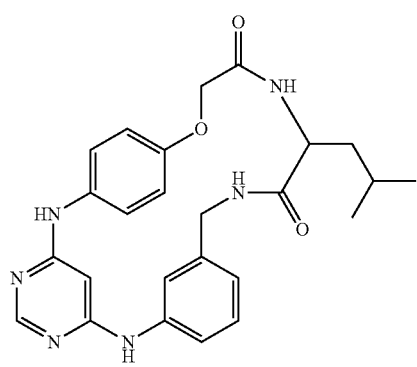
•$C_2HF_3O_2$; Co. No. 129; Ex. [B22]
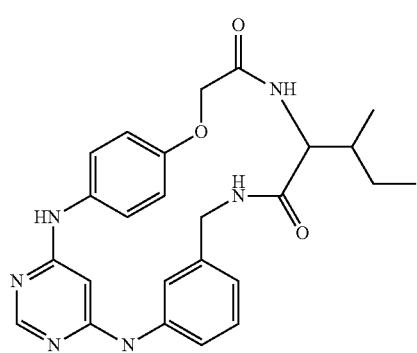
•$C_2HF_3O_2$; Co. No. 130; Ex. [B22]

TABLE F-1-continued
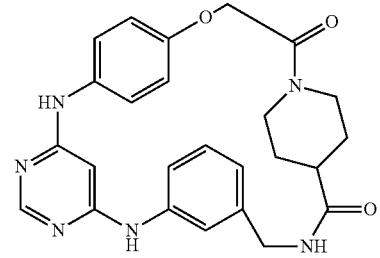
•C₂HF₃O₂; Co. No. 131; Ex. [B23]
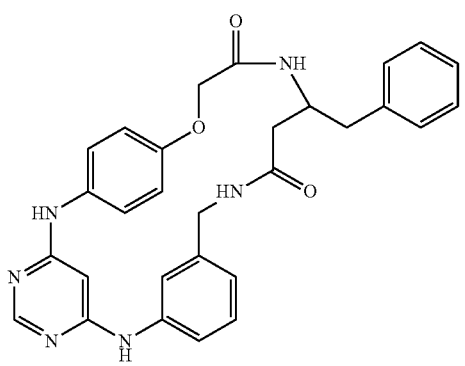
•C₂HF₃O₂; Co. No. 132; Ex. [B22]
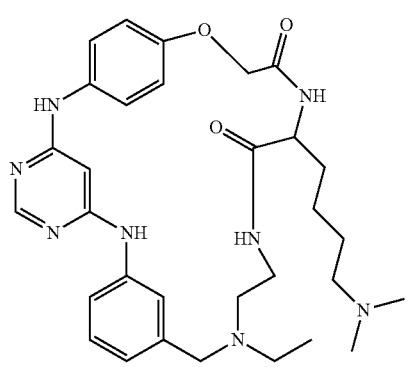
•C₂HF₃O₂; Co. No. 133; Ex. [B22]
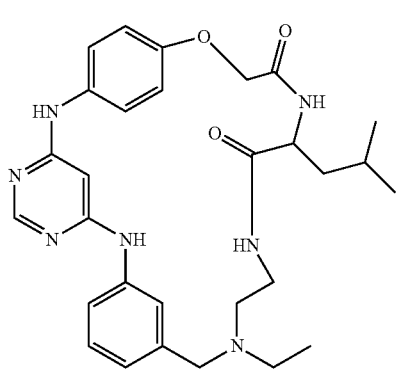
•C₂HF₃O₂; Co. No. 134; Ex. [B22]
TABLE F-1-continued
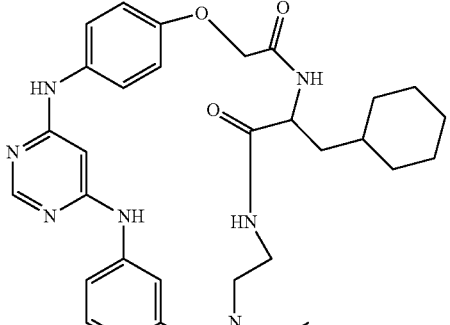
•C₂HF₃O₂; Co. No. 135; Ex. [B22]
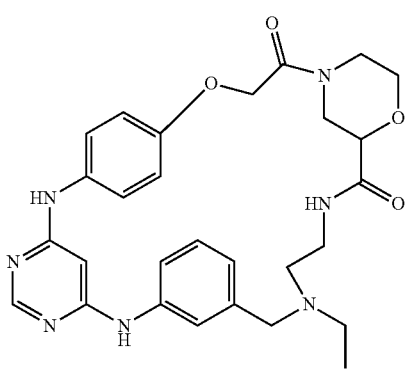
•C₂HF₃O₂; Co. No. 136; Ex. [B22]
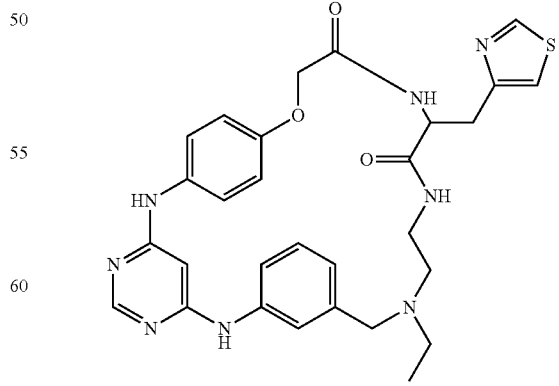
•C₂HF₃O₂; Co. No. 137; Ex. [B22]

TABLE F-1-continued
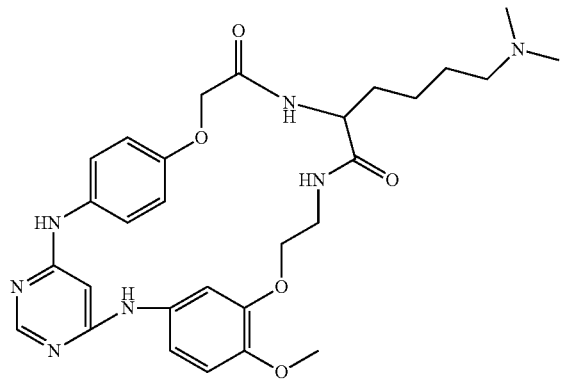
•C₂HF₃O₂; Co. No. 138; Ex. [B21]
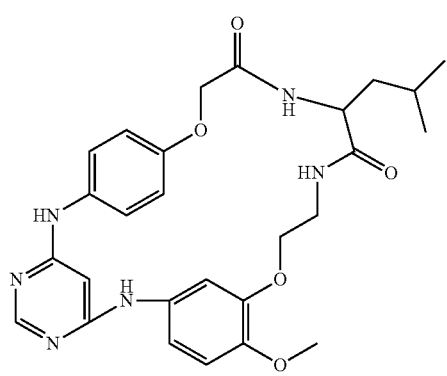
•C₂HF₃O₂; Co. No. 139; Ex. [B21]
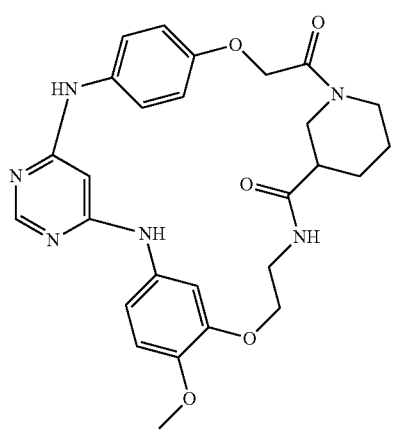
•C₂HF₃O₂; Co. No. 140; Ex. [B22]
TABLE F-1-continued
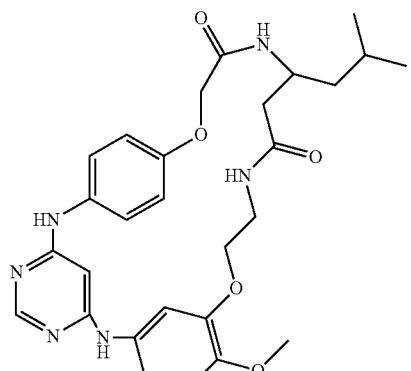
•C₂HF₃O₂; Co. No. 141; Ex. [B21]
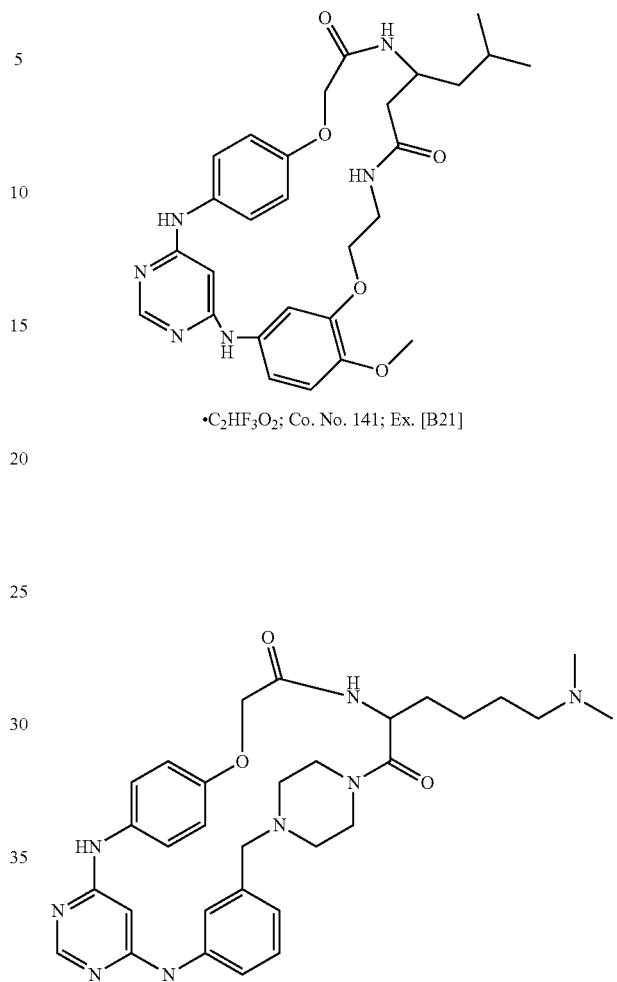
•C₂HF₃O₂; Co. No. 142; Ex. [B21]
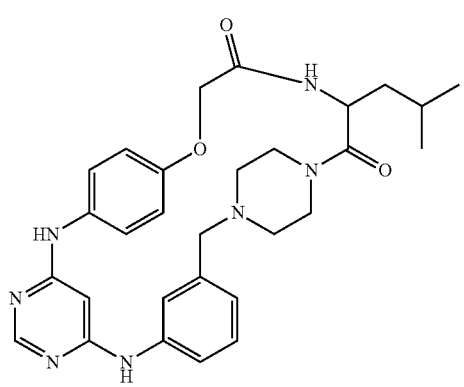
•C₂HF₃O₂; Co. No. 143; Ex. [B21]

TABLE F-1-continued
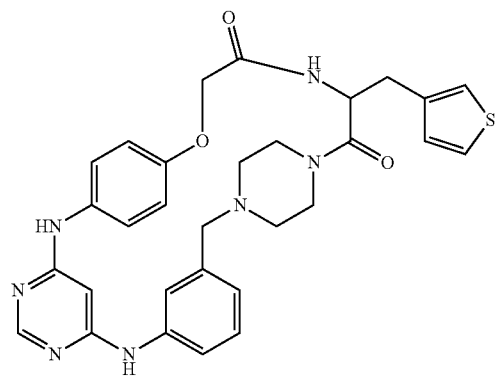
•C₂HF₃O₂; Co. No. 144; Ex. [B21]
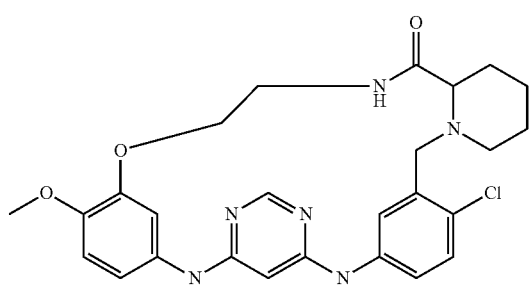
•C₂HF₃O₂; Co. No. 145; Ex. [B20];
(RS)
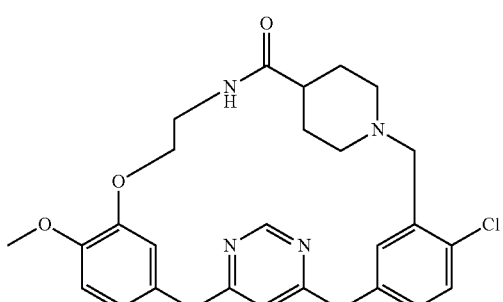
Co. No. 146; Ex. [B20]
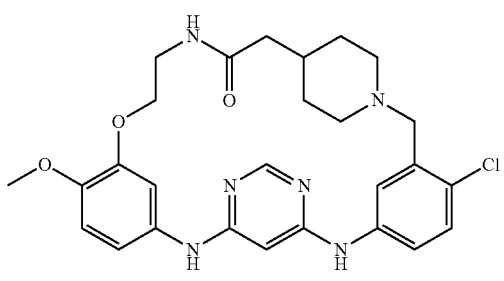
Co. No. 147; Ex. [B19]
TABLE F-1-continued
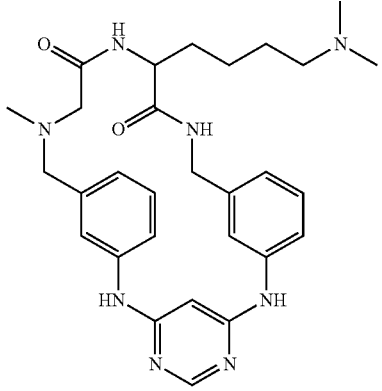
•C₂HF₃O₂; Co. No. 148; Ex. [B22]
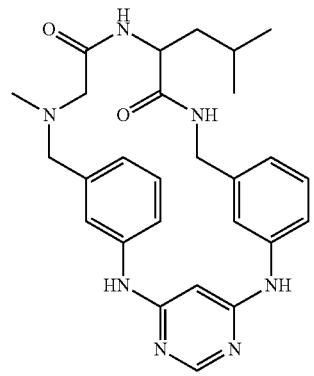
•C₂HF₃O₂; Co. No. 149; Ex. [B22]
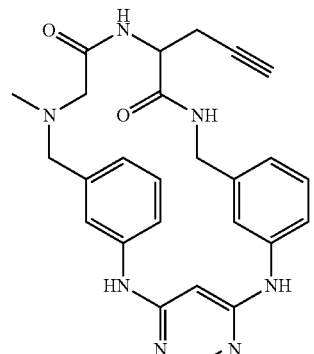
•C₂HF₃O₂; Co. No. 150; Ex. [B22]

TABLE F-1-continued
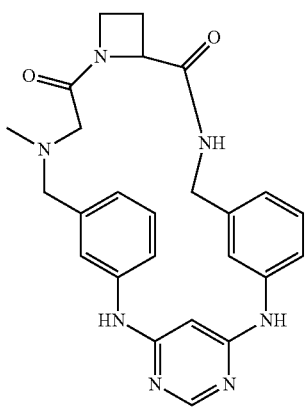
•C₂HF₃O₂; Co. No. 151; Ex. [B22]
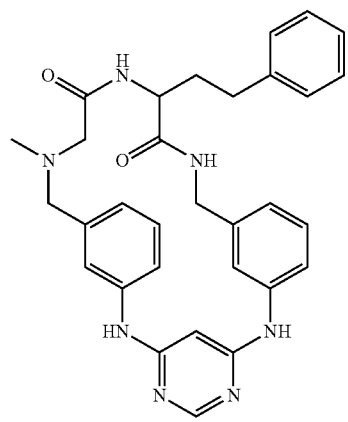
•C₂HF₃O₂; Co. No. 152; Ex. [B22]
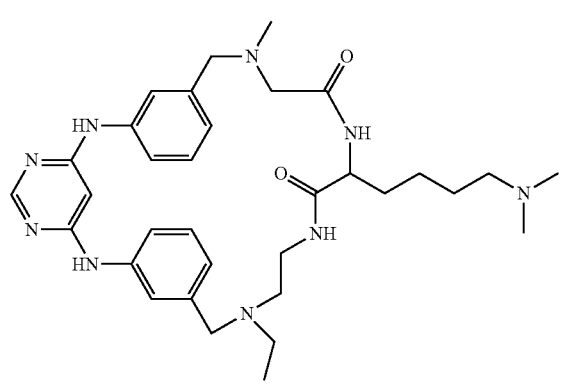
Co. No. 153; Ex. [B21]
TABLE F-1-continued
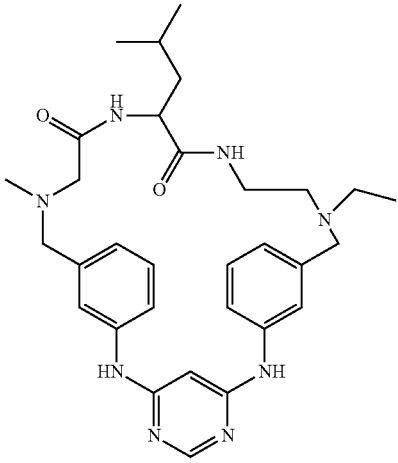
•C₂HF₃O₂; Co. No. 154; Ex. [B21]
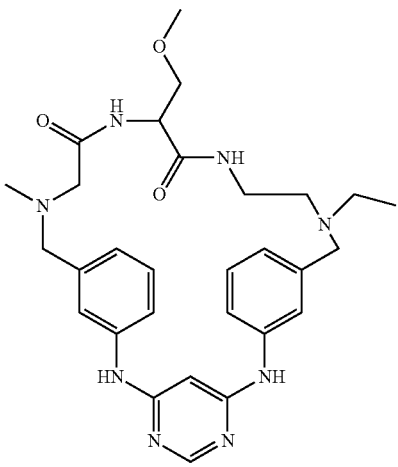
•C₂HF₃O₂; Co. No. 155; Ex. [B21]
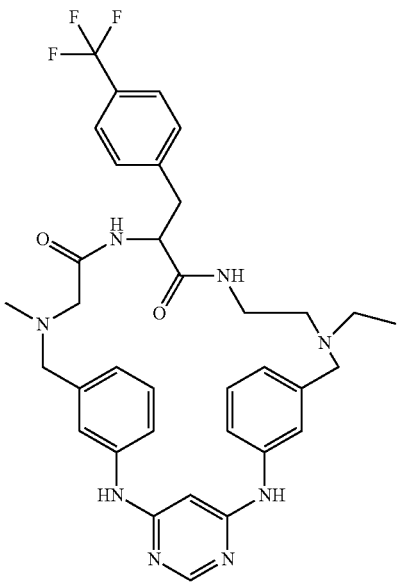
•C₂HF₃O₂; Co. No. 156; Ex. [B21]

TABLE F-1-continued
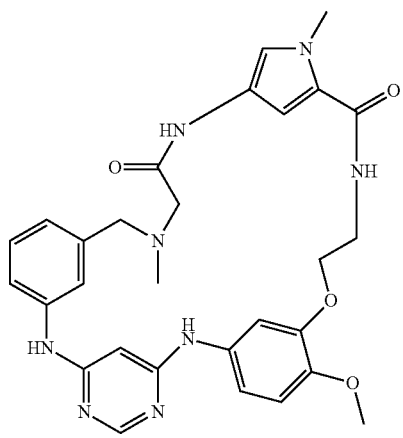
•C₂HF₃O₂; Co. No. 157; Ex. [B22]
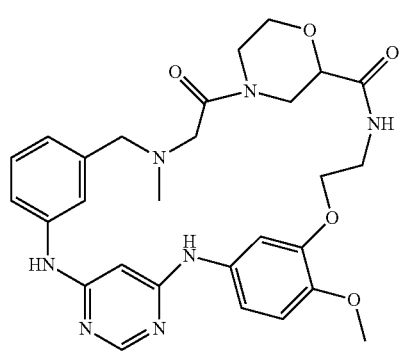
•C₂HF₃O₂; Co. No. 158; Ex. [B22];
(RS)
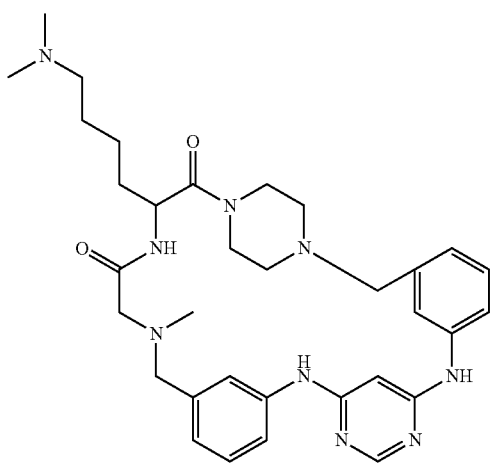
•C₂HF₃O₂; Co. No. 159; Ex. [B21]
TABLE F-1-continued
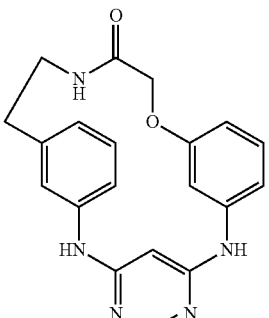
•C₂HF₃O₂; Co. No. 160; Ex. [B19]
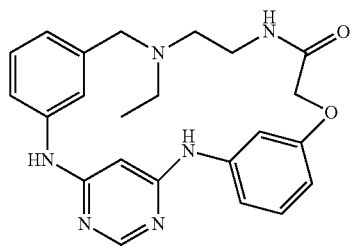
•C₂HF₃O₂; Co. No. 161; Ex. [B19]
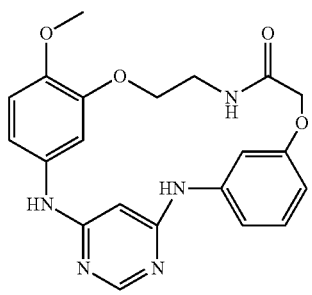
•C₂HF₃O₂; Co. No. 162; Ex. [B19]
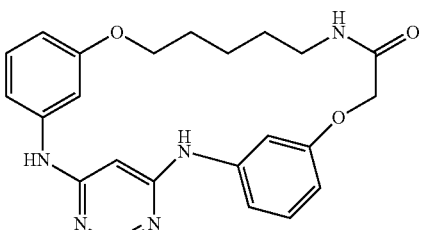
•C₂HF₃O₂; Co. No. 163; Ex. [B19]

TABLE F-1-continued
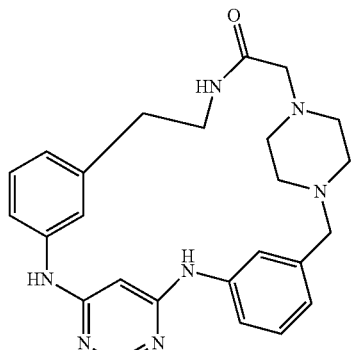
•C$_2$HF$_3$O$_2$; Co. No. 164; Ex. [B19]
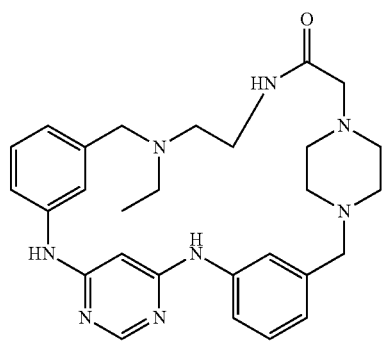
•C$_2$HF$_3$O$_2$; Co. No. 165; Ex. [B19]
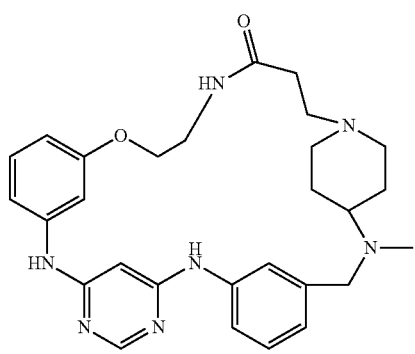
•C$_2$HF$_3$O$_2$; Co. No. 166; Ex. [B20]
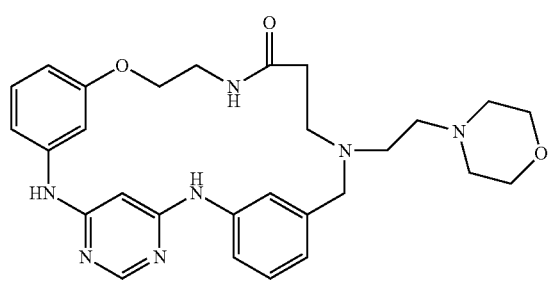
•C$_2$HF$_3$O$_2$; Co. No. 167; Ex. [B20]
TABLE F-1-continued
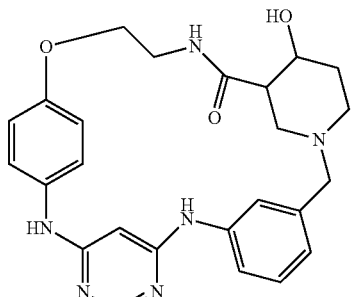
•C$_2$HF$_3$O$_2$; Co. No. 168; Ex. [B20]
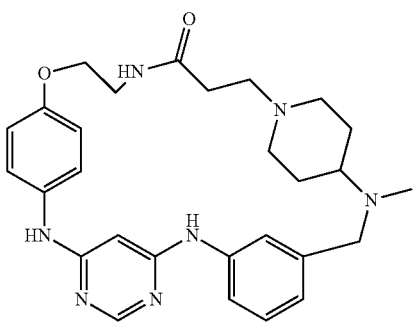
•C$_2$HF$_3$O$_2$; Co. No. 169; Ex. [B20]
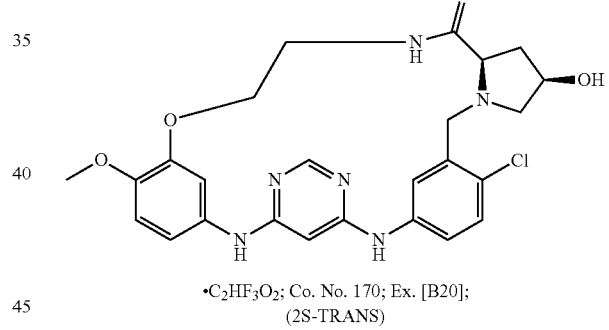
•C$_2$HF$_3$O$_2$; Co. No. 170; Ex. [B20];
(2S-TRANS)
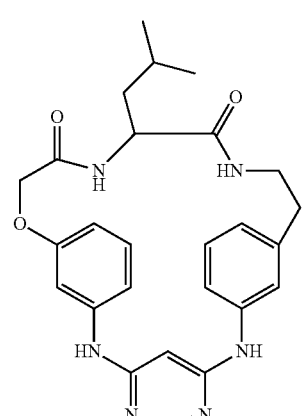
•C$_2$HF$_3$O$_2$; Co. No. 171; Ex. [B22]

TABLE F-1-continued
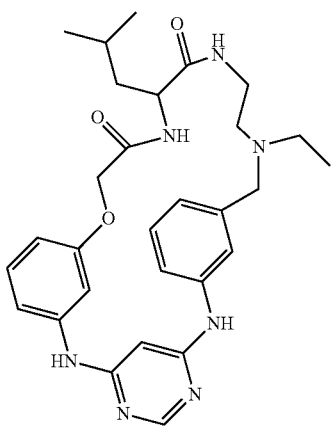
·C₂HF₃O₂; Co. No. 172; Ex. [B22]
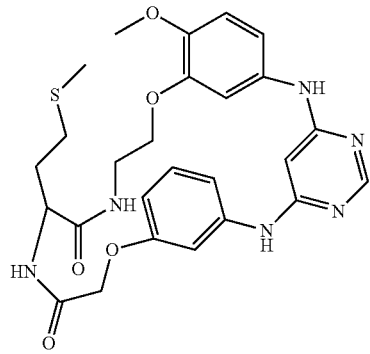
·C₂HF₃O₂; Co. No. 173; Ex. [B21]
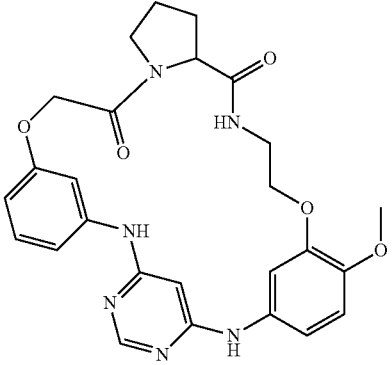
·C₂HF₃O₂; Co. No. 174; Ex. [B22]
TABLE F-1-continued
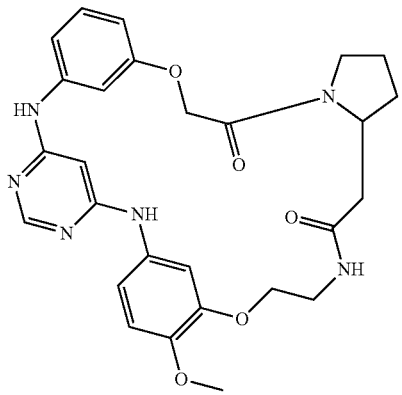
·C₂HF₃O₂; Co. No. 175; Ex. [B22]
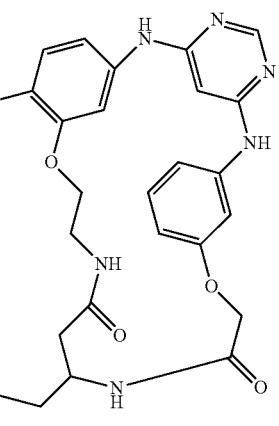
·C₂HF₃O₂; Co. No. 176; Ex. [B21]
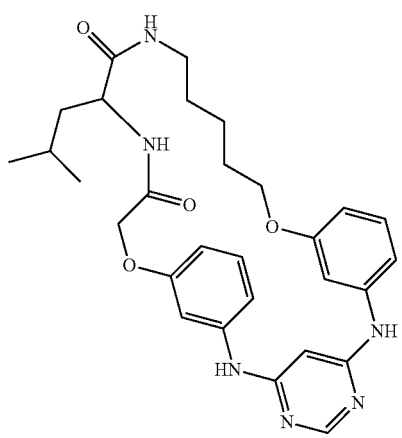
·C₂HF₃O₂; Co. No. 177; Ex. [B21]

TABLE F-1-continued
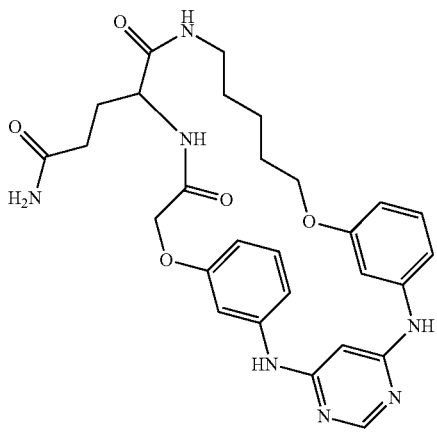
•C₂HF₃O₂; Co. No. 178; Ex. [B21]
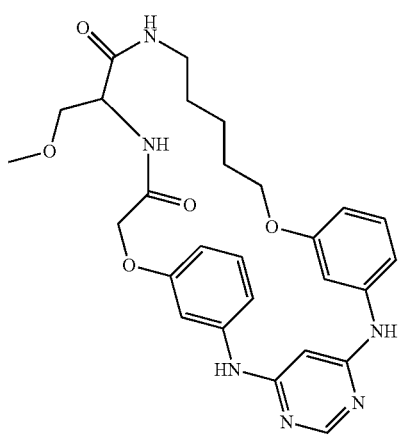
•C₂HF₃O₂; Co. No. 179; Ex. [B21]
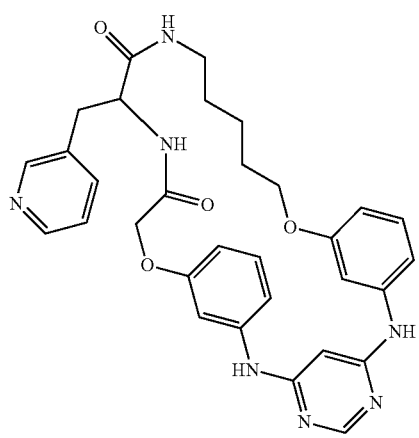
•C₂HF₃O₂; Co. No. 180; Ex. [B21]
TABLE F-1-continued
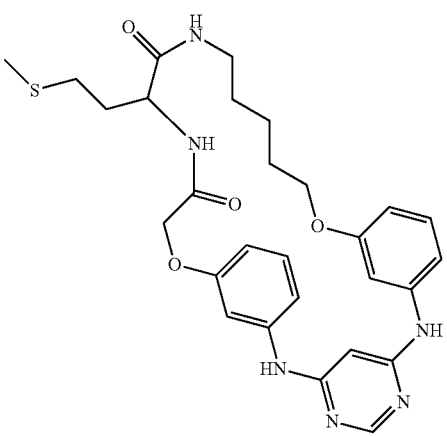
•C₂HF₃O₂; Co. No. 181; Ex. [B21]
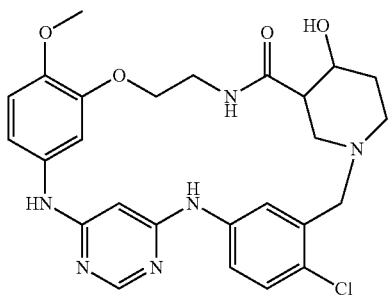
•C₂HF₃O₂; Co. No. 182; Ex. [B20]
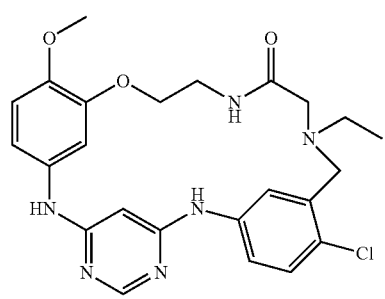
•C₂HF₃O₂; Co. No. 183; Ex. [B20]
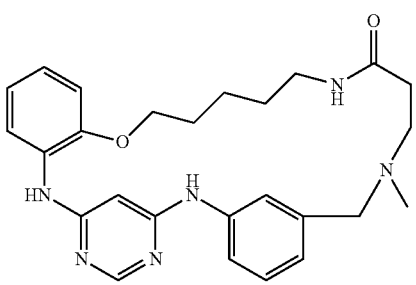
•C₂HF₃O₂; Co. No. 184; Ex. [B20]

TABLE F-1-continued
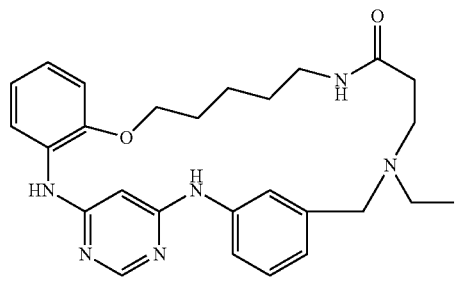
•C₂HF₃O₂; Co. No. 185; Ex. [B20]
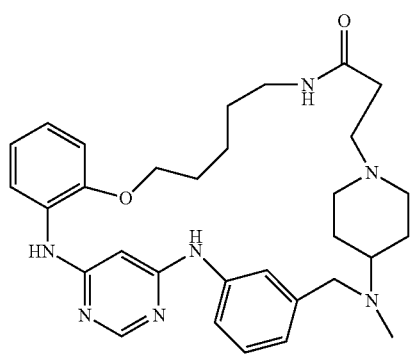
•C₂HF₃O₂; Co. No. 186; Ex. [B20]
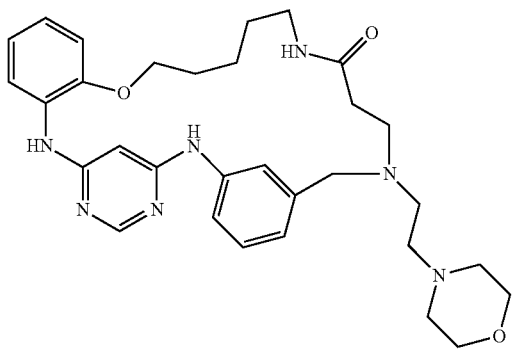
•C₂HF₃O₂; Co. No. 187; Ex. [B20]
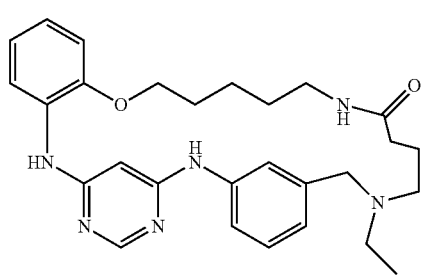
•C₂HF₃O₂; Co. No. 188; Ex. [B20]
TABLE F-1-continued
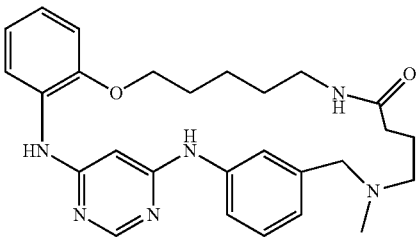
•C₂HF₃O₂; Co. No. 189; Ex. [B20]
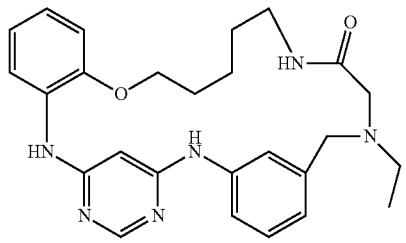
•C₂HF₃O₂; Co. No. 190; Ex. [B20]
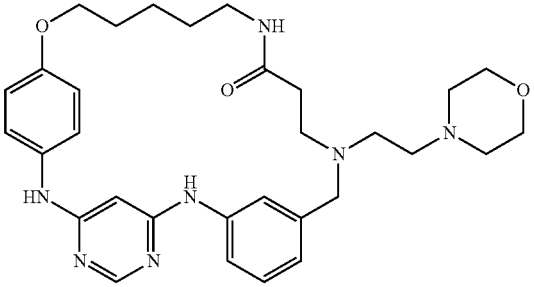
•C₂HF₃O₂; Co. No. 191; Ex. [B20]
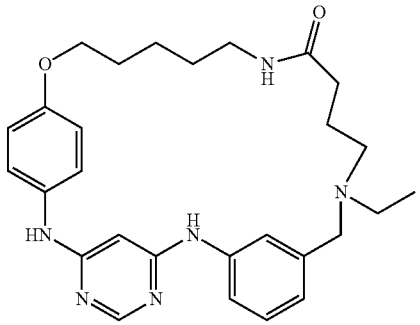
•C₂HF₃O₂; Co. No. 192; Ex. [B20]
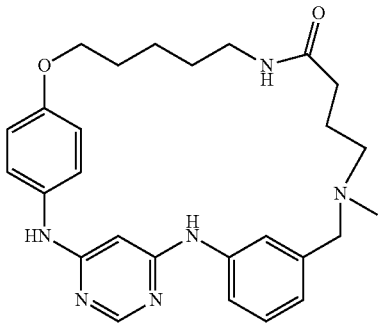
•C₂HF₃O₂; Co. No. 193; Ex. [B20]

TABLE F-1-continued
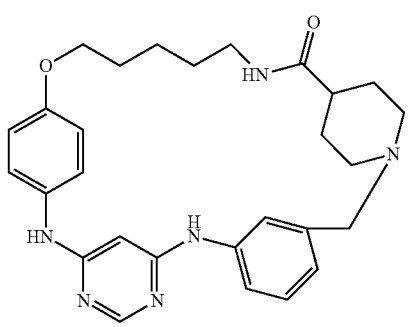
•C₂HF₃O₂; Co. No. 194; Ex. [B20]
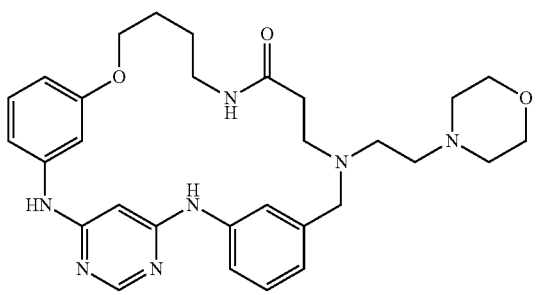
Co. No. 195; Ex. [B20]
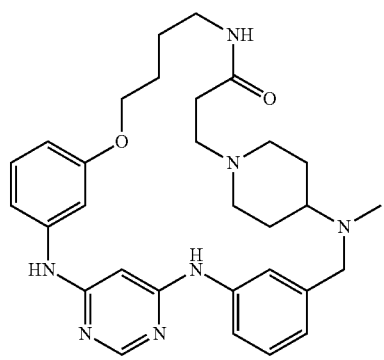
Co. No. 196; Ex. [B20]
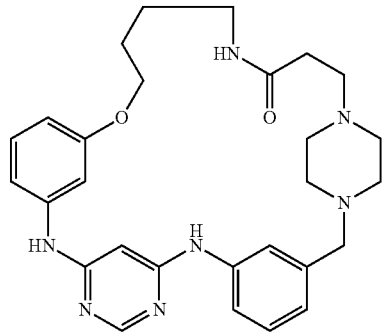
Co. No. 197; Ex. [B19]
TABLE F-1-continued
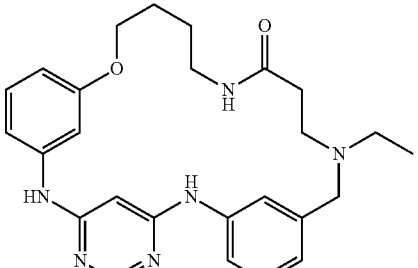
Co. No. 198; Ex. [B20]
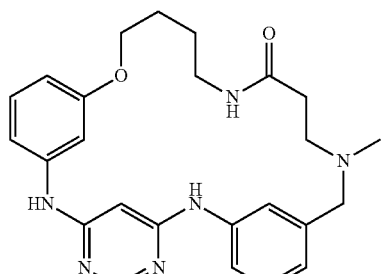
Co. No. 199; Ex. [B20]
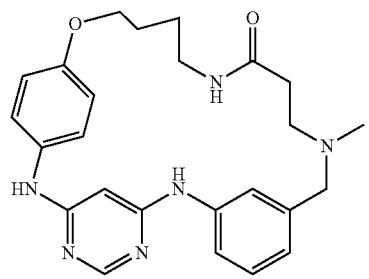
•C₂HF₃O₂; Co. No. 200; Ex. [B20]
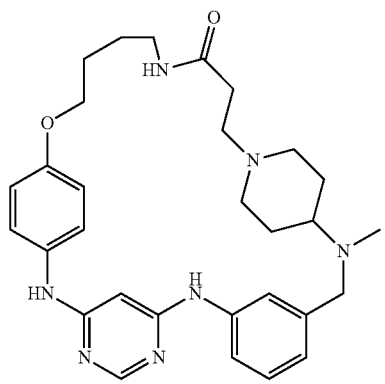
•C₂HF₃O₂; Co. No. 201; Ex. [B20]

TABLE F-1-continued
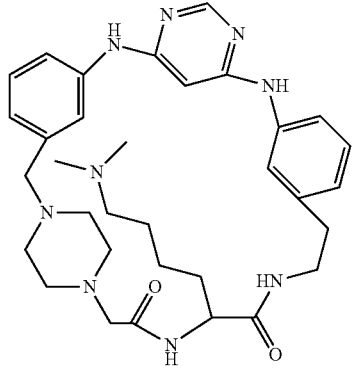
•C₂HF₃O₂; Co. No. 202; Ex. [B24]
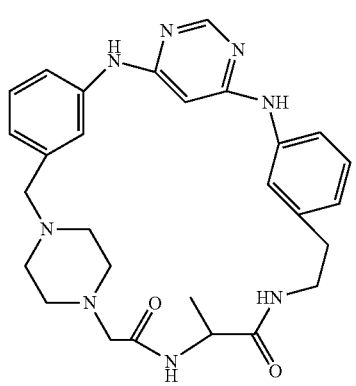
•C₂HF₃O₂; Co. No. 203; Ex. [B24]
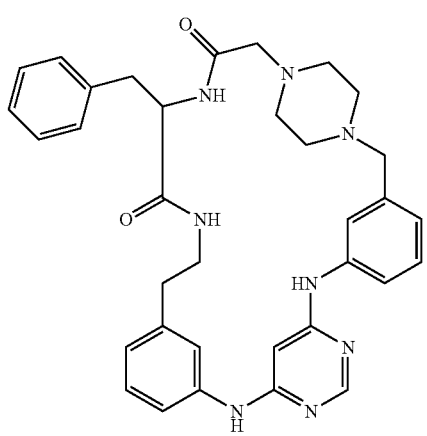
•C₂HF₃O₂; Co. No. 204; Ex. [B24]
TABLE F-1-continued
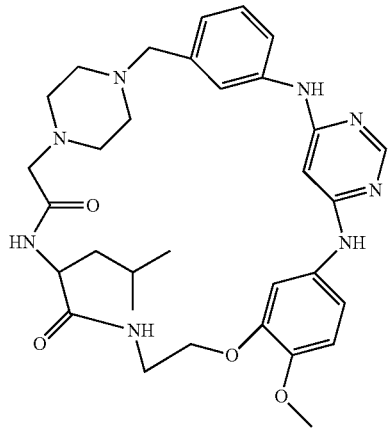
•C₂HF₃O₂; Co. No. 205; Ex. [B24]
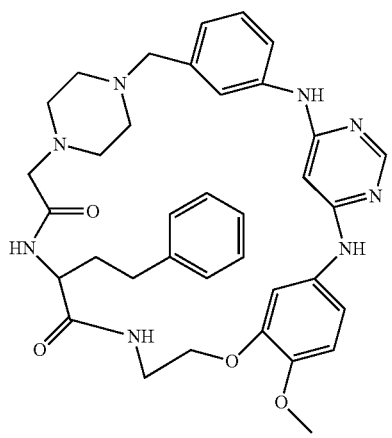
•C₂HF₃O₂; Co. No. 206; Ex. [B24]
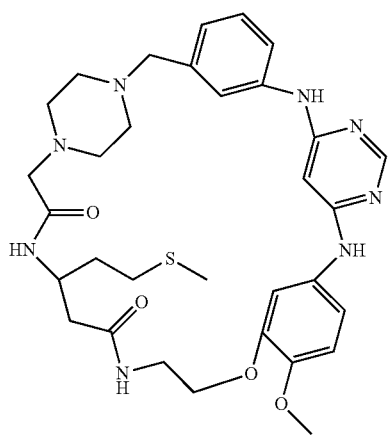
•C₂HF₃O₂; Co. No. 207; Ex. [B24]

TABLE F-1-continued
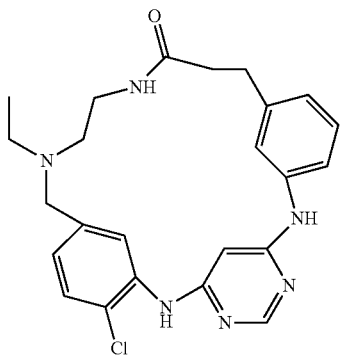
•C₂HF₃O₂; Co. No. 208; Ex. [B20]
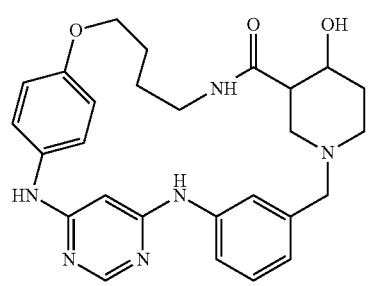
•C₂HF₃O₂; Co. No. 209; Ex. [B20]
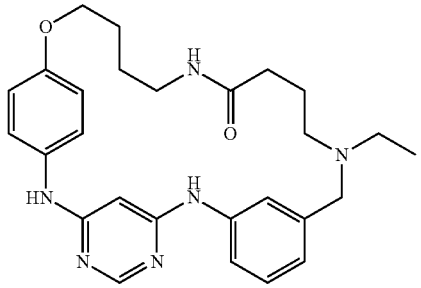
•C₂HF₃O₂; Co. No. 210; Ex. [B20]
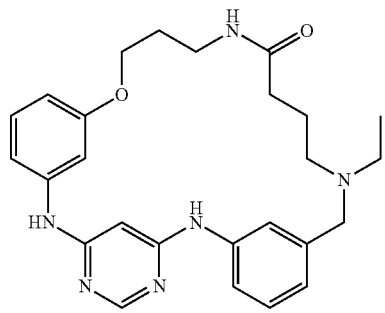
•C₂HF₃O₂; Co. No. 211; Ex. [B20]
TABLE F-1-continued
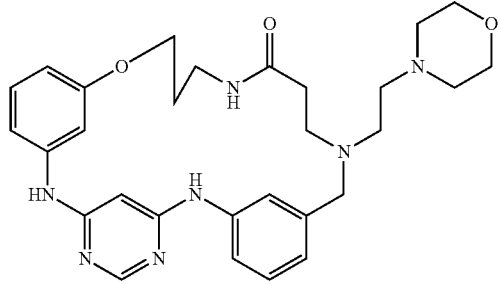
•C₂HF₃O₂; Co. No. 212; Ex. [B20]
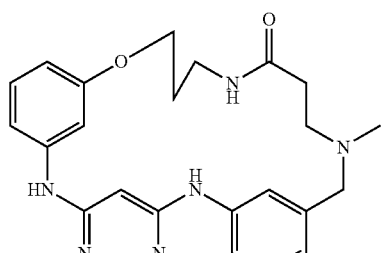
•C₂HF₃O₂; Co. No. 213; Ex. [B20]
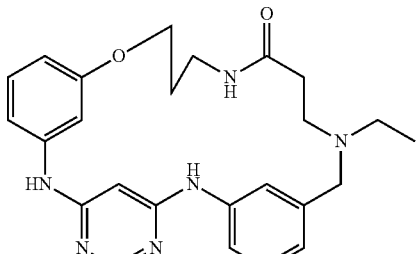
•C₂HF₃O₂; Co. No. 214; Ex. [B20]
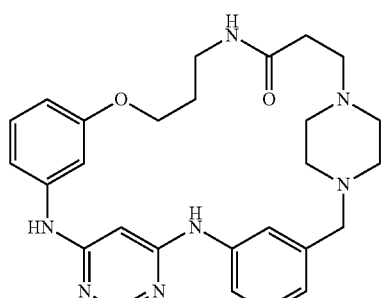
•C₂HF₃O₂; Co. No. 215; Ex. [B19]

TABLE F-1-continued
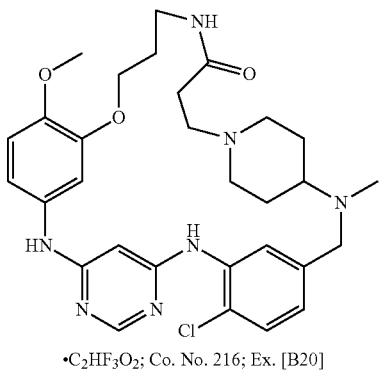 [SMILES: COc1ccc2cc1OCCCNC(=O)CCN1CCC(CC1)N(C)Cc1ccc(Cl)c(c1)Nc1cc(ncn1)N2]
•C₂HF₃O₂; Co. No. 216; Ex. [B20]
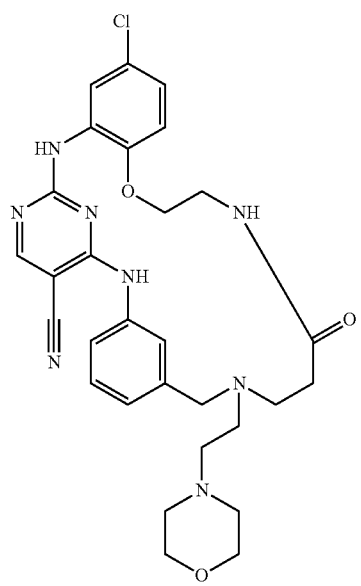
Co. No. 217; Ex. [B20]
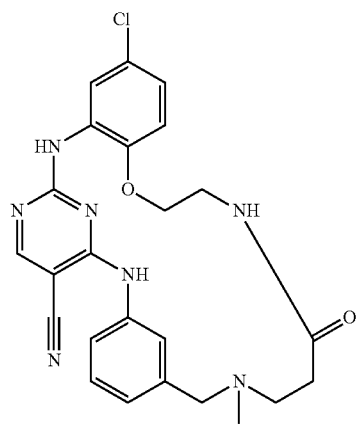
Co. No. 218; Ex. [B20]
TABLE F-1-continued
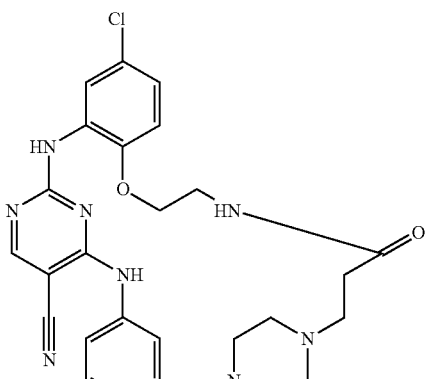
Co. No. 219; Ex. [B19]
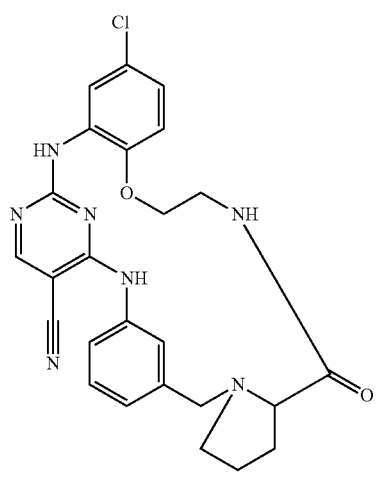
Co. No. 220; Ex. [B20]
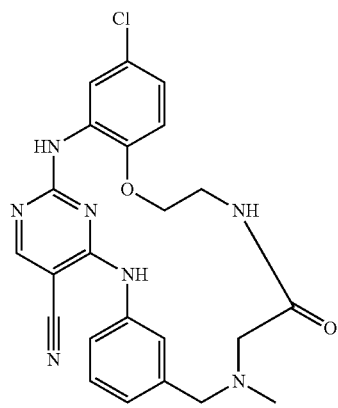
Co. No. 221; Ex. [B20]

TABLE F-1-continued
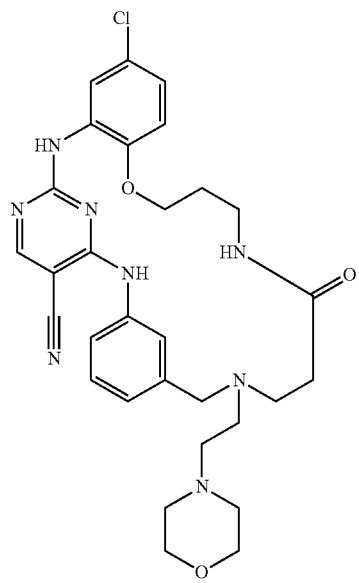
Co. No. 222; Ex. [B20]
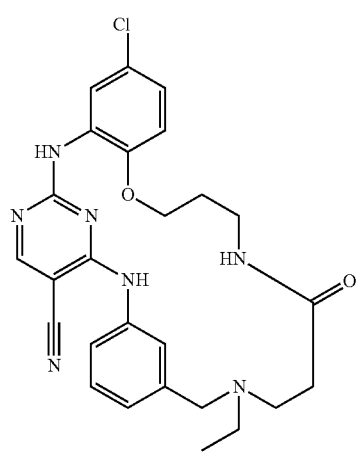
Co. No. 223; Ex. [B20]
TABLE F-1-continued
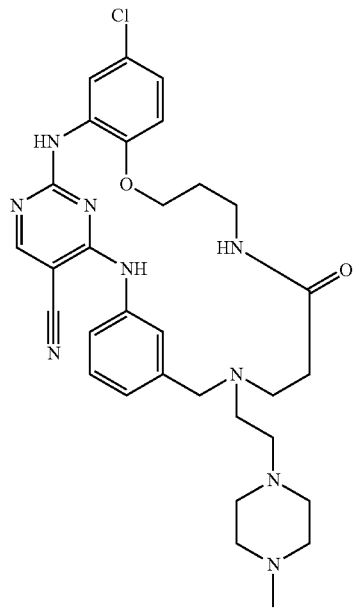
Co. No. 224; Ex. [B20]
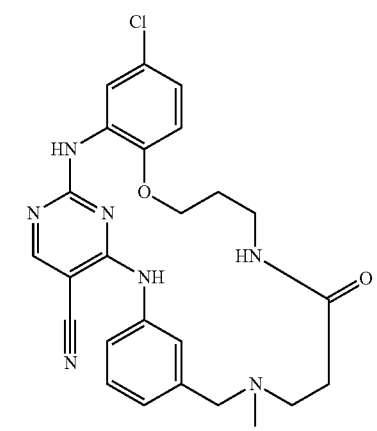
Co. No. 225; Ex. [B20]
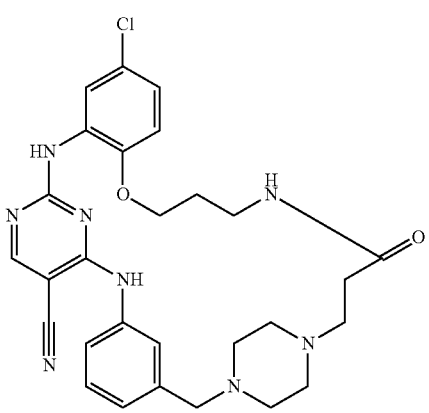
Co. No. 226; Ex. [B19]

TABLE F-1-continued
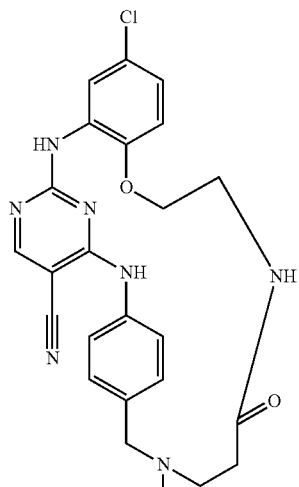
Co. No. 227; Ex. [B20]
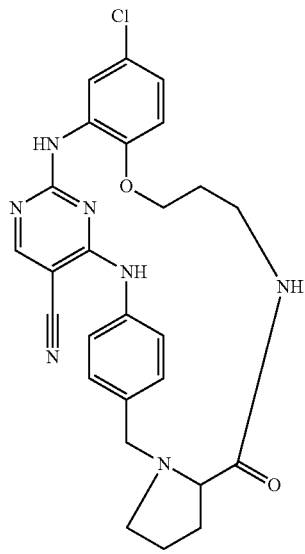
Co. No. 229; Ex. [B20]
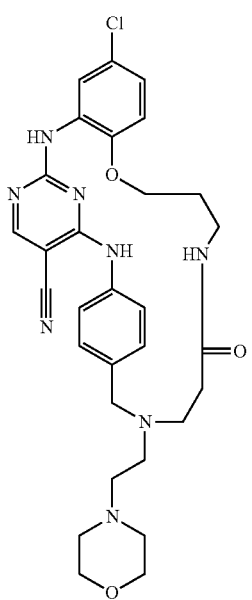
Co. No. 228; Ex. [B20]
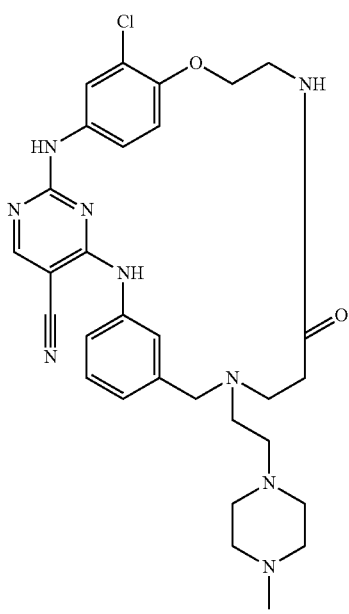
Co. No. 230; Ex. [B20]

TABLE F-1-continued
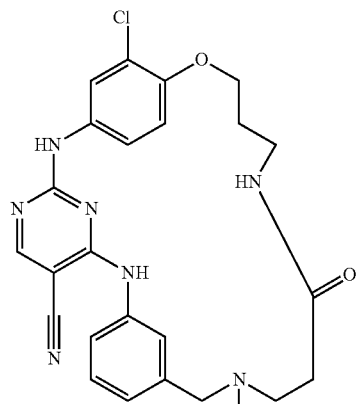
Co. No. 231; Ex. [B20]
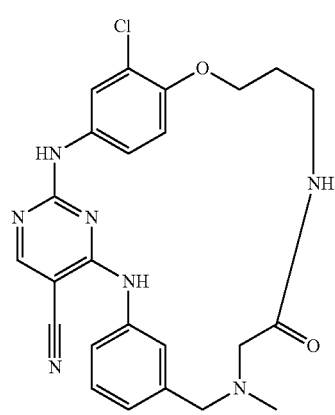
Co. No. 232; Ex. [B20]
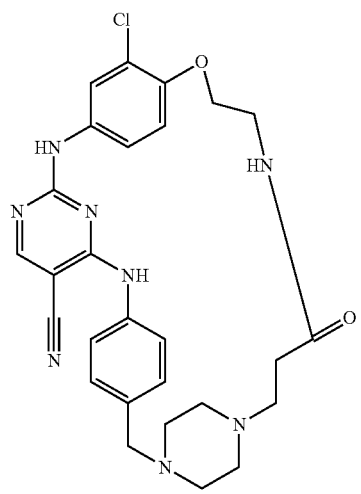
Co. No. 233; Ex. [B19]
TABLE F-1-continued
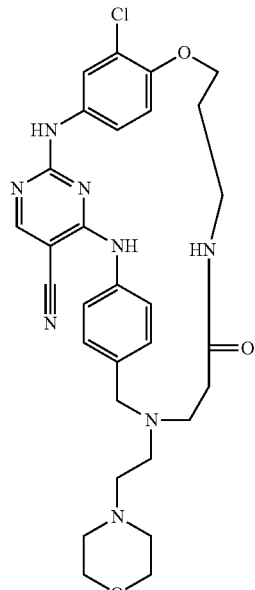
Co. No. 234; Ex. [B20]
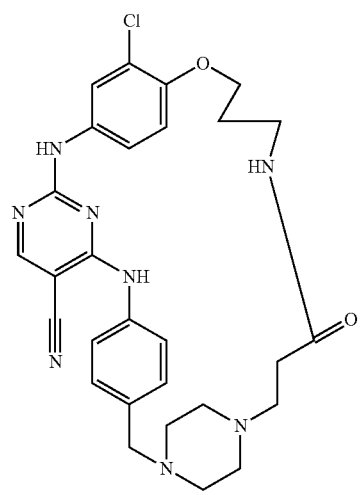
Co. No. 235; Ex. [B19]
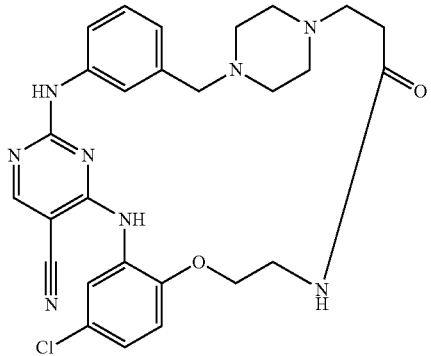
Co. No. 236; Ex. [B19]

TABLE F-1-continued
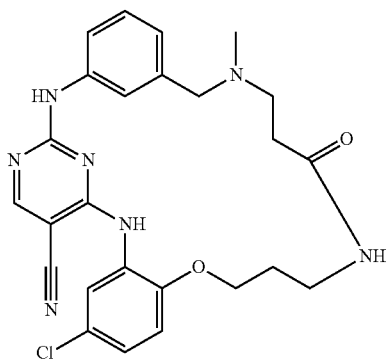
Co. No. 237; Ex. [B20]
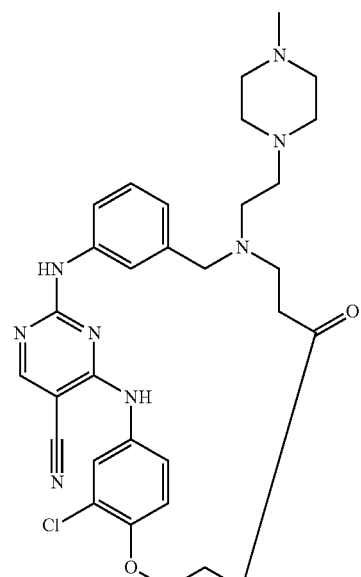
Co. No. 238; Ex. [B20]
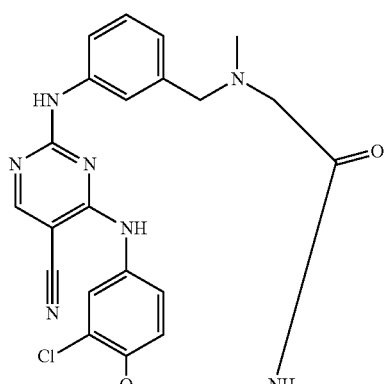
Co. No. 239; Ex. [B20]
TABLE F-1-continued
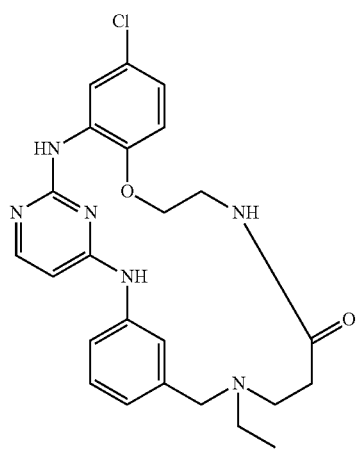
Co. No. 240; Ex. [B20]
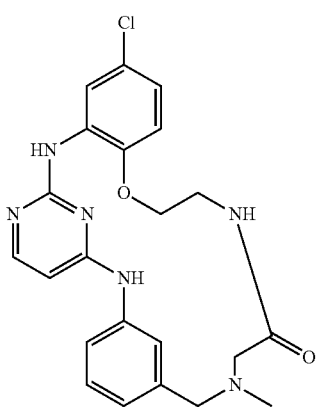
Co. No. 241; Ex. [B20]
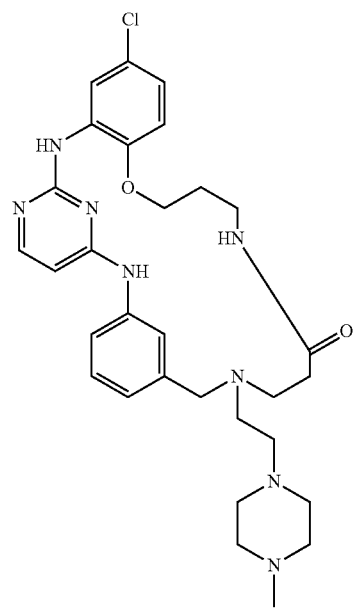
Co. No. 242; Ex. [B20]

TABLE F-1-continued
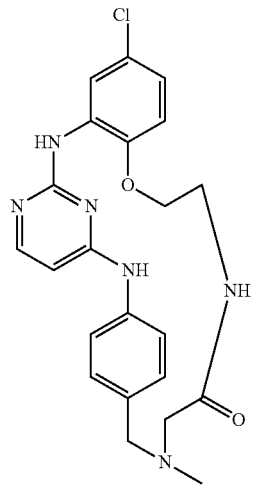
Co. No. 243; Ex. [B20]
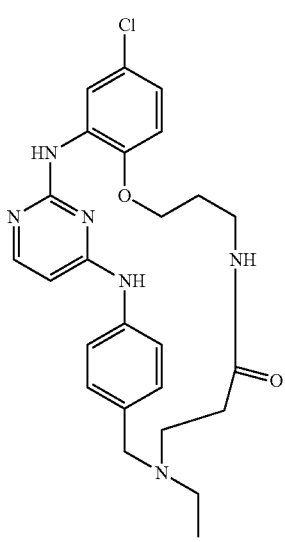
Co. No. 244; Ex. [B20]
TABLE F-1-continued
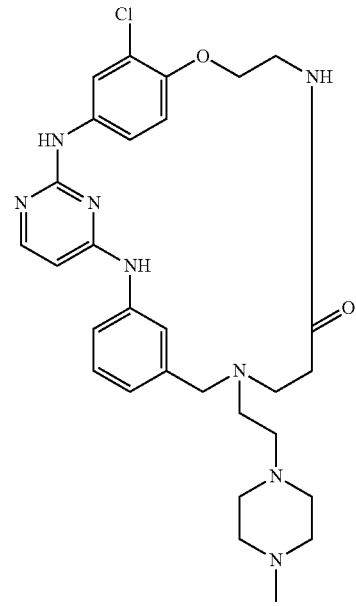
Co. No. 245; Ex. [B20]
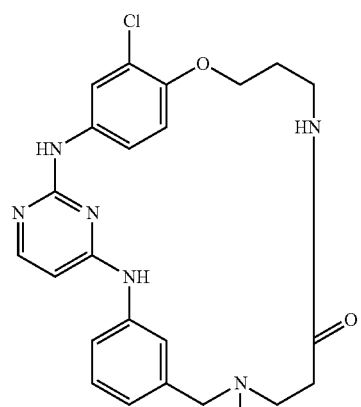
Co. No. 246; Ex. [B20]
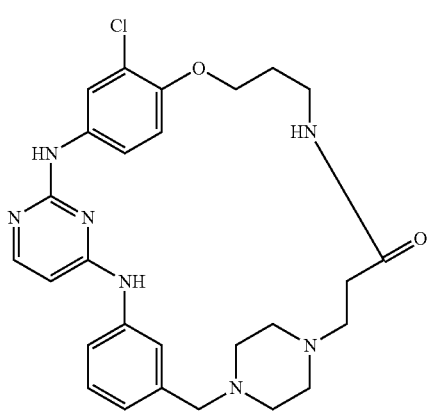
Co. No. 247; Ex. [B19]

TABLE F-1-continued
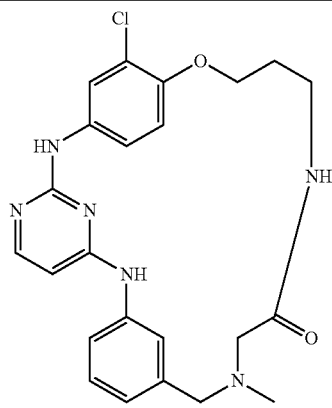
Co. No. 248; Ex. [B20]
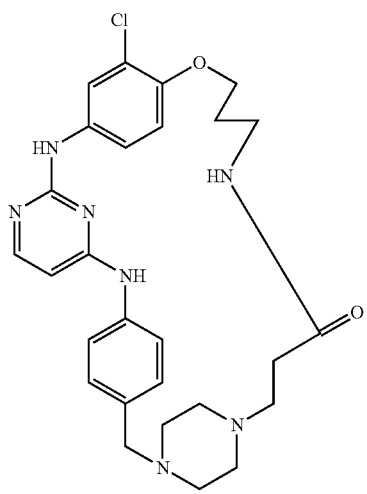
Co. No. 249; Ex. [B19]
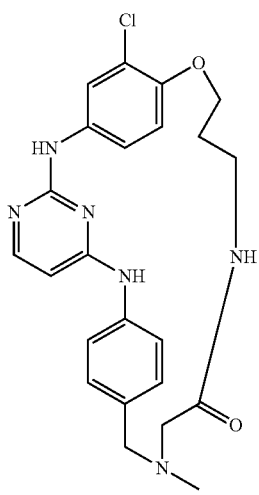
Co. No. 250; Ex. [B20]
TABLE F-1-continued
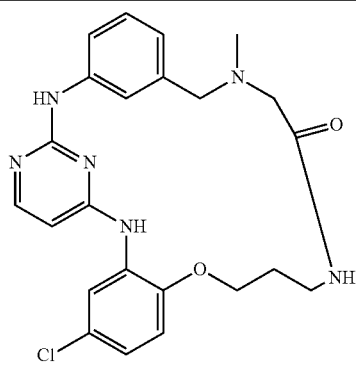
Co. No. 251; Ex. [B20]
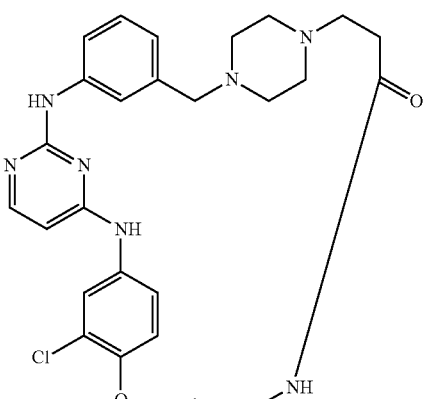
Co. No. 252; Ex. [B19]
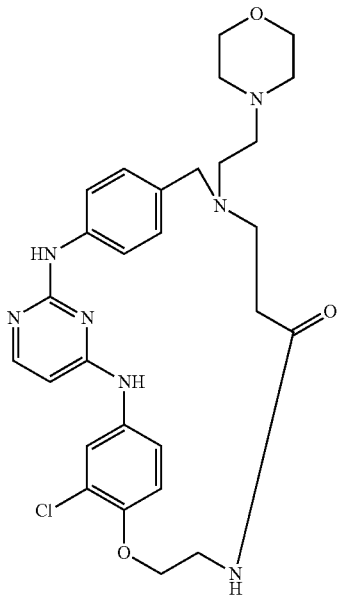
Co. No. 253; Ex. [B20]

TABLE F-1-continued
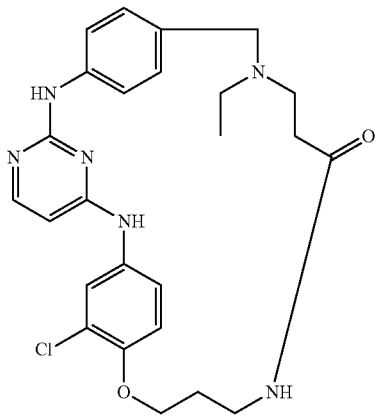
Co. No. 254; Ex. [B20]
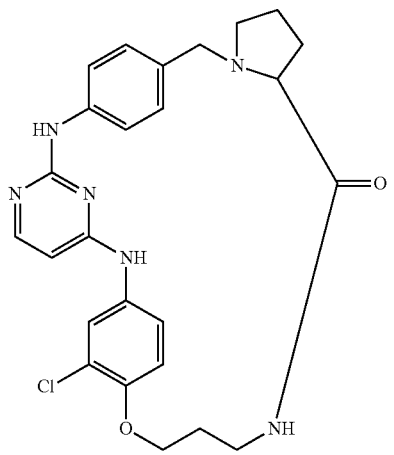
Co. No. 255; Ex. [B20]
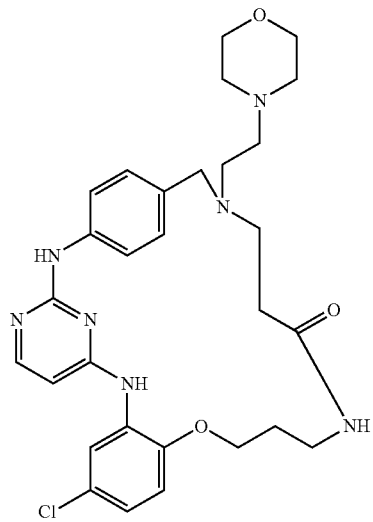
Co. No. 256; Ex. [B20]
TABLE F-1-continued
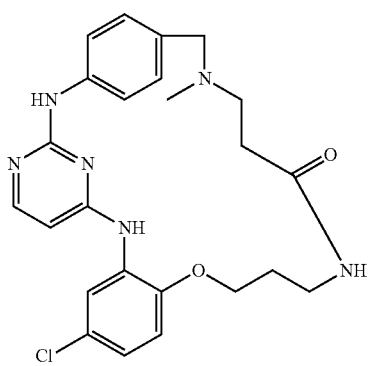
Co. No. 257; Ex. [B20]
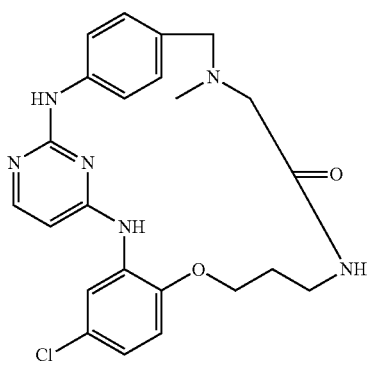
Co. No. 258; Ex. [B20]
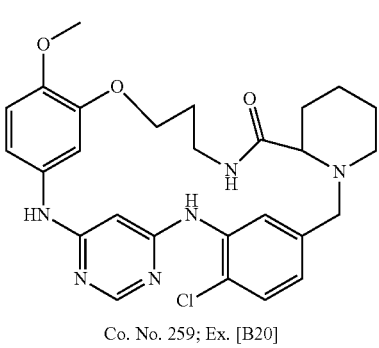 [SMILES: COc1ccc2cc1OCCCNC(=O)C1CCCCN1Cc1ccc(Cl)c(c1)Nc1cc(ncn1)N2]
Co. No. 259; Ex. [B20]
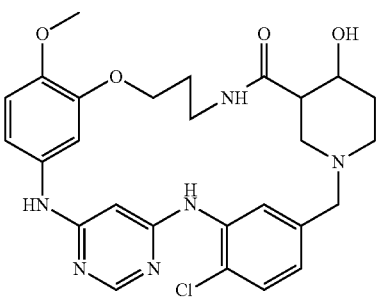
Co. No. 260; Ex. [B20]

TABLE F-1-continued

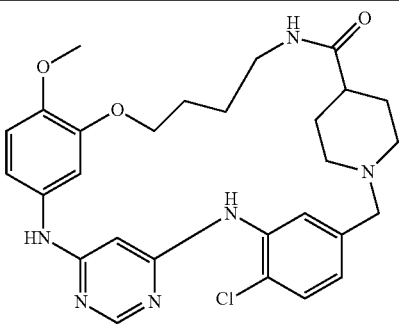

Co. No. 261; Ex. [B20]

Compound Identification

LCMS-Methods:

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode.

Method 1:

Reversed phase HPLC was carried out on a Xterra MS C18 column (3.5 mm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 uL was used.

Method 2:

Reversed phase HPLC was carried out on a Chromolith (4.6×25 mm) with a flow rate of 3 ml/min. Three mobile phases (mobile phase A 95% 25 mM ammoniumacetate+5% acetonitrile; mobile phase B: acetonitrile; mobile phase C: methanol) were employed to run a gradient condition from 96% A to 2% B and 2% C in 0.9 minutes, to 49% B and 49% C in 0.3 minute, 100% B for 0.2 minute. An injection volume of 2 uL was used.

Method 3:

Reversed phase HPLC was carried out on a Xterra MS C18 column (3.5 mm, 4.6×100 mm) with a flow rate of 1.6 ml/min. Two mobile phases (mobile phase A methanol/H2O; mobile phase B 0.1% formic acid) were employed to run a gradient condition from 100% B to 5% B 12 minutes. An injection volume of 10 uL was used.

Method 4:

Reversed phase HPLC was carried out on a Xterra MS C18 column (3.5 mm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 30% A, 35% B; 35% C in 3 minutes to 50% B and 50% C in 3.5 minutes, to 100% B in 0.5 minute. An injection volume of 10 uL was used.

Method 5:

Reversed phase HPLC was carried out on a Kromasil C18 column (3.5 mm, 4.6×100 mm) with a flow rate of 1 ml/min. Three mobile phases (mobile phase A ammoniumacetate; mobile phase B: acetonitrile; mobile phase C: formic acid) were employed to run a gradient condition from 30% A, 40% B, 30% C for 1 minute to 100% B for 5 minutes. An injection volume of 10 uL was used.

Method 6:

Reversed phase HPLC was carried out on a Xterra MS C18 column (3.5 mm, 3.9×150 mm) with a flow rate of 1 ml/min. Three mobile phases (mobile phase A ammoniumacetate; mobile phase B: acetonitrile; mobile phase C: formic acid) were employed to run a gradient condition from 85% A, 15% B for 3 minute to 80% B for 6 minutes. An injection volume of 10 uL was used.

TABLE retention time (RT in minutes) and molecular weight as the MH+

| Co. No. | method LCMS | Rt | MH+ |
|---|---|---|---|
| 2 | 1 | 3.96 | 374 |
| 3 | 1 | 3.05 | 373 |
| 5 | 1 | 3.09 | 400 |
| 6 | 3 | 7.78 | 552 |
| 7 | 1 | 6.17 | 441 |
| 8 | 1 | 3.48 | 431 |
| 9 | 4 | 5.15 | 348 |
| 10 | 1 | 4.08 | 431 |
| 11 | 1 | 3.79 | 435 |
| 12 | 6 | 8.6 | 553 |
| 13 | 6 | 7.81 | 442 |
| 14 | 1 | 2.83 | 391 |
| 15 | 1 | 4.53 | 511 |
| 16 | 5 | 2.8 | 516 |
| 17 | 4 | 5.42 | 400 |
| 18 | 1 | 4.47 | 415 |
| 19 | 1 | 4.77 | 376 |
| 20 | 3 | 6.92 | 373 |
| 21 | 1 | 4.77 | 404 |
| 22 | 1 | 4.38 | 390 |
| 23 | 2 | 0.73 | 348 |
| 25 | 3 | 9.09 | 417 |
| 26 | 1 | 5.16 | 431 |
| 27 | 3 | 8.44 | 403 |
| 28 | 3 | 9.12 | 417 |
| 31 | 3 | 6.9 | 538 |
| 34 | 1 | 5.95 | 441 |
| 37 | 1 | 7.1 | 499 |
| 41 | 1 | 3.67 | 417 |
| 42 | 2 | 0.7 | 417 |
| 43 | 3 | 3.18 | 415 |
| 44 | 2 | 0.81 | 429 |
| 45 | 1 | 3.5 | 399 |
| 46 | 4 | 5.29 | 408 |
| 47 | 2 | 0.66 | 332 |
| 48 | 2 | 0.71 | 392 |
| 49 | 2 | 0.83 | 461 |
| 50 | 4 | 5.78 | 375 |
| 51 | 4 | 5.35 | 446 |
| 52 | 4 | 5.37 | 444 |
| 53 | 2 | 0.89 | 401 |
| 54 | 2 | 0.93 | 461 |
| 55 | 2 | 0.84 | 403 |
| 56 | 2 | 0.73 | 470 |
| 57 | 2 | 4.21 | 445 |
| 58 | 2 | 3.75 | 417 |
| 59 | 2 | 0.6 | 474 |
| 61 | 2 | 0.6 | 432 |
| 62 | 1 | 3.65 | 449 |
| 63 | 2 | 0.65 | 389 |
| 64 | 2 | 0.65 | 419 |
| 65 | 2 | 0.63 | 455 |
| 66 | 4 | 4.85 | 431 |
| 67 | 4 | 5.45 | 557 |
| 68 | 4 | 5.53 | 530 |
| 69 | 4 | 6.1 | 514 |
| 70 | 4 | 5.75 | 532 |
| 71 | 4 | 6.08 | 532 |
| 72 | 4 | 5.73 | 472 |
| 73 | 4 | 5.6 | 472 |

TABLE-continued retention time (RT in minutes) and molecular weight as the MH+

| Co. No. | method LCMS | Rt | MH+ |
|---|---|---|---|
| 74 | 4 | 6.43 | 628 |
| 75 | 4 | 6.87 | 628 |
| 76 | 4 | 7.32 | 649 |
| 77 | 4 | 5.78 | 617 |
| 78 | 4 | 5.78 | 617 |
| 79 | 4 | 6.31 | 574 |
| 80 | 4 | 6.68 | 574 |
| 81 | 4 | 5.75 | 562 |
| 82 | 4 | 6.07 | 562 |
| 83 | 4 | 6.65 | 638 |
| 84 | 4 | 5.63 | 626 |
| 85 | 4 | 6.18 | 583 |
| 86 | 4 | 6.71 | 583 |
| 87 | 4 | 5.83 | 527 |
| 88 | 1 | 4.19 | 461 |
| 90 | 1 | 4.33 | 475 |
| 91 | 1 | 3.84 | 475 |
| 92 | 1 | 3.41 | 477 |
| 93 | 1 | 2.85 | 489 |
| 94 | 1 | 3.44 | 490 |
| 95 | 4 | 5.42 | 477 |
| 96 | 4 | 5.55 | 461 |
| 97 | 4 | 5.13 | 518 |
| 98 | 4 | 6.26 | 525 |
| 99 | 4 | 5.43 | 491 |
| 100 | 4 | 5.91 | 449 |
| 101 | 4 | 4.98 | 463 |
| 102 | 4 | 6.16 | 511 |
| 103 | 6 | 7.2 | 483 |
| 104 | 6 | 6.73 | 576 |
| 105 | 6 | 7.74 | 525 |
| 106 | 6 | 7.43 | 624 |
| 107 | 6 | 7.03 | 596 |
| 108 | 6 | 6.53 | 438 |
| 109 | 1 | 3.46 | 521 |
| 110 | 3 | 0.78 | 400 |
| 118 | 4 | 5.36 | 435 |
| 119 | 1 | 3.46 | 601 |
| 120 | 1 | 3.86 | 601 |
| 121 | 3 | 4.65 | 495 |
| 122 | 3 | 4.61 | 469 |
| 123 | 1 | 4.53 | 483 |
| 113 | 3 | 6.37 | 497 |
| 124 | 3 | 6.14 | 538 |
| 125 | 3 | 6.83 | 582 |
| 126 | 3 | 4.72 | 595 |
| 127 | 3 | 5.72 | 566 |
| 128 | 3 | 7.15 | 446 |
| 115 | 3 | 3.89 | 504 |
| 129 | 3 | 7.18 | 461 |
| 130 | 3 | 7.23 | 461 |
| 131 | 3 | 6.38 | 459 |
| 132 | 3 | 7.86 | 509 |
| 133 | 3 | 3.16 | 575 |
| 134 | 3 | 5.82 | 532 |
| 135 | 3 | 7.33 | 572 |
| 136 | 3 | 4.71 | 532 |
| 137 | 3 | 4.93 | 573 |
| 138 | 3 | 4.38 | 564 |
| 139 | 3 | 7.36 | 521 |
| 140 | 3 | 6.22 | 519 |
| 141 | 3 | 7.71 | 535 |
| 142 | 3 | 3.09 | 573 |
| 143 | 3 | 5.59 | 530 |
| 144 | 3 | 5.56 | 570 |
| 146 | 3 | 4.96 | 509 |
| 147 | 3 | 4.35 | 523 |
| 148 | 3 | 3.4 | 531 |
| 149 | 3 | 3.6 | 488 |
| 150 | 3 | 4.35 | 470 |
| 151 | 3 | 4.32 | 458 |
| 152 | 3 | 6.34 | 536 |
| 154 | 3 | 4.58 | 559 |
| 155 | 3 | 3.05 | 547 |
| 156 | 3 | 6.46 | 661 |
| 157 | 3 | 5.08 | 557 |
| 158 | 3 | 4.48 | 548 |
| 114 | 3 | 7.89 | 650 |
| 159 | 3 | 2.3 | 600 |
| 160 | 3 | 6.11 | 362 |
| 161 | 3 | 4.39 | 419 |
| 162 | 3 | 6.24 | 408 |
| 163 | 3 | 8.29 | 420 |
| 164 | 3 | 4.33 | 444 |
| 165 | 3 | 2.95 | 501 |
| 112 | 3 | 5.89 | 502 |
| 116 | 4 | 5.48 | 475 |
| 171 | 4 | 5.97 | 475 |
| 172 | 4 | 6.37 | 532 |
| 173 | 4 | 5.51 | 539 |
| 174 | 4 | 5.38 | 505 |
| 175 | 4 | 5.49 | 519 |
| 176 | 4 | 5.69 | 535 |
| 177 | 4 | 6.38 | 533 |
| 178 | 4 | 5.6 | 548 |
| 179 | 4 | 6.02 | 521 |
| 180 | 4 | 5.84 | 568 |
| 181 | 4 | 6.15 | 551 |
| 117 | 4 | 6.04 | 557 |
| 202 | 4 | 5.04 | 600 |
| 203 | 4 | 5.56 | 515 |
| 204 | 4 | 5.99 | 591 |
| 205 | 4 | 5.84 | 603 |
| 206 | 4 | 6.18 | 651 |
| 207 | 4 | 5.77 | 635 |
| 208 | 4 | 4.3 | 451 |

C. Pharmacological Examples

The in vitro inhibition of a panel of kinases was assessed using either the glass-fiber filter technology as described by Davies, S. P. et al., Biochem J. (2000), 351; p. 95-105.

In the glass-fiber filter technology the activity of the kinase of interest is measured using an appropriate substrate that is incubated with the aforementioned kinase protein in the presence of ($^{33}$P) radiolabeled ATP. ($^{33}$P) Phosporylation of the substrate is subsequently measured as radioactivity bound on a glassfiber-filter.

DETAILED DESCRIPTION

All kinases are pre-diluted to a 10x working concentration prior to addition into the assay. The composition of the dilution buffer for each kinase is detailed below.

| Buffer Composition | Kinase(s) |
|---|---|
| 50 mM Tris pH 7.5, 0.1 mM EGTA, 0.1 mM Na3VO4, 0.1%-mercaptoethanol, 1 mg/ml BSA | CSK, Lyn |
| 20 mM MOPS pH 7.0, 1 mM EDTA, 0.1%-mercaptoethanol, 0.01% Brij-35, 5% glycerol, 1 mg/ml BSA | Abl, EGFR, Fes, Fms, Flt3, Fyn, GSK3, Lck, Yes |

All substrates are dissolved and diluted to working stocks in de-ionised water, apart from histone H1 (10x working stock in 20 mM MOPS pH 7.4), PDKtide (10x working stock in 50 mM Tris pH 7.0) and ATF2 (which is typically stored at a 20× working stock in 50 mM Tris pH 7.5, 150 mM NaCl, 0.1 mM EGTA, 0.03% Brij-35, 50% glycerol, 1 mM benzamidine, 0.2 mM PMSF and 0.1% β-mercaptoethanol).

Example C.1

Abl Human

In a final reaction volume of 25 µl, Abl (h) (5-10 mU) is incubated with 8 mM MOPS pH 7.0, 0.2 mM EDTA, 50 µM EAIYAAPFAKKK, 10 mM MgAcetate and [-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Example C.2

CSK Human

In a final reaction volume of 25 µl, CSK (h) (5-10 mU) is incubated with 50 mM Tris pH 7.5, 0.1 mM EGTA, 0.1 mM Na3VO4, 0.1%—mercaptoethanol, 0.1 mg/ml poly(Glu, Tyr) 4:1, 10 mM MnCl2, 10 mM MgAcetate and [-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Example C.3 cSRC Human

In a final reaction volume of 25 µl, cSRC (h) (5-10 mU) is incubated with 8 mM MOPS pH 7.0, 0.2 mM EDTA, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution.

10 µl of the reaction is then spotted onto a P30 filtermat and washed three times for 5 minutes in 75 mM phosphoric acid and once in methanol prior to drying and scintillation counting.

Example C.4

EGFR Human

In a final reaction volume of 25 µl, EGFR (h) (5-10 mU) is incubated with 8 mM MOPS pH 7.0, 0.2 mM EDTA, 10 mM MnCl2, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Example C.5

Fes Human

In a final reaction volume of 25 µl, Fes (h) (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Example C.6

Flt3 Human

In a final reaction volume of 25 µl, Flt3 (h) (5-10 mU) is incubated with 8 mM MOPS pH 7.0, 0.2 mM EDTA, 50 µM EAIYAAPFAKKK, 10 mM MgAcetate and [γ-$^{33}$P-ATP] (specific activity approx. 500 cpm/pmol, concentration as required).

The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Example C.7

Fms Human

In a final reaction volume of 25 µl, Fms (h) (5-10 mU) is incubated with 8 mM MOPS pH 7.0, 0.2 mM EDTA, 250 µM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Example C.8

GSK3β Human

In a final reaction volume of 25 µl, GSK3β (h) (5-10 mU) is incubated with 8 mM MOPS pH 7.0, 0.2 mM EDTA, 20 µM YRRAAVPPSPSLSRHSSPHQS(p)EDEEE (phospho GS2 peptide), 10 mM MgAcetate and [-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 50 mM phosphoric acid and once in methanol prior to drying and scintillation counting.

Example C.9

Lck Human

In a final reaction volume of 25 µl, Lck (h) (5-10 mU) is incubated with 50 mM Tris pH 7.5, 0.1 mM EGTA, 0.1 mM Na3VO4, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution.

10 µl of the reaction is then spotted onto a P30 filtermat and washed three times for 5 minutes in 75 mM phosphoric acid and once in methanol prior to drying and scintillation counting.

Example C.10

Lyn Human

In a final reaction volume of 25 µl, Lyn (h) (5-10 mU) is incubated with 50 mM Tris pH 7.5, 0.1 mM EGTA, 0.1 mM Na3VO4, 0.1% β-mercaptoethanol, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Example C.11

Yes Human

In a final reaction volume of 25 µl, Yes (h) (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

The following tables provides the scores for the compounds according to the invention, obtained at a test concentration of 10$^{-6}$M using the above mentioned kinase assays. Score 1=10-30% inhibition, Score 2=30-60% inhibition, Score 3=60-80% inhibition and Score 4=>80% inhibition.

| Cpd No. | C1 | C2 | C3 | C4 | C4 | C6 | C7 | C8 | C9 | C10 | C11 |
|---|---|---|---|---|---|---|---|---|---|---|---|
| 103 | 4 | 2 | 4 | 4 | 3 | | | 1 | 4 | 4 | 4 |
| 12 | 2 | | | 4 | 4 | 2 | | | | 4 | 4 | 4 |
| 36 | 2 | 1 | 1 | 4 | 1 | 1 | 1 | | | 2 | 3 | 1 |
| 37 | 2 | 1 | 1 | 3 | 1 | | | 1 | 1 | 2 | 2 | 1 |

-continued

| Cpd No. | C1 | C2 | C3 | C4 | C4 | C6 | C7 | C8 | C9 | C10 | C11 |
|---|---|---|---|---|---|---|---|---|---|---|---|
| 39 | | 1 | | | 1 | | 1 | 1 | 1 | | |
| 38 | | 1 | 1 | 3 | | | 2 | 1 | | 1 | 1 |
| 40 | | | | 4 | | 1 | | 1 | 1 | | 4 |
| 8 | 1 | 1 | | 1 | | | 2 | | | 1 | 1 |
| 34 | | 1 | 1 | 2 | 1 | 1 | 1 | | 1 | 1 | 1 |
| 41 | | | | | 1 | | | 1 | | 1 | |
| 57 | | | | | | 2 | | | | | |
| 58 | | 3 | | | | | 1 | 2 | | 1 | |
| 60 | | | | | | | | 1 | | | 1 |
| 61 | | | | | | | | 3 | | | 1 |
| 109 | | | | | | | | | 1 | 1 | 1 |
| 108 | | | | | | | | | | | 1 |
| 35 | 4 | 1 | 1 | 2 | 1 | 2 | 2 | 1 | 2 | 2 | 3 |
| 42 | | 2 | 1 | | | 2 | 2 | 1 | 2 | | 3 |
| 43 | | | | 2 | | 2 | 2 | | 1 | 2 | 1 |
| 13 | 1 | | 1 | 4 | | | | | 2 | 4 | 4 |
| 105 | 4 | 2 | 4 | 4 | 3 | | 1 | 1 | 4 | 4 | 4 |
| 106 | 4 | 3 | 4 | 4 | 4 | 1 | 1 | 1 | 4 | 4 | 4 |
| 107 | 4 | 3 | 4 | 4 | 4 | | | | 4 | 4 | 4 |
| 27 | 1 | | | 1 | 1 | 3 | 2 | 2 | 2 | 1 | 1 |
| 28 | 1 | 1 | 2 | | 1 | 3 | 2 | 3 | 2 | 1 | 3 |
| 25 | 1 | 2 | 1 | 1 | 3 | 4 | 2 | 2 | 2 | 1 | 1 |
| 2 | 1 | | 2 | | 1 | 4 | 2 | 3 | 2 | 1 | 2 |
| 20 | 1 | | 1 | 1 | 1 | 2 | 1 | 3 | | | 1 |
| 29 | | 1 | | | 4 | 1 | | 2 | | | 3 |
| 26 | 1 | 1 | 1 | 1 | 2 | 3 | 2 | 1 | 1 | 2 | 1 |
| 3 | | 1 | 1 | | 1 | 2 | 2 | | 1 | | 1 |
| 18 | 1 | | | 1 | 1 | 2 | 2 | | 1 | 2 | 1 |
| 21 | 1 | | 1 | | | 3 | 2 | 1 | 2 | 1 | 1 |
| 19 | 1 | | 1 | 1 | | 2 | 1 | 1 | 2 | 1 | 2 |
| 5 | | | | | 1 | | | | | | |
| 22 | 1 | 1 | 1 | | 1 | 2 | 1 | | 1 | 1 | 1 |
| 23 | 1 | | | | 1 | 2 | | | | | |
| 31 | 2 | | 2 | 2 | | 2 | | 1 | 3 | 4 | 4 |
| 6 | | | 1 | 1 | 1 | 2 | | 2 | 2 | 1 | 2 |
| 4 | 1 | | 2 | | 2 | 4 | 3 | | 2 | 1 | 2 |
| 24 | 2 | | 1 | | | 3 | 1 | | 2 | 1 | 1 |
| 32 | 3 | 1 | 4 | 4 | 4 | 4 | 1 | 4 | 4 | 4 | 4 |
| 33 | 3 | | 4 | 3 | 2 | 4 | | 2 | 3 | 4 | 4 |

Example C.12

In Vitro Inhibition of EGFR (Flash Plate Assay)

The in vitro inhibition of EGFR was assessed using either the Flash Plate technology or the glass-fiber filter technology as described by Davies, S. P. et al., Biochem J. (2000), 351; p. 95-105. The Flash Plate technology is generally described by B. A. Brown et al. in High Throughput Screening (1997), p. 317-328. Editor(s): Devlin, John P. Publisher: Dekker, New York, N.Y.

In the Flash Plate EGFR kinase reaction assay, a kinase substrate consisting of biotinylated poly(L-glutamic acid-L-tyrosine) (poly(GT)biotin), is incubated with the aforementioned protein in the presence of ($^{33}$P) radiolabeled ATP. ($^{33}$P) phosphorylation of the substrate is subsequently measured as light energy emitted using a streptavidin-coated Flash Plate (PerkinElmer Life Sciences) by trapping and quantifying the binding of the biotin tagged and radiolabeled substrate.

DETAILED DESCRIPTION

The EGFR kinase reaction is performed at 30° C. for 60 minutes in a 96-well microtiter FlashPlate (PerkinElmer Life Sciences). For each of the tested compounds a full dose response 1.10$^{-6}$M to 1.10$^{-10}$M has been performed. IRESSA® and Tarceva™ (erlotinib) were used as reference compounds. The 100 µl reaction volume contains 54.5 mM TrisHCl pH 8.0, 10 mM MgCl$_2$, 100 M Na$_3$VO$_4$, 5.0 µM unlabeled ATP, 1 mM DTT, 0.009% BSA, 0.8 Ci AT$^{33}$P, 0.35 µg/well poly(GT)biotin and 0.5 µg EGFR-kinase domain/well.

The reaction is stopped by aspirating the reaction mixture and washing the plate 3× with 200 l wash/stop buffer (PBS+ 100 mM EDTA). After the final wash step 200 l of wash/stop buffer was added to each well and the amount of phosphorylated ($^{33}$P) Poly(GT)biotin determined by counting (30 sec/well) in a microtiterplate scintillation counter.

In the glass-fiber filter technology EGFR kinase reaction assay, a kinase substrate consisting of poly(L-glutamic acid-L-tyrosine) (poly(GT)), is incubated with the aforementioned protein in the presence of ($^{33}$P) radiolabeled ATP. ($^{33}$P) Phosporylation of the substrate is subsequently measured as radioactivity bound on a glassfiber-filter.

DETAILED DESCRIPTION

The EGFR kinase reaction is performed at 25° C. for 10 minutes in a 96-well microtiterplate. For each of the tested compounds a full dose response 1.10$^{-6}$M to 1.10$^{-10}$M has been performed. IRESSA® and Tarceva™ (erlotinib) were used as reference compounds. The 25 µl reaction volume contains 60 mM TrisHCl pH 7.5, 3 mM MgCl$_2$, 3 mM MnCl$_2$, 3 M Na$_3$VO$_4$, 50 µg/ml PEG20000, 5.0 µM unlabeled ATP, 1 mM DTT, 0.1 Ci AT$^{33}$P, 62.5 ng/well poly(GT) and 0.5 µg EGFR-kinase domain/well.

The reaction is stopped by adding 5 µl of a 3% phosphoric acid solution. 10 µl of the reaction mixture is then spotted onto a Filtermat A filter (Wallac) and washed 3 times for 5 min. in 75 mM phosphoric acid and 1 time for 5 min. in methanol prior to drying and quantification on the Typhoon (Amersham) using a LE phosphorage storage screen.

Similarly to the above the in vitro inhibition of two other kinases, i.e human ErbB2 and human ErbB4 was tested for some of the compounds according to the invention.

Example C.13

ErbB2 Human

In a final reaction volume of 25 µl, ErbB2 (h) (5-10 mU) is incubated with 8 mM MOPS pH 7.0, 0.2 mM EDTA, 10 mM MnCl2, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Example C.14

ErbB4 Human

In a final reaction volume of 25 µl, ErbB4 (h) (5-10 mU) is incubated with 8 mM MOPS pH 7.0, 0.2 mM EDTA, 10 mM MnCl2, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

The following tables provides the scores for the compounds according to the invention, obtained in these Flash Plate Assays. Score 1=pIC50<5, Score 2=pIC50 from 5-6, Score 3=pIC50>6.

| Compound No | C12 EGFR-flash Score | C13 ERBB 2 Filter Score | C14 ERBB 4 Filter Score |
|---|---|---|---|
| 112 | 3 | 3 | 3 |
| 114 | 3 | 2 | |
| 162 | 3 | 2 | 2 |
| 152 | 3 | 3 | 3 |
| 159 | 3 | 2 | |
| 148 | 3 | 2 | 2 |
| 158 | 3 | 2 | |
| 150 | 3 | 3 | 3 |
| 161 | 3 | 2 | 3 |
| 156 | 3 | 2 | 3 |
| 149 | 3 | 2 | 3 |
| 151 | 3 | 3 | 3 |
| 160 | 3 | 2 | 2 |
| 136 | 3 | | |
| 180 | 2 | | |
| 111 | 2 | | |
| 182 | 2 | | |
| 173 | 2 | | |
| 113 | 2 | | |
| 141 | 2 | | |
| 196 | 2 | | |
| 140 | 2 | | |
| 145 | 2 | | |
| 195 | 2 | | |

| Compound No | C12 EGFR-flash Score | C13 ERBB 2 Filter Score | C14 ERBB 4 Filter Score |
|---|---|---|---|
| 179 | 2 | | |
| 135 | 2 | | |
| 190 | 2 | | |
| 183 | 2 | | |
| 186 | 2 | | |
| 127 | 2 | | |
| 154 | 2 | 2 | |
| 199 | | | |
| 119 | | | |
| 197 | | | |
| 126 | | | |
| 124 | | | |
| 122 | | | |
| 153 | | 2 | |
| 163 | | 3 | |
| 164 | | 2 | 3 |
| 216 | | | 2 |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in DCM (150 ml). Then there were added DCM (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound of formula (VI)

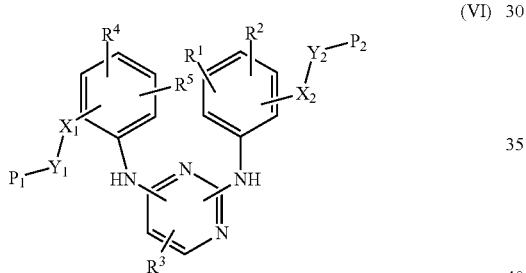

(VI)

the pharmaceutically acceptable addition salts and the stereochemically isomeric forms thereof, wherein $P_1$ and $P_2$ each independently represent hydroxy, halo, hydroxycarbonyl-, halocarbonyl-, amino or —$NHR^{29}$;

$Y_1$ and $Y_2$ each independently represent $C_{1-7}$alkyl, $C_{3-7}$alkenyl, $Het^{27}$, $Het^{28}$-CO, $Het^{29}$-$C_{1-5}$alkyl, $L^2$-NH, $L^1$-NH—CO, $L^3$-CO, $L^3$-CO—NH, CO—$C_{1-6}$alkyl, NH—CO—$C_{1-3}$alkyl, $C_{1-3}$alkyl-$NR^{11}$—$CH_2$, or $CH_2$—CO—NH—$C_{1-3}$alkyl; $X^1$ represents a direct bond, O, —O—$C_{1-2}$alkyl, CO, CO—$C_{1-2}$alkyl, $NR^{16}$—$C_{1-2}$alkyl, CO—$NR^{17}$, $Het^{23}$-$C_{1-2}$alkyl, or $C_{1-2}$alkyl;

$X^2$ represents a direct bond, 0, —O—$C_{1-2}$alkyl, CO, CO—$C_{1-2}$alkyl, $NR^{18}$—$C_{1-2}$alkyl, CO—$NR^{16}$, $Het^{24}$-$C_{1-2}$alkyl, or $C_{1-2}$alkyl;

$R^1$ represents hydrogen, halo, $C_{1-6}$alkyloxy or $C_{1-6}$alkyloxy substituted with $Het^1$ or $C_{1-4}$alkyloxy;

$R^2$ represents hydrogen or halo;

$R^3$ represents hydrogen or cyano;

$R^4$ represents hydrogen or halo;

$R^5$ represents hydrogen, halo, $C_{1-6}$alkyloxy or $C_{1-6}$alkyloxy substituted with $Het^2$ or $C_{1-4}$alkyloxy;

$R^{11}$ represents hydrogen or $C_{1-4}$alkyl or $Het^{17}$-$C_{1-4}$alkyl;

$R^{16}$ and $R^{18}$ each independently represent hydrogen, $C_{1-4}$alkyl or $Het^{17}$-$C_{1-4}$alkyl;

$R^{17}$ and $R^{19}$ each independently represent hydrogen;

$R^{29}$ represents hydrogen, $C_{1-4}$alkyl, or $Het^{31}$-$C_{1-4}$alkyl; wherein $Het^{31}$ represents a heterocycle selected from morpholinyl, pyrrolidinyl, 2-pyrrolidinonyl, piperazinyl or piperidinyl;

$L^1$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl; in particular $L^1$ represents $C_{1-8}$alkyl optionally substituted with phenyl, methylsulfide, hydroxy, thiol, amino, mono- or di($C_{1-4}$alkyl)-amine or imidazoyl $L^2$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$L^3$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$Het^1$ represents morpholinyl, oxazolyl, isoxazolyl, or piperazinyl; $Het^2$ represents morpholinyl, oxazolyl, isoxazolyl, or piperazinyl;

$Het^{17}$ represents morpholinyl, pyrrolidinyl, piperazinyl or piperidinyl wherein said $Het^{17}$ is optionally substituted with one or two substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{22}$ represents a heterocycle selected from morpholinyl, piperazinyl or piperidinyl wherein said $Het^{22}$ is optionally substituted with $C_{1-4}$alkyl;

$Het^{23}$ and $Het^{24}$ each independently represent a heterocycle selected from pyrrolidinyl, piperazinyl or piperidinyl, wherein said $Het^{23}$ and $Het^{24}$ is optionally substituted with $Het^{22}$-carbonyl;

$Het^{27}$ and $Het^{29}$ each independently represent a heterocycle selected from morpholinyl, pyrrolidinyl, -pyrrolidinonyl, quinolinyl, isoquinolinyl, decahydroquinolinyl, piperazinyl or piperidinyl wherein said $Het^{27}$ and $Het^{29}$ are optionally substituted with one or where possible two or more substituents selected from hydroxy, $Het^{22}$-carbonyl-, $C_{1-4}$alkyl, hydroxy-$C_{1-4}$alkyl- or polyhydroxy-$C_{1-4}$alkyl-;

$Het^{28}$ represents a heterocycle selected from morpholinyl, pyrrolidinyl, 2-pyrrolidinonyl, piperazinyl or piperidinyl wherein said $Het^{28}$ is optionally substituted with one or where possible two or more substituents selected from hydroxy, $C_{1-4}$alkyl, hydroxy-$C_{1-4}$alkyl- or polyhydroxy-$C_{1-4}$alkyl.

2. A compound of formula (VII)

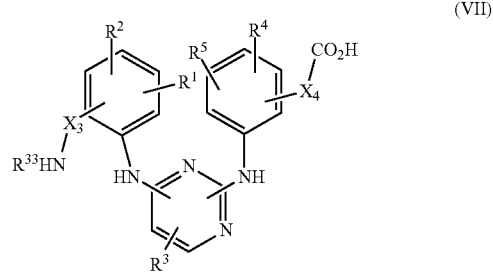

(VII)

the pharmaceutically acceptable addition salts and the stereochemically isomeric forms thereof, wherein $X_3$ and $X_4$ each independently represent a direct bond, $C_{1-7}$alkyl, $C_{3-7}$alkenyl, $C_{3-7}$alkynyl, wherein said $C_{1-7}$alkyl, $C_{3-7}$alkenyl, $C_{3-7}$alkynyl are optionally substituted with one or where possible two or more substituents selected from amino, mono- or di($C_{1-4}$alkyl)amino, aminosulfonyl, mono- or di($C_{1-4}$alkyl)aminosulfonyl, $C_{1-4}$alkylsulfide, $C_{1-4}$alkylsulfoxide, $C_{1-4}$alkylsulfonyl and $C_{1-4}$alkyloxycarbonylamino;

or $X_3$ and $X_4$ each independently represent $C_{1-5}$alkyl-O—$C_{1-5}$alkyl, $C_{1-5}$alkyl-$NR^{30}$—$C_{1-5}$alkyl, $C_{1-2}$alkyl-CO-$Het^{10}$, $Het^{23}$, $CR^8R^9$ or O—$C_{1-2}$alkyl with the oxygen atom attached to the phenyl ring;

$R^1$ represents hydrogen, cyano, halo, hydroxy, formyl, $C_{1-6}$alkoxy-, $C_{1-6}$alkyl-, halo-phenyl-carbonylamino-, $Het^{20}$, $C_{1-6}$alkoxy- substituted with halo, $Het^1$ or $C_{1-4}$alkyloxy-, or $R^1$ represents $C_{1-6}$alkyl substituted with one or where possible two or more substituents selected from hydroxy, $Het^{18}$ or halo;

$R^2$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^3$ represents hydrogen, cyano, nitro, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

$R^4$ represents hydrogen, cyano, halo, hydroxy, hydroxycarbonyl-, $C_{1-4}$alkyloxycarbonyl-, $C_{1-4}$alkylcarbonyl-, aminocarbonyl-, mono- or di($C_{1-4}$alkyl)aminocarbonyl-, $C_{1-4}$alkyl-, $C_{2-6}$alkynyl-, $C_{3-6}$cycloalkyloxy-, aminosulfonyl, mono- or di($C_{1-4}$alkyl)aminosulfonyl, $C_{1-4}$alkylsulfide, $C_{1-4}$alkylsulfoxide, $C_{1-4}$alkylsulfide or $C_{1-6}$alkoxy-;

$R^5$ represents hydrogen, cyano, halo, hydroxy, formyl, $C_{1-6}$alkoxy-, $C_{1-6}$alkyl-, halo-phenyl-carbonylamino-, $Het^{21}$, $C_{1-6}$alkoxy- substituted with halo, $Het^2$ or $C_{1-4}$alkyloxy-, or $R^5$ represents $C_{1-6}$alkyl substituted with one or where possible two or more substituents selected from hydroxy, $Het^{19}$ or halo;

$R^8$ and $R^9$ each independently represents hydrogen or $C_{1-4}$alkyl optionally substituted with phenyl, indolyl, methylsulfide, hydroxy, thiol, hydroxyphenyl, $C_{1-4}$alkyloxyphenyl-, aminocarbonyl, hydroxycarbonyl, amino, mono- or di($C_{1-4}$alkyl)-amine-, imidazoyl, cyano, polyhalo$C_{1-4}$alkylphenyl, $C_{1-4}$alkyloxy, pyridinyl, $C_{3-6}$cycloalkyl or guanidino;

$R^{30}$ represents hydrogen, $C_{1-4}$alkyl, $Het^{11}$, $Het^{12}$-$C_{1-4}$alkyl, phenyl-$C_{1-4}$alkyl, phenyl or mono- or di($C_{1-4}$alkyl)amino-$C_{1-4}$alkyl-carbonyl wherein said $R^{30}$ is optionally substituted with hydroxy, amino, mono- or di($C_{1-4}$alkyl)amino, pyrimidinyl or $C_{1-4}$alkyloxy;

$R^{33}$ represents hydrogen, $C_{1-4}$alkyl, $Het^{14}$ or $C_{1-4}$alkyl substituted with one or where possible two or more substituents selected from hydroxy, amino, mono- or di($C_{1-4}$alkyl)amino, phenyl, $Het^{15}$ or $C_{1-2}$alkyloxy;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^2$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^2$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{10}$ represents a heterocycle selected from pyrrolidinyl, 2-pyrrolidinonyl, piperazinyl or piperidinyl wherein said $Het^{10}$ is optionally substituted with one or where possible two or more substituents selected from hydroxy, $C_{1-4}$alkyl, hydroxy-$C_{1-4}$alkyl- or polyhydroxy-$C_{1-4}$alkyl-;

$Het^{11}$ represent a heterocycle selected from pyrrolidinyl or piperidinyl wherein said $Het^{11}$ is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{12}$ represent a heterocycle selected from morpholinyl, pyrrolidinyl, piperazinyl or piperidinyl wherein said $Het^{12}$ is optionally substituted with one or where possible two or more substituents selected from $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

$Het^{14}$ represent a heterocycle selected from pyrrolidinyl or piperidinyl wherein said pyrrolidinyl or piperazinyl are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represents a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{18}$ or $Het^{19}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{20}$ and $Het^{21}$ each independently represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^{20}$ or $Het^{21}$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{22}$ represents a heterocycle selected from morpholinyl, pyrrolidinyl, piperazinyl or piperidinyl wherein said $Het^{22}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{23}$ represents a heterocycle selected from pyrrolidinyl, 2-pyrrolidinonyl, quinolinyl, isoquinolinyl, decahydroquinolinyl, piperazinyl or piperidinyl wherein said $Het^{23}$ is optionally substituted with one or where possible two or more substituents selected from hydroxy, $Het^{25}$, $Het^{22}$-carbonyl, $C_{1-4}$alkyl, hydroxy-$C_{1-4}$alkyl- or polyhydroxy-$C_{1-4}$alkyl-; and $Het^{25}$ represents a heterocycle selected from morpholinyl, pyrrolidinyl, piperazinyl or piperidinyl wherein said $Het^{25}$ is optionally substituted with one or where possible two or more substituents selected from $C_{1-4}$alkyl, $C_{3-6}$cycloalkyl,
hydroxy-$C_{1-4}$alkyl-, $C_{1-4}$alkyloxy$C_{1-4}$alkyl or polyhydroxy-$C_{1-4}$alkyl-;

provided said intermediate of formula (VII) is other than 2-[[2-[(3-aminophenyl)amino]-4-pyrimidinyl]amino]-Benzoic acid.

3. A compound according to claim 2 wherein;

$Y_1$ and $Y_2$ each independently represent $C_{1-7}$alkyl, $C_{3-7}$alkenyl, $Het^{27}$, $Het^{28}$-CO, $L^1$-NH, CO—$C_{1-3}$alkyl, $C_{1-3}$alkyl-$NR^{11}$—$CH_2$ or $CH_2$—CO—NH—$C_{1-3}$alkyl;

$X^2$ represents a direct bond, O, —O—$C_{1-2}$alkyl, CO, CO—$C_{1-2}$alkyl, $NR^{18}$—$C_{1-2}$alkyl, CO—$NR^{16}$, $Het^{24}$-$C_{1-2}$alkyl, or $C_{1-2}$alkyl;

$R^1$ represents hydrogen, halo, $C_{1-6}$alkyloxy or $C_{1-6}$alkyloxy substituted with $Het^1$ or $C_{1-4}$alkyloxy;

$R^2$ represents hydrogen or halo;

$R^3$ represents hydrogen or cyano;

$R^4$ represents hydrogen or halo;

$R^5$ represents hydrogen, halo, $C_{1-6}$alkyloxy or $C_{1-6}$alkyloxy substituted with $Het^2$ or $C_{1-4}$alkyloxy;

$R^{11}$ represents hydrogen or $C_{1-4}$alkyl or $Het^{17}$-$C_{1-4}$alkyl;

$R^{16}$ and $R^{18}$ each independently represent hydrogen, $C_{1-4}$alkyl or $Het^{17}$-$C_{1-4}$alkyl;

$R^{17}$ and $R^{19}$ each independently represent hydrogen;

$L^1$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$L^2$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$L^3$ represents $C_{1-8}$alkyl optionally substituted with phenyl, methylsulfide, mono- or di($C_{1-4}$alkyl)amino, cyano, polyhalo$C_{1-4}$alkylphenyl, $C_{1-4}$alkyloxy, pyridinyl, imidazolyl or $C_{3-6}$cycloalkyl;

$Het^1$ represents morpholinyl, oxazolyl, isoxazolyl, or piperazinyl;

$Het^2$ represents morpholinyl, oxazolyl, isoxazolyl, or piperazinyl;

$Het^{22}$ represents a heterocycle selected from morpholinyl, piperazinyl or piperidinyl wherein said $Het^{22}$ is optionally substituted with $C_{1-4}$alkyl;

$Het^{23}$ and $Het^{24}$ each independently represent a heterocycle selected from pyrrolidinyl, piperazinyl or piperidinyl, wherein said $Het^{23}$ and $Het^{24}$ is optionally substituted with $Het^{22}$-carbonyl;

$Het^{27}$ and $Het^{29}$ each independently represent a heterocycle selected from morpholinyl, pyrrolidinyl, -pyrrolidinonyl, quinolinyl, isoquinolinyl, decahydroquinolinyl, piperazinyl or piperidinyl wherein said $Het^{27}$ and $Het^{29}$ are optionally substituted with one or where possible two or more substituents selected from hydroxy, $Het^{22}$-carbonyl-, $C_{1-4}$alkyl, hydroxy-$C_{1-4}$alkyl- or polyhydroxy-$C_{1-4}$alkyl-;

$Het^{28}$ represents a heterocycle selected from morpholinyl, pyrrolidinyl, 2-pyrrolidinonyl, piperazinyl or piperidinyl wherein said $Het^{28}$ is optionally substituted with one or where possible two or more substituents selected from hydroxy, $C_{1-4}$alkyl, hydroxy-$C_{1-4}$alkyl- or polyhydroxy-$C_{1-4}$alkyl-.

4. A compound according to claim 2 wherein;

$X_3$ and $X_4$ each independently represent a direct bond, $C_{1-7}$alkyl, $C_{3-7}$alkenyl, $C_{1-5}$alkyl-$NR^{30}$—$C_{1-5}$alkyl, $Het^{23}$, $CR^8R^9$ or O—$C_{1-2}$alkyl with the oxygen atom attached to the phenyl ring;

$R^1$ represents hydrogen, halo, $C_{1-6}$alkyloxy-, or $C_{1-6}$alkyloxy substituted with $Het^1$ or $C_{1-4}$alkyloxy;

$R^2$ represents hydrogen of halo;

$R^3$ represents hydrogen, cyano or nitro; in particular hydrogen or cyano;

$R^4$ represents hydrogen or halo;

$R^5$ represents hydrogen, halo, $C_{1-6}$alkyloxy-, or $C_{1-6}$alkyloxy substituted with $Het^2$ or $C_{1-4}$alkyloxy;

$R^8$ and $R^9$ each independently represents hydrogen or $C_{1-4}$alkyl optionally substituted with phenyl, methylsulfide, hydroxy, thiol, amino, mono- or di($C_{1-4}$alkyl)-amine-, or imidazoyl;

$R^{30}$ represents hydrogen, $C_{1-4}$alkyl or $Het^{12}$-$C_{1-4}$alkyl;

$R^{33}$ represents hydrogen, $C_{1-4}$alkyl or $Het^{15}$-$C_{1-4}$alkyl;

$Het^1$ represents morpholinyl;

$Het^2$ represents morpholinyl;

$Het^{12}$ represents pyrrolidinyl or piperazinyl wherein said $Het^{12}$ is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-; in particular $Het^{12}$ represents pyrrolidinyl or piperazinyl;

$Het^{15}$ represents pyrrolidinyl or piperazinyl wherein said $Het^{15}$ is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-; in particular $Het^{15}$ represents pyrrolidinyl or piperazinyl; and $Het^{23}$ represents a heterocycle selected from pyrrolidinyl, decahydroquinolinyl or pyridinyl wherein said $Het^{23}$ is optionally substituted with one or where possible two or more substituents selected from hydroxy or $C_{1-4}$alkyl.

* * * * *